(12) United States Patent
Ryckman et al.

(10) Patent No.: US 8,853,235 B2
(45) Date of Patent: Oct. 7, 2014

(54) POLYMORPHS AND SALTS OF A KINASE INHIBITOR

(75) Inventors: David M. Ryckman, San Diego, CA (US); Michael Schwaebe, San Diego, CA (US)

(73) Assignee: Senhwa Biosciences, Inc., New Taipei (TW)

( * ) Notice: Subject to any disclaimer, the term of this patent is extended or adjusted under 35 U.S.C. 154(b) by 469 days.

(21) Appl. No.: 12/952,879

(22) Filed: Nov. 23, 2010

(65) Prior Publication Data

US 2011/0160240 A1     Jun. 30, 2011

Related U.S. Application Data

(60) Provisional application No. 61/263,638, filed on Nov. 23, 2009.

(51) Int. Cl.
*A61K 31/4375* (2006.01)
*C07D 471/04* (2006.01)
*A61K 31/54* (2006.01)

(52) U.S. Cl.
CPC .............. *A61K 31/54* (2013.01); *C07D 471/04* (2013.01)
USPC ........................................... 514/290; 546/81

(58) Field of Classification Search
USPC ........................................... 546/81; 514/290
See application file for complete search history.

(56) References Cited

U.S. PATENT DOCUMENTS

| 4,666,922 | A | 5/1987 | Smith et al. |
| 4,954,507 | A | 9/1990 | Weber et al. |
| 5,464,781 | A | 11/1995 | Armitage et al. |
| 6,723,734 | B2 | 4/2004 | Kim et al. |
| 2009/0239859 | A1 | 9/2009 | Chua et al. |

FOREIGN PATENT DOCUMENTS

WO     2008/028168     *   3/2008

OTHER PUBLICATIONS

Byrn et al, 1995, Pharmaceutical Solids. A strategic approach to regulatory considerations.*
Berge S. et al , 1977, Pharmaceutical Salts.*
ICH, Harmonised Tripartite Guidelines and decision trees, 1999.*
Young, "International Search Report," 3 pages, PCT appl. No. PCT/US10/57838, United States Patent and Trademark Office (mailed Feb. 7, 2011).
Young, "Written Opinion of the International Searching Authority," 9 pages, PCT appl. No. PCT/US10/57838, United States Patent and Trademark Office (mailed Feb. 7, 2011).

* cited by examiner

*Primary Examiner* — Rita Desai
(74) *Attorney, Agent, or Firm* — Cooley LLP

(57) ABSTRACT

The present invention relates to novel crystalline polymorphic salt forms of 5-(3-chlorophenylamino)benzo[c][2,6]naphthyridine-8-carboxylic acid, processes for the preparation thereof, compositions thereof and their use in methods of treatment and prevention of conditions mediated by casein kinase (CK) and/or poly(ADP-ribose)polymerase (PARP).

36 Claims, 86 Drawing Sheets

Figure 25
Lysine Salt - PLM (x20)
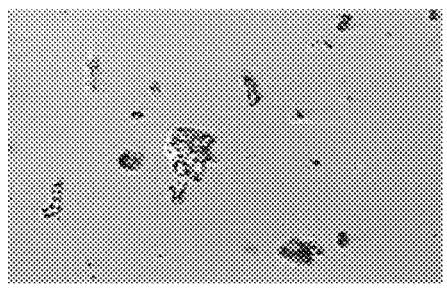
iPrOH
2BuOH
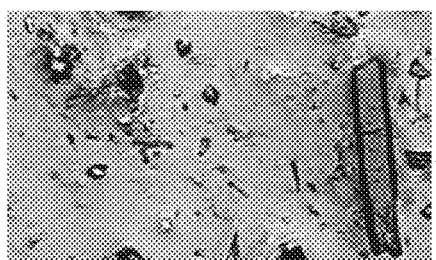
iPrOH : H$_2$O
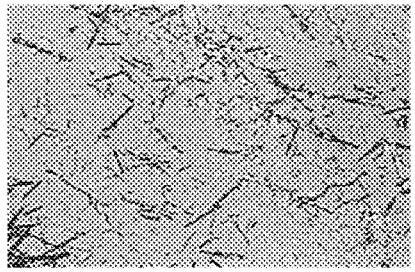
DMF Figure 28
Zinc acetate - PLM (X20)
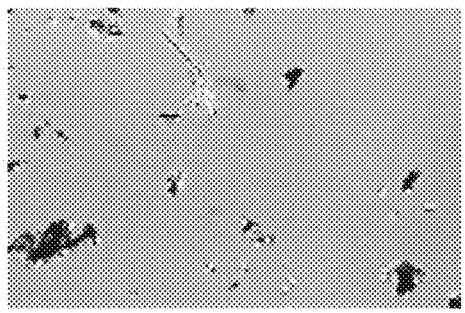
EtOH
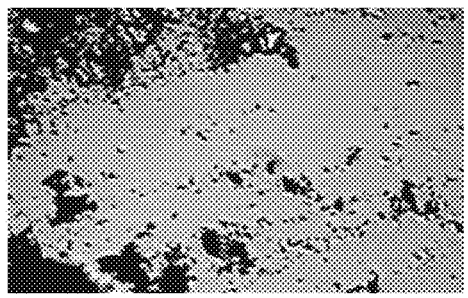
iPrOH
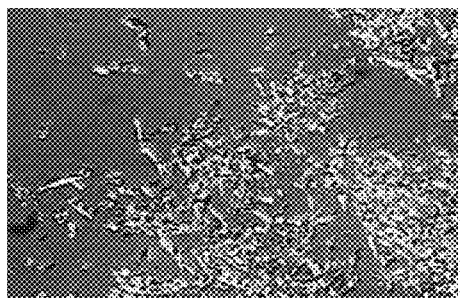
2BuOH
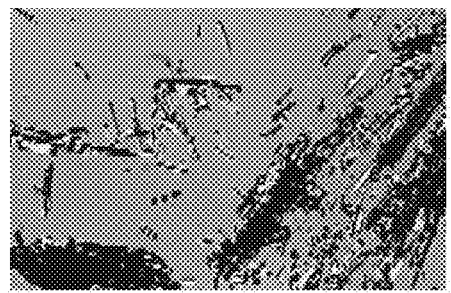
iPrOH : $H_2O$ zinc acetate salts - XRPD Figure 31
N-methylglucamine - PLM (x20)
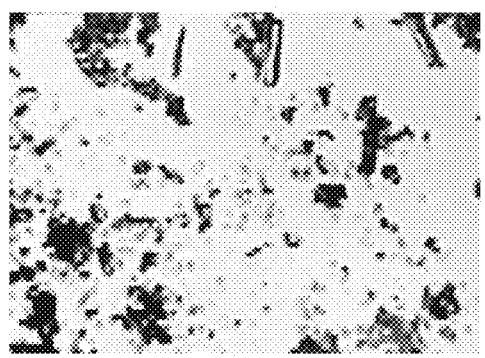
EtOH
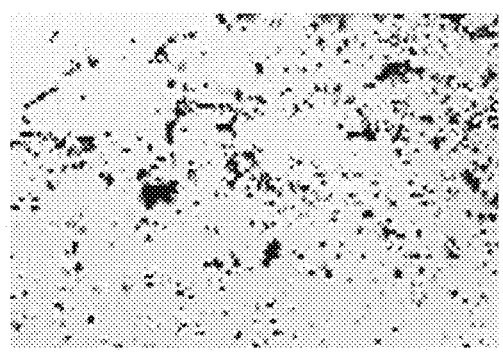
iPrOH
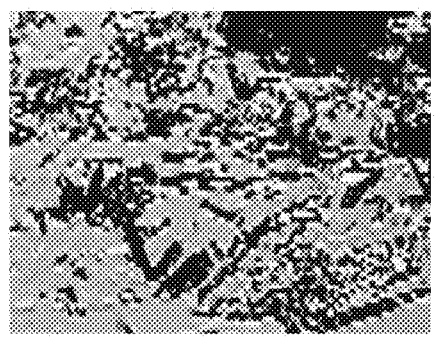
2BuOH
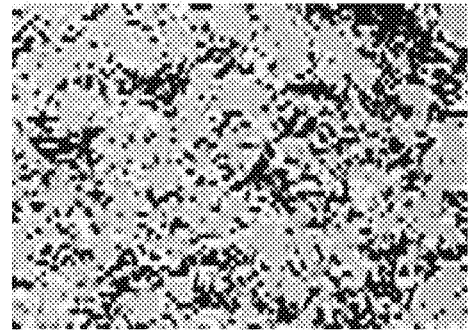
iPrOH : H$_2$O N-methylglucamine (from EtoH) - XRPD Figure 34
Ammonium hydroxide salt - PLM (x20)
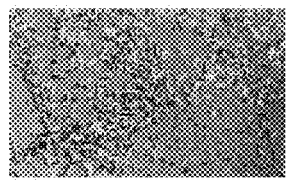 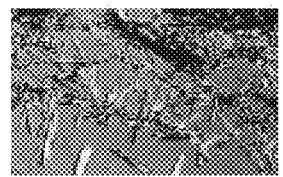 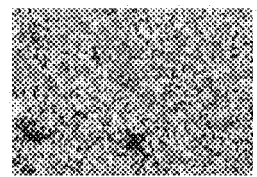
EtOH   /PrOH   2BuOH
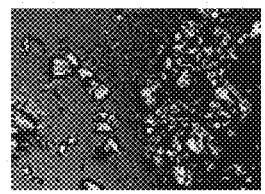 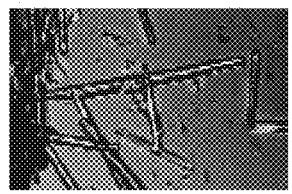
/PrOH : H₂O   DMF Figure 36
Choline hydroxide salt - PLM
EtOH
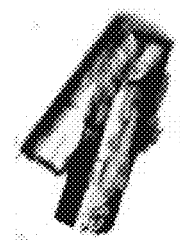
*i*PrOH (x40)
2BuOH
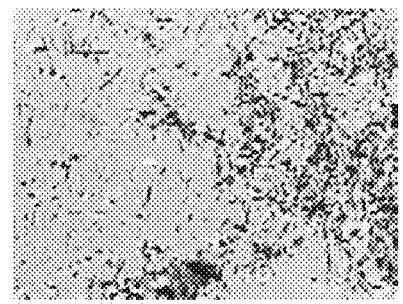
*i*PrOH : H$_2$O Figure 38
Ca(OH)$_2$ salt (1:1) - PLM (x20)
 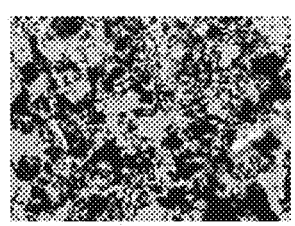 
EtOH　　　　　　　　　$^i$PrOH　　　　　　　　　2BuOH
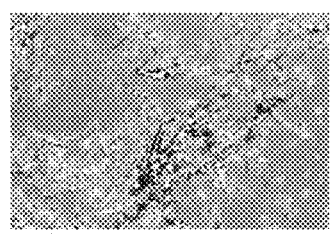 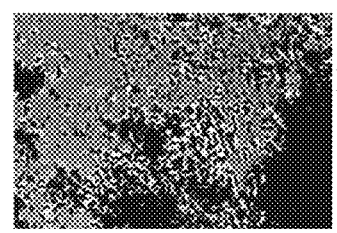
$^i$PrOH:H$_2$O　　　　　　　　　DMF Figure 42
Mg(OH)$_2$ salt (1:1) - PLM
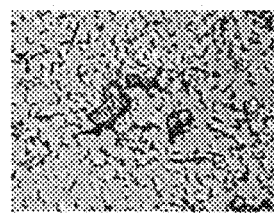
EtOH
$i$PrOH
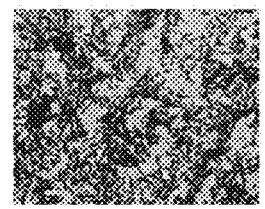
2BuOH
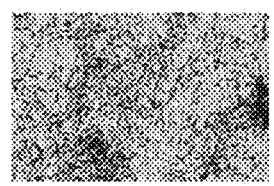
$i$PrOH : H$_2$O
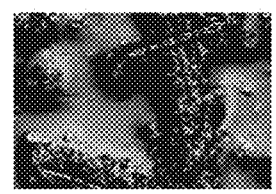
DMF Figure 45
KOH salt - PLM
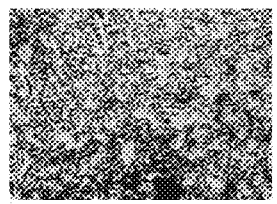  
EtOH    iPrOH    2BuOH
 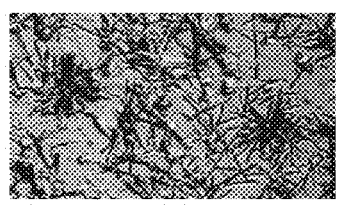
iPrOH:H₂O    DMF K salt - TGA & DSC Figure 49
Arginine Salt
Polarised light microscopy (PLM)
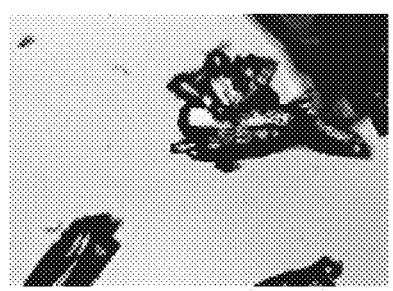
EtOH (x20)
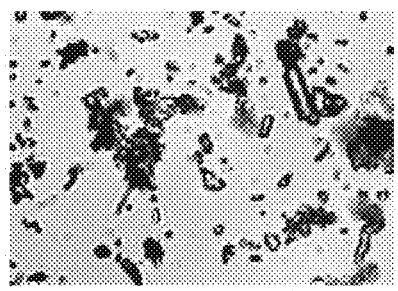
iPrOH (x40)
2BuOH (x40)
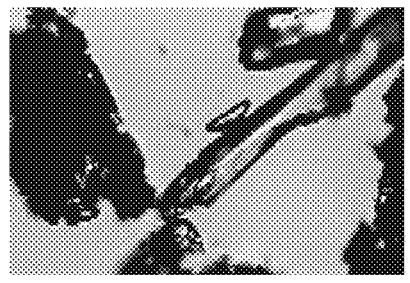
iPrOH:H$_2$O (x20)

Arginine (from EtOH) - XRPD

Figure 60
a)
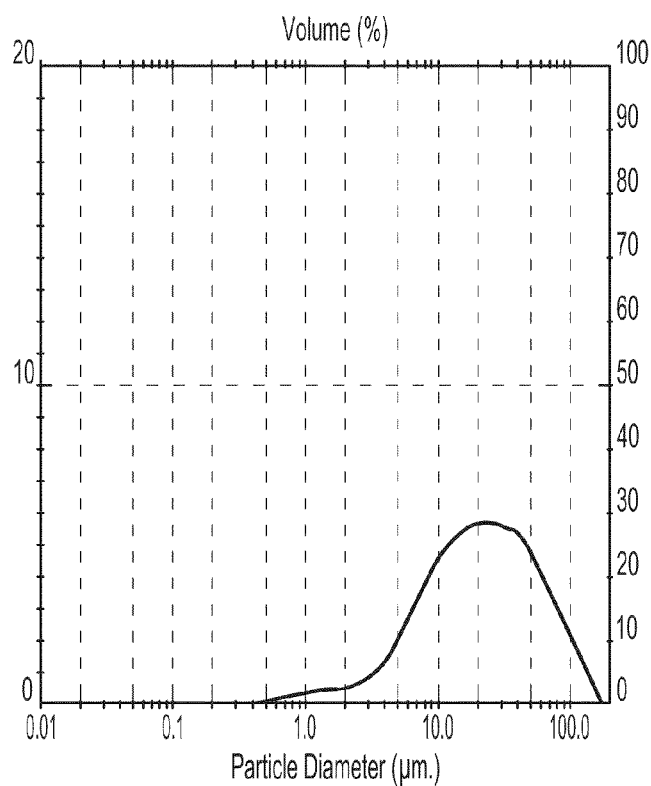
b)
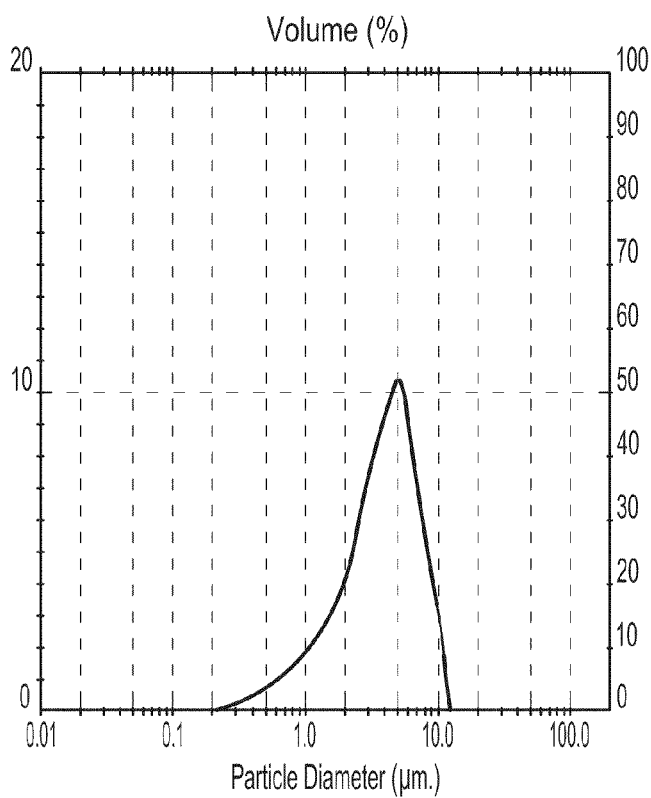

Figure 64
Tromethamine (TRIS) salt - PLM (X20)
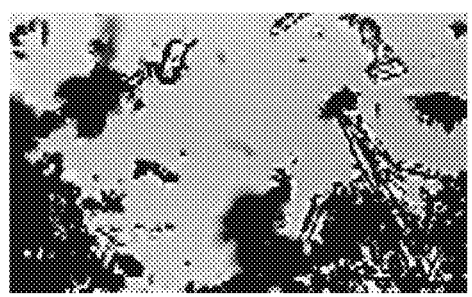
EtOH
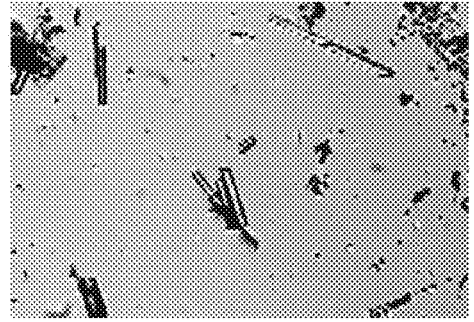
iPrOH
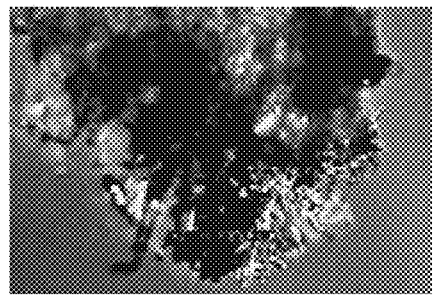
2BuOH
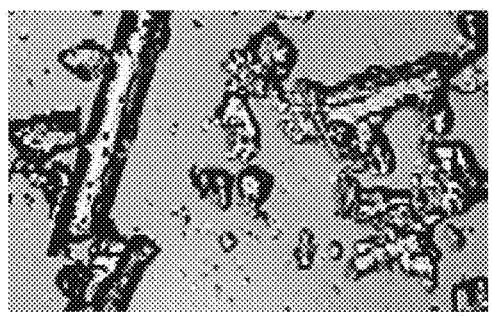
iPrOH : H$_2$O Tromethamine salt - XRPD Figure 75
A)
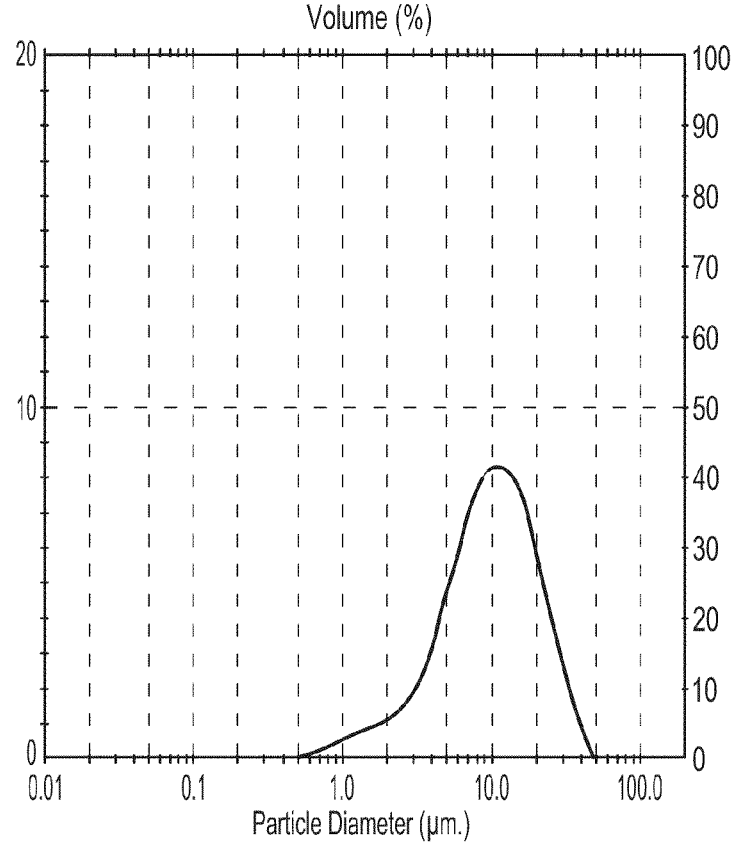
B)
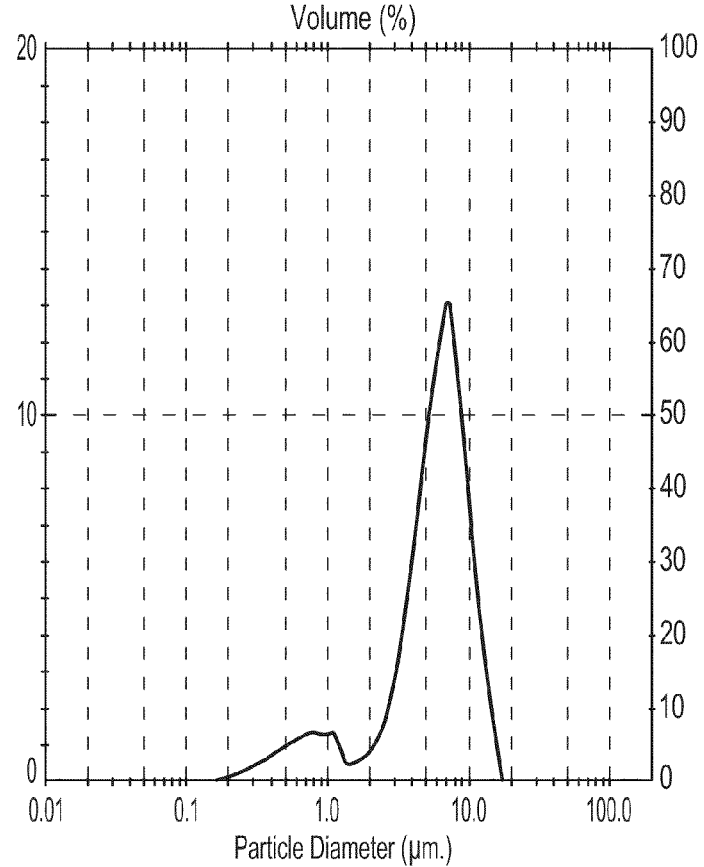

Figure 81

|  | Free-acid | Sodium salt |
|---|---|---|
| Ethanol 200 proof | < 2 | < 2 |
| Isopropanol | < 2 | < 2 |
| Acetone | < 2 | < 2 |
| Methylene chloride | < 2 | < 2 |
| PEG400 | < 2 | ~ 20 |
| Benzyl alcohol | < 2 | ~ 2 |
| Propylene glycol | < 2 | < 14 |
| Labrasol | < 2 | ~ 9 |
| Polysorbate 80 | < 2 | ~ 2 |

POLYMORPHS AND SALTS OF A KINASE INHIBITOR

CROSS-REFERENCE TO RELATED APPLICATION

This application claims the benefit of U.S. Provisional Application No. 61/263,638, filed on Nov. 23, 2009 and entitled "POLYMORPHS AND SALTS OF A KINASE INHIBITOR", the disclosures of which are hereby incorporated by reference in their entireties for all purposes.

FIELD OF THE INVENTION

The invention relates in part to novel crystalline polymorphic and salt forms of 5-(3-chlorophenylamino)benzo[c][2,6]naphthyridine-8-carboxylic acid having certain biological activities that include, but are not limited to, inhibiting cell proliferation, modulating serine-threonine protein kinase activity and modulating polymerase activity. The polymorphs and salts of the invention can modulate casein kinase (CK) activity (e.g., CK2 activity) and/or poly(ADP-ribose)polymerase (PARP) activity. The invention also relates in part to methods for using such forms, processes for their preparation, and compositions thereof.

BRIEF SUMMARY OF THE INVENTION

In one aspect is provided a solid salt of compound (I):

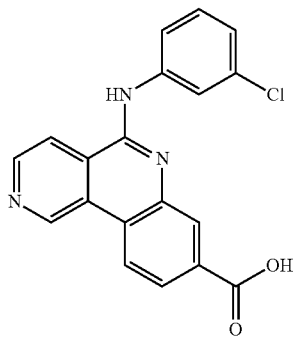

(I)

5-(3-chlorophenylamino)benzo[c][2,6]naphthyridine-8-carboxylic acid

In one variation, the salt is a sodium salt (e.g., a solid amorphous sodium salt or crystalline sodium salt). In one variation, the crystalline sodium salt of compound (I) is any polymorph of a sodium salt described herein (e.g., polymorph Form II, III, IV, V, VI, VII, VIII, IX, X, XI, or XII). The salt forms described herein (e.g., the sodium salt of compound I) may have drastically improved solubility properties over the corresponding free acid, and are surprisingly more soluble in organic solvents than the acid. The specific polymorph forms described herein are advantageous over the known solid form of the acid of compound (I) by virtue of improved handling characteristics, lower tendency to aggregate, improved suitability for forming cohesive solid forms (tablets), improved stability for long term storage, better solubility, and/or improved solubility profiles. The acid form of Compound I has very low water solubility, while the salts have much higher solubility not only in water, but also in other solvents suitable for pharmaceutical use.

In particular embodiments, Form II is advantageous because it can be prepared consistently, while other polymorphs of the sodium salt often interconvert on handling or upon exposure to moist air. Indeed, some of the other forms can be converted into Form II readily, and conditions for such interconversion are described herein. Consistent physical properties greatly facilitate handling, and preparation of solid dosage forms on production scale; thus it is advantageous to use a polymorph that is stable under normal handling conditions. Thus in one embodiment, the polymorph of Form II is utilized.

In one variation, the polymorph of compound (I) is a sodium salt polymorph of Form II. In some embodiments, the polymorph is characterized as having any one or combination of powder X-ray diffraction pattern peaks of 2θ at about 5.2°, 7.1°, 10.4°, 11.9°, 15.1°, 15.6°, 16.1°, 17.3°, 17.7°, 19.3°, 20.3°, 21.1°, 24.6°, 26.2°, 27.2°, 28.3°, 28.9°, 30.6°, 36.7°, 37.4°, 39.1°, 41.4°, 44.4°, 45.0°, 46.4° and 48.1°. In some embodiments, the polymorph is characterized by having powder X-ray diffraction pattern peaks of 2θ at about 26.2°, and 27.2°. In some embodiments, the polymorph is characterized by having powder X-ray diffraction pattern peaks of 2θ at about 10.4°, 11.9°, 15.1°, 15.6°, 26.2° and 27.2°. In some embodiments, the polymorph is characterized by having the powder X-ray diffraction pattern substantially as shown in FIG. 2. In some embodiments, the polymorph is further characterized by having a water content between about 13% and about 17%. In some embodiments, the water content is about 15%. In some embodiments, the polymorph is further characterized by having an endotherm at about 90° C. as shown by DSC. In some embodiments, the polymorph is characterized as having any one or combination of Raman peaks at e.g., about 997.8, 1170.0, 1264.4, 1350.6, 1402.7, 1426.5, 1464.7, 1513.8, 1537.7, 1546.4, 1605.4 and 1605.4 cm$^{-1}$. In some embodiments, the polymorph is characterized as having a Raman spectrum substantially as shown in FIG. 20. In some embodiments, the polymorph is substantially pure.

In one variation, the polymorph of compound (I) is a sodium salt polymorph of Form III. In some embodiments, the polymorph is characterized as having any one or combination of powder X-ray diffraction pattern peaks of 2θ at about 5.2°, 7.1°, 7.4°, 8.2°, 9.0°, 10.4°, 12.0°, 13.3°, 14.7°, 15.7°, 16.1°, 16.5°, 17.0°, 17.5°, 17.8°, 18.6°, 19.4°, 20.0°, 21.0°, 21.3°, 22.2°, 23.0°, 24.4°, 25.0°, 25.9°, 26.1°, 27.1°, 27.8°, 29.7°, 30.8°, 32.2° and 44.6°. In some embodiments, the polymorph is characterized by having powder X-ray diffraction pattern peaks of 2θ at about 25.9°, 27.1° and 27.9°. In some embodiments, the polymorph is characterized by having powder X-ray diffraction pattern peaks of 2θ at about 8.2°, 25.9°, 26.1°, 27.1° and 27.9°. In some embodiments, the polymorph is characterized by having the powder X-ray diffraction pattern substantially as shown in FIG. 7. In some embodiments, the polymorph is further characterized by having a water content between about 3% and about 7%. In some embodiments, the water content is about 5%. In some embodiments, the polymorph is further characterized by having an endotherm at about 120° C. as shown by DSC. In some embodiments, the polymorph is characterized as having any one or combination of Raman peaks at e.g., about 994.6, 1081.9, 1212.1, 1244.5, 1346.7, 1403.5, 1431.2, 1465.1, 1512.3 and 1603.5 cm$^{-1}$. In some embodiments, the polymorph is characterized as having a Raman spectrum substantially as shown in FIG. 20. In some embodiments, the polymorph is substantially pure.

In one variation, the polymorph of compound (I) is a sodium salt polymorph of Form IV. In some embodiments, the polymorph is characterized as having any one or combination of powder X-ray diffraction pattern peaks of 2θ at about 5.4°, 8.0°, 10.8°, 11.9°, 14.7°, 16.1°, 16.9°, 17.9°, 19.5°, 20.0°, 20.6°, 21.6°, 22.8°, 24.1°, 24.6°, 25.3°, 26.9°, 28.7°, 29.5°, 32.6°, 34.0°, 35.8°, 36.4° and 38.0°. In some embodiments, the polymorph is characterized by having powder X-ray diffraction pattern peaks of 2θ at about 22.8° and 25.3°. In some embodiments, the polymorph is characterized by having powder X-ray diffraction pattern peaks of 2θ at about 19.5°, 21.6°, 22.8°, 24.1°, 24.6°, 25.3°, 26.9° and 29.5°. In some embodiments, the polymorph is characterized by having the powder X-ray diffraction pattern substantially as shown in FIG. 11. In some embodiments, the polymorph is further characterized by having a water content of less than about 5%. In some embodiments, the polymorph has a water content of about 2%. In some embodiments, the polymorph is further characterized by having an endotherm at about 100° C. as shown by DSC. In some embodiments, the polymorph is characterized as having any one or combination of Raman peaks at e.g., about 1342.9, 1402.5, 1416.3, 1427.3, 1463.4, 1517.9, 1559.2 and 1608.3 cm$^{-1}$. In some embodiments, the polymorph is characterized as having a Raman spectrum substantially as shown in FIG. 20. In some embodiments, the polymorph is substantially pure.

In one variation, the polymorph of compound (I) is a sodium salt polymorph of Form V. In some embodiments, the polymorph is characterized as having any one or combination of powder X-ray diffraction pattern peaks of 2θ at about 6.1°, 9.9°, 10.6°, 11.1°, 12.3°, 14.4°, 15.3°, 18.5°, 19.7°, 20.1°, 21.8°, 22.4°, 24.2°, 24.9°, 26.8°, 28.2°, 31.3°, 33.0°, 36.5°, 40.6°, 41.1°, 42.6°, 44.5°, 45.8° and 47.7°. In some embodiments, the polymorph is characterized by having the powder X-ray diffraction pattern peaks of 2θ at about 12.3° and 31.3°. In some embodiments, the polymorph is characterized by having powder X-ray diffraction pattern peaks of 2θ at about 12.3°, 21.8°, 22.4° and 31.3°. In some embodiments, the polymorph is characterized by having powder X-ray diffraction pattern substantially as shown in FIG. 16. In some embodiments, the polymorph is substantially pure.

In one variation, the polymorph of compound (I) is a sodium salt polymorph of Form VI. In some embodiments, the polymorph is characterized as having any one or combination of powder X-ray diffraction pattern peaks of 2θ at about 6.8°, 9.5°, 10.3°, 11.4°, 14.6°, 16.1°, 16.9°, 17.3°, 18.1°, 18.7°, 20.7°, 22.2°, 23.4°, 24.6°, 26.0°, 28.5°, 31.7°, 32.4°, 33.4°, 37.7° and 39.5°. In some embodiments, the polymorph is characterized by having powder X-ray diffraction pattern peaks of 2θ at about 20.7° and 26.0°: In some embodiments, the polymorph is characterized by having powder X-ray diffraction pattern peaks of 2θ at about 11.4°, 14.6°, 16.1°, 20.7° and 26.0°. In some embodiments, the polymorph is characterized by having the powder X-ray diffraction pattern substantially as shown in FIG. 17. In some embodiments, the polymorph is substantially pure.

In one variation, the polymorph of compound (I) is a sodium salt polymorph of Form VII. In some embodiments, the polymorph is characterized as having any one or combination of powder X-ray diffraction pattern peaks of 2θ at about 9.2°, 9.8°, 10.4°, 11.7°, 12.2°, 13.7°, 13.8°, 14.4°, 15.3°, 15.9°, 17.7°, 18.5°, 19.7°, 20.5°, 21.0°, 21.5°, 21.9°, 23.4°, 24.1°, 24.5°, 25.1°, 25.9°, 26.6°, 26.9°, 27.6°, 28.2°, 29.3°, 29.8°, 30.3°, 31.1°, 32.0°, 33.0°, 33.3°, 34.2°, 34.6°, 35.4°, 36.2°, 36.8°, 37.4°, 38.1°, 39.1°, 40.2°, 40.6°, 41.2°, 43.2°, 44.2°, 45.2°, 46.5° and 47.6°. In some embodiments, the polymorph is characterized by having powder X-ray diffraction pattern peaks of 2θ at about 12.7° and 17.7°. In some embodiments, the polymorph is characterized by having powder X-ray diffraction pattern peaks of 2θ at about 11.7°, 12.2°, 13.8°, 14.4°, 15.9°, 17.7°, 18.5° and 19.7°. In some embodiments, the polymorph is characterized by having the powder X-ray diffraction pattern substantially as shown in FIG. 18A. In some embodiments, the polymorph is further characterized by having a water content between about 3% and about 7%. In some embodiments, the water content is about 5%. In some embodiments, the polymorph is substantially pure.

In one variation, the polymorph of compound (I) is a sodium salt polymorph of Form VIII. In some embodiments, the polymorph is characterized as having any one or combination of powder X-ray diffraction pattern peaks of 2θ at about 10.2°, 14.0°, 14.4°, 15.0°, 18.4°, 19.7°, 20.4°, 20.8°, 22.6°, 24.4°, 24.9°, 25.4°, 26.3°, 27.4°, 29.0°, 30.3°, 31.6°, 32.5°, 33.5°, 36.0°, 36.7°, 38.2°, 42.5°, 43.1°, 44.6° and 46.4°. In some embodiments, the polymorph is characterized by having powder X-ray diffraction pattern peaks of 2θ at about 24.4° and 25.4°. In some embodiments, the polymorph is characterized by having powder X-ray diffraction pattern peaks of 2θ at about 10.2°, 14.0°, 14.4°, 18.4°, 24.4°, 24.9° and 25.4°. In some embodiments, the polymorph is characterized by having the powder X-ray diffraction pattern substantially as shown in FIG. 19. In some embodiments, the polymorph is substantially pure.

In one variation, the polymorph of compound (I) is a sodium salt polymorph of Form IX. In some embodiments, the polymorph is characterized as having any one or combination of powder X-ray diffraction pattern peaks of 2θ at about 7.8°, 8.3°, 9.2°, 10.1°, 10.8°, 14.0°, 14.2°, 14.9°, 15.8°, 16.0°, 16.5°, 17.3°, 18.2°, 21.2°, 23.9°, 24.4°, 24.9°, 25.7°, 26.5°, 32.1° and 33.2°. In some embodiments, the polymorph is characterized by having powder X-ray diffraction pattern peaks of 2θ at about 15.8° and 16.5°. In some embodiments, the polymorph is characterized by having powder X-ray diffraction pattern peaks of 2θ at about 14.2°, 15.8°, 16.0° and 16.5°. In some embodiments, the polymorph is characterized by having the powder X-ray diffraction, pattern substantially as shown in FIG. 21. In some embodiments, the polymorph is substantially pure.

In one variation, the polymorph of compound (I) is a sodium salt polymorph of Form X. In some embodiments, the polymorph is characterized as having any one or combination of powder X-ray diffraction pattern peaks of 2θ at about 5.2°, 5.5°, 8.3°, 9.2°, 10.0°, 10.9°, 12.4°, 13.8°, 14.9°, 15.3°, 16.8°, 17.6°, 18.2°, 18.6°, 19.7°, 20.9°, 21.2°, 22.2°, 22.7°, 23.2°, 23.6°, 24.1°, 25.3° 26.1°, 27.2°, 27.7°, 28.4°, 29.8°, 30.7°, 32.1°, 32.9°, 33.9°, 35.9°, 37.8°, 39.9°, 41.2°, 42.6°, 43.1°, 44.6° and 46.6°. In some embodiments, the polymorph is characterized by having powder X-ray diffraction pattern peaks of 2θ at about 23.6° and 28.4°. In some embodiments, the polymorph is characterized by having powder X-ray diffraction pattern peaks of 2θ at about 13.8°, 23.6°, 25.3° and 28.4°. In some embodiments, the polymorph is characterized by having the powder X-ray diffraction pattern substantially as shown in FIG. 22. In some embodiments, the polymorph is substantially pure.

In one variation, the polymorph of compound (I) is a sodium salt polymorph of Form XI. In some embodiments, the polymorph is characterized as having any one or combination of powder X-ray diffraction pattern peaks of 2θ at about 5.1°, 5.5°, 6.0°, 8.2°, 9.2°, 9.9°, 10.2°, 12.1°, 13.2°, 14.2°, 14.7°, 15.0°, 16.5°, 17.3°, 17.7°, 18.3°, 20.3°, 21.5°, 22.0°, 22.6°, 24.4°, 24.9°, 26.4°, 27.2°, 27.7°, 28.5°, 28.8°, 29.2°, 29.6°, 30.7°, 32.1°, 34.5°, 36.0°, 40.0°, 40.8°, 41.9° and 45.5°. In some embodiments, the polymorph is characterized by having powder X-ray diffraction pattern peaks of 2θ at about 24.4°, 24.9° and 26.4°. In some embodiments, the polymorph is characterized by having powder X-ray diffraction pattern peaks of 2θ at about 22.6°, 24.4°, 24.9°, 26.4°, 28.5° and 30.7°. In some embodiments, the polymorph is characterized by having the powder X-ray diffraction pattern substantially as shown in FIG. 23. In some embodiments, the polymorph is substantially pure.

In one variation, the polymorph of compound (I) is a sodium salt polymorph of Form XII. In some embodiments, the polymorph is characterized as having any one or combination of powder X-ray diffraction pattern peaks of 2θ at about 5.1°, 6.3°, 6.9°, 7.4°, 10.1°, 11.0°, 13.4°, 14.8°, 15.3°, 15.7°, 16.3°, 19.2°, 20.5°, 21.3°, 21.9°, 22.6°, 23.8°, 24.9°, 25.5°, 26.3°, 27.1°, 27.6°, 28.8°, 29.3°, 29.9°, 30.7°, 32.2°, 33.3°, 36.8°, 38.3°, 40.5°, 41.5°, 43.3° and 48.5°. In some embodiments, the polymorph is characterized by having powder X-ray diffraction pattern peaks of 2θ at about 26.3° and 30.7°. In some embodiments, the polymorph is characterized by having powder X-ray diffraction pattern peaks of 2θ at about 14.8°, 21.9°, 23.8°, 26.3°, 27.6°, and 30.7°. In some embodiments, the polymorph is characterized by having the powder X-ray diffraction pattern substantially as shown in FIG. 24. In some embodiments, the polymorph is substantially pure.

In one aspect is provided a process for producing a crystalline polymorph of the sodium salt of compound (I). In one variation, the crystalline polymorph of compound (I) is any polymorph of a sodium salt described herein (e.g., polymorph Form II, III, IV, V, VI, VII, VIII, IX, X, XI, or XII).

In one variation is provided a process for producing the sodium salt polymorph of Form II comprising exposing amorphous Form I sodium salt of compound (I) to moist air. In some embodiments, the moist air has a relative humidity of greater than about 60%. In some embodiments, the moist air has a relative humidity from about 30% to about 60%. In some of these embodiments, exposing amorphous Form I sodium salt of compound (I) to moist air occurs at room temperature, or from about room temperature to about 40° C., or from about 30° C. to about 50° C., or about 40° C.

In one variation is provided a process for producing the sodium salt polymorph of Form III comprising preparing a mixture (e.g., slurry) of amorphous Form I sodium salt of compound (I) in isopropyl alcohol. In some embodiments, the mixture is temperature cycled (e.g., from about room temperature to about 40° C. over about 4 hours). In some embodiments, the mixture is temperature cycled for at least about 1, 2, 3, 4, or more days.

In one variation is provided a process for producing the sodium salt polymorph of Form IV comprising preparing a mixture (e.g., slurry) of amorphous Form I sodium salt of compound (I) in ethyl acetate. In some embodiments, the mixture is temperature cycled (e.g., from about room temperature to about 40° C. over about 4 hours). In some embodiments, the mixture is temperature cycled for at least about 1, 2, 3, 4, or more days.

In one variation is provided a process for producing the sodium salt polymorph of Form V comprising preparing a mixture (e.g., slurry) of amorphous Form I sodium salt of compound (I) in THF and water. In some embodiments, the ratio of THF to water is between about 50:50 to about 90:10, or about 60:40 to about 80:20, or about 65:35 to about 75:15, or about 70:30. In some embodiments, the mixture is temperature cycled (e.g., from about room temperature to about 40° C. over about 4 hours). In some embodiments, the mixture is temperature cycled for at least about 1, 2, 3, 4, or more days.

In one variation is provided a process for producing the sodium salt polymorph of Form VI comprising exposing the sodium salt polymorph of Form IV to dry air. In some embodiments, the dry air has a relative humidity of less than about 60%, or about 50%, or about 40%, or about 30%, or about 20%, or about 10%. In some embodiments, exposing the sodium salt polymorph of Form VI to dry air occurs at a temperature of greater or about any one of 40° C., 50° C., 60° C., 70° C., 80° C., or 90° C.

In one variation is provided a process for producing the sodium salt polymorph of Form VII comprising exposing the amorphous Form I sodium salt of compound (I) to moist air for greater than 1 month (or greater than 2 months, or 3 month, or 4 months). In some embodiments, the moist air has a relative humidity of greater than about 60% (e.g., greater than or about 75%). In some embodiments, the moist air has a relative humidity from about 30% to about 80%, or about 50% to about 75%. In some of these embodiments, exposing amorphous Form I sodium salt of compound (I) to moist air occurs at room temperature, or from about room temperature to about 40° C., or from about 30° C. to about 50° C., or about 40° C.

In one variation is provided a process for producing the sodium salt polymorph of Form VIII comprising melting the sodium salt polymorph of Form II or Form IV, followed by slow cooling. In some embodiments, the slow cooling (e.g., to room temperature) occurs over at least about any of 1, 2, 4, 8, 16, or 24 hours.

In one variation is provided a process for producing the sodium salt polymorph of Form IX comprising preparing a mixture (e.g., a slurry) of amorphous Form I sodium salt of compound (I) in water (e.g., 100% water). In some embodiments, the mixture is temperature cycled (e.g., from about room temperature to about 40° C. over about 4 hours). In some embodiments, the mixture is temperature cycled for at least about 1, 2, 3, 4, or more days.

In one variation is provided a process for producing the sodium salt polymorph of Form X comprising preparing a mixture (e.g., slurry) of amorphous Form I sodium salt of compound (I) in alcohol/H$_2$O. In some embodiments, the ratio of alcohol to water is between about 60:40 to about 80:20, or about 65:35 to about 75:15, or about 70:30. In some embodiments, the alcohol is ethanol and/or isopropanol. In some embodiments, the mixture is temperature cycled (e.g., from about room temperature to about 40° C. over about 4 hours). In some embodiments, the mixture is temperature cycled for at least about 1, 2, 3, 4, or more days.

In one variation is provided a process for producing the sodium salt polymorph of Form XI comprising preparing a mixture (e.g., slurry) of amorphous Form I sodium salt of compound (I) in alcohol/H$_2$O. In some embodiments, the ratio of alcohol to water is less than 70:30. In some embodiments, the ration of alcohol to water is between about 50:50 to about 70:30, or about 50:50 to about 60:40. In some embodiments, the alcohol is ethanol and/or isopropanol. In some embodiments, the alcohol is isopropanol. In some embodiments, the mixture is temperature cycled (e.g., from about room temperature to about 40° C. over about 4 hours). In some embodiments, the mixture is temperature cycled for at least about 1, 2, 3, 4, or more days.

In one variation is provided a process for producing the sodium salt polymorph of Form XII comprising preparing a mixture (e.g., slurry) of amorphous Form I sodium salt of compound (I) in acetone/H$_2$O. In some embodiments, the ratio of alcohol to water is between about 50:50 to about 90:10, or about 60:40 to about 80:20, or about 65:35 to about 75:15, or about 70:30. In some embodiments, the mixture is temperature cycled (e.g., from about room temperature to about 40° C. over about 4 hours). In some embodiments, the mixture is temperature cycled for at least about 1, 2, 3, 4, or more days.

In one aspect is provided an L-Lysine salt of compound (I) (e.g., a solid amorphous L-Lysine salt or crystalline L-Lysine salt). In one variation, the L-Lysine salt is a crystalline polymorph of Form XIII. In some embodiments, the polymorph is characterized as having any one or combination of powder X-ray diffraction pattern peaks of 2θ at about 11.7°, 14.7°, 15.1°, 15.7°, 16.7°, 18.5°, 19.2°, 19.6°, 20.5°, 21.5°, 23.0°, 23.9°, 25.1°, 25.7°, 26.6°, 27.3°, 28.7° and 29.0°. In some embodiments, the polymorph is characterized by having powder X-ray diffraction pattern peaks of 2θ at about 25.1° and 26.6°. In some embodiments, the polymorph is characterized by having powder X-ray diffraction pattern peaks of 2θ at about 16.7°, 19.2°, 25.1°, 25.7°, 26.6° and 27.3°. In some embodiments, the polymorph is characterized by having the powder X-ray diffraction pattern substantially as shown in FIG. 27. In some embodiments, the polymorph is characterized as having any one or combination of Raman peaks at e.g., about 1610.1, 1519.5, 1470.5, 1412.2, 1356.9, 1242.3, 1092.6, 1001.9, 861.0, 749.0 and 335.7 cm$^{-1}$. In some embodiments, the polymorph is characterized as having a Raman spectrum substantially as shown in FIG. 26. In some embodiments, the polymorph or salt is substantially pure.

In one aspect is provided a process for producing an L-Lysine salt of compound (I) (e.g., Form XIII polymorph), comprising preparing a mixture (e.g., a slurry) of compound (I) in a solvent (e.g., EtOH, iPrOH, 2-BuOH, DMF, or iPrOH:H$_2$O) followed by the addition of L-lysine (e.g., equal to or greater than about 1 equivalent). In some embodiments, the mixture is temperature cycled (e.g., from about room temperature to about 40° C. over about 4 hours). In some embodiments, the mixture is temperature cycled for at least about 1, 2, 3, 4, or more days.

In one aspect is provided a zinc salt of compound (I) (e.g., a solid amorphous zinc salt or crystalline zinc salt). In one variation, the zinc salt is a crystalline polymorph of Form XIV. In one variation, the zinc salt is a crystalline polymorph of Form XIV-A. In some embodiments, the polymorph is characterized as having any one or combination of powder X-ray diffraction pattern peaks of 2θ at about 10.4°, 12.7°, 14.7°, 15.8°, 16.1°, 16.8°, 17.8°, 18.8°, 19.0°, 19.6°, 20.5°, 21.6°, 22.4°, 23.3°, 24.3°, 26.0°, 27.6° and 28.7°. In some embodiments, the polymorph is characterized by having powder X-ray diffraction pattern peaks of 2θ at about 24.3° and 26.0°. In some embodiments, the polymorph is characterized by having powder X-ray diffraction pattern peaks of 2θ at about 17.8°, 22.4°, 23.3°, 24.3°, 26.0° and 27.6°. In some embodiments, the polymorph is characterized by having the powder X-ray diffraction pattern substantially as shown in FIG. 30 (top). In some embodiments, the polymorph is characterized as having any one or combination of Raman peaks at e.g., about 1607.8, 1525.6, 1468.8, 1411.0, 1353.5, 1248.8, 1096.2, 1002.3, 882.7 and 743.3 cm$^{-1}$. In some embodiments, the polymorph is characterized as having a Raman spectrum substantially as shown in FIG. 29A. In one variation, the calcium salt is a crystalline polymorph of Form XIV-B. In some embodiments, the polymorph is characterized as having any one or combination of powder X-ray diffraction pattern peaks of 2θ at about 12.3°, 13.5°, 14.1°, 14.8°, 15.8°, 17.6°, 19.0°, 19.5°, 20.2°, 22.6°, 23.4°, 24.2°, 24.6°, 25.4°, 25.9°, 27.3°, 28.0° and 29.5°. In some embodiments, the polymorph is characterized by having powder X-ray diffraction pattern peaks of 2θ at about 19.0° and 25.9°. In some embodiments, the polymorph is characterized by having powder X-ray diffraction pattern peaks of 2θ at about 15.8°, 17.6°, 19.0°, 19.5°, 20.2°, 22.6°, 25.4° and 25.9°. In some embodiments, the polymorph is characterized by having the powder X-ray diffraction pattern substantially as shown in FIG. 30 (bottom). In some embodiments, the polymorph is characterized as having any one or combination of Raman peaks at e.g., about 1604.9, 1552.3, 1521.1, 1467.1, 1408.3, 1352.5, 1275.9, 1239.0, 1093.0, 1001.4 and 506.8 cm$^{-1}$. In some embodiments, the polymorph is characterized as having a Raman spectrum substantially as shown in FIG. 29B. In some embodiments, the polymorph or salt is substantially pure.

In one aspect is provided a process for producing a zinc salt of compound (I) (e.g., a Form XIV polymorph), comprising preparing a mixture (e.g., a slurry) of compound (I) in a solvent (e.g., EtOH, iPrOH, 2-BuOH, DMF, or iPrOH:H$_2$O) followed by the addition of zinc acetate (e.g., equal to or greater than about 1 equivalent). In some embodiments, the solvent is EtOH and the zinc salt is a polymorph Form XIV-A. In some embodiments, the solvent is 2-BuOH and the zinc salt is a polymorph Form XIV-B. In some embodiments, the mixture is temperature cycled (e.g., from about room temperature to about 40° C. over about 4 hours). In some embodiments, the mixture is temperature cycled for at least about 1, 2, 3, 4, or more days.

In one aspect is provided an N-methylglucamine salt of compound (I) (e.g., a solid amorphous N-methylglucamine salt or crystalline N-methylglucamine salt). In one variation, the N-methylglucamine salt is a crystalline polymorph of Form XV. In some embodiments, the polymorph is characterized as having any one or combination of powder X-ray diffraction pattern peaks of 2θ at about 11.1°, 12.0°, 12.8°, 13.9°, 14.7°, 15.7°, 16.7°, 17.2°, 17.7°, 18.3°, 18.8°, 19.6°, 20.2°, 21.0°, 21.4°, 22.9°, 23.8°, 24.4°, 25.2°, 26.2°, 26.7°, 27.7°, 28.0°, 28.5° and 29.4°. In some embodiments, the polymorph is characterized by having powder X-ray diffraction pattern peaks of 2θ at about 26.7° and 28.5°. In some embodiments, the polymorph is characterized by having powder X-ray diffraction pattern peaks of 2θ at about 13.9°, 21.4°, 22.9°, 23.8°, 24.4°, 26.7° and 28.5°. In some embodiments, the polymorph is characterized by having the powder X-ray diffraction pattern substantially as shown in FIG. 33. In some embodiments, the polymorph is characterized as having any one or combination of Raman peaks at e.g., about 1607.1, 1521.1, 1469.4, 1411.3, 1350.4, 1261.7, 1091.4, 999.1, 869.1, 746.6, 646.6 and 510.7 cm$^{-1}$. In some embodiments, the polymorph is characterized as having a Raman spectrum substantially as shown in FIG. 32. In some embodiments, the polymorph or salt is substantially pure.

In one aspect is provided a process for producing an N-methylglucamine salt of compound (I) (e.g., Form XV polymorph), comprising preparing a mixture (e.g., a slurry) of compound (I) in a solvent (e.g., EtOH, iPrOH, 2-BuOH, DMF, or iPrOH:H$_2$O) followed by the addition of N-methylglucamine (e.g., equal to or greater than about 1 equivalent). In some embodiments, the mixture is temperature cycled (e.g., from about room temperature to about 40° C. over about 4 hours). In some embodiments, the mixture is temperature cycled for at least about 1, 2, 3, 4, or more days.

In one aspect is provided an ammonium salt of compound (I) (e.g., a solid amorphous ammonium salt or crystalline ammonium salt). In one variation, the ammonium salt is a crystalline polymorph of Form XVI. In some embodiments, the polymorph is characterized as having any one or combination of Raman peaks at e.g., about 1694.2, 1624.7, 1605.0, 1523.7, 1474.6, 1430.1, 1355.9, 1289.0, 1242.2, 1096.1, 1002.2, 858.0 and 748.4 cm$^{-1}$. In some embodiments, the polymorph is characterized as having a Raman spectrum substantially as shown in FIG. 35. In some embodiments, the polymorph or salt is substantially pure.

In one aspect is provided a process for producing an ammonium salt of compound (I) (e.g., Form XVI polymorph), comprising preparing a mixture (e.g., a slurry) of compound (I) in a solvent (e.g., EtOH, iPrOH, 2-BuOH, DMF, or iPrOH:H$_2$O) followed by the addition of ammonium hydroxide (e.g., equal to or greater than about 1 equivalent). In some embodiments, the mixture is temperature cycled (e.g., from about room temperature to about 40° C. over about 4 hours). In some embodiments, the mixture is temperature cycled for at least about 1, 2, 3, 4, or more days.

In one aspect is provided a choline salt of compound (I) (e.g., a solid amorphous choline salt or crystalline choline salt). In one variation, the choline salt is a crystalline polymorph of Form XVII. In some embodiments, the polymorph is characterized as having any one or combination of Raman peaks at e.g., about 1702.28, 1617.60, 1603.99, 1523.05, 1474.05, 1427.05, 1406.77, 1357.53, 1344.03, 1286.98, 1235.41, 1092.50, 997.61, 845.88 and 749.61 cm$^{-1}$. In some embodiments, the polymorph is characterized as having a Raman spectrum substantially as shown in FIG. 37. In some embodiments, the polymorph or salt is substantially pure.

In one aspect is provided a process for producing a choline salt of compound (I) (e.g., Form XVII polymorph), comprising preparing a mixture (e.g., a slurry) of compound (I) in a solvent (e.g., EtOH, iPrOH, 2-BuOH, DMF, or iPrOH:H$_2$O) followed by the addition of choline hydroxide (e.g., equal to or greater than about 1 equivalent). In some embodiments, the mixture is temperature cycled (e.g., from about room temperature to about 40° C. over about 4 hours). In some embodiments, the mixture is temperature cycled for at least about 1, 2, 3, 4, or more days.

In one aspect is provided a calcium salt of compound (I) (e.g., a solid amorphous calcium salt or crystalline calcium salt). In some embodiments, the ratio of compound (I) to calcium is 1:1. In some embodiments, the ratio of compound (I) to calcium is 2:1. In one variation, the calcium salt is a crystalline polymorph of Form XVIII-A. In some embodiments, the polymorph is characterized as having any one or combination of Raman peaks at e.g., about 1606.7, 1519.3, 1462.2, 1408.6, 1241.6, 1089.3, 999.8, 868.7, 745.4, 509.6 and 131.3 cm$^{-1}$. In some embodiments, the polymorph is characterized as having a Raman spectrum substantially as shown in FIG. 39. In some embodiments, the polymorph has a ratio of compound (I) to calcium of 1:1. In one variation, the calcium salt is a crystalline polymorph of Form XVIII-B. In some embodiments, the polymorph is characterized as having any one or combination of Raman peaks at e.g., about 1605.0, 1519.8, 1467.5, 1428.7, 1349.4, 1260.5, 1092.4, 998.5, 870.1, 746.0 and 512.4 cm$^{-1}$. In some embodiments, the polymorph is characterized as having a Raman spectrum substantially as shown in FIG. 40. In some embodiments, the polymorph has a ratio of compound (I) to calcium of 1:1. In one variation, the calcium salt is a crystalline polymorph of Form XVIII-C. In some embodiments, the polymorph is characterized as having any one or combination of Raman peaks at e.g., about 1701.4, 1604.4, 1522.3, 1473.6, 1425.8, 1345.7, 1286.3, 1234.6, 1091.5, 997.1, 844.6, 749.4, 281.3 and 136.3 cm$^{-1}$. In some embodiments, the polymorph is characterized as having a Raman spectrum substantially as shown in FIG. 41. In some embodiments, the polymorph has a ratio of compound (I) to calcium of 1:1. In some embodiments, the polymorph or salt is substantially pure.

In one aspect is provided a process for producing a calcium salt of compound (I) (e.g., a Form XVIII polymorph), comprising preparing a mixture (e.g., a slurry) of compound (I) in a solvent (e.g., EtOH, iPrOH, 2-BuOH, DMF, or iPrOH:H$_2$O) followed by the addition of calcium hydroxide (e.g., equal to or greater than about 1 equivalent). In some embodiments, the solvent is EtOH and the calcium salt is polymorph Form XVIII-A. In some embodiments, the solvent is iPrOH:H$_2$O and the calcium salt is polymorph Form XVIII-B. In some embodiments, the solvent is 2-BuOH and the calcium salt is polymorph Form XVIII-C. In some embodiments, the mixture is temperature cycled (e.g., from about room temperature to about 40° C. over about 4 hours). In some embodiments, the mixture is temperature cycled for at least about 1, 2, 3, 4, or more days.

In one aspect is provided a magnesium salt of compound (I) (e.g., a solid amorphous magnesium salt or crystalline magnesium salt). In some embodiments, the ratio of compound (I) to magnesium is 1:1. In some embodiments, the ratio of compound (I) to magnesium is 2:1. In one variation, the magnesium salt is a crystalline polymorph of Form XIX-A. In some embodiments, the polymorph is characterized as having any one or combination of Raman peaks at e.g., about 1702.5, 1605.0, 1522.5, 1473.8, 1426.1, 1346.1, 1286.2, 1234.8, 1158.8, 1091.8, 996.9, 844.8 and 747.6 cm$^{-1}$. In some embodiments, the polymorph is characterized as having a Raman spectrum substantially as shown in FIG. 43. In some embodiments, the polymorph has a ratio of compound (I) to magnesium of 1:1. In another variation, the magnesium salt is a crystalline polymorph of Form XIX-B. In some embodiments, the polymorph is characterized as having any one or combination of Raman peaks at e.g., about 1606.7, 1518.9, 1466.1, 1429.0, 1407.3, 1348.1, 1258.7, 1092.3, 999.3, 868.9 and 743.6 cm$^{-1}$. In some embodiments, the polymorph is characterized as having a Raman spectrum substantially as shown in FIG. 44. In some embodiments, the polymorph has a ratio of compound (I) to magnesium of 1:1. In some embodiments, the polymorph or salt is substantially pure.

In one aspect is provided a process for producing a magnesium salt of compound (I) (e.g., a Form XIX polymorph), comprising preparing a mixture (e.g., a slurry) of compound (I) in a solvent (e.g., EtOH, iPrOH, 2-BuOH, DMF, or iPrOH:H$_2$O) followed by the addition of magnesium hydroxide (e.g., equal to or greater than about 1 equivalent). In some embodiments, the magnesium salt is polymorph Form XIX-A. In some embodiments, the magnesium salt is polymorph Form XIX-B. In some embodiments, the mixture is temperature cycled (e.g., from about room temperature to about 40° C. over about 4 hours). In some embodiments, the mixture is temperature cycled for at least about 1, 2, 3, 4, or more days.

In one aspect is provided a potassium salt of compound (I) (e.g., a solid amorphous potassium salt or crystalline potassium salt). In one variation, the potassium salt is a crystalline polymorph of Form XX. In some embodiments, the polymorph is characterized as having any one or combination of powder X-ray diffraction pattern peaks of 2θ at about 7.7°, 9.4°, 11.8°, 12.0°, 12.3°, 14.7°, 15.6°, 16.7°, 18.9°, 19.7°, 24.1°, 24.6°, 25.3°, 26.1°, 26.7°, 27.8°, 28.4°, 29.8°, 30.6°, 31.5°, 32.1° and 33.7°. In some embodiments, the polymorph is characterized by having powder X-ray diffraction pattern peaks of 2θ at about 15.6° and 18.9°. In some embodiments, the polymorph is characterized by having powder X-ray diffraction pattern peaks of 2θ at about 15.6°, 18.9°, 19.7°, 24.6°, 26.7° and 28.4°. In some embodiments, the polymorph is characterized by having the powder X-ray diffraction pattern substantially as shown in FIG. 47. In some embodiments, the polymorph is further characterized by having an endotherm at about 100° C. In some embodiments, the polymorph is characterized as having any one or combination of Raman peaks at e.g., about 1609.2, 1518.9, 1472.8, 1411.9, 1360.9, 1093.9, 1001.5 and 754.5 cm$^{-1}$. In some embodiments, the polymorph is characterized as having a Raman spectrum substantially as shown in FIG. 46. In some embodiments, the polymorph or salt is substantially pure.

In one aspect is provided a process for producing a potassium salt of compound (I) (e.g., Form XX polymorph), comprising preparing a mixture (e.g., a slurry) of compound (I) in a solvent (e.g., EtOH, iPrOH, 2-BuOH, DMF, or iPrOH:H$_2$O) followed by the addition of potassium hydroxide (e.g., equal to or greater than about 1 equivalent). In some embodiments, the mixture is temperature cycled (e.g., from about room temperature to about 40° C. over about 4 hours). In some embodiments, the mixture is temperature cycled for at least about 1, 2, 3, 4, or more days.

In one aspect is provided an L-Arginine salt of compound (I) (e.g., a solid amorphous L-Arginine salt or crystalline L-Arginine salt). In one variation, the L-Arginine salt is a crystalline polymorph of Form XXII. In some embodiments, the polymorph is characterized as having any one or combination of powder X-ray diffraction pattern peaks of 2θ at about 10.5°, 11.6°, 15.0°, 16.3°, 16.6°, 18.3°, 19.4°, 20.2°, 21.2°, 22.3°, 23.2°, 24.5°, 25.3°, 26.2°, 26.8° and 27.7°. In some embodiments, the polymorph is characterized by having powder X-ray diffraction pattern peaks of 2θ at about 15.0° and 25.3°. In some embodiments, the polymorph is characterized by having powder X-ray diffraction pattern peaks of 2θ at about 15.0°, 22.3°, 24.5°, 25.3°, 26.2° and 26.8°. In some embodiments, the polymorph is characterized by having the powder X-ray diffraction pattern substantially as shown in FIG. 51. In some embodiments, the polymorph is further characterized by having an endotherm at about 215° C. In some embodiments, the polymorph is characterized as having any one or combination of Raman peaks at e.g., about 3085.3, 1606.6, 1518.5, 1405.9, 1348.2, 1245.9, 1087.9, 998.7, 868.8, 745.6 and 509.2 cm$^{-1}$. In some embodiments, the polymorph is characterized as having a Raman spectrum substantially as shown in FIG. 50. In some embodiments, the polymorph or salt is substantially pure.

In one aspect is provided a process for producing an L-Arginine salt of compound (I) (e.g., Form XXI polymorph), comprising preparing a mixture (e.g., a slurry) of compound (I) in a solvent (e.g., EtOH, iPrOH, 2-BuOH, DMF, or iPrOH:H$_2$O) followed by the addition of L-Arginine (e.g., equal to or greater than about 1 equivalent). In some embodiments, the mixture is temperature cycled (e.g., from about room temperature to about 40° C. over about 4 hours). In some embodiments, the mixture is temperature cycled for at least about 1, 2, 3, 4, or more days.

In one aspect is provided a TRIS salt of compound (I) (e.g., a solid amorphous TRIS salt or crystalline TRIS salt). In one variation, the TRIS salt is a crystalline polymorph of Form XXII. In some embodiments, the polymorph is characterized as having any one or combination of powder X-ray diffraction pattern peaks of 2θ at about 10.23°, 10.8°, 11.3°, 13.1°, 13.8°, 14.5°, 15.3°, 16.0°, 17.5°, 18.4°, 19.8°, 20.7°, 21.5°, 22.8°, 23.3°, 24.1°, 24.4°, 25.1°, 25.8°, 26.4°, 27.6° and 28.8°. In some embodiments, the polymorph is characterized by having powder X-ray diffraction pattern peaks of 2θ at about 16.0° and 25.8°. In some embodiments, the polymorph is characterized by having powder X-ray diffraction pattern peaks of 2θ at about 16.0°, 19.8°, 25.1°, 25.8° and 27.6°. In some embodiments, the polymorph is characterized by having the powder X-ray diffraction pattern substantially as shown in FIG. 66. In some embodiments, the polymorph is further characterized by having an endotherm at about 135° C. In some embodiments, the polymorph is further characterized by having two endotherms between about 130° C. and about 150° C. In some embodiments, the polymorph is characterized as having any one or combination of Raman peaks at e.g., about 1609.3, 1519.8, 1468.8, 1408.5, 1347.5, 1251.0, 1089.8, 1002.9, 869.5, 746.1 and 514.5 cm$^{-1}$. In some embodiments, the polymorph is characterized as having a Raman spectrum substantially as shown in FIG. 65. In some embodiments, the polymorph or salt is substantially pure.

In one aspect is provided a process for producing a TRIS salt of compound (I) (e.g., Form XXII polymorph), comprising preparing a mixture (e.g., a slurry) of compound (I) in a solvent (e.g., EtOH, iPrOH, 2-BuOH, DMF, or iPrOH:H$_2$O) followed by the addition of TRIS (e.g., equal to or greater than about 1 equivalent). In some embodiments, the mixture is temperature cycled (e.g., from about room temperature to about 40° C. over about 4 hours). In some embodiments, the mixture is temperature cycled for at least about 1, 2, 3, 4, or more days.

In one aspect is provided a composition comprising a salt of compound (I) described herein (e.g., sodium, L-lysine, zinc, methylglucamine, ammonium, choline, calcium (such as 1:1 or 2:1 calcium), magnesium (such as 1:1 or 2:1 magnesium), potassium, or tris(hydroxymethyl)aminomethane (TRIS)), and a pharmaceutically acceptable carrier. In one variation is provided a polymorph described herein (e.g., polymorph Form II, III, IV, V, VI, VII, VIII, IX, X, XI, XII, XIII, XIV, XV, XVI, XVII, XVIII, XIX, XX, XXI, or XXII), and a pharmaceutically acceptable carrier. In some variations, the composition comprises an effective amount of the salt or polymorph and a pharmaceutically acceptable carrier. In some embodiments, the composition further comprising a compound that is capable of inhibiting PARP and/or CK2, or a pharmaceutically acceptable salt or solvate thereof.

In one aspect is provided a method of modulating the activity of a PARP protein, the method comprising contacting the protein with an effective amount compound (I), wherein compound (I) is derived from a salt form described herein, such as an amorphous salt or crystalline polymorph salt (e.g., polymorph Form II, III, IV, V, VI, VII, VIII, IX, X, XI, XII, XIII, XIV, XV, XVI, XVII, XVIII, XIX, XX, XXI, or XXII). In some embodiments, the activity of the PARP protein is inhibited. In some embodiments, PARP protein is contacted in a cell. In other embodiments, PARP protein is contacted in a cell-free system.

In one aspect is provided a method for inhibiting cell proliferation comprises contacting cells with an effective amount of compound (I), wherein compound (I) is derived from a salt form described herein, such as an amorphous salt or crystalline polymorph salt (e.g., polymorph Form II, III, IV, V, VI, VII, VIII, IX, X, XI, XII, XIII, XIV, XV, XVI, XVII, XVIII, XIX, XX, XXI, or XXII). In some embodiments, the cells are in a cancer cell line. In some embodiments, the cancer cell line is a breast cancer, prostate cancer, pancreatic cancer, lung cancer, hemopoietic cancer, colorectal cancer, skin cancer, ovary cancer cell line. In some embodiments, the cells are in a tumor in a subject. In some embodiments, contacting cells induces cell apoptosis. In some embodiments, the cells are from an eye of a subject having macular degeneration. In some embodiments, the cells are in a subject having macular degeneration.

In one aspect is provided a method of treating a condition mediated a PARP protein in an individual in need thereof, the method comprising administering to the individual an effective amount of a salt form described herein, such as an amorphous salt or crystalline polymorph salt (e.g., polymorph Form II, III, IV, V, VI, VII, VIII, IX, X, XI, XII, XIII, XIV, XV, XVI, XVII, XVIII, XIX, XX, XXI, or XXII). In some embodiments, the condition is cancer. In some embodiments, the cancer is selected from breast cancer, prostate cancer, pancreatic cancer, lung cancer, hemopoietic cancer, colorectal cancer, skin cancer, and ovary cancer.

In one aspect is provided a method for treating a condition related to aberrant cell proliferation, the method comprising administering to an individual in need thereof an effective amount of a salt form described herein, such as an amorphous salt or crystalline polymorph salt (e.g., polymorph Form II, III, IV, V, VI, VII, VIII, IX, X, XI, XII, XIII, XIV, XV, XVI, XVII, XVIII, XIX, XX, XXI, or XXII). In some embodiments, the cell proliferative condition is a tumor-associated cancer. In some embodiments, the cancer is of the breast, prostate, pancreas, lung, colorectum, skin, or ovary. In some embodiments, the cell proliferative condition is a non-tumor cancer. In some embodiments, the non-tumor cancer is a hematopoietic cancer. In some embodiments, the cell proliferative condition is macular degeneration.

In one aspect is provided a method of treating pain or inflammation in an individual in need thereof, comprising administering to the individual an effective amount of a salt form described herein, such as an amorphous salt or crystalline polymorph salt (e.g., polymorph Form II, III, IV, V, VI, VII, VIII, IX, X, XI, XII, XIII, XIV, XV, XVI, XVII, XVIII, XIX, XX, XXI, or XXII).

In one aspect is provided a method of inhibiting angiogenesis in an individual in need thereof, comprising administering to the individual an effective amount of a salt form described herein, such as an amorphous salt or crystalline polymorph salt (e.g., polymorph Form II, III, IV, V, VI, VII, VIII, IX, X, XI, XII, XIII, XIV, XV, XVI, XVII, XVIII, XIX, XX, XXI, or XXII).

In one aspect is provided a method of treating cancer or an inflammatory disorder in individual in need thereof, comprising administering to the individual an effective amount of a salt form described herein, such as an amorphous salt or crystalline polymorph salt (e.g., polymorph Form II, III, IV, V, VI, VII, VIII, IX, X, XI, XII, XIII, XIV, XV, XVI, XVII, XVIII, XIX, XX, XXI, or XXII); and administering an additional pharmaceutical agent, additional treatment modality, or combination thereof. In some embodiments, the additional pharmaceutical agent is a compound that is capable of inhibiting PARP and/or CK2, or a pharmaceutically acceptable salt or solvate thereof. In some embodiments, the crystalline polymorph and the additional pharmaceutical agent are combined into one pharmaceutical composition. In some embodiments, administering the additional pharmaceutical agent, additional treatment modality, or combination thereof is performed concurrently with administering the crystalline polymorph. In some embodiments, administering the additional pharmaceutical agent, additional treatment modality, or combination thereof is performed after administering the crystalline polymorph. In some embodiments, administering the additional pharmaceutical agent, additional treatment modality, or combination thereof is performed prior to administering the crystalline polymorph.

In one aspect is provided a salt form described herein, such as an amorphous salt or crystalline polymorph salt (e.g., polymorph Form II, III, IV, V, VI, VII, VIII, IX, X, XI, XII, XIII, XIV, XV, XVI, XVII, XVIII, XIX, XX, XXI, or XXII) use as a medicament.

In one aspect is provided the use of one or more salt forms described herein, such as an amorphous salt or crystalline polymorph salt (e.g., polymorph Form II, III, IV, V, VI, VII, VIII, IX, X, XI, XII, XIII, XIV, XV, XVI, XVII, XVIII, XIX, XX, XXI, or XXII) for the manufacture of a medicament for the treatment or prevention of a condition mediated by PARP activity. In some embodiments, the condition is cancer.

In one aspect is provided the use of one or more salt forms described herein, such as an amorphous salt or crystalline polymorph salt (e.g., polymorph Form II, III, IV, V, VI, VII, VIII, IX, X, XI, XII, XIII, XIV, XV, XVI, XVII, XVIII, XIX, XX, XXI, or XXII) for the treatment or prevention of a condition mediated by PARP activity. In some embodiments, the condition is cancer.

In one aspect is provided a kit for the treatment or prevention in an individual with cancer, comprising a salt form described herein, such as an amorphous salt or crystalline polymorph salt (e.g., polymorph Form II, III, IV, V, VI, VII, VIII, IX, X, XI, XII, XIII, XIV, XV, XVI, XVII, XVIII, XIX, XX, XXI, or XXII) and packaging. In one variation is provided a kit for the treatment or prevention in an individual with cancer, comprising a composition of the polymorphs described herein and packaging.

BRIEF DESCRIPTION OF THE FIGURES

FIG. 25 depicts Polarized light microscopy (PLM) results for the L-Lysine salt polymorph from the indicated solvents.

FIG. 28 depicts PLM results for the zinc salt polymorph from the indicated solvents.

FIG. 31 depicts PLM results for the N-methylglucamine salt polymorph from the indicated solvents.

FIG. 34 depicts PLM results for the ammonium salt polymorph from the indicated solvents.

FIG. 36 depicts PLM results for the choline salt polymorph from the indicated solvents.

FIG. 38 depicts PLM results for the calcium salt polymorphs from the indicated solvents.

FIG. 42 depicts PLM results for the magnesium salt polymorph from the indicated solvents.

FIG. 45 depicts PLM results for the potassium salt polymorph from the indicated solvents.

FIG. 49 depicts PLM results for the L-Arginine salt polymorph from the indicated solvents.

FIG. 60 depicts particle size distribution of the (a) pre-micronized and (b) micronized L-Arginine salt polymorph.

FIG. 64 depicts PLM results for the Tromethamine (TRIS) salt polymorph from the indicated solvents.

FIG. 75 depicts particle size distribution of the (a) pre-micronized and (b) micronized TRIS salt polymorph.

FIG. 81 depicts the solubility of the sodium salt of compound (I) compared to the free acid compound (I) in various organic solvents.

DETAILED DESCRIPTION OF THE INVENTION

Described herein are crystalline polymorphic and salt forms of compound (I):

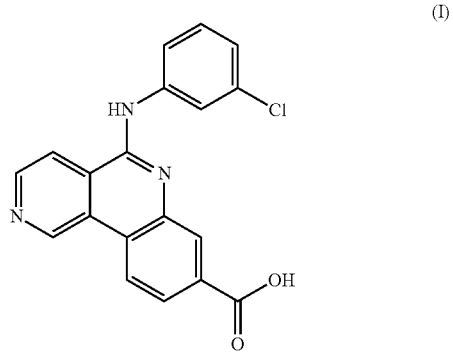 [SMILES: O=C(O)c1ccc2c(c1)nc(Nc1cccc(Cl)c1)c1ccncc12]

(I)

5-(3-chlorophenylamino)benzo[c][2,6]naphthyridine-8-carboxylic acid

Compound (I) has certain biological activities that include, but are not limited to, inhibiting cell proliferation, inhibiting angiogenesis, and modulating protein kinase activity. These compounds can modulate casein kinase 2 (CK2) activity, Pim kinase activity, and/or Fms-like tyrosine kinase 3 (Flt) activity and thus affect biological functions that include but are not limited to, inhibiting gamma phosphate transfer from ATP to a protein or peptide substrate, inhibiting angiogenesis, inhibiting cell proliferation and inducing cell apoptosis, for example. Also provided are methods for preparing novel polymorphic forms of compound (I) and methods of using thereof. Also provided are compositions comprising the above-described forms of compound (I) in combination with other agents (e.g., one or more additional pharmaceutical agents), and methods for using such in combination with other agents.

As is well known to the skilled artisan, variations in the salt form and/or crystal structure of a pharmaceutical drug substance often affect the dissolution rate (which may affect bioavailability, etc.), manufacturability (e.g., ease of handling, ability to consistently prepare doses of known strength) and stability (e.g., thermal stability, shelf life, etc.) of a pharmaceutical drug product, particularly when formulated in a solid oral dosage form.

Compound I has been described as the free acid in copending U.S. application Ser. No. 11/849,230 (US2009/0105233; the content of which is hereby incorporated by reference) as a kinase inhibitor useful for treatment of conditions, e.g., various proliferative disorders. Solutions of its salts are also mentioned.

Experimentation with a plethora of crystallization conditions (e.g., various solvents, solvent mixtures, varying cooling rates, etc.) revealed that the production of a particular polymorph described herein was unpredictable, thus, specific processes for consistently producing these polymorphs were developed. These methods allowed the preparation and characterization of the novel salt and polymorphic forms disclosed herein. The processes for the preparation of and characterization of these forms are described in greater detail below. These salt and/or crystalline forms of compound (I) may have particularly desirable characteristics in the solid form, such as dissolution rate, absorption and stability.

Figure 82:
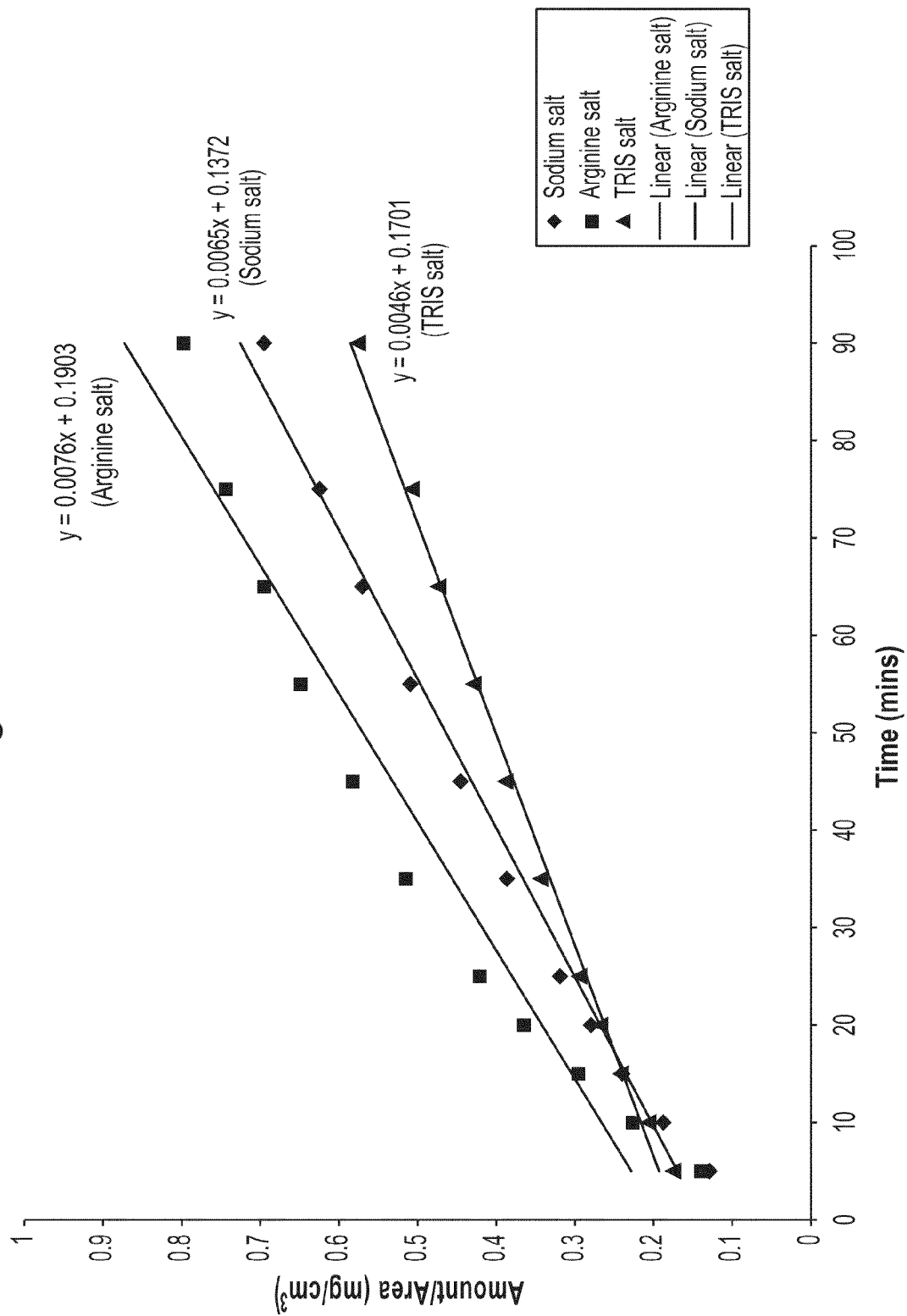
FIG. 82 depicts the Intrinsic Dissolution Rate of Sodium, L-Arginine, and TRIS salts of compound (I) in 0.1N HCl.
Figure 83:
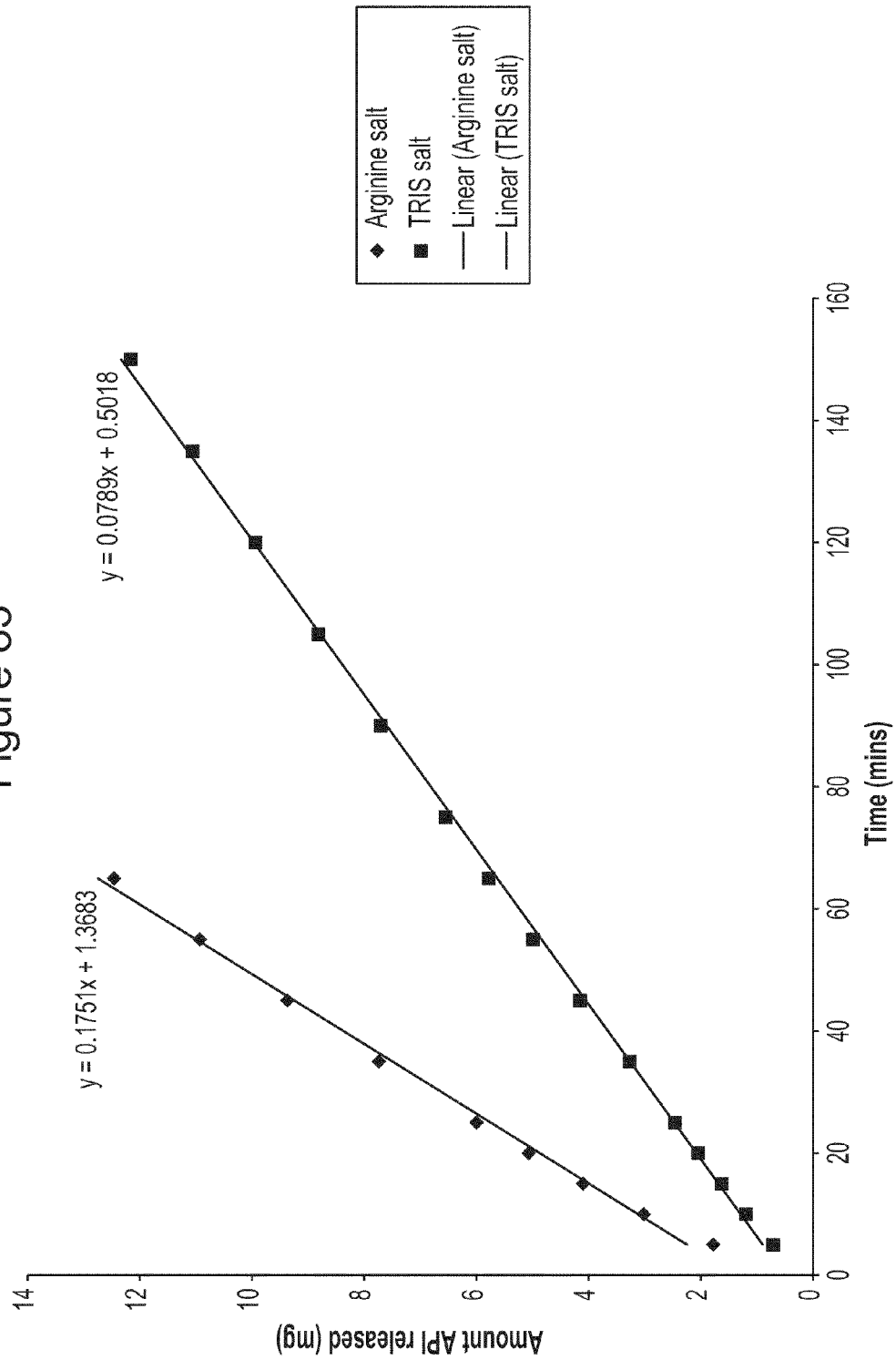
FIG. 83 depicts the Intrinsic Dissolution Rate of L-Arginine and TRIS salts of compound (I) at pH 6.8.

For example, while it might be expected that a salt would be more soluble in aqueous solutions than the corresponding acid, it has been found that the sodium salt in its amorphous form is more soluble in organic solvents than the acid is; see for example the data in FIG. 81. Moreover, certain specific salts and specific polymorphs exhibit higher intrinsic solubility and/or faster dissolution rates than others, which is advantageous for handling and formulation purposes. For example, the amorphous sodium salt and Form II polymorph of the sodium salt are significantly more soluble than other polymorphs; and the arginine and TRIS salts are also particularly easily dissolved. See FIGS. 82-83.

Accordingly, in one aspect is provided salt forms of compound (I), e.g., compound (I) in the form of a salt having any one of the following species as a counterion: sodium, lysine, zinc, methylglucamine, ammonium, choline, calcium (such as 1:1 or 2:1 calcium), magnesium (such as 1:1 or 2:1 magnesium), potassium, arginine, and tris(hydroxymethyl)aminomethane (TRIS). In some of these embodiments, the indicated salt is in a solid form (e.g., a solid amorphous sodium salt).

In another aspect is provided polymorphic forms of compound (I), namely, polymorph Form II, III, IV, V, VI, VII, VIII, IX, X, XI, XII, XIII, XIV, XV, XVI, XVII, XVIII, XIX, or XX. Each of these is a crystalline form of a salt of compound (I). Forms II-VIII are all forms of the sodium salt of compound (I), while each of forms IX-XX are crystalline polymorphs of other salts. These polymorphs of salts of compound (I) are useful for the preparation of solid dosage forms of a pharmaceutical composition that exhibits the biological activities of compound (I), including efficacy for treating proliferative disorders as discussed herein. Some of the polymorphs of the sodium salt (II-VIII) are also useful for preparing other polymorphic forms as explained herein. The novel crystalline forms may be more readily purified, such as by crystallization and/or recrystallization, than the free carboxylic acid or non-crystalline forms of compound (I).

In another aspect, the invention provides a method to make specific polymorphs of the salts of compound (I), as further described herein.

In another aspect are provided methods of treating a condition that is responsive to compound (I) (e.g., a condition mediated by a PARP and/or CK2 protein) using a salt form described herein, such as an amorphous salt or crystalline polymorph salt, namely, polymorph Form II, III, IV, V, VI, VII, VIII, IX, X, XI, XII, XIII, XIV, XV, XVI, XVII, XVIII, XIX, or XX. Such conditions include pain, inflammation, angiogenesis, and cell proliferation (e.g., cancer).

In some embodiments, the methods and compositions described herein can be used as a mixture of two or more of these polymorphs; mixtures of polymorphs are sometimes useful. In some embodiments, the methods and compositions described herein can be used as a mixture of one or more of these polymorphs with an additional pharmaceutical agent, as described herein.

Also provided are kits, compositions, combination therapies and unit dosage forms of the polymorphs described herein.

ABBREVIATIONS AND DEFINITIONS

Nomenclature of some compounds described herein may be identified using ChemDraw Ultra Version 10.0, available from CambridgeSoft®.

As used herein, "amorphous" refers to a material that contains too little crystal content to yield a discernable pattern by XRPD or other diffraction techniques. Glassy materials are contemplated to be amorphous. Amorphous materials do not have a true crystal lattice, and are consequently glassy rather than true solids, technically resembling very viscous non-crystalline liquids. Rather than true solids, glasses may better be described as quasi-solid amorphous material. Thus an amorphous material refers to a quasi-solid glassy material. Precipitation of a compound from solution, often effected by rapid evaporation of solvent, may favor amorphous forms of a compound.

As used herein, "crystalline" refers to a material that contains a specific compound, which may be hydrated and/or solvated, and has sufficient crystal content to exhibit a discernable diffraction pattern by X-ray powder diffraction (XRPD) or other diffraction techniques. Crystalline polymorphs may be characterized by a number of additional analytical techniques, including infrared spectra (e.g., FT-IR (Fourier Transform-IR)), differential scanning calorimetry (DSC), density, crystal group, and solubility. A crystalline material that is obtained from a solvent by direct crystallization of a compound dissolved in a solution or interconversion of crystals obtained under different crystallization conditions, may have crystals that contain the solvent. The specific solvent composition and physical properties of crystallization (e.g., rate of crystallization, temperature) collectively termed crystallization conditions, may cause one crystal form to dominate and may result in crystalline material having physical and chemical properties that are unique to the crystallization conditions.

The salt forms of the invention can be formed from the parent compound, i.e., Compound (I), due to the ionizable groups of the parent compound. These salts may be acid addition salts involving inorganic or organic acids or the salts may, in the case of acidic forms of the parent compound of the invention be prepared from inorganic or organic bases. Frequently, the salts are prepared or used as pharmaceutically acceptable salts prepared as addition products of pharmaceutically acceptable acids or bases. Suitable pharmaceutically acceptable acids and bases are well-known in the art, such as hydrochloric, sulphuric, hydrobromic, acetic, lactic, citric, or tartaric acids for forming acid addition salts, and potassium hydroxide, sodium hydroxide, ammonium hydroxide, caffeine, various amines, and the like for forming basic salts. Methods for preparation of the appropriate salts are well-established in the art. In some cases, the compounds may contain both an acidic and a basic functional group, in which case they may have two ionized groups and yet have no net charge. Standard methods for the preparation of pharmaceutically acceptable salts and their formulations are well known in the art, and are disclosed in various references, including for example, "*Remington: The Science and Practice of Pharmacy*", A. Gennaro, ed., 20th edition, Lippincott, Williams & Wilkins, Philadelphia, Pa.

Further more, the present salt forms may be anhydrous or contain solvent(s), such as water. In some embodiments, the present salt forms comprise solvate, such as hydrate.

"Solvate", as used herein, means a compound formed by solvation (the combination of solvent molecules with molecules or ions of the solute), or an aggregate that consists of a solute ion or molecule, i.e., a compound of the invention, with one or more solvent molecules. When water is the solvent, the corresponding solvate is "hydrate". Examples of hydrate include, but are not limited to, hemihydrate, monohydrate, dihydrate, trihydrate, hexahydrate, etc. It should be understood by one of ordinary skill in the art that the pharmaceutically acceptable salt, and/or prodrug of the present salt form may also exist to include a solvate. The solvate is typically formed via hydration which is either part of the preparation of the present salt form or through natural absorption of moisture by the anhydrous salt form of the present invention.

As used herein, "treatment", "treating", or "treat" is an approach for obtaining beneficial or desired results, including clinical results. For purposes herein, beneficial or desired results include, but are not limited to, one or more of the following: decreasing one more symptoms resulting from the condition (e.g., cancer), diminishing the extent of the disease, stabilizing the condition (e.g., preventing or delaying the worsening of the condition, such as cancer), delay or slowing the progression of the condition, ameliorating the disease state, decreasing the dose of one or more other medications required to treat the condition, increasing the quality of life of an individual who has been or is suspected of having the condition, and/or prolonging survival (including overall survival and progression free survival). Also encompassed by "treatment" is a reduction of pathological consequence of cancer. The methods described herein contemplate any one or more of these aspects of treatment.

As used herein, "delaying" with respect to a condition means to defer, hinder, slow, retard, stabilize, and/or postpone development of, and/or one or more symptoms of the condition (e.g., cancer). This delay can be of varying lengths of time, depending on the history of the disease and/or individual being treated. As is evident to one skilled in the art, a sufficient or significant delay can, in effect, encompass prevention, in that the individual does not develop the condition (e.g., cancer). A method that "delays" development of cancer is a method that reduces the probability of disease development in a given time frame and/or reduces the extent of the condition in a given time frame, when compared to not using the method. Such comparisons are typically based on clinical studies, using a statistically significant number of subjects. Cancer development can be detectable using standard methods, such as routine physical exams or x-ray. Development may also refer to disease progression that may be initially undetectable and includes occurrence and onset.

As used herein, an "at risk" individual with respect to a condition is an individual who is at risk of developing a condition (e.g., cancer). An individual "at risk" may or may not have a detectable condition, and may or may not have displayed symptoms associated with a detectable condition prior to the treatment methods described herein. "At risk" denotes that an individual has one or more so-called risk factors, which are measurable parameters that correlate with development of the condition. An individual having one or more of these risk factors has a higher probability of developing the condition than an individual without these risk factor(s).

As used herein, "pharmaceutically acceptable" with respect to a material refers to a material that is not biologically or otherwise unsuitable, e.g., the material may be incorporated (e.g., at the time of manufacturing or administration) into a pharmaceutical composition administered to an individual without causing any significant undesirable biological effects or interacting in a deleterious manner with any of the other components of the composition in which it is contained. As used herein, the term "pharmaceutically acceptable carrier," refers to, for example, solvents, stabilizers, pH-modifiers, tonicity modifiers, adjuvants, binders, diluents, etc., known to the skilled artisan that are suitable for administration to an individual (e.g., a human). Combinations of two or more carriers are also contemplated. The pharmaceutically acceptable carrier(s) and any additional components, as described herein, should be compatible for use in the intended route of administration (e.g., oral) for a particular dosage form. Such suitability will be easily recognized by the skilled artisan, particularly in view of the teaching provided herein. Pharmaceutically acceptable carriers or excipients have preferably met the required standards of toxicological and manufacturing testing and/or are included on the Inactive Ingredient Guide prepared by the U.S. Food and Drug administration.

With respect to treatment, an "effective amount," as used herein refers to an amount that results in a desired pharmacological and/or physiological effect for a specified condition (e.g., cancer) or one or more of its symptoms and/or to completely or partially prevent the occurrence or recurrence of the condition or symptom thereof and/or may be therapeutic in terms of a partial or complete cure for the condition and/or adverse effect attributable to the condition (e.g., cancer). In reference to conditions described herein (e.g., cancer), a pharmaceutically or therapeutically effective amount may comprise an amount sufficient to, among other things, reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; prevent growth and/or kill existing cancer cells; be cytostatic and/or cytotoxic; restore or maintain vasculostasis or prevention of the compromise or loss or vasculostasis; reduction of tumor burden; reduction of morbidity and/or mortality; and/or relieve to some extent one or more of the symptoms associated with the cancer. The effective amount may extend progression free survival (e.g. as measured by Response Evaluation Criteria for Solid Tumors, RECIST, or CA-125 changes), result in an objective response (including a partial response or a complete response), increase overall survival time, and/or improve one or more symptoms of cancer (e.g. as assessed by FOSI). In certain embodiments, the pharmaceutically effective amount is sufficient to prevent the condition, as in being administered to an individual prophylactically. Effective amount includes the eradication or amelioration of the underlying condition being treated and/or eradication or amelioration of one or more of the symptoms associated with the underlying condition such that the individual reports an improvement in feeling or condition (e.g., decreased pain intensity and/or duration), notwithstanding that the individual may still be afflicted with the underlying disease. Effective amount also includes halting or slowing the progression of the disease (e.g., cancer), regardless of whether improvement or the disease or condition is realized.

The "effective amount" may vary depending on the composition being administered, the condition being treated/prevented (e.g., the type of cancer), the severity of the condition being treated or prevented, the age, body size, weight, and relative health of the individual, the route and form of administration, the judgment of the attending medical or veterinary practitioner (if applicable), and other factors appreciated by the skilled artisan in view of the teaching provided herein. An effective amount may be assessed, for example, by using data from one or more clinical, physiological, biochemical, histological, electrophysiological, and/or behavioral evaluations.

As is understood in the art, an "effective amount" may be administered in one or more doses, i.e., a single dose or multiple doses may be required to achieve the desired treatment endpoint. An effective amount may be considered in the context of administering one or more additional pharmaceutical agents, and a polymorph may be considered to be given in an effective amount if, in conjunction with one or more additional pharmaceutical agents, one or more desirable or beneficial result(s) may be or are achieved.

When used with respect to methods of treatment/prevention and the use of the polymorphs and compositions thereof described herein, an individual "in need thereof" may be an individual who has been diagnosed with, previously treated for, and/or suspected of having the condition to be treated (e.g., a proliferative disease such as cancer). With respect to prevention, the individual in need thereof may also be an individual who is at risk for a condition (e.g., a family history of the condition, life-style factors indicative of risk for the condition, etc.).

In some embodiments, the individual is a mammal, including, but not limited to, bovine, horse, feline, rabbit, canine, rodent, or primate. In some embodiments, the mammal is a primate. In some embodiments, the primate is a human. In some embodiments, the individual is human, including adults, children, infants, and preemies. In some embodiments, the individual is a non-mammal. In some variations, the primate is a non-human primate such as chimpanzees and other apes and monkey species. In some embodiments, the mammal is a farm animal such as cattle, horses, sheep, goats, and swine; pets such as rabbits, dogs, and cats; laboratory animals including rodents, such as rats, mice, and guinea pigs; and the like. In some embodiments, the individual is a non-mammal, including, but not limited to, birds, and the like. The term "individual" does not denote a particular age or sex.

With respect to the polymorphs described herein, "combination therapy" means a first therapy that includes a polymorph in conjunction with a second therapy (e.g., surgery and/or an additional pharmaceutical agent) useful for treating, stabilizing, preventing, and/or delaying the disease or condition. Administration in "conjunction with" another compound includes administration in the same or different composition(s), either sequentially, simultaneously, or continuously, through the same or different routes. In some embodiments, the combination therapy optionally includes one or more pharmaceutically acceptable carriers or excipients, non-pharmaceutically active compounds, and/or inert substances.

As used herein, the term "additional pharmaceutical agent," with respect to the polymorphs described herein refers to an active agent other than the specified polymorph, (e.g., a drug and/or a different polymorphic form), which is administered to elicit a therapeutic effect. The pharmaceutical agent(s) may be directed to a therapeutic effect related to the condition that the polymorph is intended to treat or prevent (e.g., cancer) or, the pharmaceutical agent may be intended to treat or prevent a symptom of the underlying condition (e.g., tumor growth, hemorrhage, ulceration, pain, enlarged lymph nodes, cough, jaundice, swelling, weight loss, cachexia, sweating, anemia, paraneoplastic phenomena, thrombosis, etc.) or to further reduce the appearance or severity of side effects of the polymorph.

Reference to "about" a value or parameter herein includes (and describes) variations that are directed to that value or parameter per se. For example, a description referring to "about Y" includes the description of "Y". When used in combination with measured values, "about" includes a range that encompasses at least the uncertainty associated with the method of measuring the particular value, and can include a range of plus or minus one or two standard deviations around the stated value. When used to describe estimated values or compound dosages, it includes a range of plus or minus 10% of the stated value, or in some embodiments a range of plus or minus 5% around the stated value.

As used herein and in the appended claims, the singular forms "a," "or," and "the" include plural referents unless the context clearly dictates otherwise. It is understood that aspect and variations described herein include "consisting" and/or "consisting essentially of" aspects and variations. The terms "a" and "an" do not denote a limitation of quantity, but rather denote the presence of at least one of the referenced item. The terms "a" and "an" are used interchangeable with "one or more" or "at least one". The term "or" or "and/or" is used as a function word to indicate that two words or expressions are to be taken together or individually. The terms "comprising", "having", "including", and "containing" are to be construed as open-ended terms (i.e., meaning "including, but not limited to"). The endpoints of all ranges directed to the same component or property are inclusive and independently combinable.

The terms "salt form(s) of the invention", "these salt forms", "such salt form(s)", "the salt form(s)", and "the present salt form(s)" refer to salt forms described herein, such as an amorphous salt form or crystalline polymorph salt form (e.g., polymorph Form II, III, IV, V, VI, VII, VIII, IX, X, XI, XII, XIII, XIV, XV, XVI, XVII, XVIII, XIX, XX, XXI, or XXII). Furthermore, the present salt forms can modulate, i.e., inhibit or enhance, the biological activity of a CK2 protein, a Pim protein or both, and thereby is also referred to herein as a "modulator(s)" or "CK2 and/or Pim modulator(s)".

Unless defined otherwise or clearly indicated by context, all technical and scientific terms and abbreviations used herein have the same meaning as commonly understood by one of ordinary skill in the art to which this invention belongs.

Amorphous Sodium Salt of 5-(3-chlorophenylamino) benzo[c][2,6]naphthyridine-8-carboxylic acid (Form I)

Figure 1:
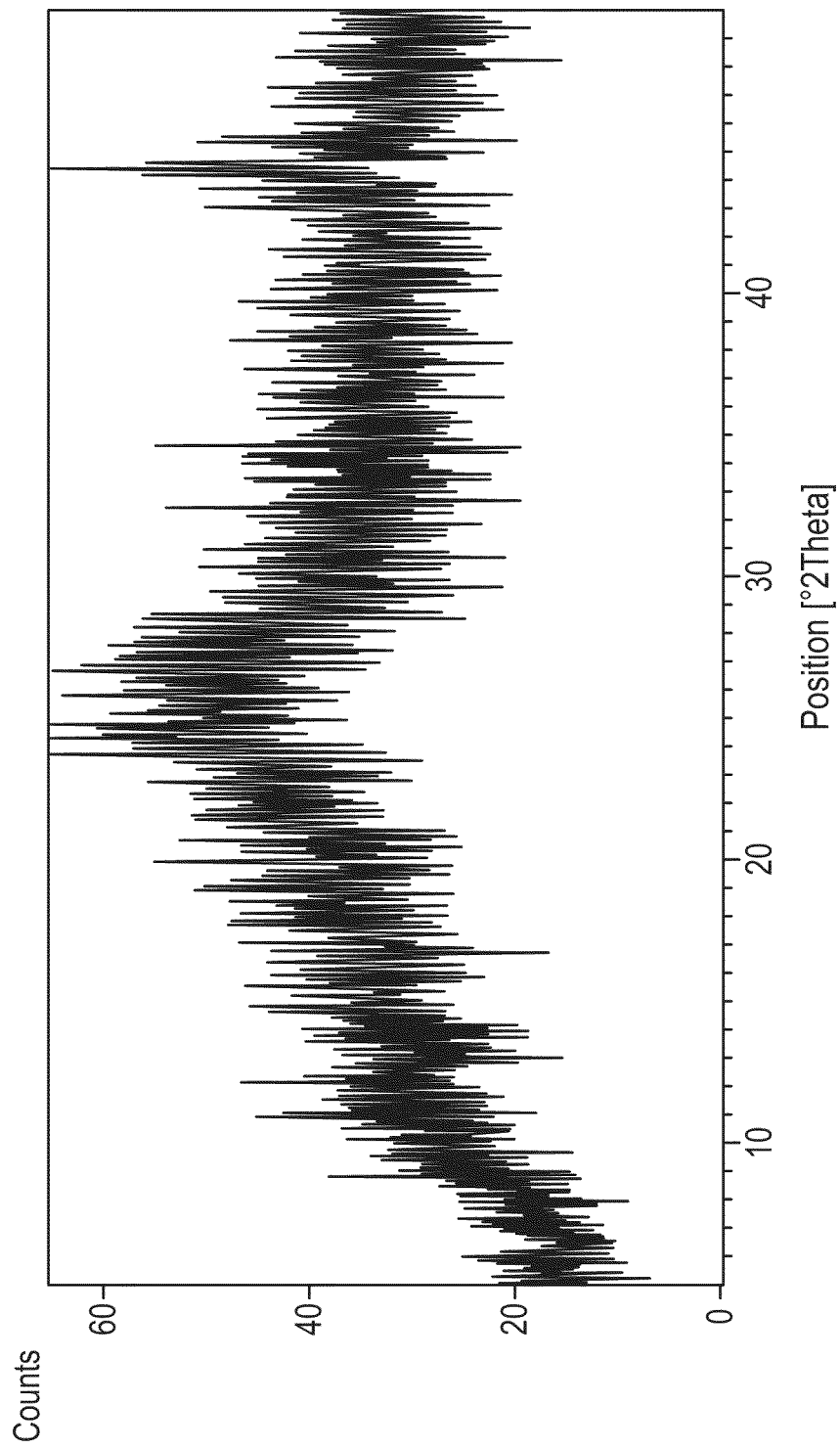
FIG. 1 depicts the powder x-ray diffraction pattern of the sodium salt of 5-(3-chlorophenylamino)benzo[c][2,6]naphthyridine-8-carboxylic acid (compound (I)) in amorphous form.

The amorphous sodium salt of compound I can be prepared from the free acid using standard techniques known in the art and identified by its lack of discernable diffraction pattern in XRPD (see FIG. 1). Preparation of the free acid is shown below in the Experimental section and described in copending U.S. application Ser. No. 11/849,230 (US2009/0105233) and U.S. application Ser. No. 12/396,084 (Protein Kinase Modulators). The content of both of these applications is hereby incorporated by reference.

The amorphous form is anhydrous and will stay amorphous e.g., under dry conditions less than 30° C. The amorphous form is an off-white to yellow solid with a melting point of approximately 418.91° C. The major Infrared Absorption (IR) wavenumbers for the amorphous form are shown below in Table 1.

TABLE 1

Major IR Absorption wavenumber assignments for the Amorphous Sodium Salt (Form I).

| Wavenumber ($cm^{-1}$) | Assignment |
|---|---|
| 3632 | NH Stretch |
| 3307 | NH Stretch |
| 1581 | Aryl COO Stretch Asym |
| 1555 | Aryl COO Stretch Asym |
| 1400 | Aryl COO Stretch Sym |

TABLE 1-continued

Major IR Absorption wavenumber assignments for the Amorphous Sodium Salt (Form I).

| Wavenumber ($cm^{-1}$) | Assignment |
|---|---|
| 1076 | Aryl Cl M-Substitution Vibration |
| 769 | Aryl Cl Stretch |

Figure 20:
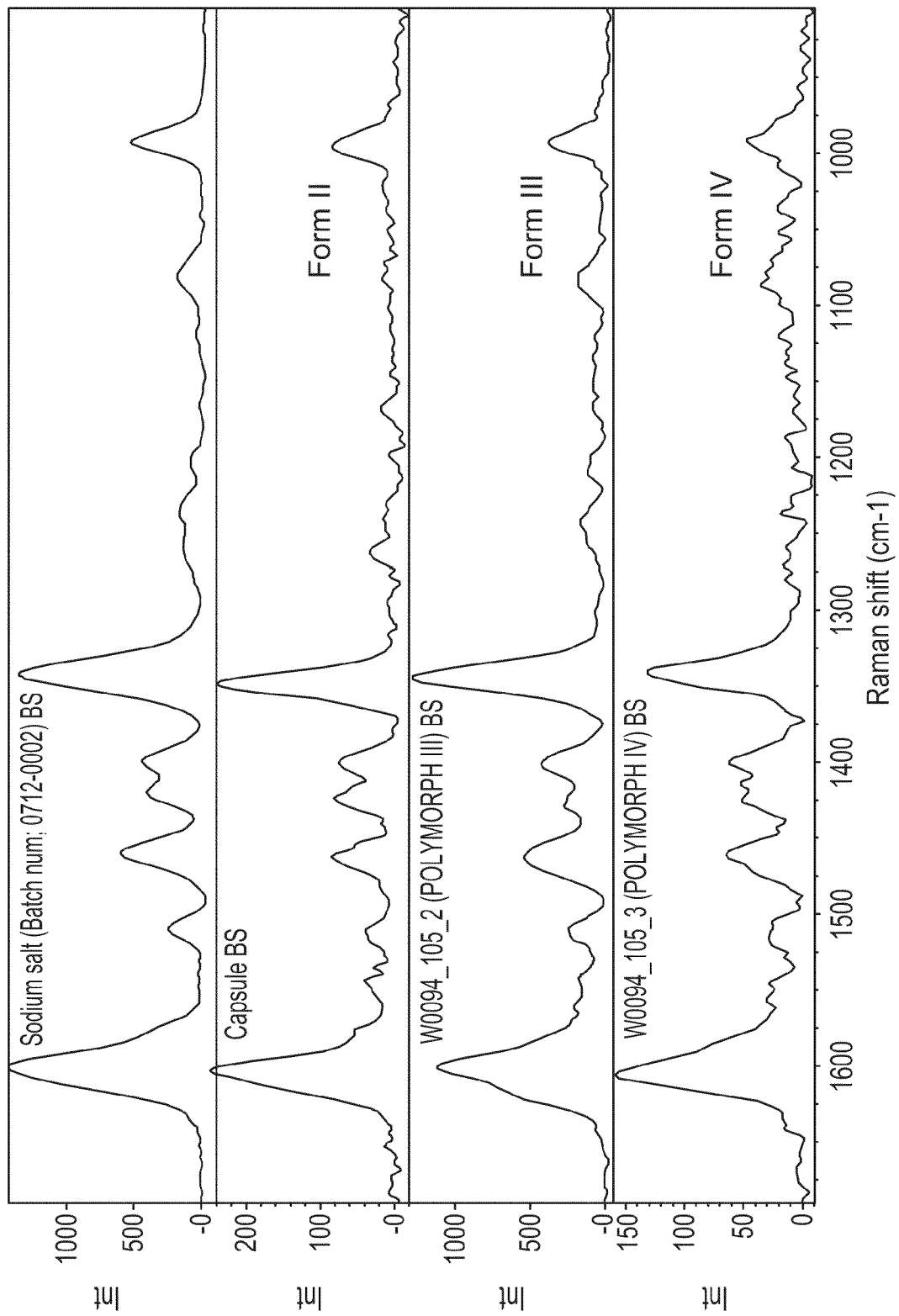
FIG. 20 depicts Raman spectra for the Forms I-IV.

Raman spectra for the amorphous Form I is shown in FIG. 20. Peak assignments ($cm^{-1}$) and corresponding intensities are shown in Table 2.

TABLE 2

Raman assignments for the Amorphous Sodium Salt (Form I).

| Wavenumber ($cm^{-1}$) | Intensity |
|---|---|
| 994.38 | 505.231 |
| 1082.91 | 160.045 |
| 1240.15 | 143.893 |
| 1344.35 | 1341.864 |
| 1401.86 | 419.044 |
| 1422.06 | 386.1 |
| 1462.28 | 584.876 |
| 1512.36 | 232.123 |
| 1603.22 | 1428.857 |

Polymorphs of 5-(3-chlorophenylamino)benzo[c][2,6]naphthyridine-8-carboxylic acid Crystalline Sodium Salt of 5-(3-chlorophenylamino) benzo[c][2,6]naphthyridine-8-carboxylic acid (Form II)

The Form II polymorph of the sodium salt of compound I can be made by exposure of the amorphous Form I material to moist air (e.g., RH>60% in a fluid bed 'dryer' acting as a controlled flow of humidity). In some instances preferred drying conditions are exposure of Form I to atmospheric humidity (about 30% to 60%), either at room temperature or at about 40° C. (in an open oven). Only some initial conversion to Form II was obtained by slurrying in organic solvent/water (e.g., EtOH/water) at a ratio of 10:90.

Figure 2:
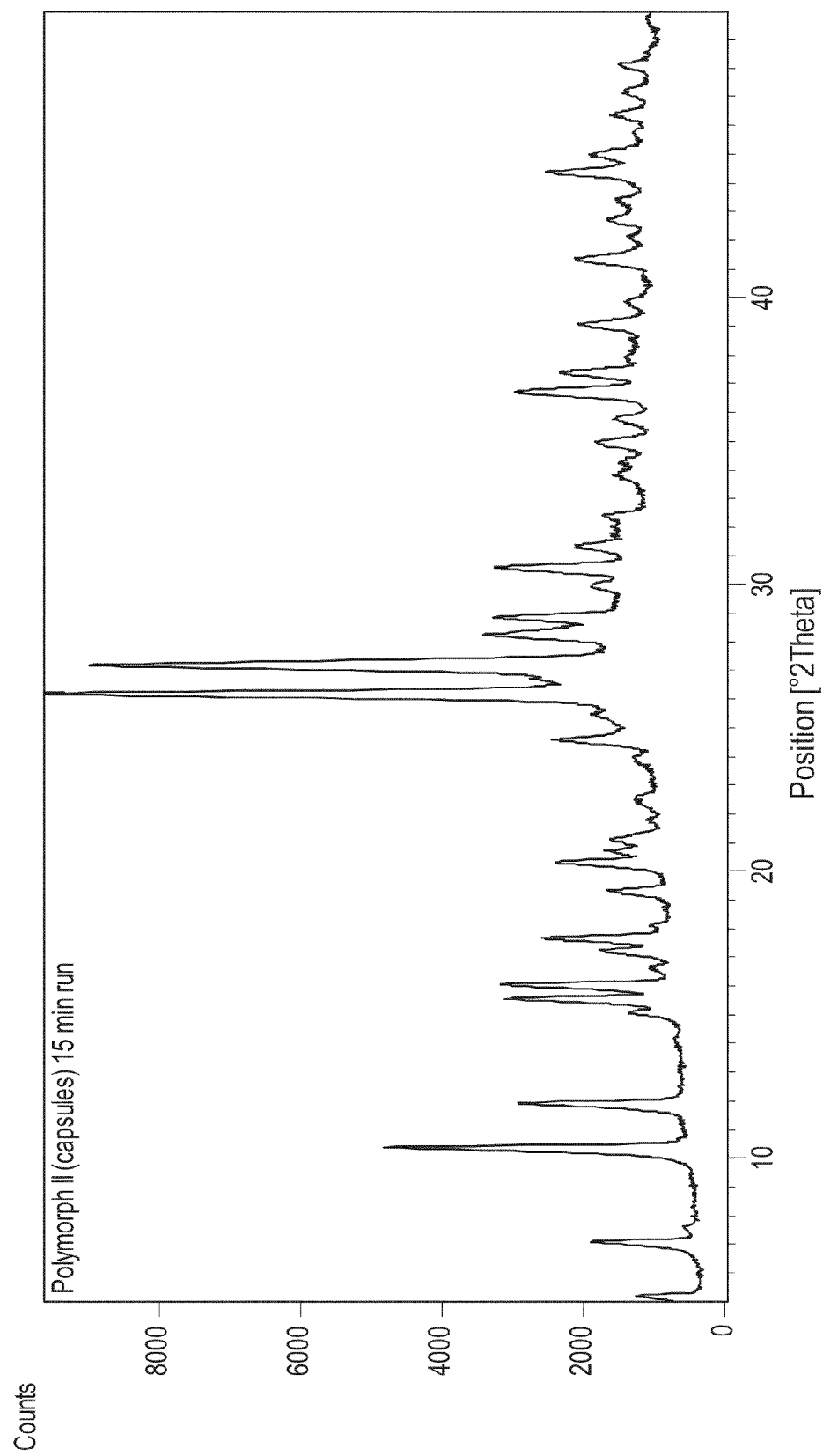
FIG. 2 depicts the powder x-ray diffraction pattern of polymorph Form II.

The XRPD pattern of Form II is shown in FIG. 2, indicating 2θ diffraction lines at e.g., about 5.2°, 7.1°, 10.4°, 11.9°, 15.1°, 15.6°, 16.1°, 17.3°, 17.7°, 19.3°, 20.3°, 21.1°, 24.6°, 26.2°, 27.2°, 28.3°, 28.9°, 30.6°, 36.7°, 37.4°, 39.1°, 41.4°, 44.4°, 45.0°, 46.4° and 48.1°, with major 2θ diffraction lines at e.g., about 10.4°, 26.2° and 27.2°.

Figure 3:
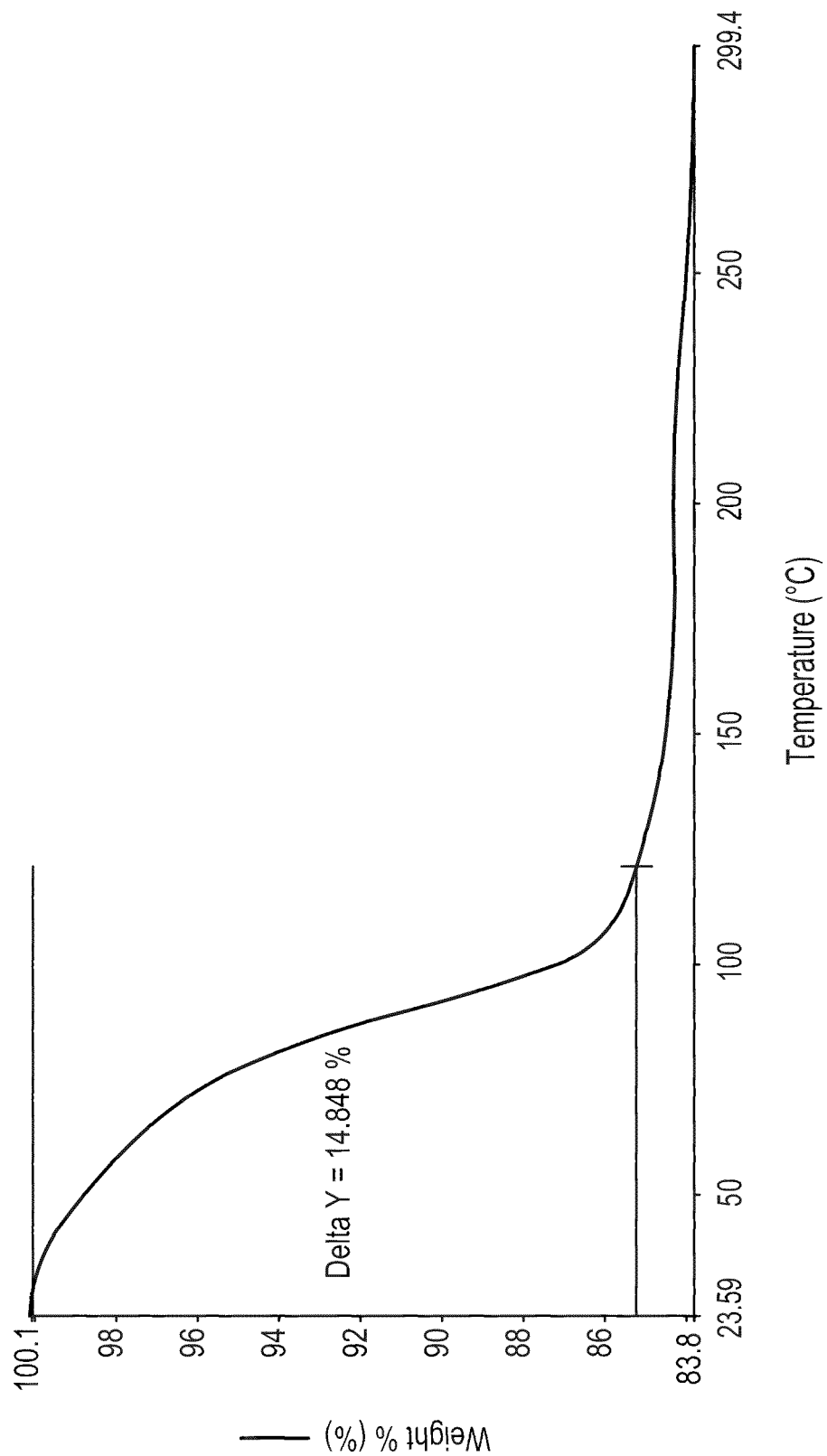
FIG. 3 depicts the Thermogravimetric Analysis (TGA) data of polymorph Form II.
Figure 4:
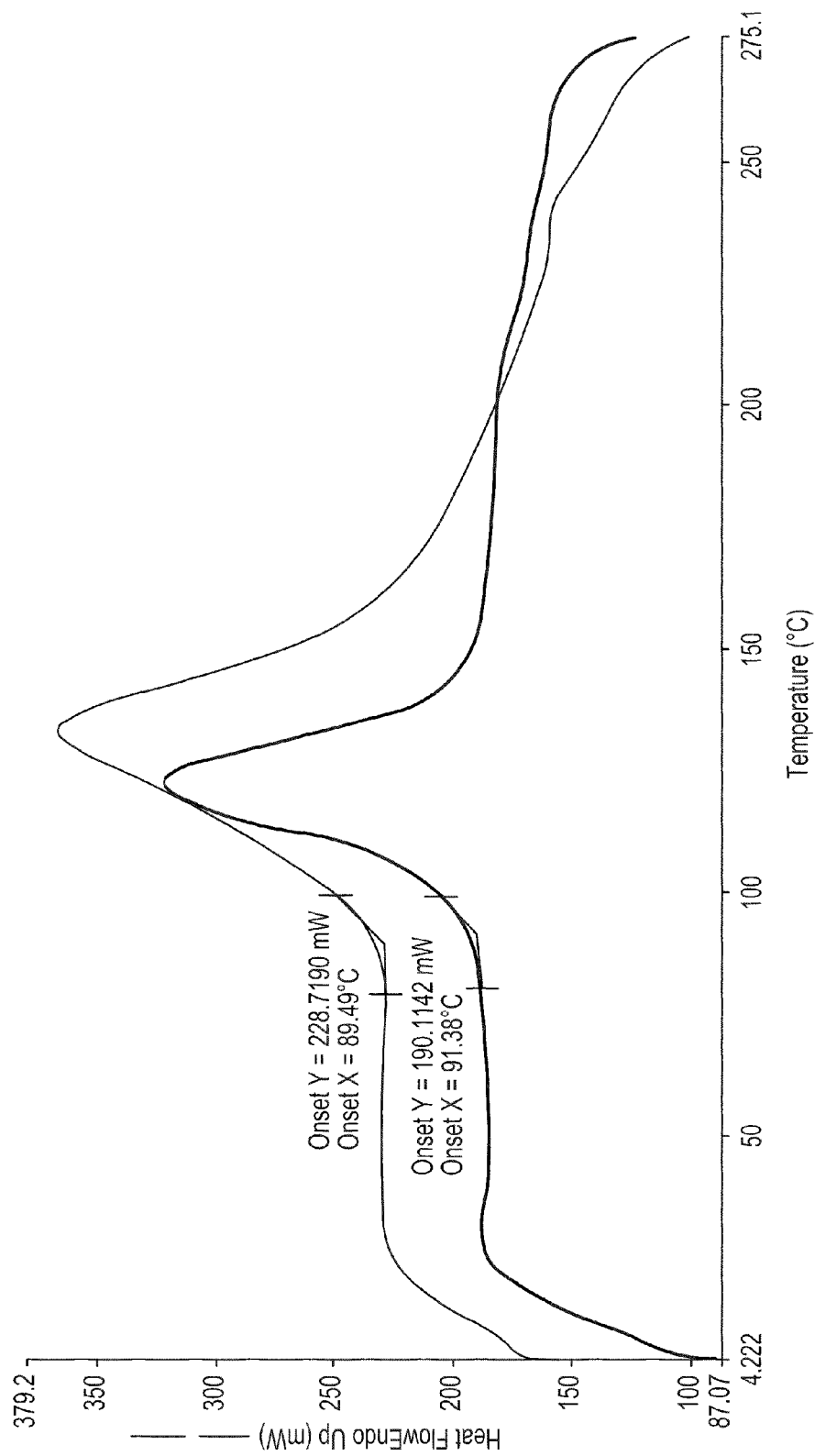
FIG. 4 depicts a Differential Scanning Calorimetry (DSC) thermogram of polymorph Form II.
Figure 5:
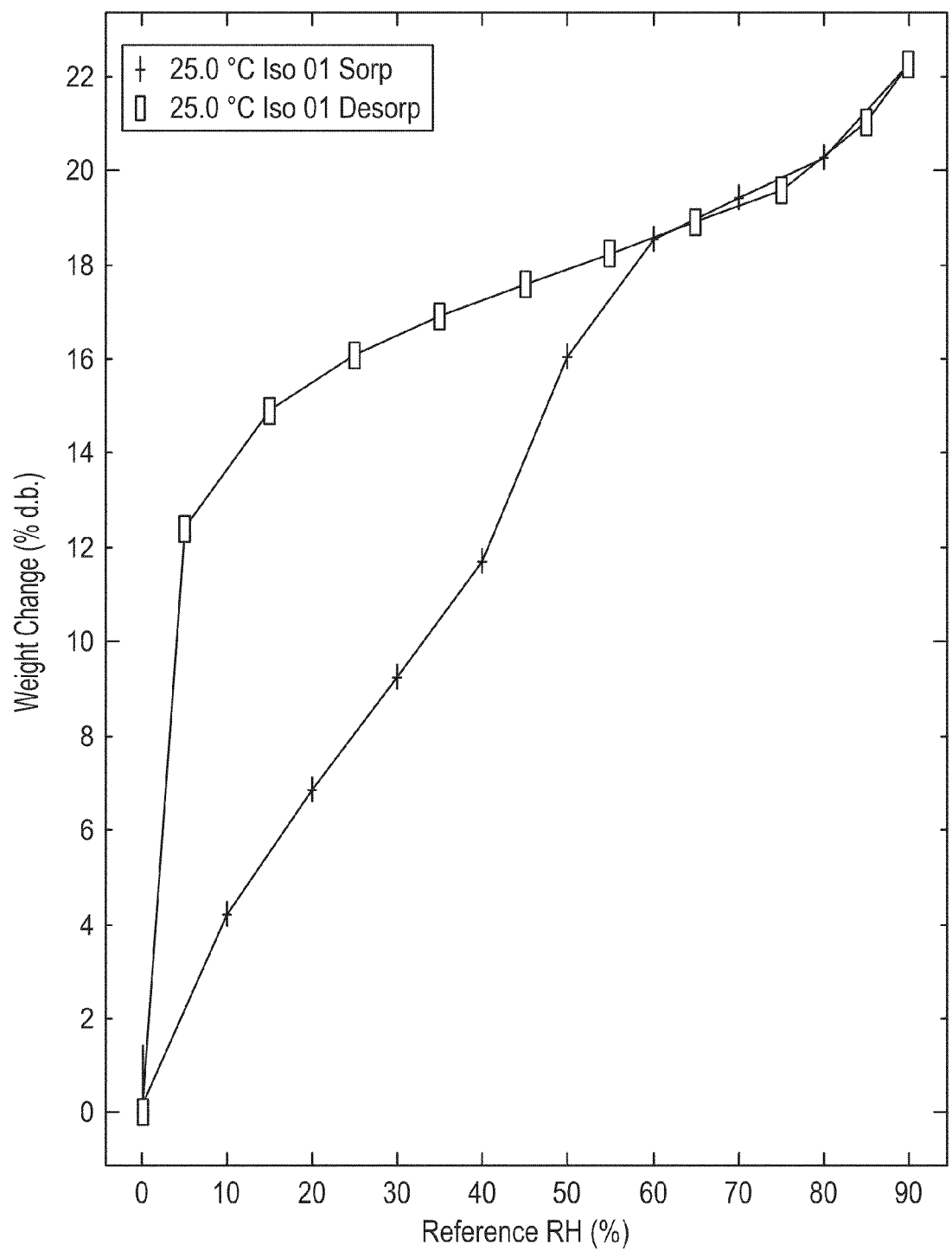
FIG. 5 depicts the Gravimetric Vapor Sorption (GVS) data of in polymorph Form II.

Thermogravimetric Analysis (TGA) data for Form II (FIG. 3) indicates significant weight loss of about 15% out to about 125° C., suggesting the Form II polymorph is a trihydrate (weight loss equates to about 3 moles of water). Differential Scanning Calorimetry (DSC) data for Form II (FIG. 4) shows an endotherm at about 90° C. which coincides with the TGA analysis. Gravimetric Vapor Sorption (GVS) data for Form II (FIG. 5) displays about 12% uptake of water between the normal operating range of 20-70% RH, indicating the hydroscopic nature of Form II. Form II showed a moderate hydroscopicity in RH range of about 10% to about 70% with about 8% weight gain. No further form conversion was observed in the GVS cycle (from about 10% to about 90%, repeated).

Raman spectra for the polymorph Form II is shown in FIG. 20. Peak assignments ($cm^{-1}$) and corresponding intensities are shown in Table 3.

TABLE 3

Raman assignments for the Form II polymorph of the sodium salt.

| Wavenumber (cm$^{-1}$) | Intensity |
|---|---|
| 997.78 | 80.591 |
| 1169.94 | 15.292 |
| 1264.42 | 30.285 |
| 1350.64 | 237.913 |
| 1402.66 | 72.003 |
| 1426.54 | 78.963 |
| 1464.65 | 81.484 |
| 1513.78 | 36.193 |
| 1537.74 | 24.465 |
| 1546.42 | 37.735 |
| 1605.42 | 247.304 |

Figure 6:
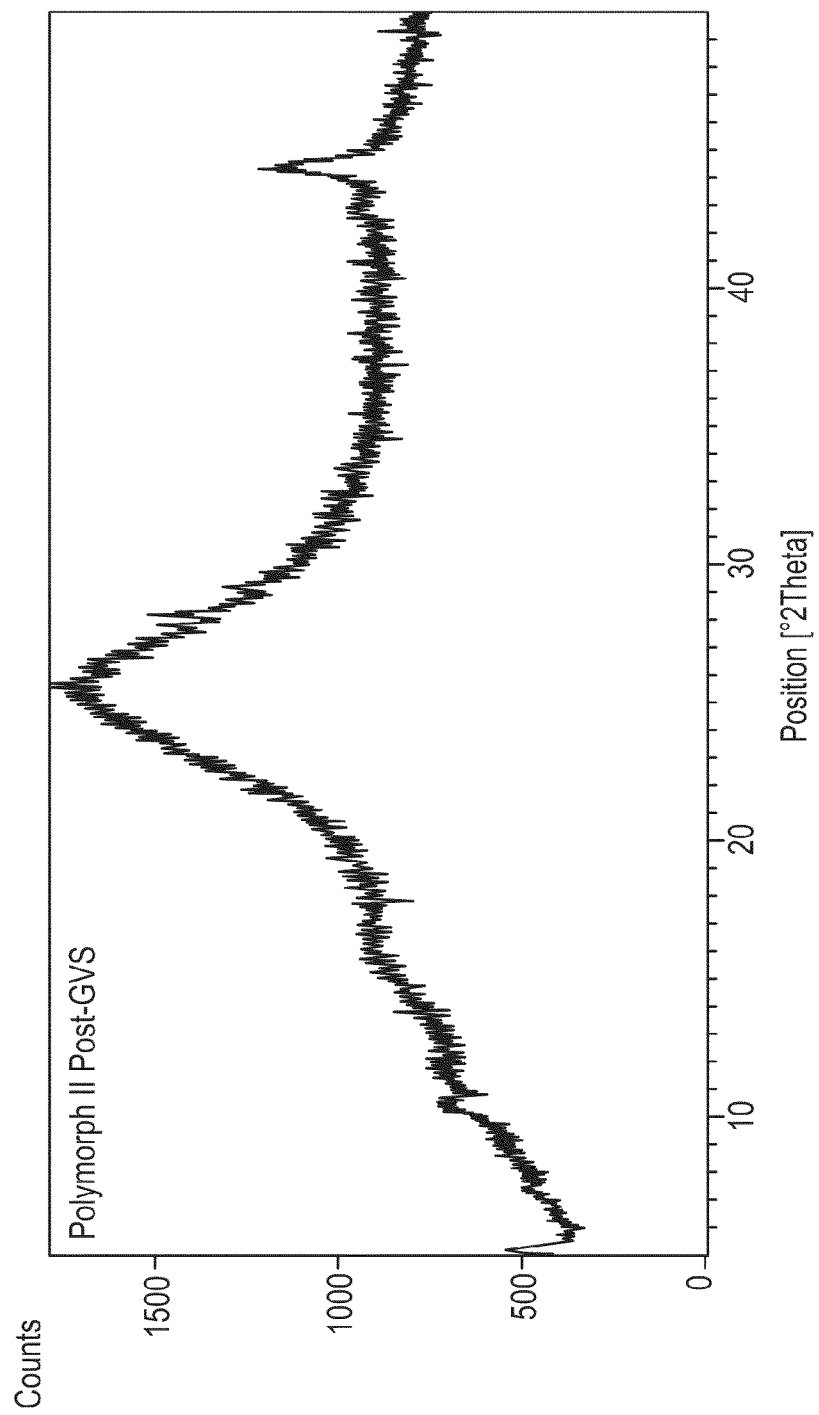
FIG. 6 depicts the powder x-ray diffraction pattern of polymorph Form II after storage for 5 days at 80° C.

Upon drying the Form II samples (e.g., at 80° C. for about 24 hours and prolonged drying at 60° C.), the Form II polymorph is converted to amorphous material (see FIG. 6). XPRD analysis of the post-GVS experiment sample showed amorphous content.

Crystalline Sodium Salt of 5-(3-chlorophenylamino)benzo[c][2,6]naphthyridine-8-carboxylic acid (Form III)

The Form III polymorph of the sodium salt of compound I can be made by slurrying the amorphous Form I material (e.g., about 100 mg) in isopropyl alcohol (e.g., about 1.5 mL) and allowing the sample to temperature cycle over 2 days.

Figure 7:
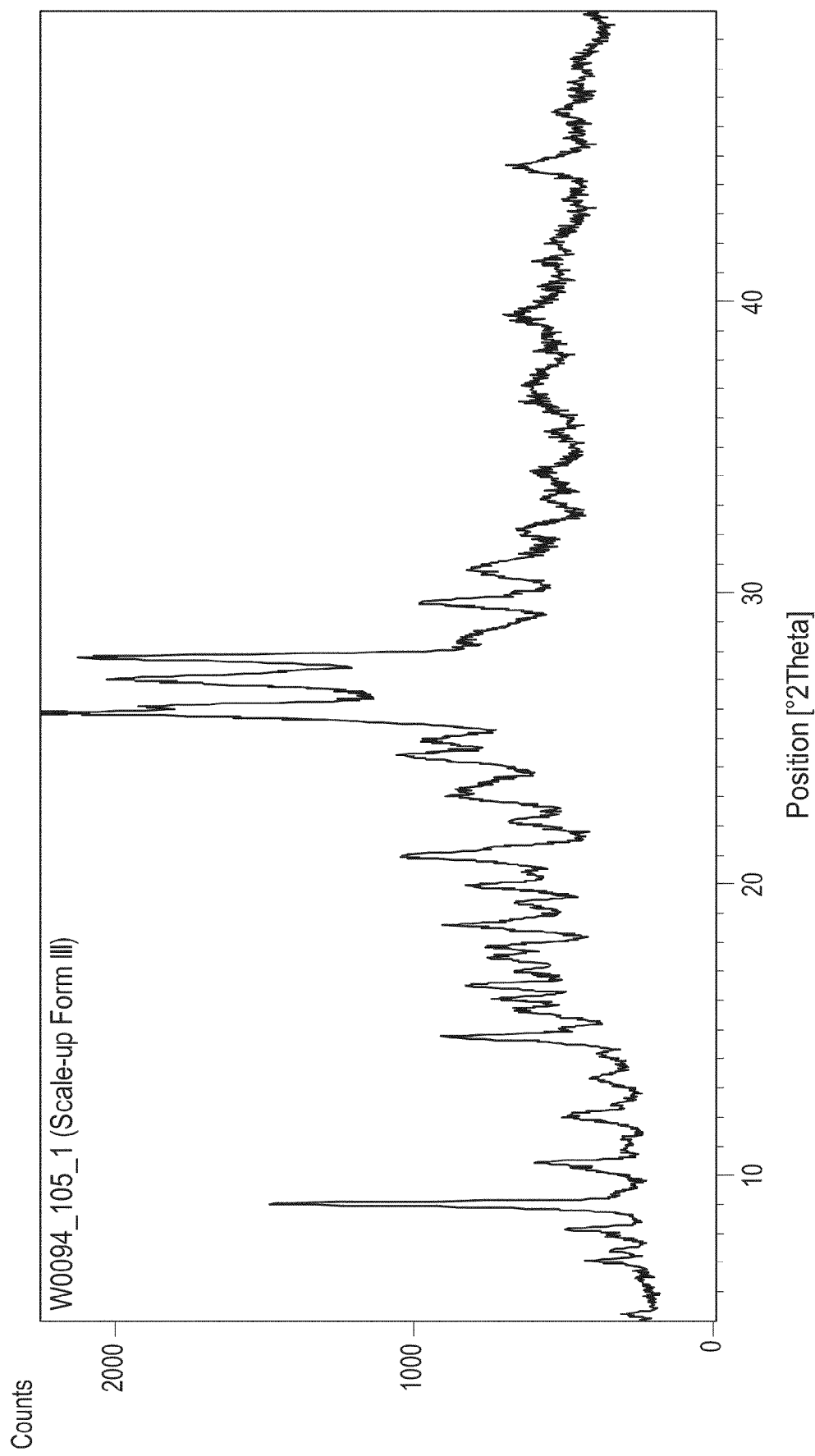
FIG. 7 depicts the powder x-ray diffraction pattern of polymorph Form III.

The XRPD pattern of Form III is shown in FIG. 7, indicating 2θ diffraction lines at e.g., about 5.2°, 7.1°, 7.4°, 8.2°, 9.0°, 10.4°, 12.0°, 13.3°, 14.7°, 15.7°, 16.1°, 16.5°, 17.0°, 17.5°, 17.8°, 18.6°, 19.4°, 20.0°, 21.0°, 21.3°, 22.2°, 23.0°, 24.4°, 25.0°, 25.9°, 26.1°, 27.1°, 27.8°, 29.7°, 30.8°, 32.2° and 44.6°, with major 2θ diffraction lines at e.g., about 8.2°, 25.9°, 26.1° and 27.9°.

Figure 8:
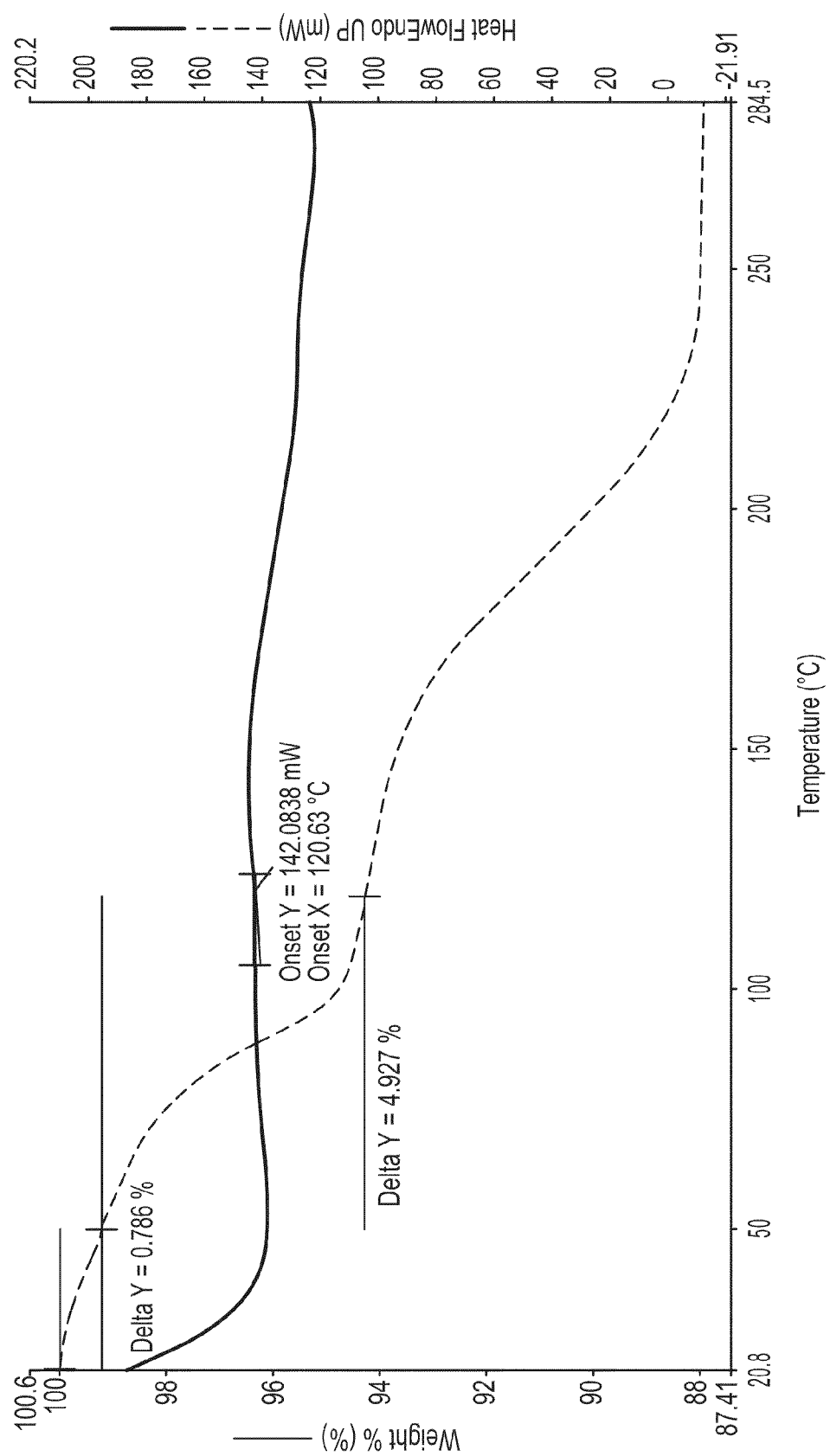
FIG. 8 depicts TGA and DSC data of polymorph Form III.
Figure 9:
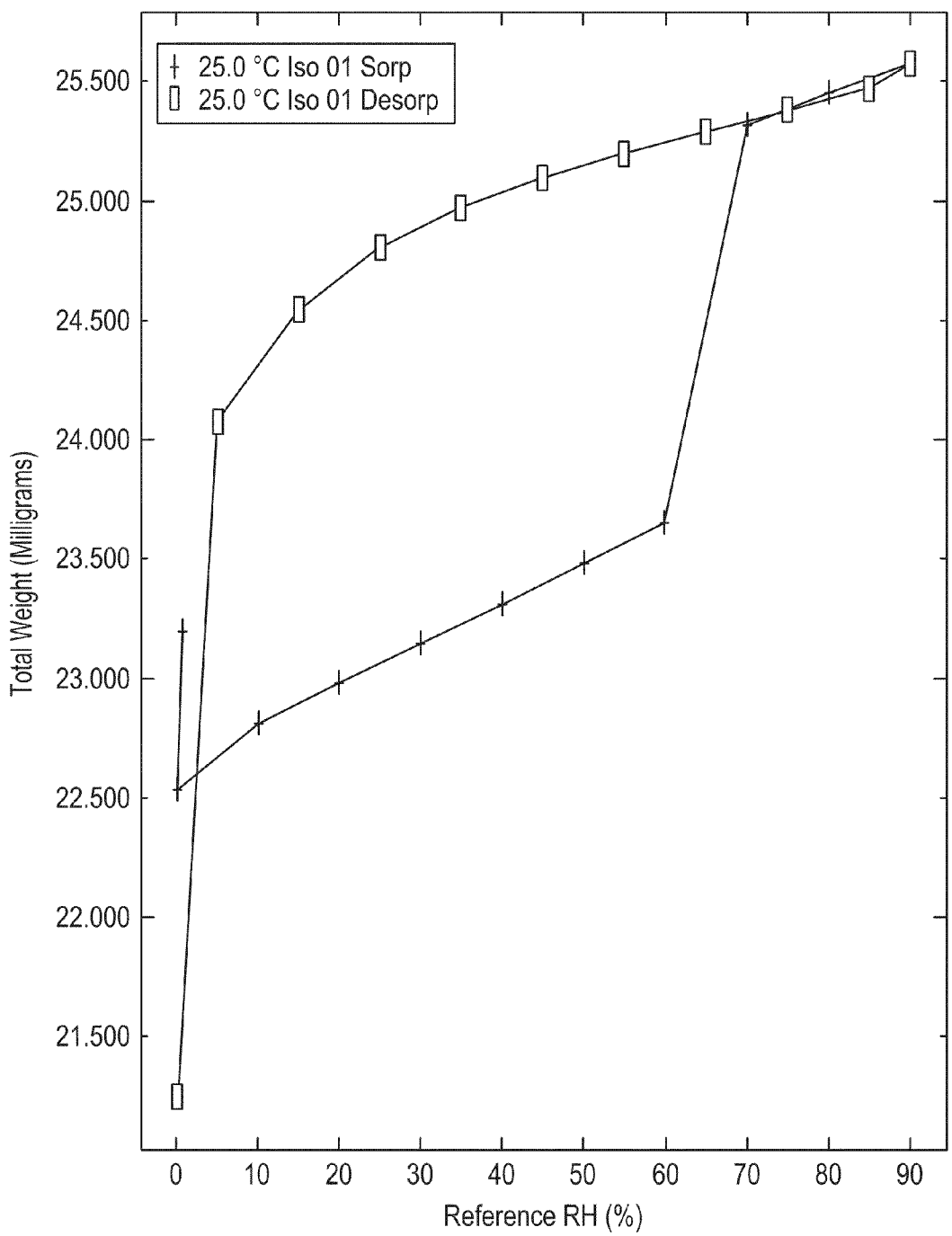
FIG. 9 depicts the GVS data of in polymorph Form III.
Figure 10:
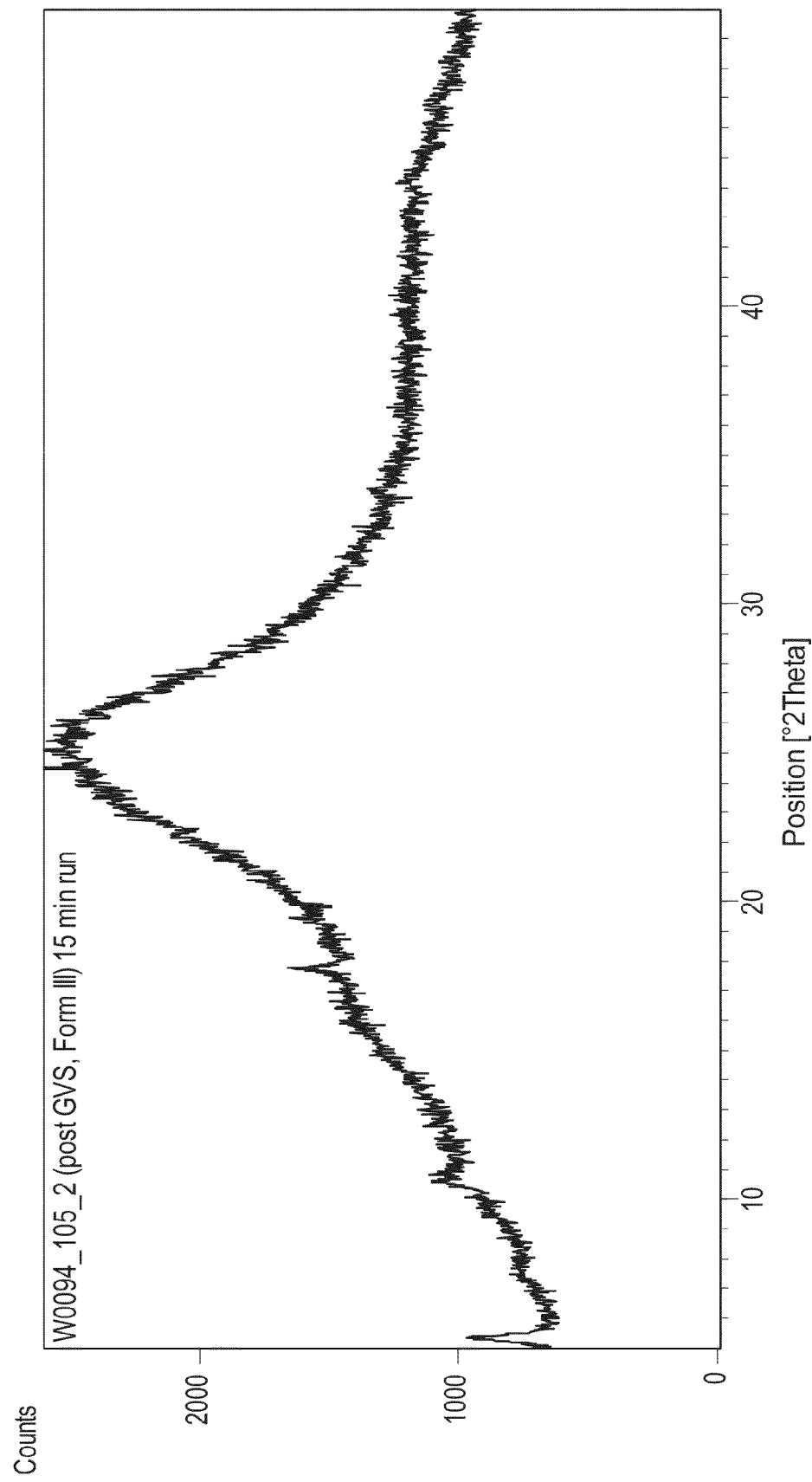
FIG. 10 depicts the powder x-ray diffraction pattern of polymorph Form III after drying.

Thermogravimetric Analysis (TGA) data for Form III (see FIG. 8) indicates an initial weight loss of less than about 1% to about 50° C. and a subsequent weight loss of about 5% through about 120° C., followed by main degradation at about 150° C. The TGA data suggests that the Form III polymorph is hydrate (weight loss equates to about 1 moles of water). Differential Scanning Calorimetry (DSC) data for Form III (see FIG. 8) shows a broad endotherm at about 120° C. indicating a possible solvent or water loss (followed by events at higher temperature likely the result of degradation). Gravimetric Vapor Sorption (GVS) data for Form III (FIG. 9) displays an initial weight loss due to an initially wet sample. GVS data shows Form III is hydroscopic, absorbing 11% on sorption and retaining water on desorption until 5%, wherein the mass drops significantly. XPRD analysis of the post-GVS experiment sample showed amorphous content (FIG. 10).

Raman spectra for the polymorph Form III is shown in FIG. 20. Peak assignments (cm$^{-1}$) and corresponding intensities are shown in Table 4.

TABLE 4

Raman assignments for the Form III polymorph of the sodium salt.

| Wavenumber (cm$^{-1}$) | Intensity |
|---|---|
| 994.61 | 362.088 |
| 1081.85 | 165.508 |
| 1212.05 | 102.279 |
| 1244.54 | 154.328 |
| 1346.68 | 1277.688 |
| 1403.53 | 410.611 |

TABLE 4-continued

Raman assignments for the Form III polymorph of the sodium salt.

| Wavenumber (cm$^{-1}$) | Intensity |
|---|---|
| 1431.16 | 257.099 |
| 1465.13 | 526.681 |
| 1512.25 | 231.499 |
| 1603.46 | 1109.713 |

5 day stability studies of Form III indicate the material reverts to Form II at 40° C./75% RH within about 24 hours. Storage studies at about 80° C. over about 5 days resulted in less crystalline appearance as shown by XPRD, while 5 day light studies indicated no physical change by XRPD for the duration of the study.

Crystalline Sodium Salt of 5-(3-chlorophenylamino)benzo[c][2,6]naphthyridine-8-carboxylic acid (Form IV)

The Form IV polymorph of the sodium salt of compound I can be made by slurrying the amorphous Form I material (e.g., about 100 mg) in ethyl acetate (e.g., about 1.5 mL) and allowing the sample to temperature cycle over 2 days.

Figure 11:
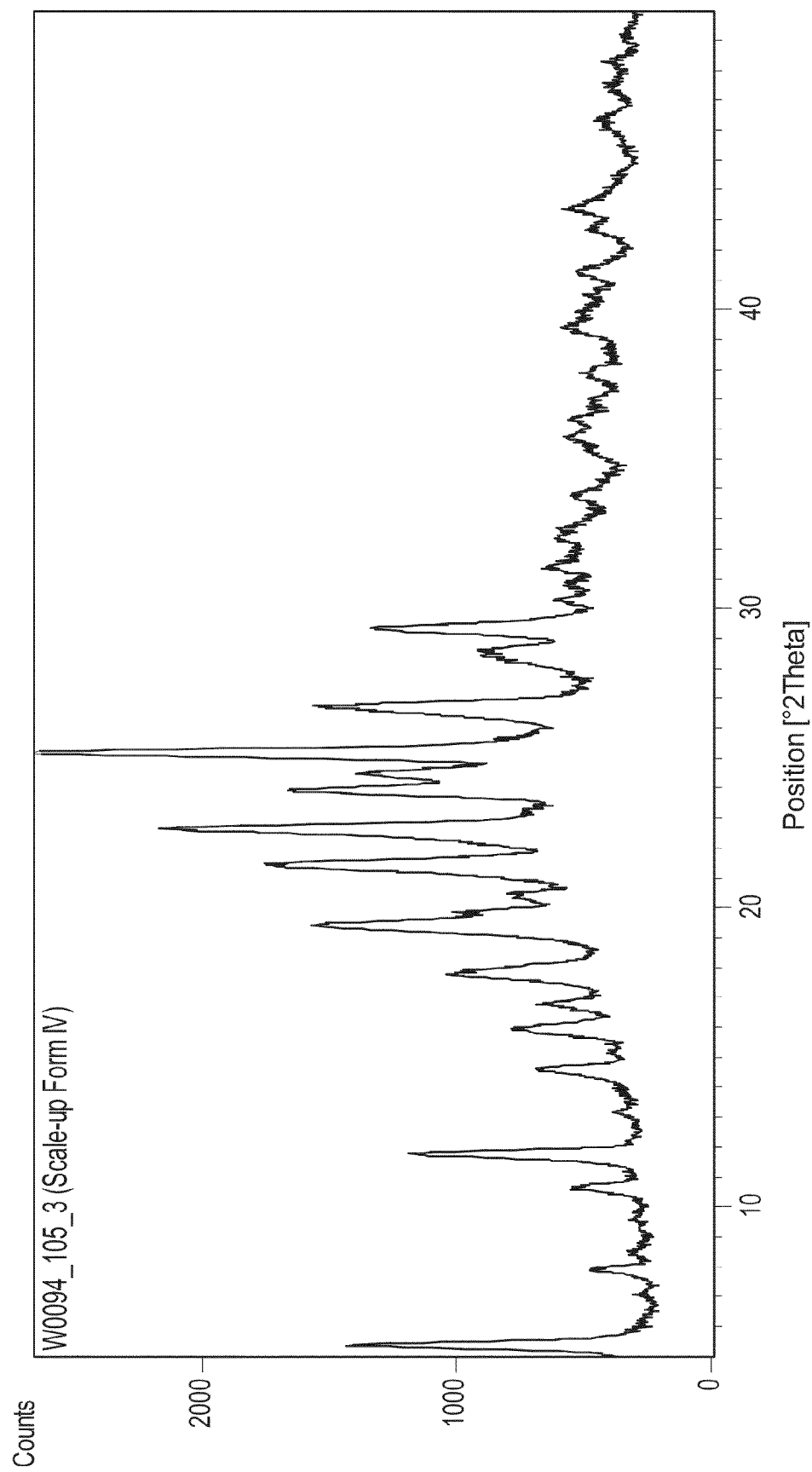
FIG. 11 depicts the powder x-ray diffraction pattern of polymorph Form IV.

The XRPD pattern of Form IV is shown in FIG. 11, indicating 2θ diffraction lines at e.g., about 5.4°, 8.0°, 10.8°, 11.9°, 14.7°, 16.1°, 16.9°, 17.9°, 19.5°, 20.0°, 20.6°, 21.6°, 22.8°, 24.1°, 24.6°, 25.3°, 26.9°, 28.7°, 29.5°, 32.6°, 34.0°, 35.8°, 36.4° and 38.0°, with major 2θ diffraction lines at e.g., about 21.6°, 22.8° and 25.3°.

Figure 12:
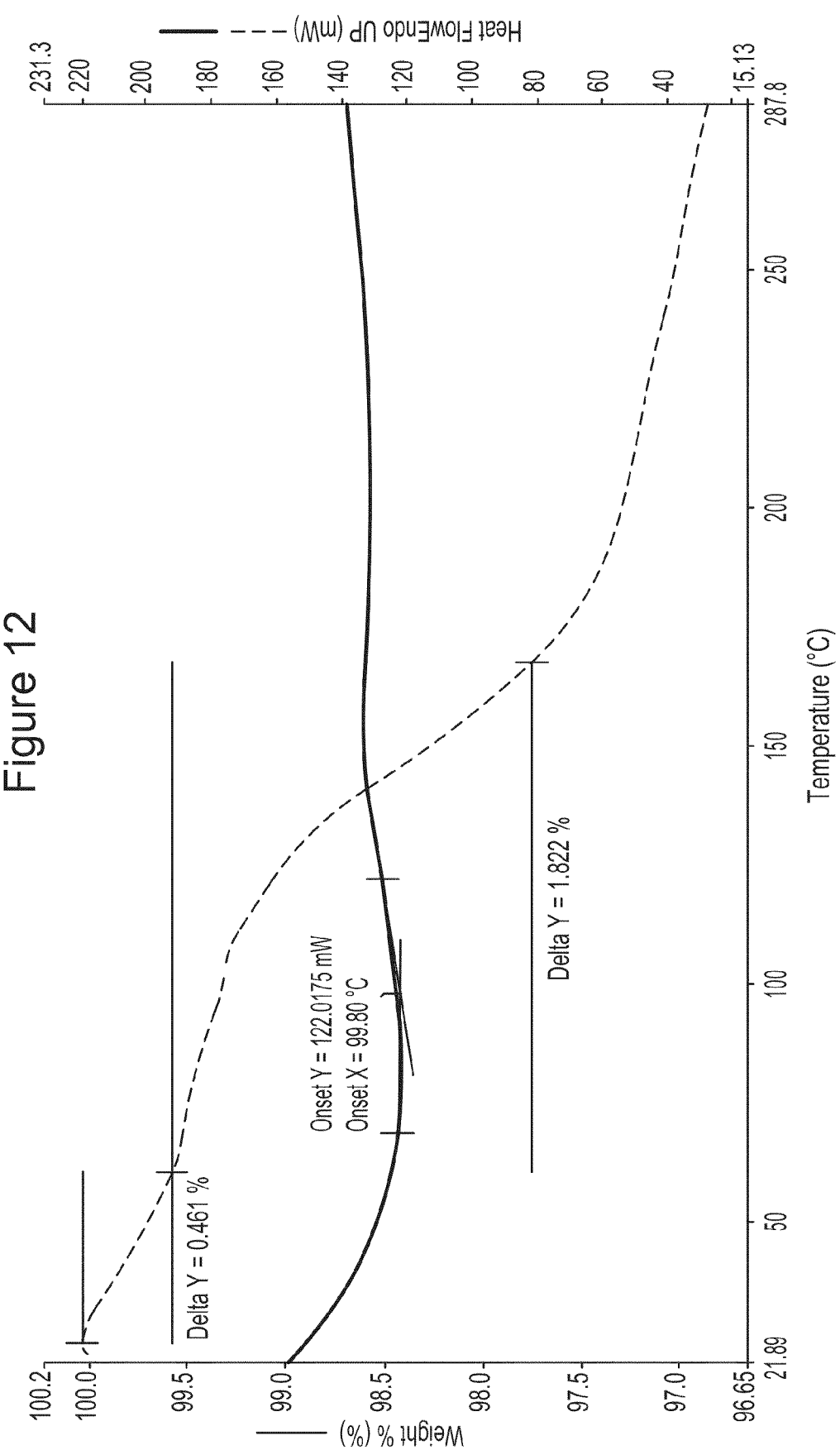
FIG. 12 depicts TGA and DSC data of polymorph Form IV.
Figure 13:
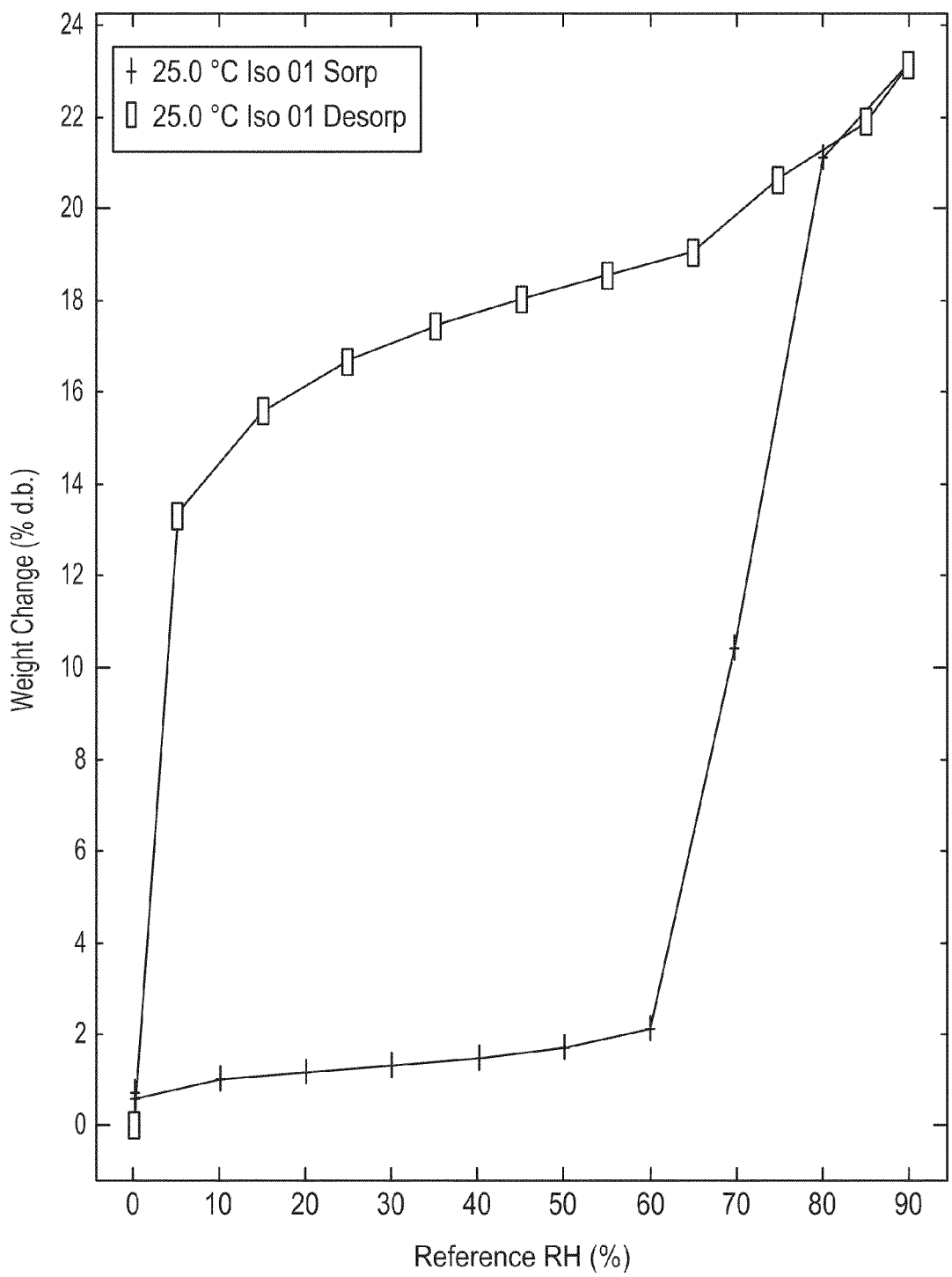
FIG. 13 depicts GVS data of in polymorph Form IV.
Figure 14:
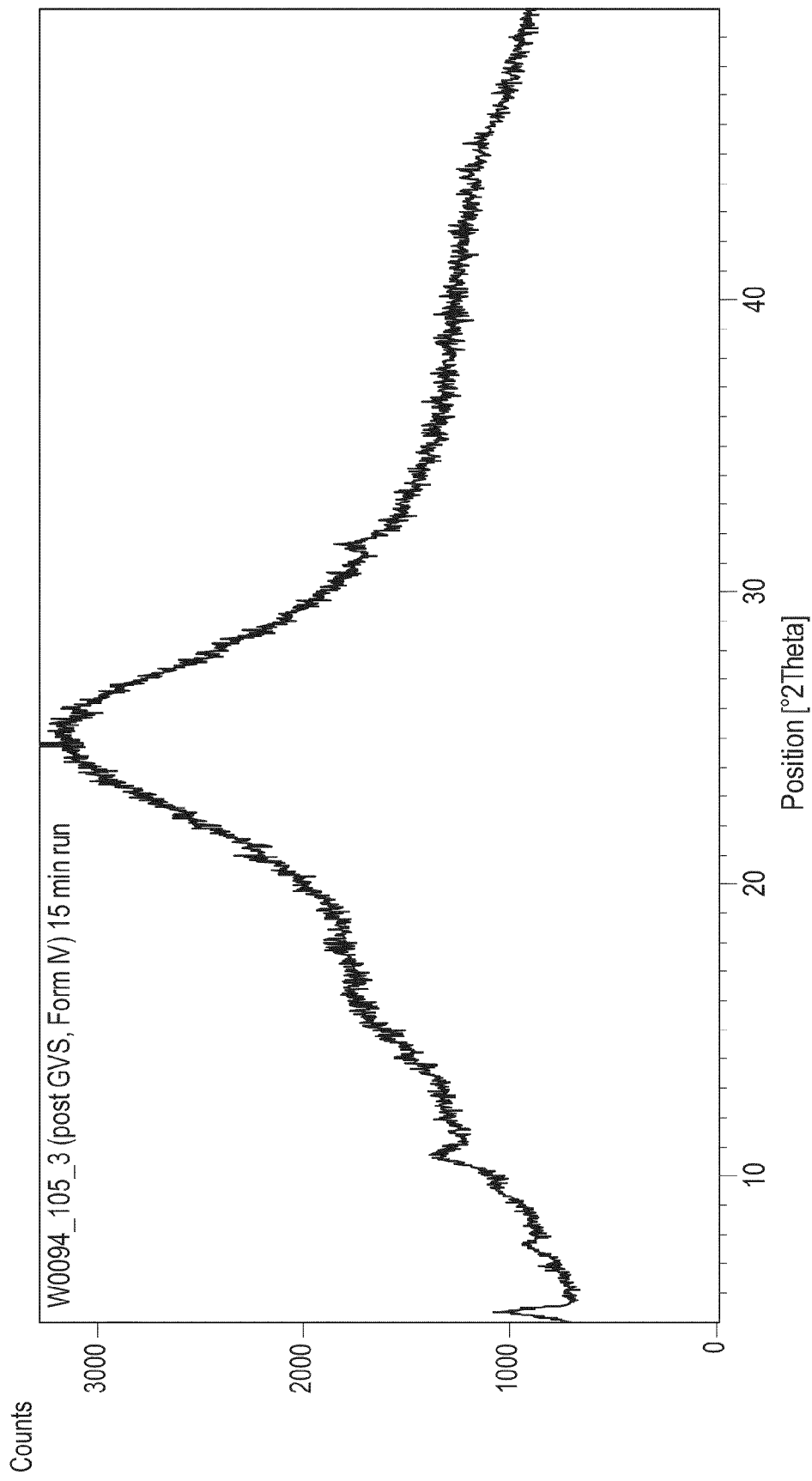
FIG. 14 the powder x-ray diffraction pattern of polymorph Form IV after treatment under GVS conditions.
Figure 17:
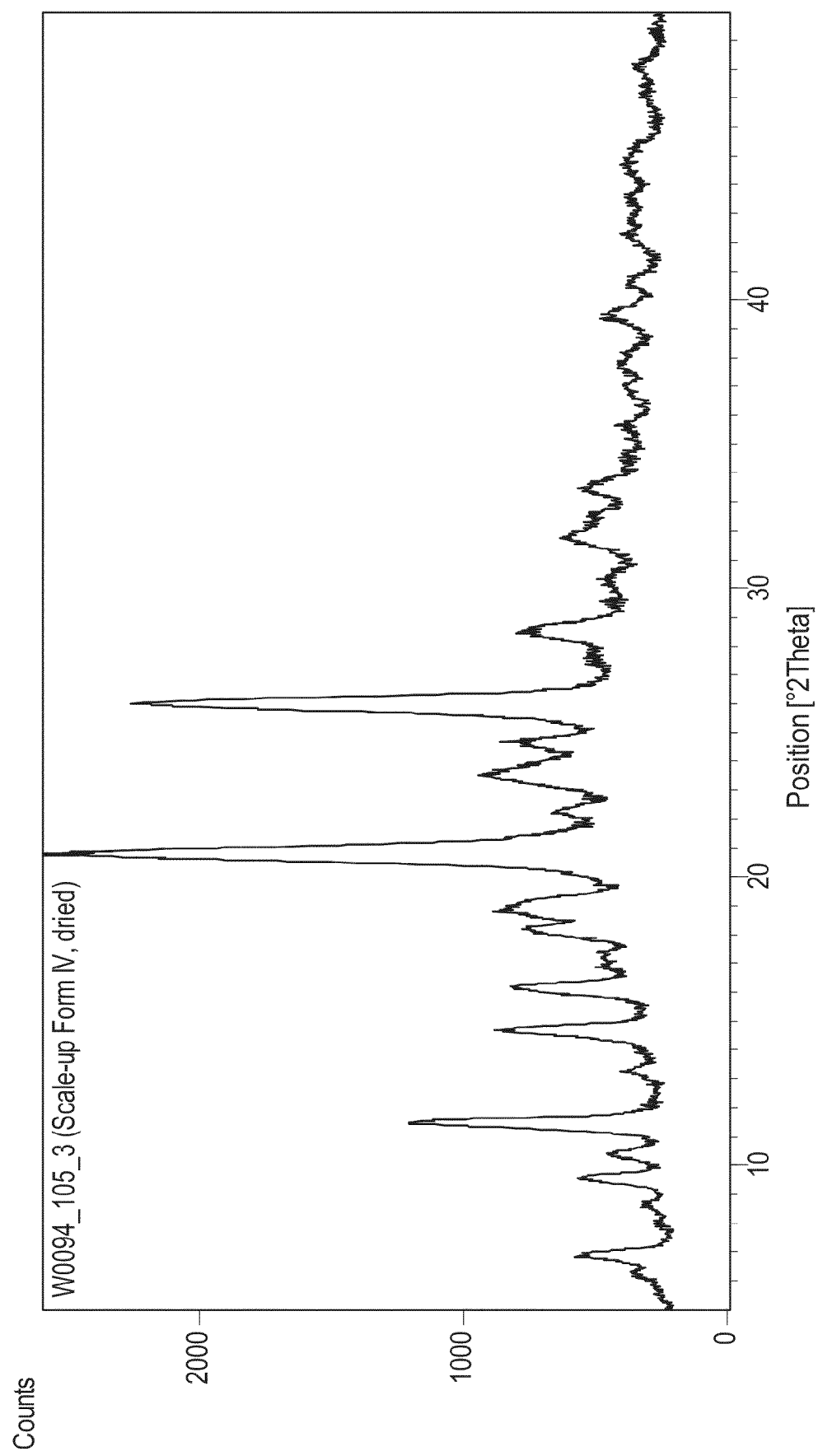
FIG. 17 depicts the powder x-ray diffraction pattern of polymorph Form VI.

Upon drying Form IV at 50° C., the sample converts to another crystalline polymorph (Form VI, see FIG. 17 and comments below). Thermogravimetric Analysis (TGA) data for Form IV (see FIG. 12) indicates an initial weight loss of about 2% through about 160° C. which equates to about 0.5 moles of water (thus, a possible hemihydrate). No additional TGA events were observed except the main degradation at about 160° C. Differential Scanning Calorimetry (DSC) data for Form IV (see FIG. 12) shows a broad endotherm at about 100° C. indicating a possible solvent or water loss (followed by events at higher temperature likely the result of degradation). Gravimetric Vapor Sorption (GVS) data for Form IV (FIG. 13) indicates that on sorption there is about 1% uptake of water between about 20-60% RH. The data shows a further approximately 8% rapid uptake between about 60-70% RH. On desorption the sample retains water until about 5%, where the mass drops significantly. XPRD analysis of the post-GVS experiment sample showed amorphous content (FIG. 14).

Raman spectra for the polymorph Form IV is shown in FIG. 20. Peak assignments (cm$^{-1}$) and corresponding intensities are shown in Table 5.

TABLE 5

Raman assignments for the Form IV polymorph of the sodium salt.

| Wavenumber (cm$^{-1}$) | Intensity |
|---|---|
| 1342.88 | 131.373 |
| 1402.47 | 60.609 |
| 1416.29 | 51.566 |
| 1427.31 | 50.167 |
| 1463.41 | 62.865 |
| 1517.89 | 26.637 |
| 1559.22 | 29.457 |
| 1608.25 | 158.008 |

Figure 15:
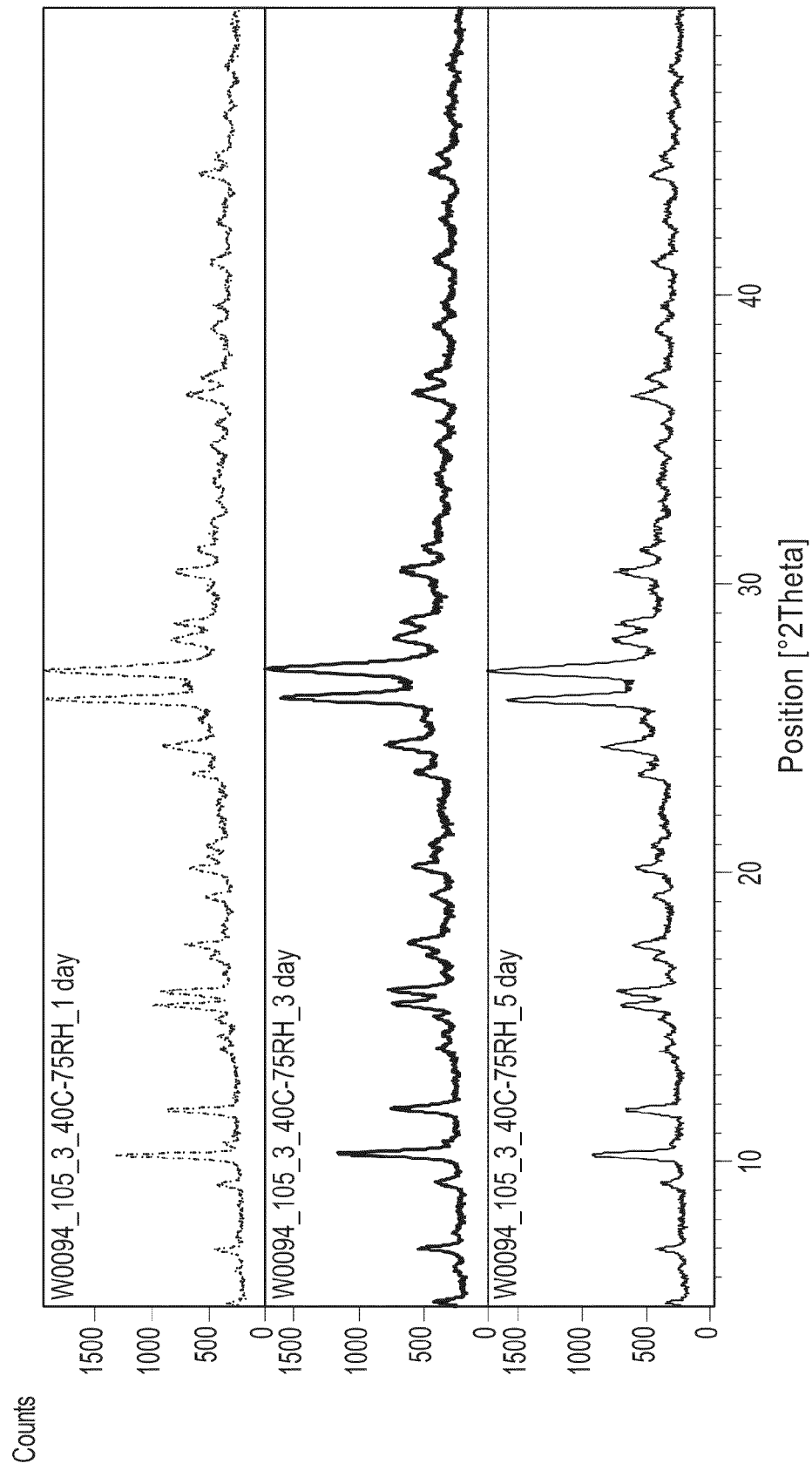
FIG. 15 depicts the powder x-ray diffraction pattern of polymorph Form IV after storage for 1 day (top), 3 days (middle) and 5 days (bottom) at 80° C.

5 day stability studies of Form IV indicate the material reverts to Form II at 40° C./75% RH within about 24 hours. Storage studies at about 80° C. over about 5 days resulted in no physical change as shown by XPRD (see FIG. 15). Likewise, 5 day light studies indicated no physical change by XRPD.

Crystalline Sodium Salt of 5-(3-chlorophenylamino) benzo[c][2,6]naphthyridine-8-carboxylic acid (Form V)

The Form V polymorph of the sodium salt of compound I can be made by slurrying the amorphous Form I (10 mg) material in a 70:30 THF/water mixture (100 µL) and allowing the sample to temperature cycle over 2 days (40° C./RT, 4 hour periods at each temperature and checked periodically for crystalline material).

Figure 16:
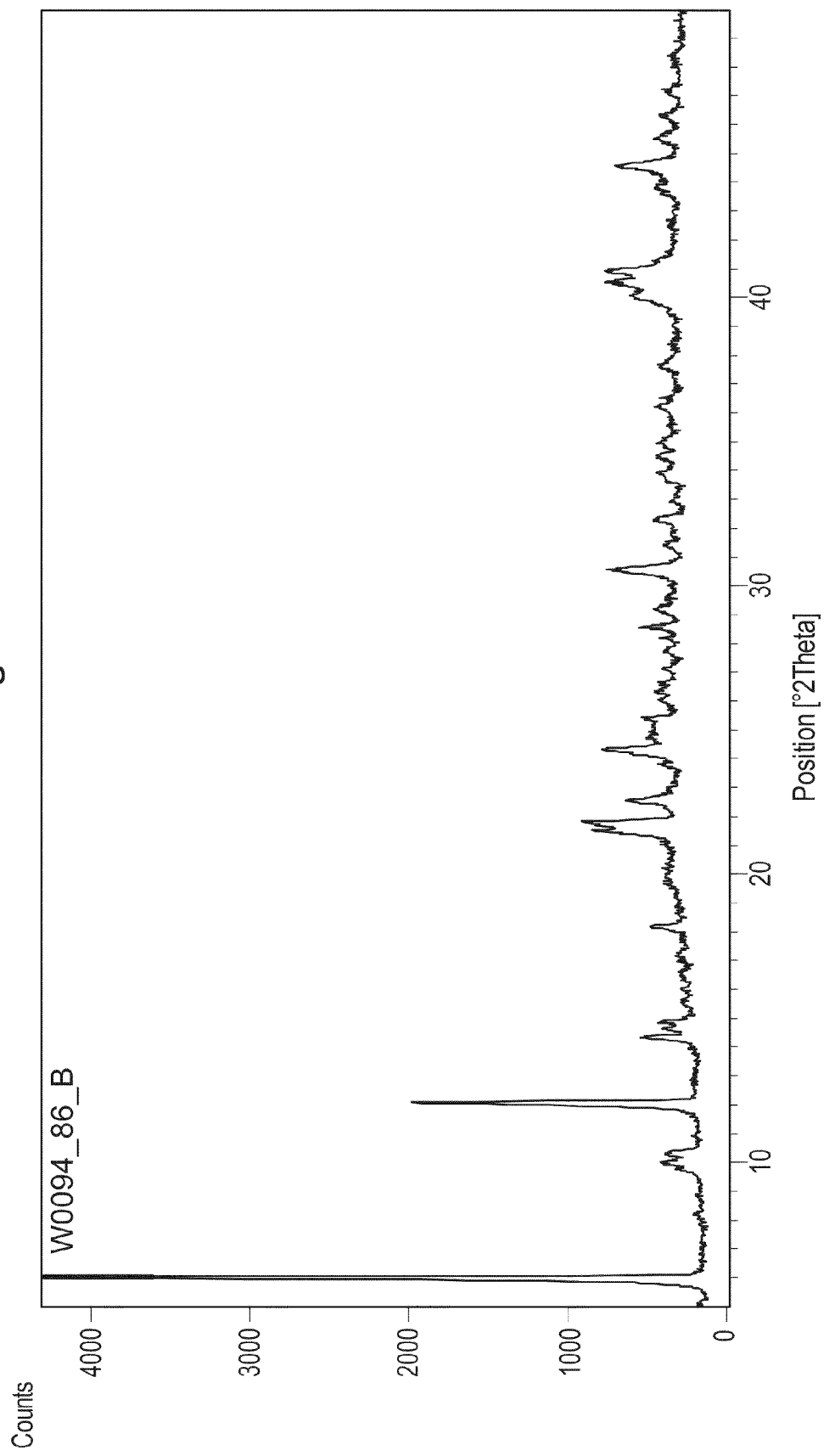
FIG. 16 depicts the powder x-ray diffraction pattern of polymorph Form V.

The XRPD pattern of Form V is shown in FIG. 16, indicating 2θ diffraction lines at e.g., about 6.1°, 9.9°, 10.6°, 11.1°, 12.3°, 14.4°, 15.3°, 18.5°, 19.7°, 20.1°, 21.8°, 22.4°, 24.2°, 24.9°, 26.8°, 28.2°, 31.3°, 33.0°, 36.5°, 40.6°, 41.1°, 42.6°, 44.5°, 45.8° and 47.7°, with major 2θ diffraction lines at e.g., about 12.3°, 21.8°, 22.4° and 31.3°.

Crystalline Sodium Salt of 5-(3-chlorophenylamino) benzo[c][2,6]naphthyridine-8-carboxylic acid (Form VI)

As previously described, the Form VI polymorph can be obtained by drying (e.g., at 50° C. or 80° C.) of Form IV. The XRPD pattern of Form VI (FIG. 17) indicates 2θ diffraction lines at e.g., about 6.8°, 9.5°, 10.3°, 11.4°, 14.6°, 16.1°, 16.9°, 17.3°, 18.1°, 18.7°, 20.7°, 22.2°, 23.4°, 24.6°, 26.0°, 28.5°, 31.7°, 32.4°, 33.4°, 37.7° and 39.5°, with major 2θ diffraction lines at e.g., about 11.4°, 20.7° and 26.0°.

Crystalline Sodium Salt of 5-(3-chlorophenylamino) benzo[c][2,6]naphthyridine-8-carboxylic acid (Form VII)

The Form VII polymorph of the sodium salt of compound I can be made by storage of amorphous Form I for three months at 40° C. in 75% RH.

Figure 18A:
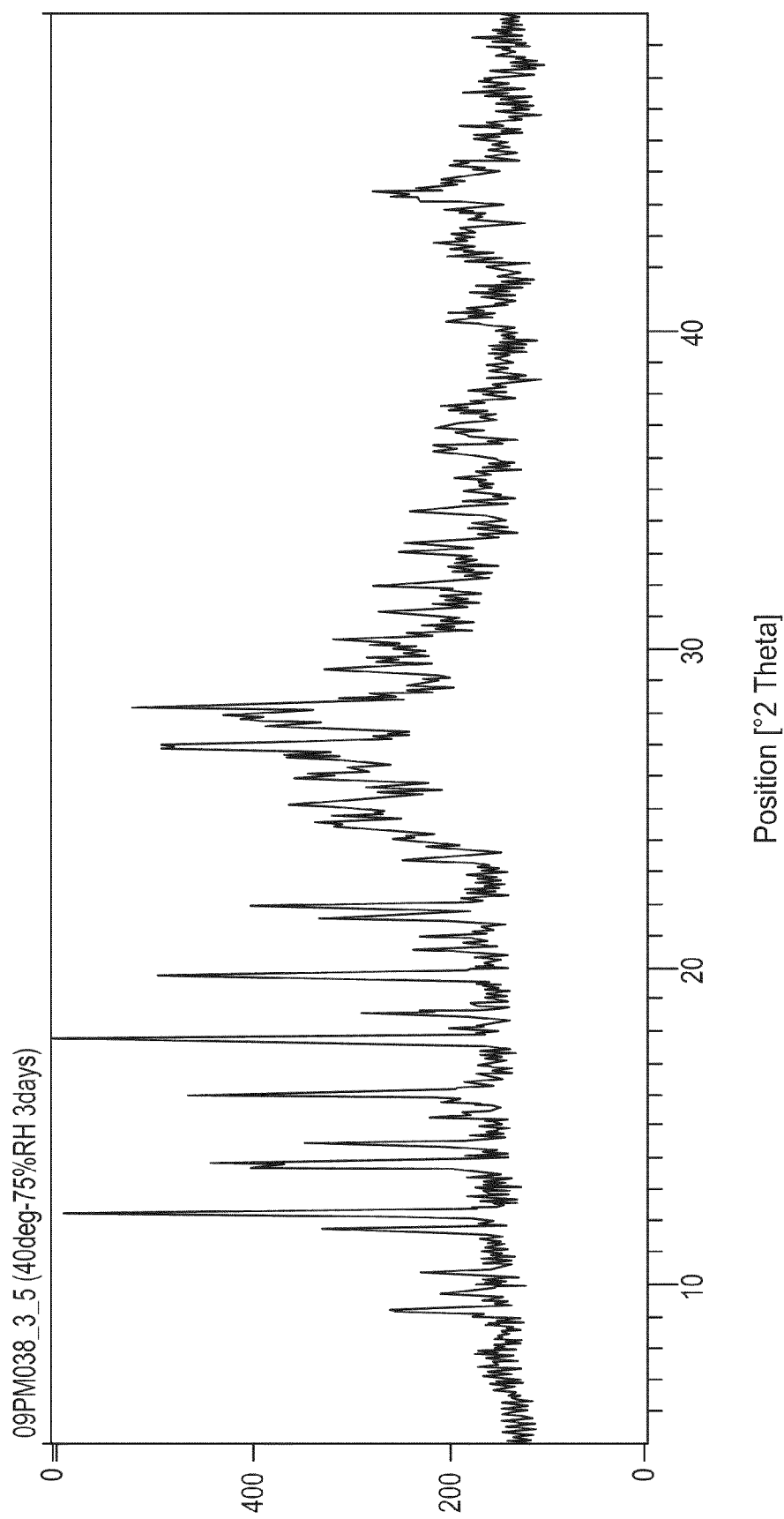
FIG. 18A depicts the powder x-ray diffraction pattern of polymorph Form VII.

The XRPD pattern of Form VII is shown in FIG. 18A, indicating 2θ diffraction lines at e.g., about 9.2°, 9.8°, 10.4°, 11.7°, 12.2°, 13.7°, 13.8°, 14.4°, 15.3°, 15.9°, 17.7°, 18.5°, 19.7°, 20.5°, 21.0°, 21.5°, 21.9°, 23.4°, 24.1°, 24.5°, 25.1°, 25.9°, 26.6°, 26.9°, 27.6°, 28.2°, 29.3°, 29.8°, 30.3°, 31.1°, 32.0°, 33.0°, 33.3°, 34.2°, 34.6°, 35.4°, 36.2°, 36.8°, 37.4°, 38.1°, 39.1°, 40.2°, 40.6°, 41.2°, 43.2°, 44.2°, 45.2°, 46.5° and 47.6°, with major 2θ diffraction lines at e.g., about 12.2°, 15.9° and 17.7°.

Figure 18B:
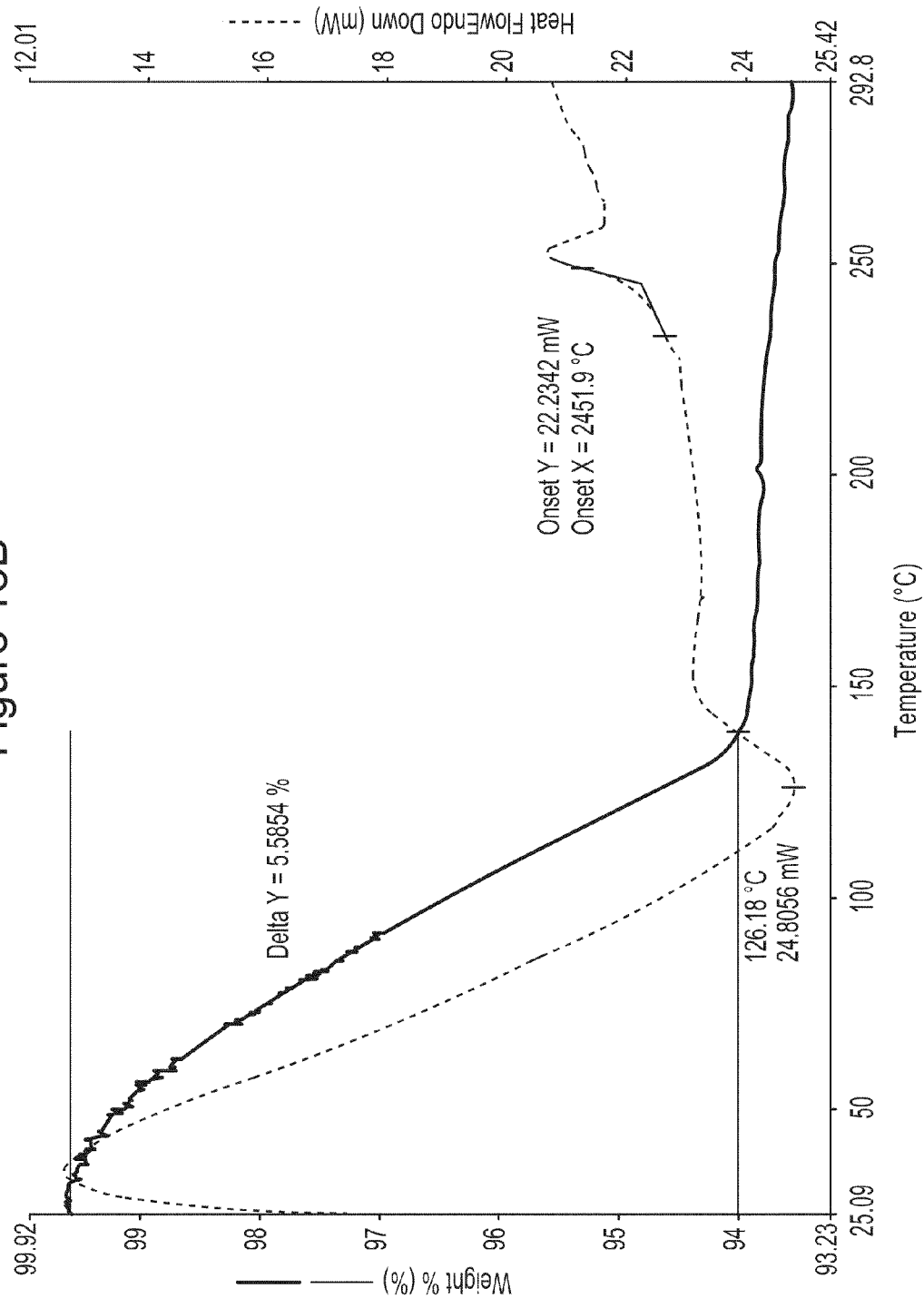
FIG. 18B depicts TGA data of polymorph Form VII. DTA (dashed line) was monitored for reference.
Figure 18C:
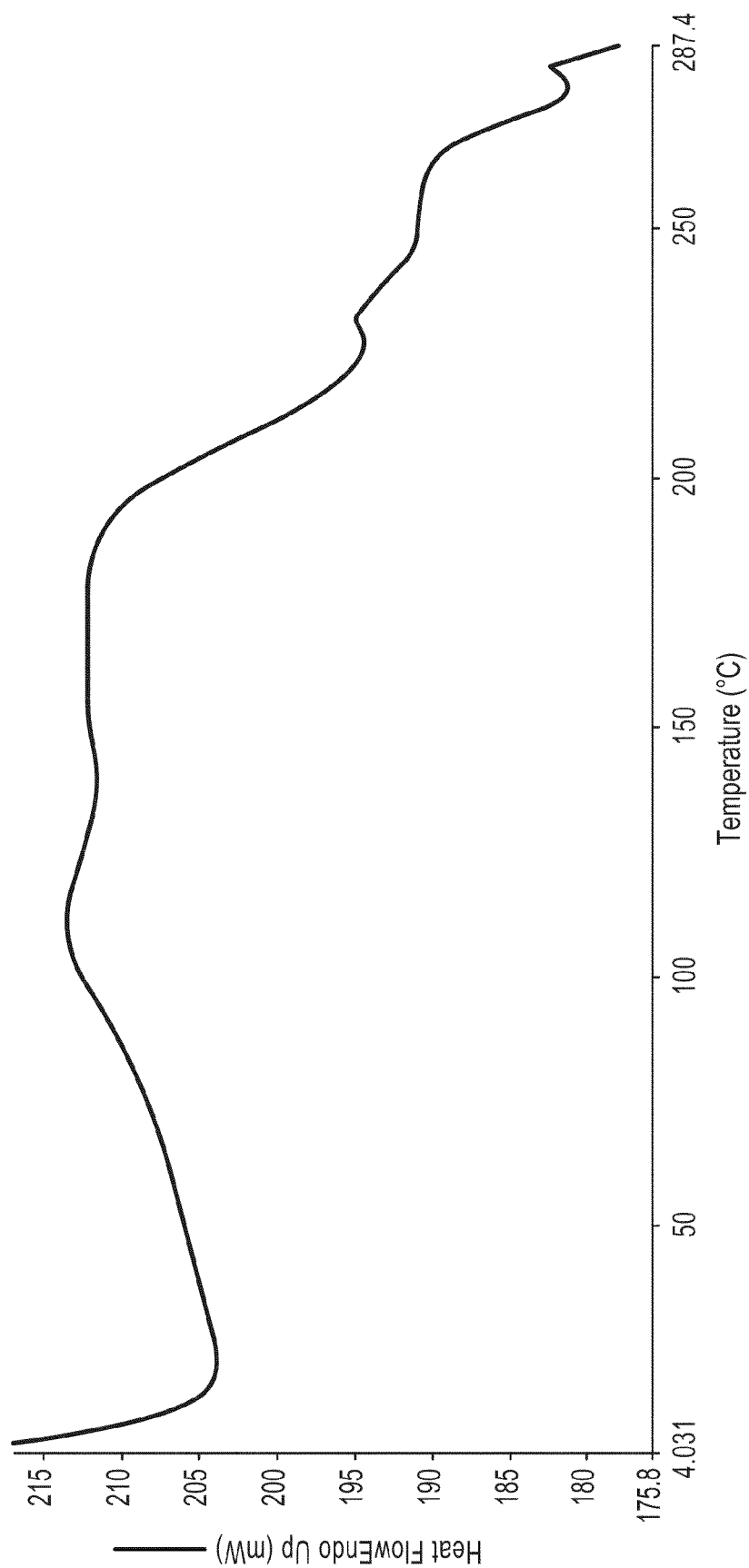
FIG. 18C depicts DSC data of polymorph Form VII.

Thermogravimetric Analysis (TGA) data for Form VII (see FIG. 18B) indicates an initial weight loss of about 5.6% (~30° C. through about 126° C.) which suggests a possible monohydrate. No additional TGA events were observed even through about 300° C., indicating a potential high temperature form and/or possible melting and cooling without degradation. Differential Scanning Calorimetry (DSC) data for Form VII is shown in FIG. 18C. Stability studies of Form VII indicate the polymorph is stable under ambient conditions and at 40° C./75% relative humidity after seven days (as shown by XRPD).

Crystalline Sodium Salt of 5-(3-chlorophenylamino) benzo[c][2,6]naphthyridine-8-carboxylic acid (Form VIII)

The Form VIII polymorph of the sodium salt of compound I can be made from Form II or Form VII by melting, followed by slowly cooling.

Figure 19:
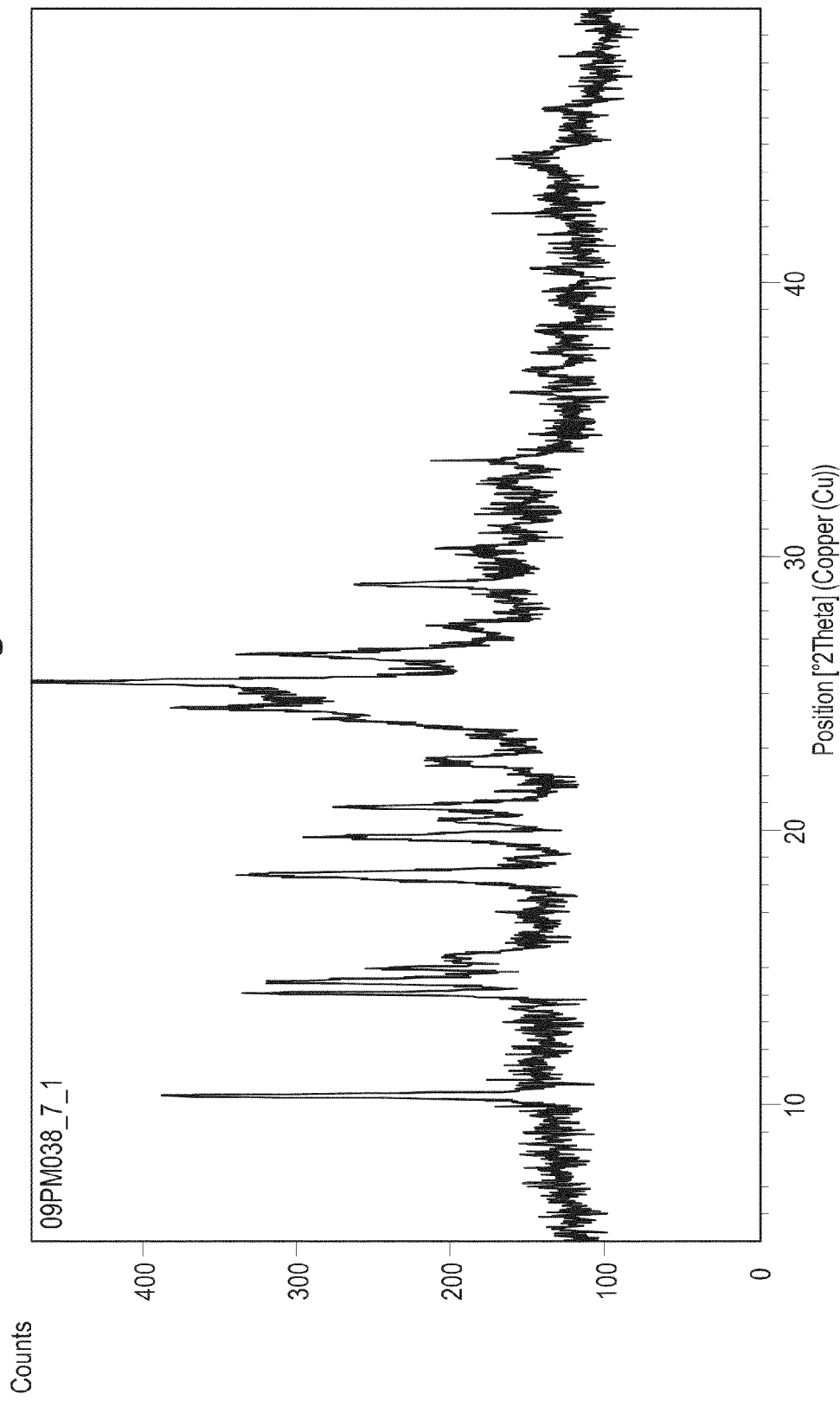
FIG. 19 depicts the powder x-ray diffraction pattern of polymorph Form VII.

The XRPD pattern of Form VIII is shown in FIG. 19, indicating 2θ diffraction lines at e.g., about 10.2°, 14.0°, 14.4°, 15.0°, 18.4°, 19.7°, 20.4°, 20.8°, 22.6°, 24.4°, 24.9°, 25.4°, 26.3°, 27.4°, 29.0°, 30.3°, 31.6°, 32.5°, 33.5°, 36.0°, 36.7°, 38.2°, 42.5°, 43.1°, 44.6° and 46.4°, with major 2θ diffraction lines at e.g., about 10.2°, 18.4°, 24.4° and 25.4°.

Crystalline Sodium Salt of 5-(3-chlorophenylamino) benzo[c][2,6]naphthyridine-8-carboxylic acid (Form IX)

The Form IX polymorph of the sodium salt of compound I can be made by slurrying the amorphous Form I material in 100% $H_2O$ and allowing the sample to temperature cycle over 2 days as described herein (10 mg in 100 µL solvent, temperature cycled between 25° C. and 50° C. for 4 hour periods over 16 hours (50° C./RT, 4 hour periods at each temperature), then drying of the resulting solids under gentle conditions.

Figure 21:
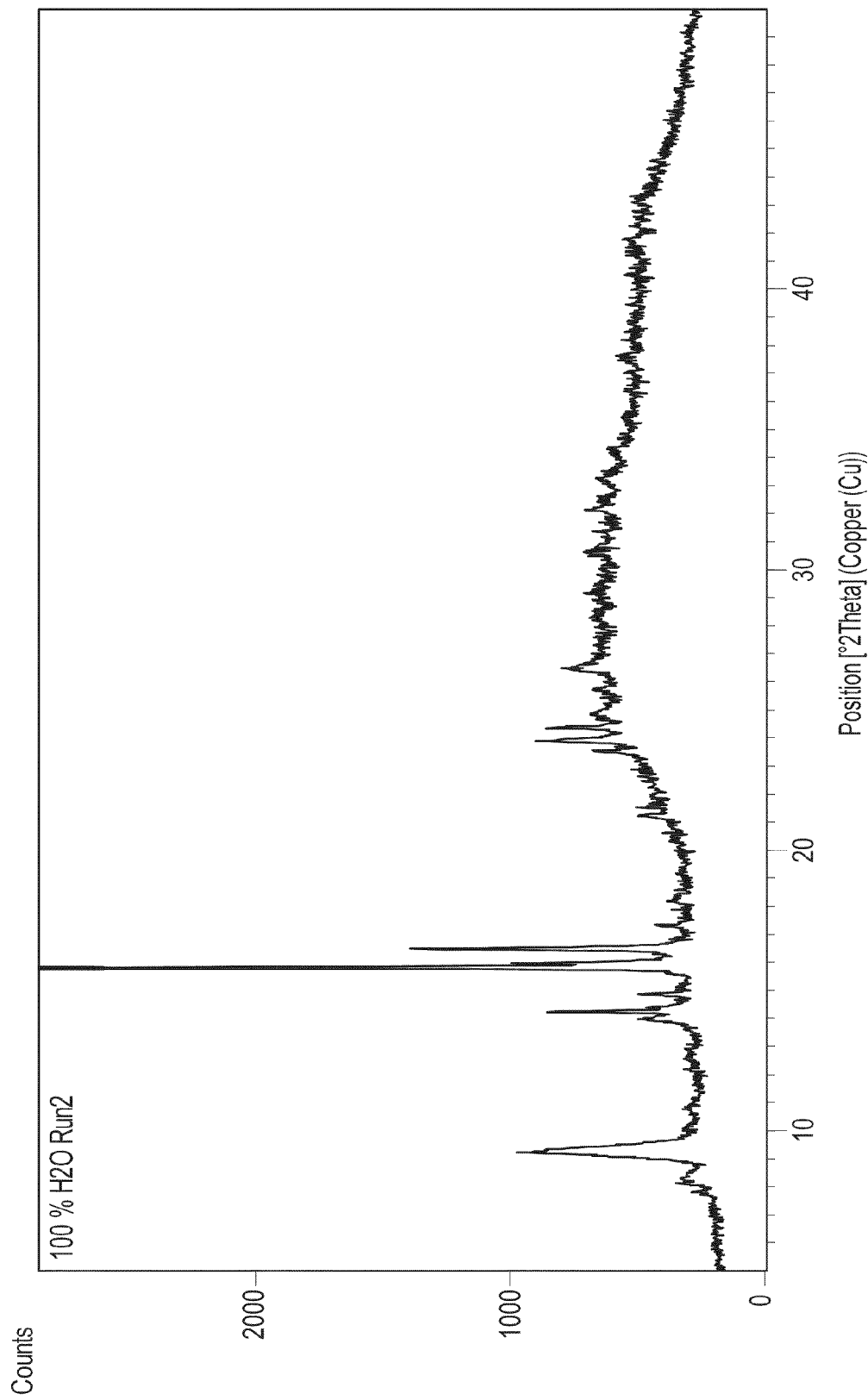
FIG. 21 depicts the powder x-ray diffraction pattern of Form IX.

The XRPD pattern of Form IX is shown in FIG. 21, indicating 2θ diffraction lines at e.g., about 7.8°, 8.3°, 9.2°, 10.1°, 10.8°, 14.0°, 14.2°, 14.9°, 15.8°, 16.0°, 16.5°, 17.3°, 18.2°, 21.2°, 23.9°, 24.4°, 24.9°, 25.7°, 26.5°, 32.1° and 33.2°, with major 2θ diffraction lines at e.g., about 15.8° and 16.5°.

Crystalline Sodium Salt of 5-(3-chlorophenylamino) benzo[c][2,6]naphthyridine-8-carboxylic acid (Form X)

The Form X polymorph of the sodium salt of compound I can be made by slurrying the amorphous Form I material in EtOH:$H_2O$ and i-PrOH:$H_2O$ (70:30), allowing the sample to temperature cycle over 2 days as described herein (e.g., 10 mg in 100 µL solvent, 50° C./RT, 4 hour periods at each temperature).

Figure 22:
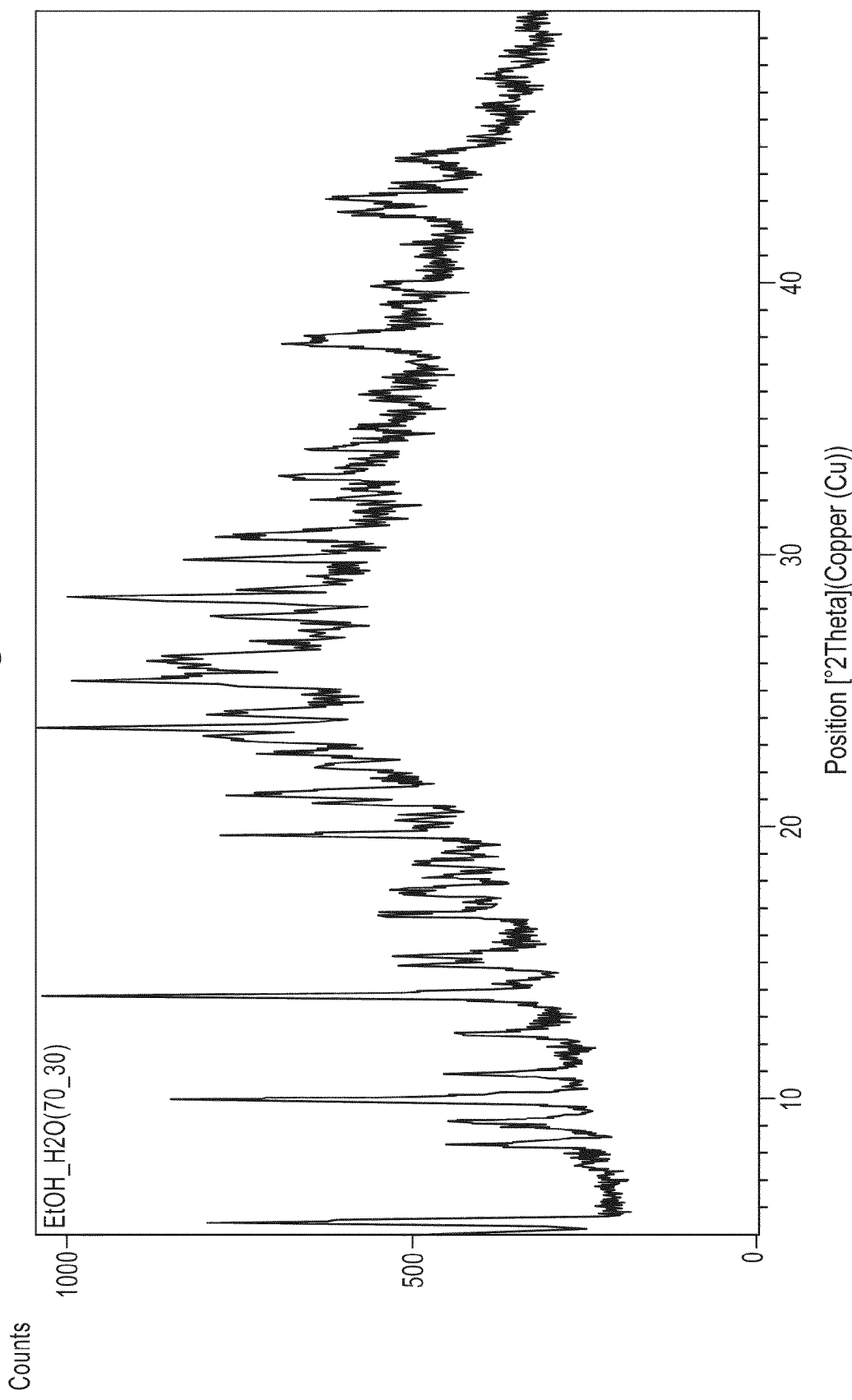
FIG. 22 depicts the powder x-ray diffraction pattern of Form X.

The XRPD pattern of Form X is shown in FIG. 22, indicating 2θ diffraction lines at e.g., about 5.2°, 5.5°, 8.3°, 9.2°, 10.0°, 10.9°, 12.4°, 13.8°, 14.9°, 15.3°, 16.8°, 17.6°, 18.2°, 18.6°, 19.7°, 20.9°, 21.2°, 22.2°, 22.7°, 23.2°, 23.6°, 24.1°, 25.3° 26.1°, 27.2°, 27.7°, 28.4°, 29.8°, 30.7°, 32.1°, 32.9°, 33.9°, 35.9°, 37.8°, 39.9°, 41.2°, 42.6°, 43.1°, 44.6° and 46.6°, with major 2θ diffraction lines at e.g., about 23.6°, 25.3° and 28.4°.

Crystalline Sodium Salt of 5-(3-chlorophenylamino) benzo[c][2,6]naphthyridine-8-carboxylic acid (Form XI)

The Form XI polymorph of the sodium salt of compound I can be made by slurrying the amorphous Form I material in i-PrOH:$H_2O$ (50:50 or 60:40), allowing the sample to temperature cycle over 2 days as described herein. (e.g., 10 mg in 100 µL solvent, 50° C./RT, 4 hour periods at each temperature).

Figure 23:
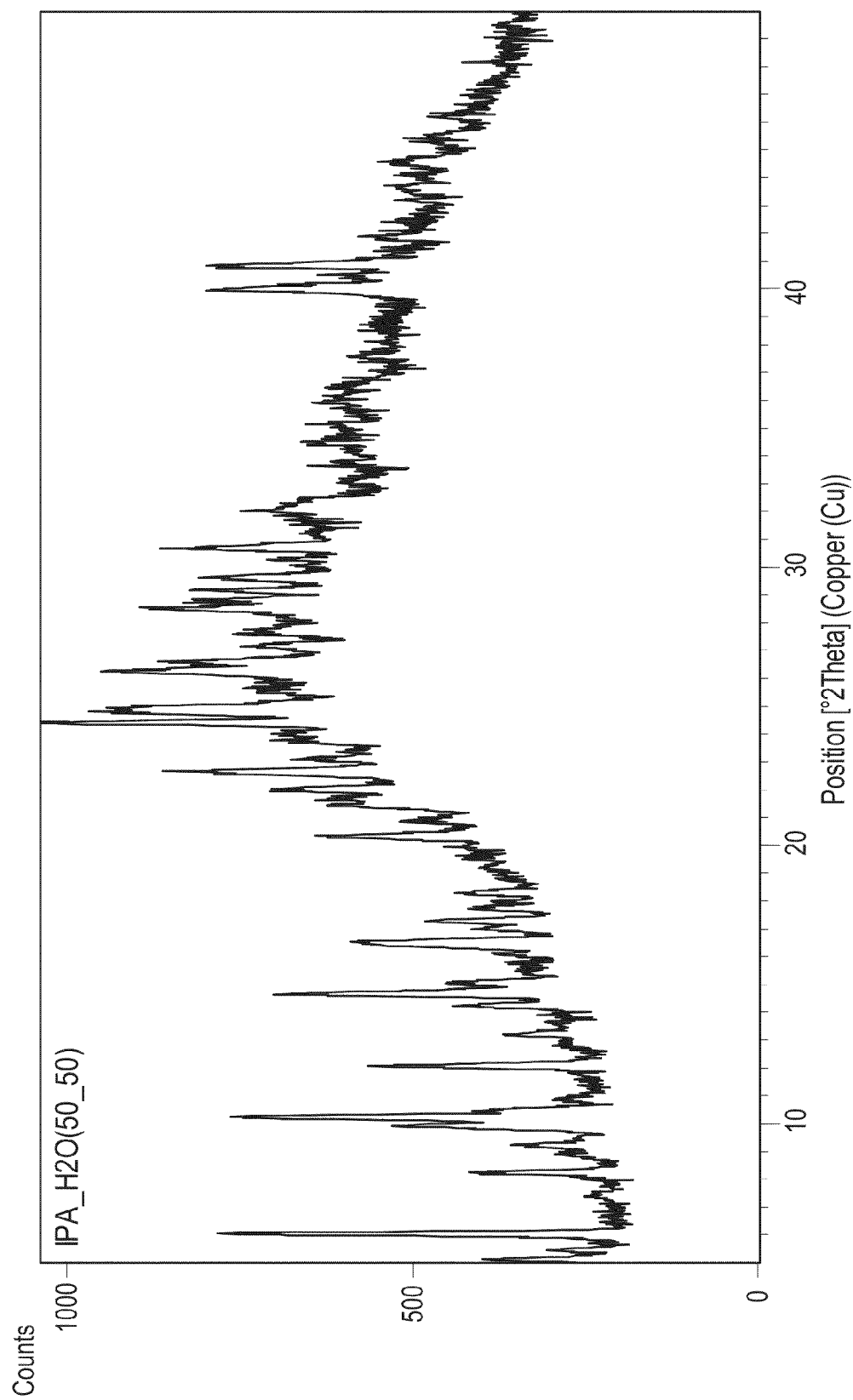
FIG. 23 depicts the powder x-ray diffraction pattern of Form XI.

The XRPD pattern of Form XI is shown in FIG. 23, indicating 2θ diffraction lines at e.g., about 5.1°, 5.5°, 6.0°, 8.2°, 9.2°, 9.9°, 10.2°, 12.1°, 13.2°, 14.2°, 14.7°, 15.0°, 16.5°, 17.3°, 17.7°, 18.3°, 20.3°, 21.5°, 22.0°, 22.6°, 24.4°, 24.9°, 26.4°, 27.2°, 27.7°, 28.5°, 28.8°, 29.2°, 29.6°, 30.7°, 32.1°, 34.5°, 36.0°, 40.0°, 40.8°, 41.9° and 45.5°, with major 2θ diffraction lines at e.g., about 24.4°, 24.9° and 26.4°.

Crystalline Sodium Salt of 5-(3-chlorophenylamino) benzo[c][2,6]naphthyridine-8-carboxylic acid (Form XII)

The Form XII polymorph of the sodium salt of compound I can be made by slurrying the amorphous Form I material in Acetone:H$_2$O, allowing the sample to temperature cycle over 2 days as described herein (e.g., 10 mg in 100 µL solvent, 50° C./RT, 4 hour periods at each temperature).

Figure 24:
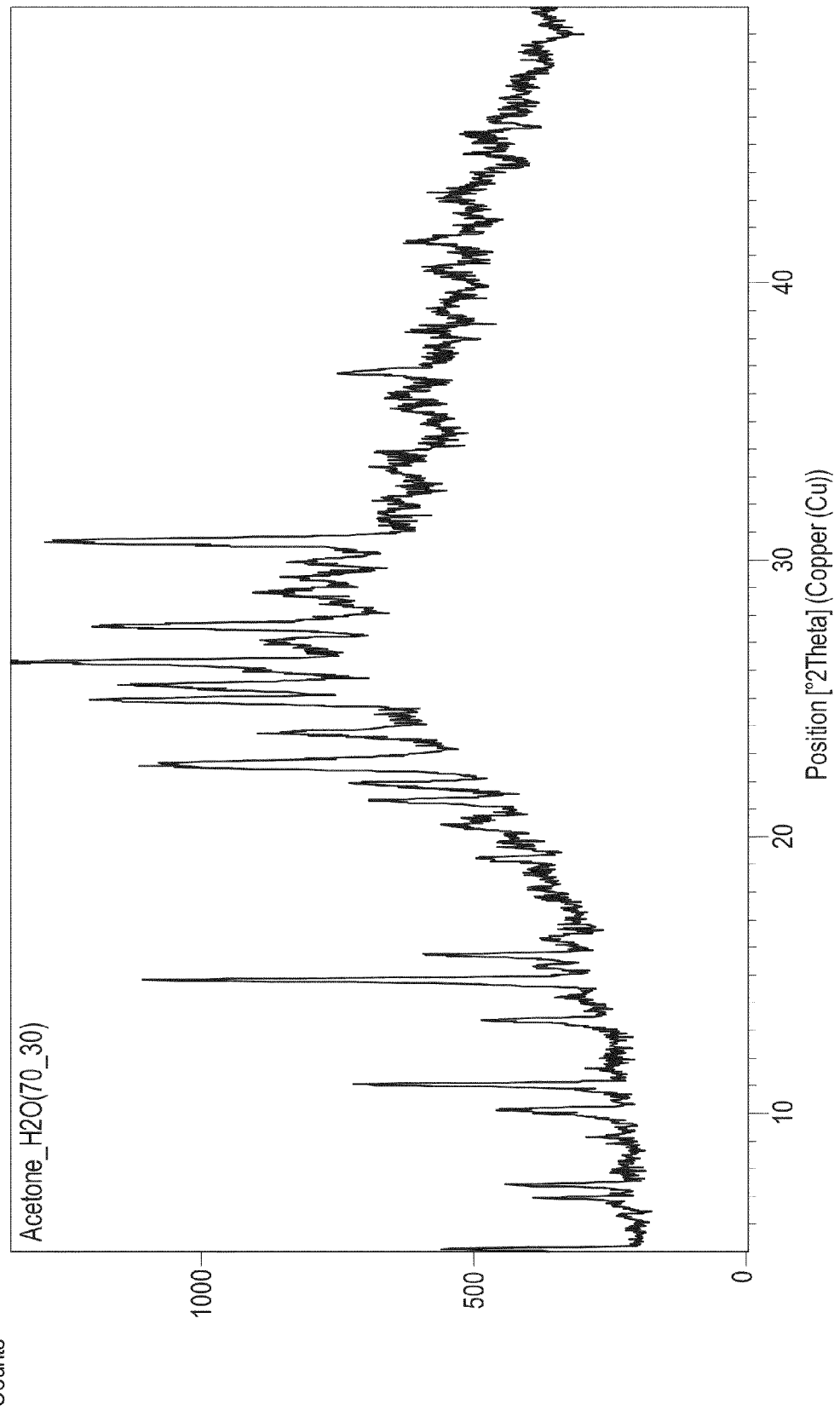
FIG. 24 depicts the powder x-ray diffraction pattern of Form XII.

The XRPD pattern of Form XII is shown in FIG. 24, indicating 2θ diffraction lines at e.g., about 5.1°, 6.3°, 6.9°, 7.4°, 10.1°, 11.0°, 13.4°, 14.8°, 15.3°, 15.7°, 16.3°, 19.2°, 20.5°, 21.3°, 21.9°, 22.6°, 23.8°, 24.9°, 25.5°, 26.3°, 27.1°, 27.6°, 28.8°, 29.3°, 29.9°, 30.7°, 32.2°, 33.3°, 36.8°, 38.3°, 40.5°, 41.5°, 43.3° and 48.5°, with major 2θ diffraction lines at e.g., about 26.3°, 27.6° and 30.7°.

Crystalline L-Lysine Salt of 5-(3-chlorophenylamino)benzo[c][2,6]naphthyridine-8-carboxylic acid (Form XIII)

The Form XIII polymorph (L-lysine salt) of compound I can be made by following the general methods described below in the Experimental section. Briefly, amorphous Form I (10 mg) material is slurried in 50-200 mL solvent (e.g., EtOH, iPrOH, 2BuOH, DMF, or iPrOH:H$_2$O), followed by the addition of 1 equivalent of base solution (1.0M in water) and treated as described.

Figure 26:
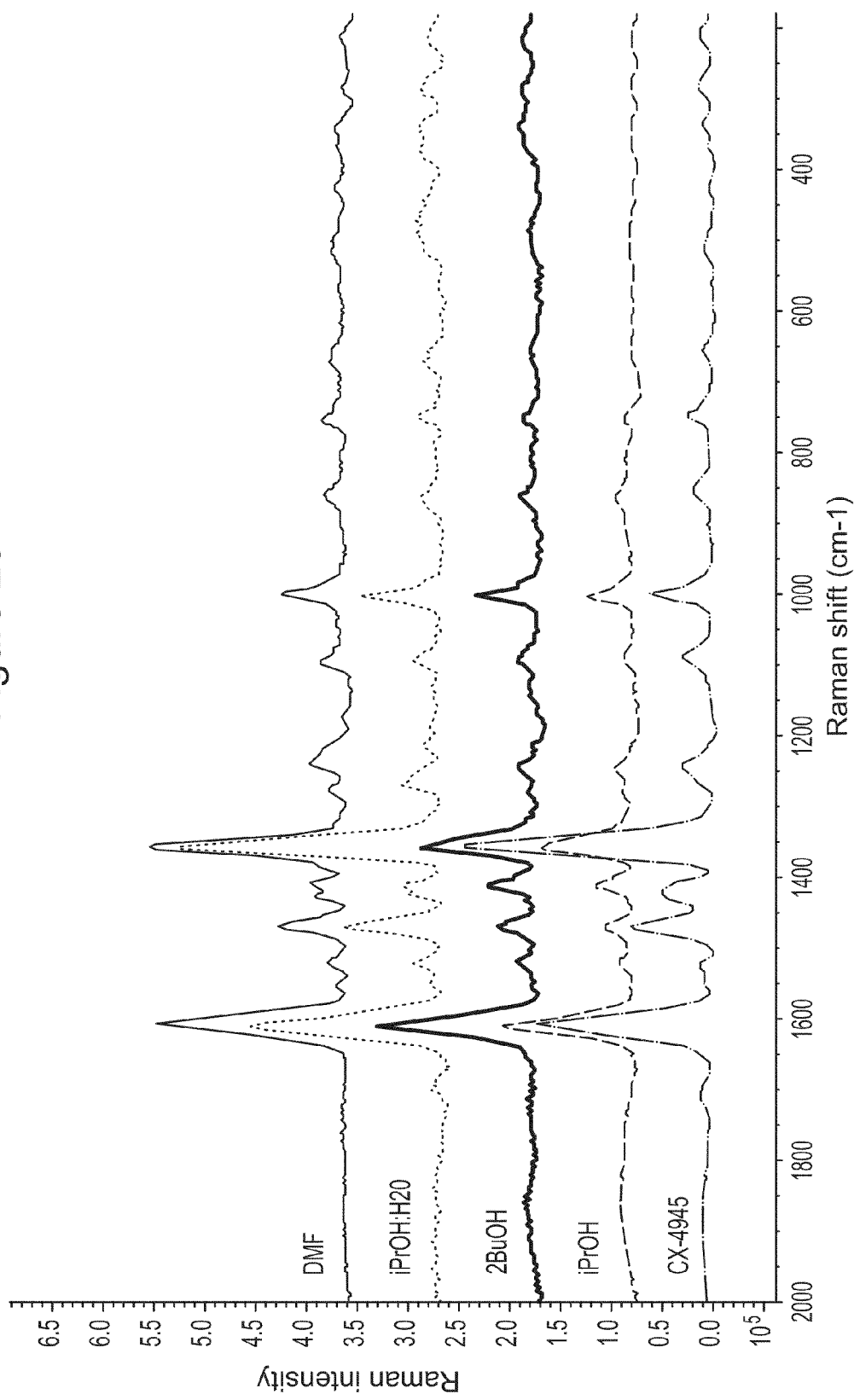
FIG. 26 depicts Raman spectra for the L-Lysine salt polymorph from the indicated solvents.
Figure 27:
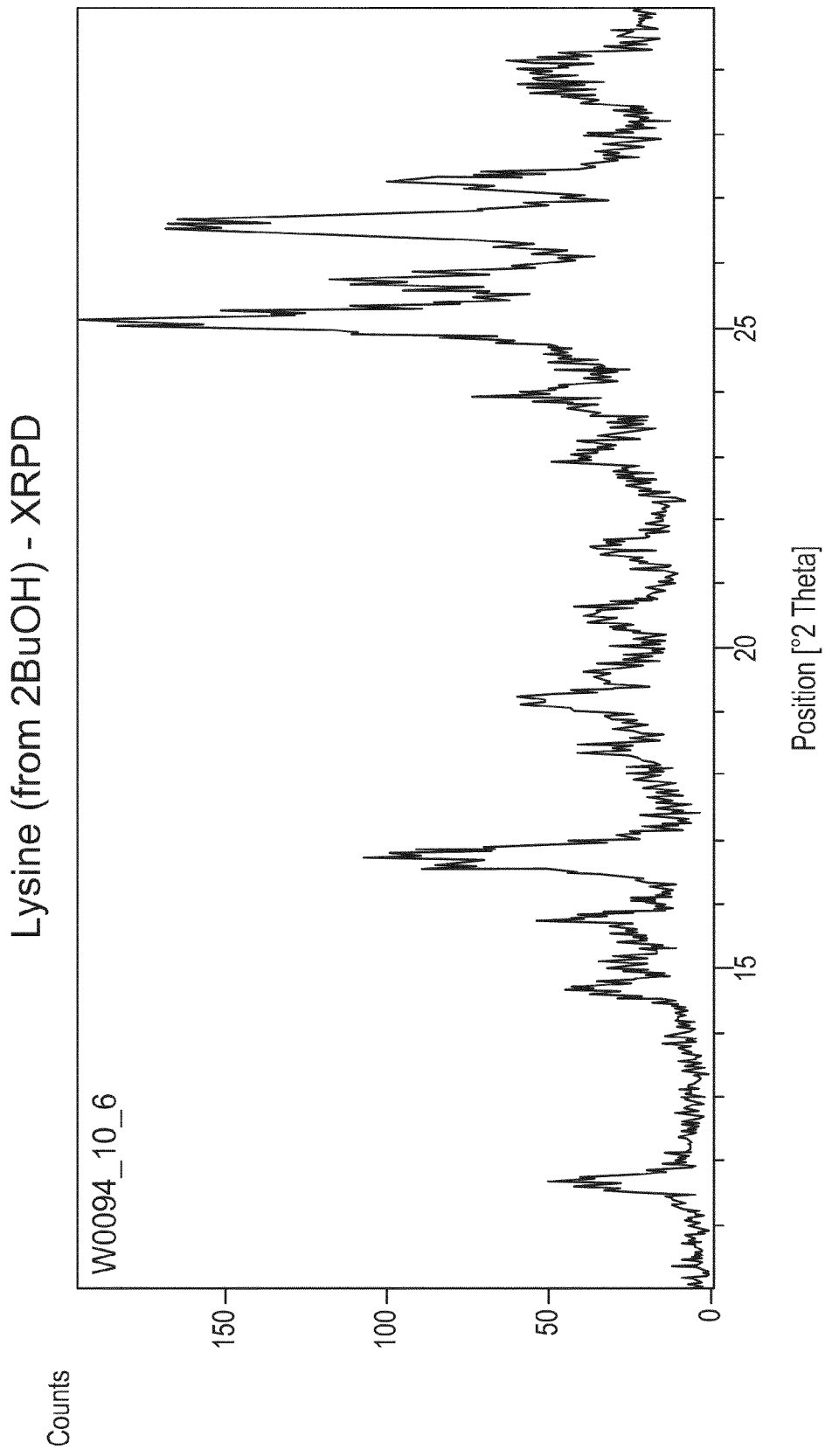
FIG. 27 depicts the powder x-ray diffraction pattern of L-Lysine salt polymorph.

The Polarized light microscopy (PLM) of FIG. 25 indicates crystalline needles of the Form XIII polymorph from iPrOH, 2-BuOH, iPrOH:H$_2$O, and DMF. The Raman spectra for the Form XIII polymorph from various solvents is shown in FIG. 26 indicating peak assignments at e.g., about 1610.07, 1519.46, 1470.53, 1412.24, 1356.85, 1242.30, 1092.55, 1001.86, 860.95, 748.98 and 335.65 cm$^{-1}$. The XRPD pattern of Form XIII polymorph from 2-BuOH (FIG. 27) indicates 2θ diffraction lines at e.g., about 11.7°, 14.7°, 15.1°, 15.7°, 16.7°, 18.5°, 19.2°, 19.6°, 20.5°, 21.5°, 23.0°, 23.9°, 25.1°, 25.7°, 26.6°, 27.3°, 28.7° and 29.0°, with major 2θ diffraction lines at e.g., about 16.7°, 25.1° and 26.6°.

Crystalline Zinc Salt of 5-(3-chlorophenylamino)benzo[c][2,6]naphthyridine-8-carboxylic acid (Form XIV)

The Form XIV polymorph (zinc salt) of compound I can be made by following the general methods described below in the Experimental section. Multiple polymorphic forms may be generated dependent on solvent choice, as indicated below based on XRPD and Raman spectra analysis.

Figure 29A:
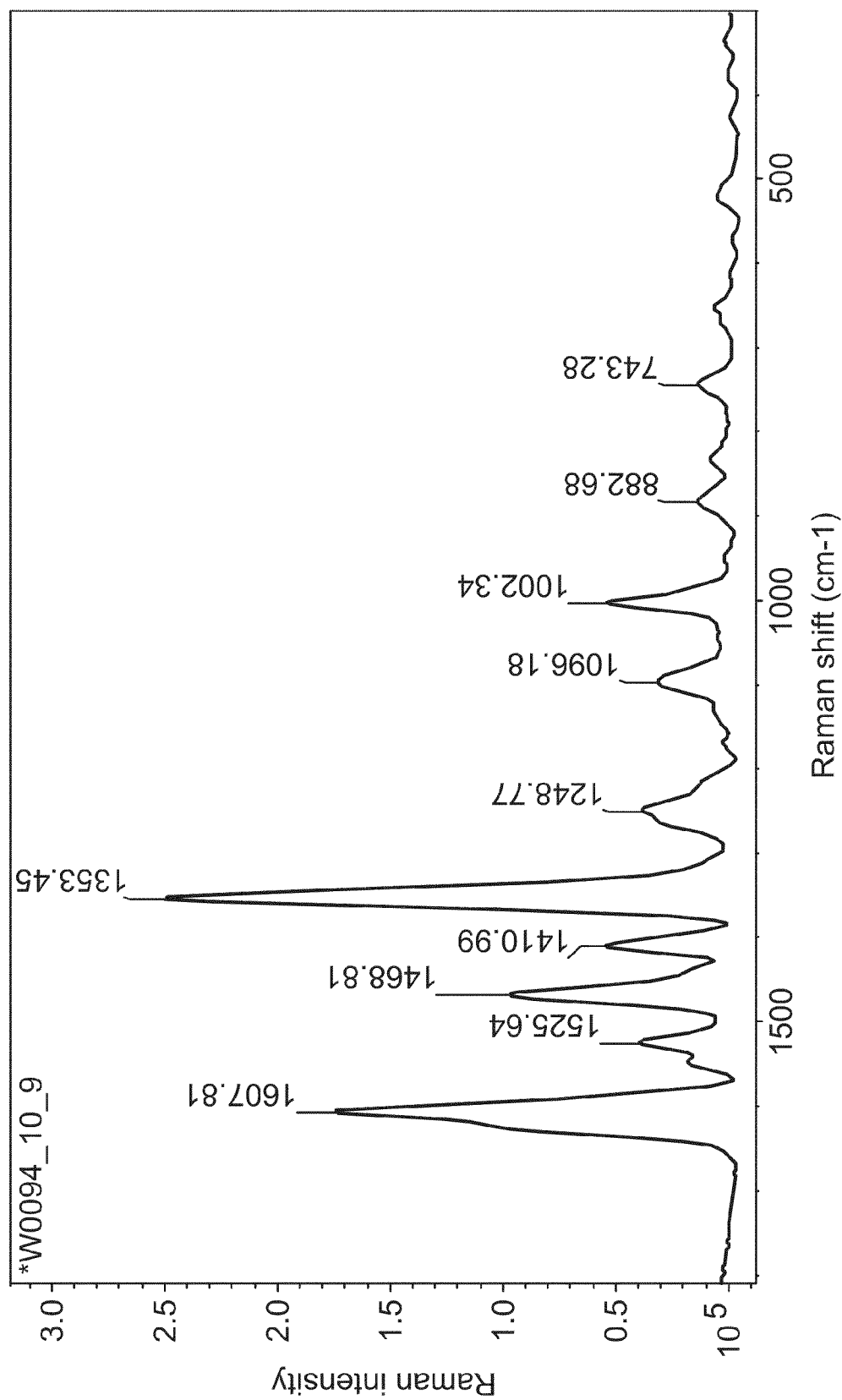
FIG. 29A depicts Raman spectra for the zinc salt polymorph from the EtOH (Form XIV-A).
Figure 29B:
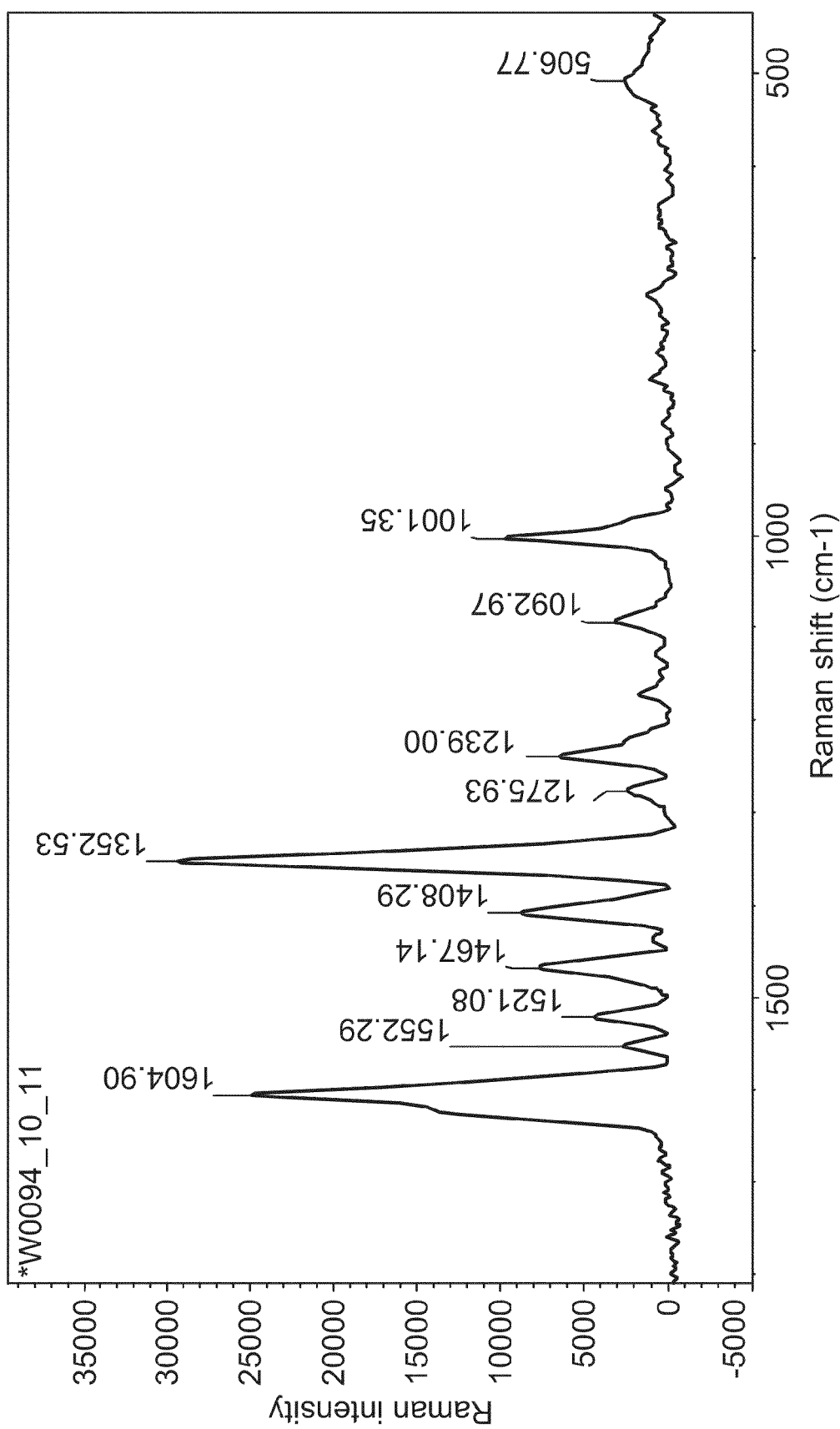
FIG. 29B depicts Raman spectra for the zinc salt polymorph from the 2-BuOH (Form XIV-B).
Figure 30:
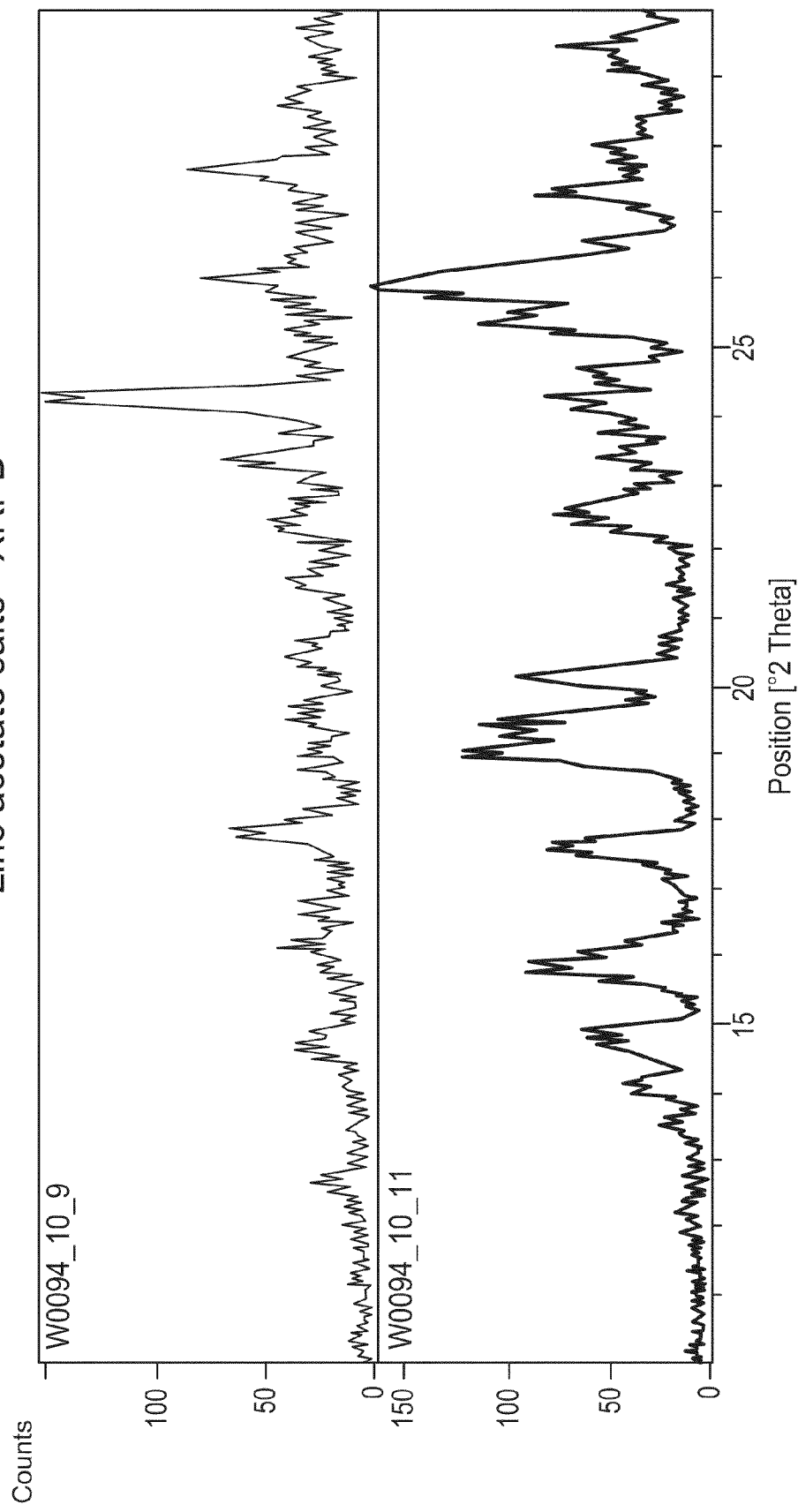
FIG. 30 depicts the powder x-ray diffraction patterns of two zinc salt polymorphs (top: Form XIV-A; bottom: Form XIV-B).

The Polarized light microscopy (PLM) shown in FIG. 28 indicates crystalline needles of the Form XIV polymorph from EtOH, iPrOH, 2-BuOH, and iPrOH:H$_2$O. The Raman spectra for the Form XIV polymorph from EtOH (Form XIV-A) is shown in FIG. 29A indicating peak assignments at e.g., about 1607.81, 1525.64, 1468.81, 1410.99, 1353.45, 1248.77, 1096.18, 1002.34, 882.68 and 743.28 cm$^{-1}$. The XRPD pattern of Form XIV-A polymorph (FIG. 30; top) indicates 2θ diffraction lines at e.g., about 10.4°, 12.7°, 14.7°, 15.8°, 16.1°, 16.8°, 17.8°, 18.8°, 19.0°, 19.6°, 20.5°, 21.6°, 22.4°, 23.3°, 24.3°, 26.0°, 27.6° and 28.7°, with major 2θ diffraction lines at e.g., about 24.3°, 26.0° and 27.6°. The Raman spectra for the Form XIV polymorph from 2-BuOH (Form XIV-B) is shown in FIG. 29B indicating peak assignments at e.g., about 1604.90, 1552.29, 1521.08, 1467.14, 1408.29, 1352.53, 1275.93, 1239.00, 1092.97, 1001.35 and 506.77 cm$^{-1}$. The XRPD pattern of Form XIV-B polymorph (FIG. 30; bottom) indicates 2θ diffraction lines at e.g., about 12.3°, 13.5°, 14.1°, 14.8°, 15.8°, 17.6°, 19.0°, 19.5°, 20.2°, 22.6°, 23.4°, 24.2°, 24.6°, 25.4°, 25.9°, 27.3°, 28.0° and 29.5°, with major 2θ diffraction lines at e.g., about 19.0°, 19.5° and 25.9°.

A third polymorphic form (Form XIV-C) contains a Raman spectra indicating peak assignments at e.g., about 1859.83, 1607.09, 1522.59, 1469.53, 1438.29, 1413.54, 1353.62, 1244.69, 1089.86, 1000.50, 746.44 cm$^{-1}$. The XRPD pattern of Form XIV-C indicates 2θ diffraction lines at e.g., about 11.4°, 15.9°, 16.9°, 18.2°, 19.4°, 20.9°, 22.0°, 22.6°, 24.6°, 25.5°, 26.7°, 27.6°, 29.0°.

Crystalline N-methylglucamine Salt of 5-(3-chlorophenylamino)benzo[c][2,6]naphthyridine-8-carboxylic acid (Form XV)

The Form XV polymorph (N-methylglucamine salt) of compound I can be made by following the general methods described below in the Experimental section.

Figure 32:
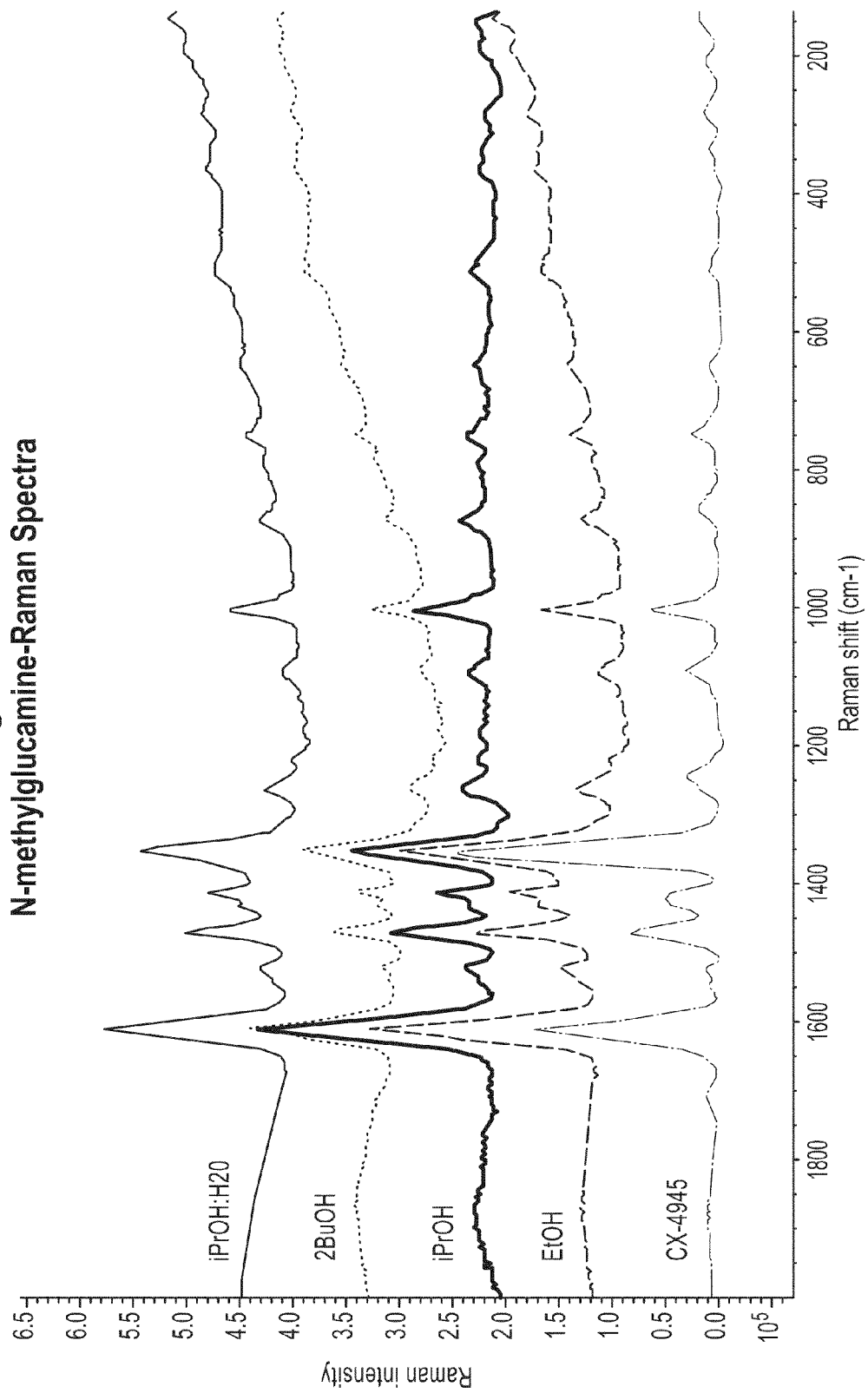
FIG. 32 depicts Raman spectra for the N-methylglucamine salt polymorph from the indicated solvents.
Figure 33:
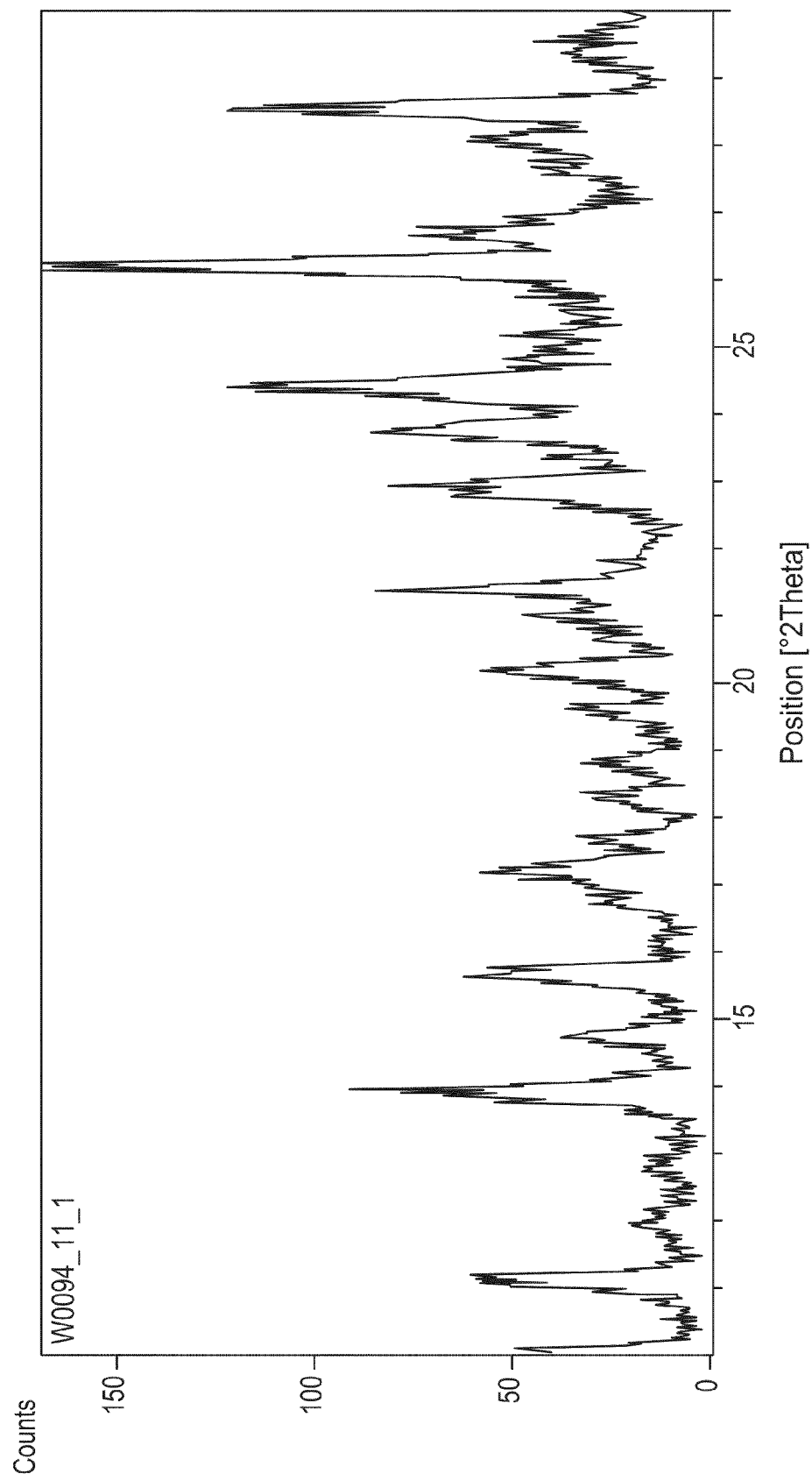
FIG. 33 depicts the powder x-ray diffraction pattern of the N-methylglucamine salt polymorph.

The Polarized light microscopy (PLM) shown in FIG. 31 indicates crystalline solid as possible plates and/or needles of the Form XV polymorph from EtOH, iPrOH, 2-BuOH, and iPrOH:H$_2$O. The Raman spectra for the Form XV polymorph from various solvents is shown in FIG. 32 indicating peak assignments at e.g., about 1607.12, 1521.08, 1469.40, 1411.25, 1350.43, 1261.73, 1091.38, 999.11, 869.09, 746.56, 646.59 and 510.73 cm$^{-1}$. The XRPD pattern of Form XV polymorph (FIG. 33) indicates 2θ diffraction lines at e.g., about 11.1°, 12.0°, 12.8°, 13.9°, 14.7°, 15.7°, 16.7°, 17.2°, 17.7°, 18.3°, 18.8°, 19.6°, 20.2°, 21.0°, 21.4°, 22.9°, 23.8°, 24.4°, 25.2°, 26.2°, 26.7°, 27.7°, 28.0°, 28.5° and 29.4°, with major 2θ diffraction lines at e.g., about 24.4°, 26.7° and 28.5°.

Crystalline Ammonium Salt of 5-(3-chlorophenylamino)benzo[c][2,6]naphthyridine-8-carboxylic acid (Form XVI)

Figure 35:
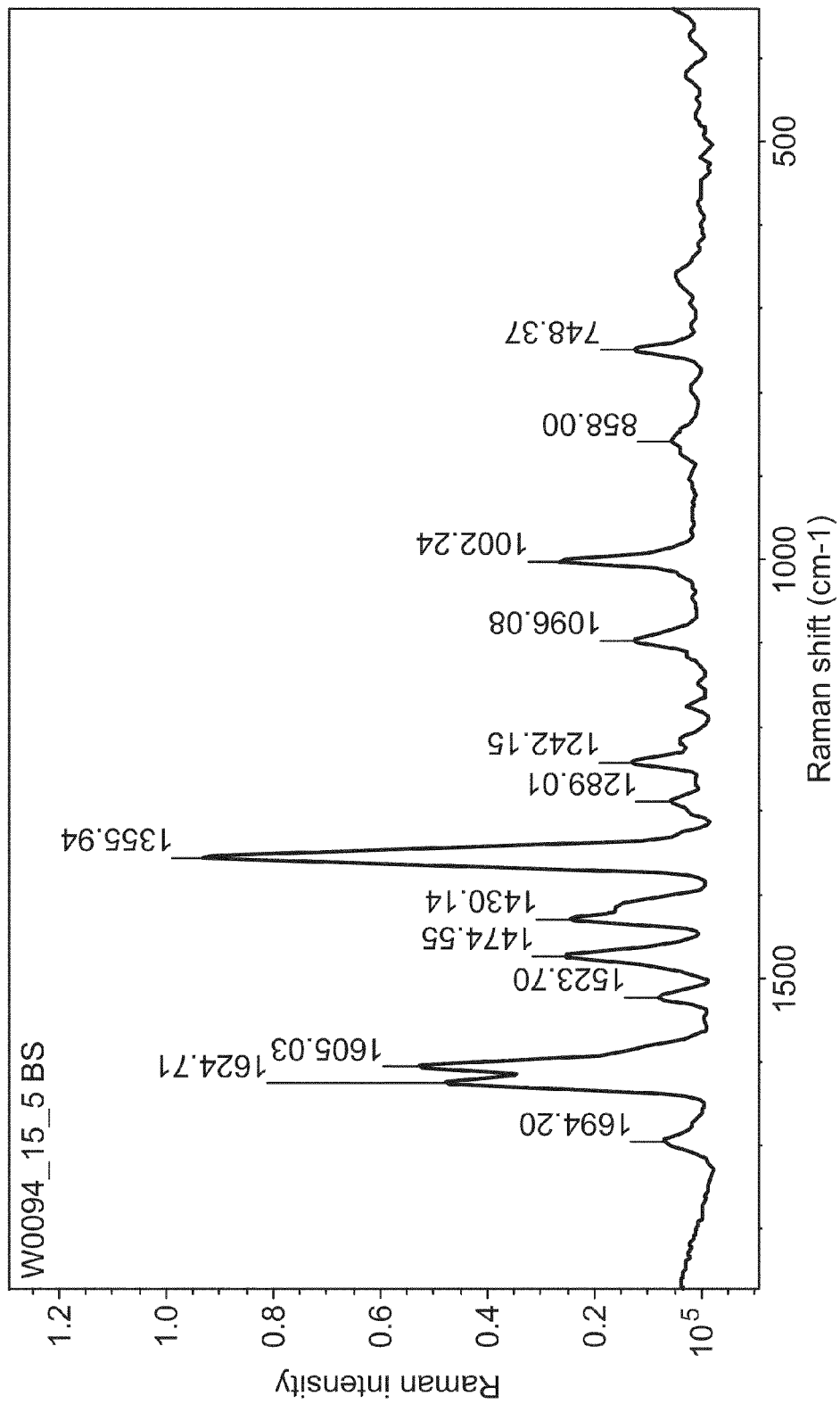
FIG. 35 depicts a Raman spectrum for the ammonium salt polymorph.

The Form XII polymorph (ammonium salt) of compound I can be made by following the general methods described below in the Experimental section. The Polarized light microscopy (PLM) shown in FIG. 34 indicates crystalline needles of the Form XVI polymorph from EtOH, iPrOH, 2-BuOH, iPrOH:H$_2$O, and DMF. The Raman spectra for the Form XVI polymorph is shown in FIG. 35 indicating peak assignments at e.g., about 1694.20, 1624.71, 1605.03, 1523.70, 1474.55, 1430.14, 1355.94, 1289.01, 1242.15, 1096.08, 1002.24, 858.00 and 748.37 cm$^{-1}$.

Crystalline Choline Salt of 5-(3-chlorophenylamino)benzo[c][2,6]naphthyridine-8-carboxylic acid (Form XVII)

The Form XVII polymorph (choline salt) of compound I can be made by following the general methods described below in the Experimental section.

Figure 37:
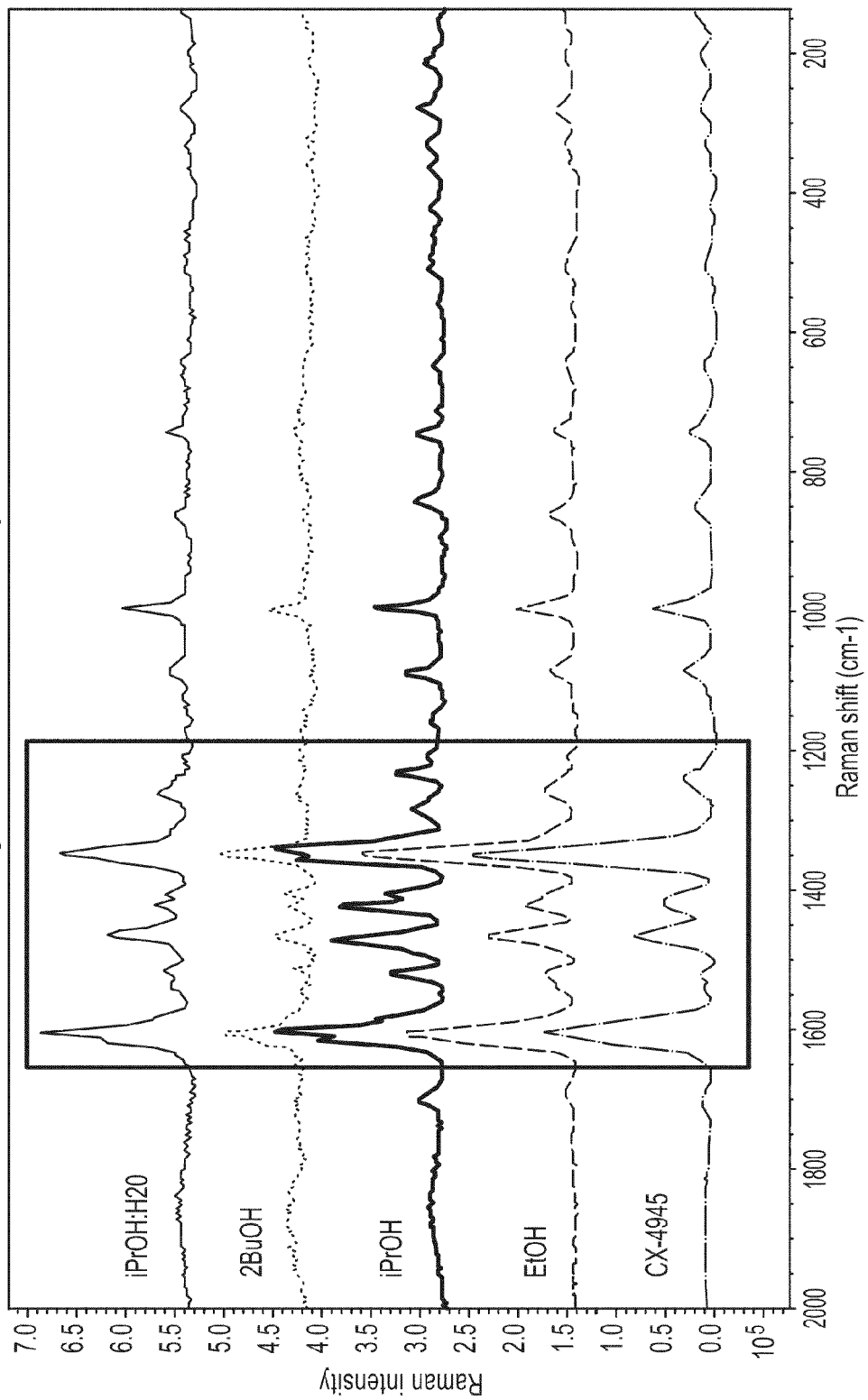
FIG. 37 depicts Raman spectra for the choline salt polymorph from the indicated solvents.

The Polarized light microscopy (PLM) shown in FIG. 36 indicates crystalline needles of the Form XVII polymorph from EtOH, iPrOH, 2-BuOH, and iPrOH:H$_2$O. The Raman spectra for the Form XVII polymorph from various solvents is shown in FIG. 37 indicating peak assignments at e.g., about 1702.28, 1617.60, 1603.99, 1523.05, 1474.05, 1427.05, 1406.77, 1357.53, 1344.03, 1286.98, 1235.41, 1092.50, 997.61, 845.88 and 749.61 cm$^{-1}$.

Crystalline Calcium Salt of 5-(3-chlorophenylamino)benzo[c][2,6]naphthyridine-8-carboxylic acid (Form XVIII)

The Form XVIII polymorphs (calcium salt) of compound I can be made by following the general methods described below in the Experimental section. Three polymorphic forms may be generated dependent on solvent choice, as indicated below based on Raman spectra analysis.

Figure 39:
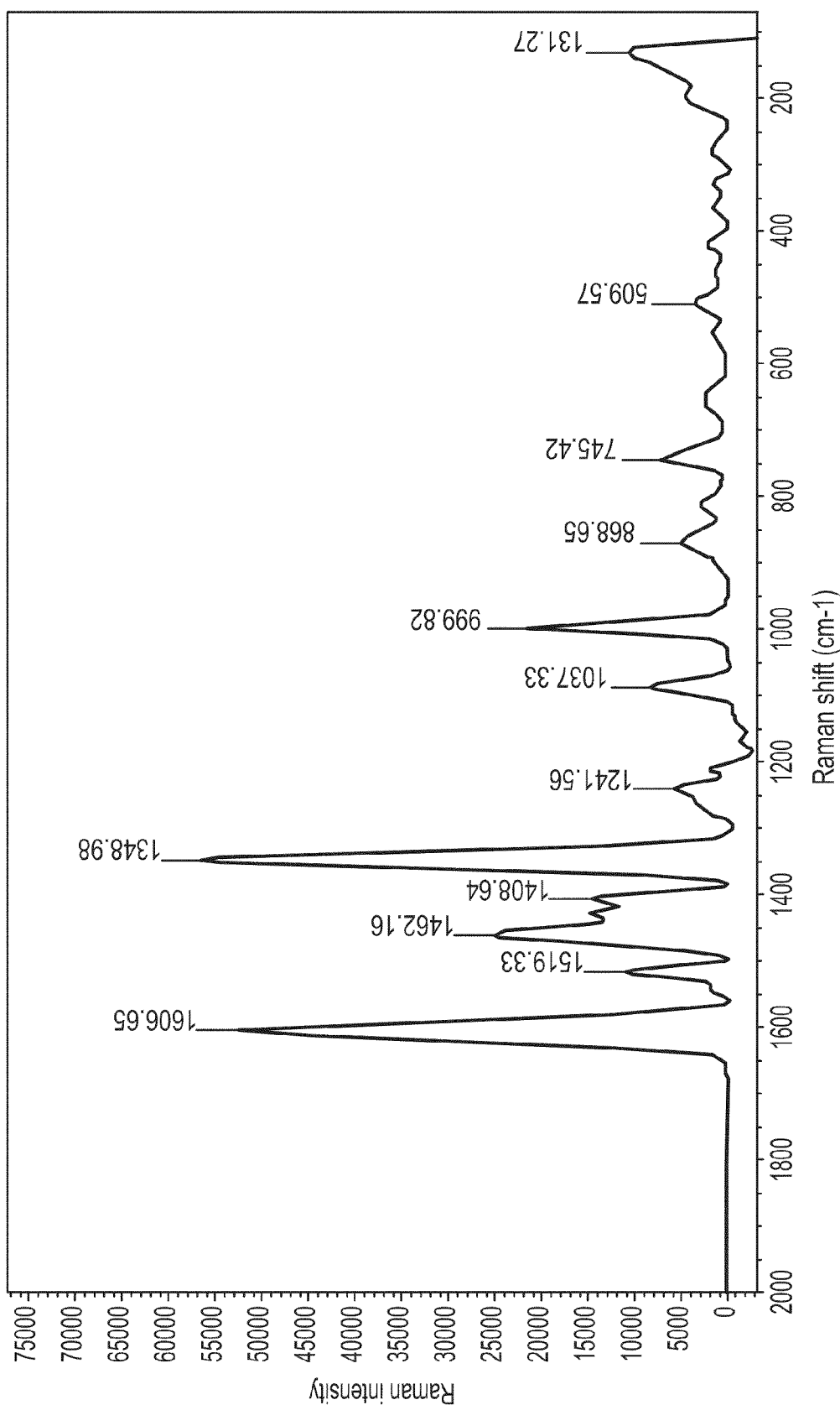
FIG. 39 depicts Raman spectra for the calcium salt polymorph Form XVIII-A from EtOH.
Figure 40:
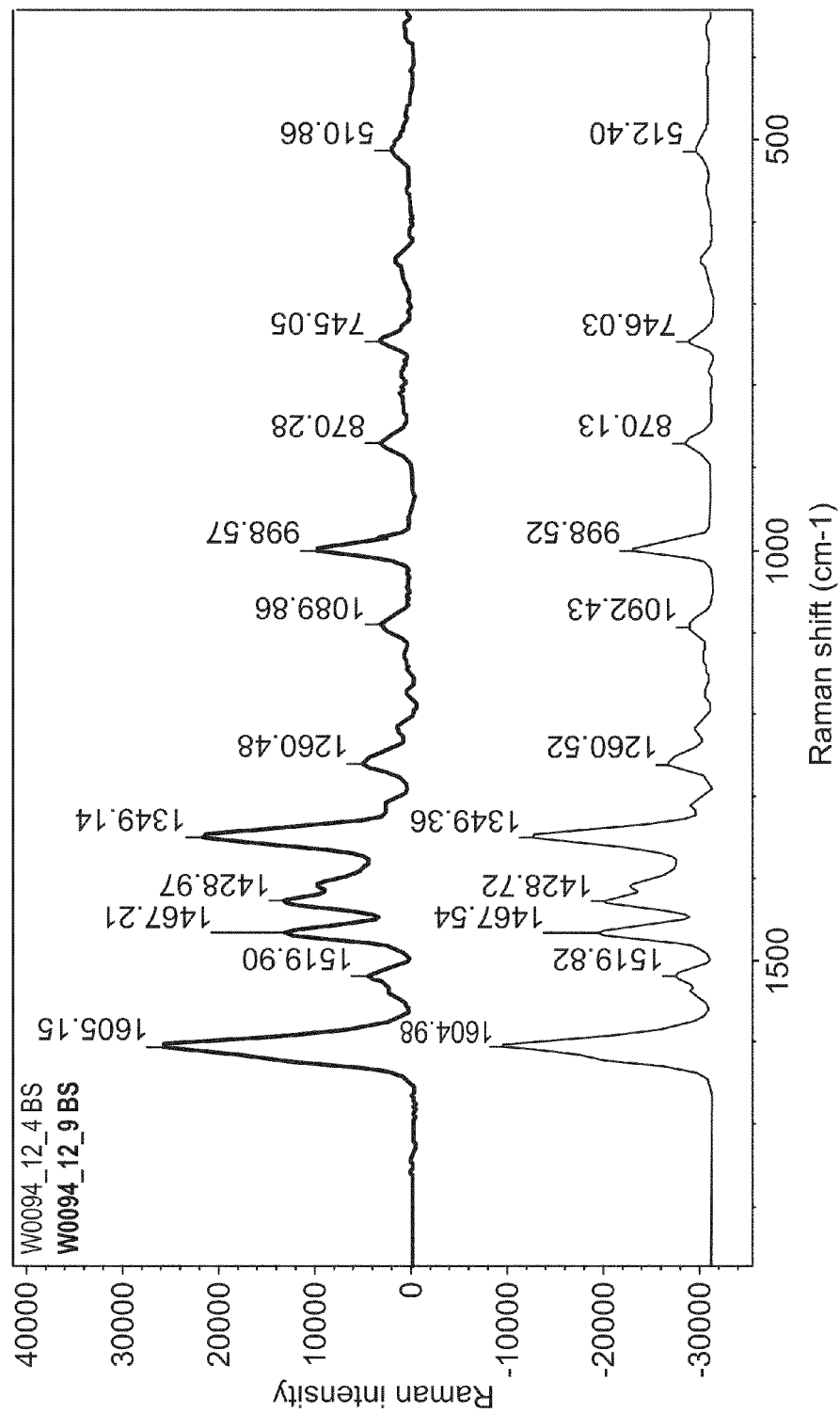
FIG. 40 depicts Raman spectra for the calcium salt polymorph Form XVIII-B from iPrOH:H$_2$O.
Figure 41:
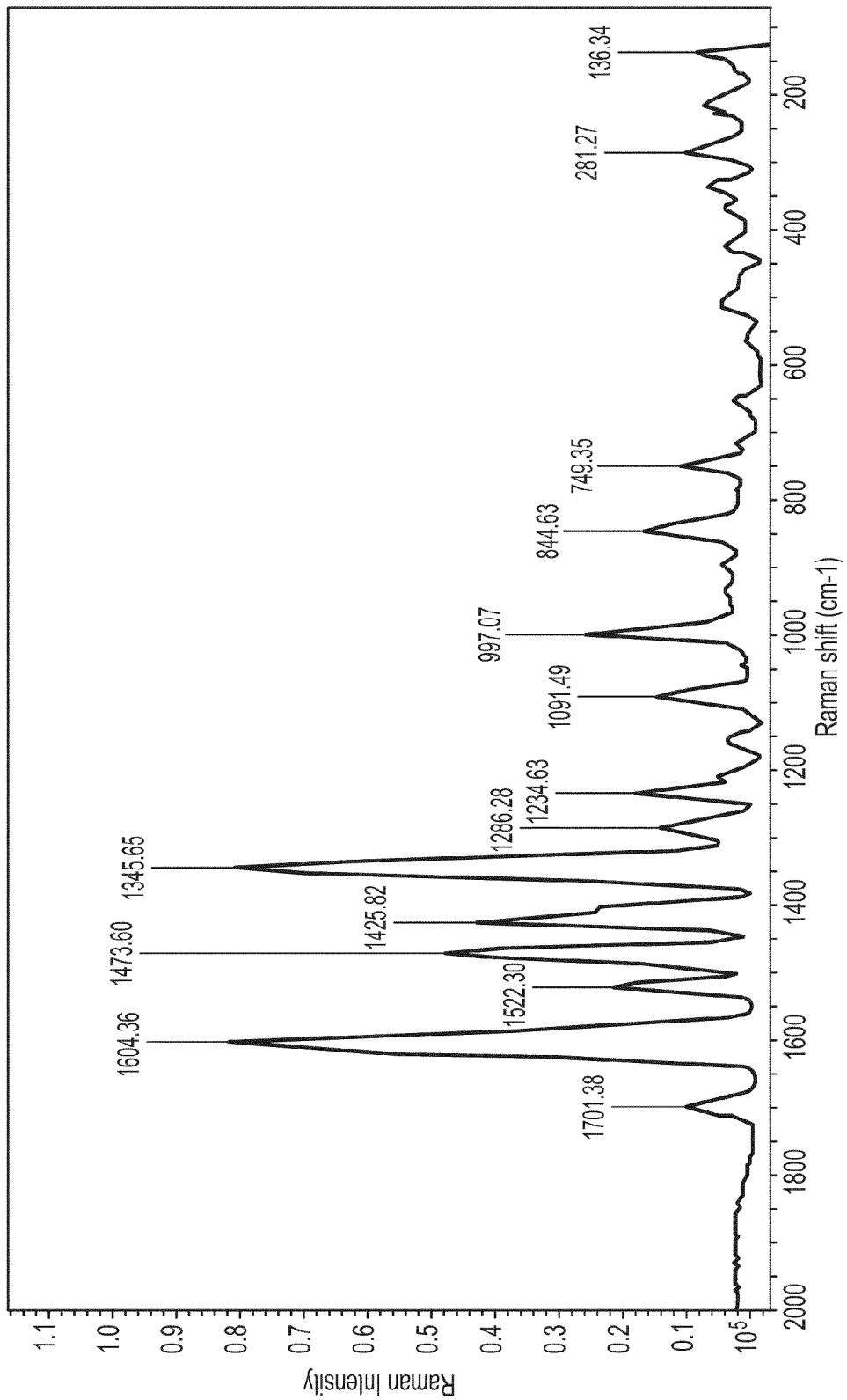
FIG. 41 depicts Raman spectra for the calcium salt polymorph Form XVIII-C from 2-BuOH.

The Polarized light microscopy (PLM) shown in FIG. 38 (from a 1:1 ratio of Ca to compound I) indicates crystalline solid as possible plates and/or needles of the Form XVIII polymorphs from EtOH, iPrOH, 2-BuOH, iPrOH:H$_2$O and DMF. The Raman spectra for the Form XVIII polymorph from EtOH (Form XVIII-A) is shown in FIG. 39 indicating peak assignments at e.g., about 1606.65, 1519.33, 1462.15, 1408.64, 1241.56, 1089.33, 999.82, 868.65, 745.42, 509.57 and 131.27 cm$^{-1}$. The Raman spectra for the Form XVIII polymorph from iPrOH:H$_2$O (Form XVIII-B) is shown in FIG. 40 indicating peak assignments at e.g., about 1604.98, 1519.82, 1467.54, 1428.72, 1349.36, 1260.52, 1092.43, 998.52, 870.13, 746.03 and 512.4 cm$^{-1}$. The Raman spectra for the Form XVIII polymorph from 2-BuOH (Form XVIII-C) is shown in FIG. 41 indicating peak assignments at e.g., about 1701.38, 1604.36, 1522.30, 1473.60, 1425.82, 1345.65, 1286.28, 1234.63, 1091.49, 997.07, 844.63, 749.35, 281.27 and 136.34 cm$^{-1}$.

Crystalline Magnesium Salt of 5-(3-chlorophenylamino)benzo[c][2,6]naphthyridine-8-carboxylic acid (Form XIX)

The Form XIX polymorphs (magnesium salt) of compound I can be made by following the general methods described below in the Experimental section. Two polymorphic forms may be generated as indicated below based on Raman spectra analysis.

Figure 43:
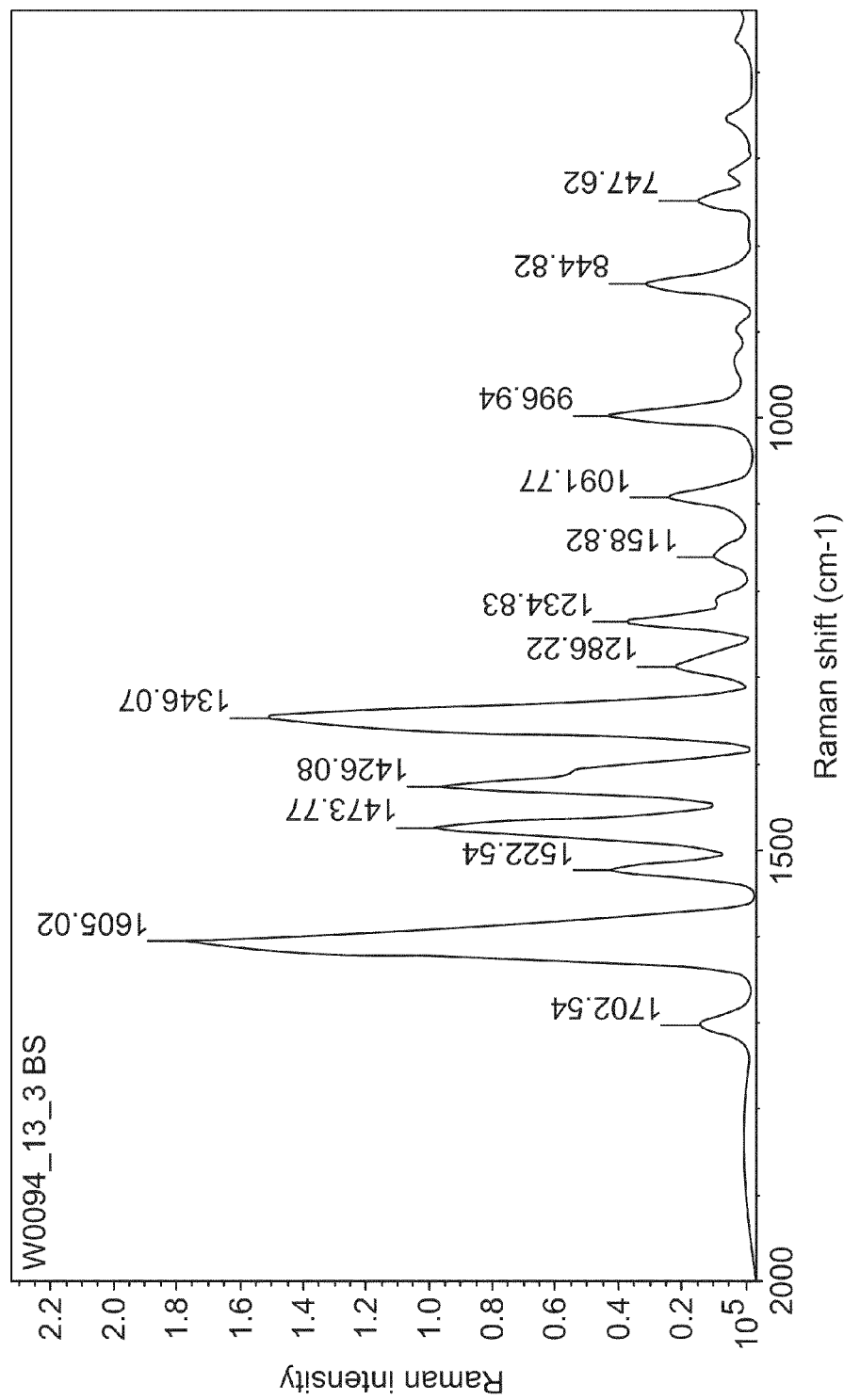
FIG. 43 depicts Raman spectra for the magnesium salt polymorph form XIX-A.
Figure 44:
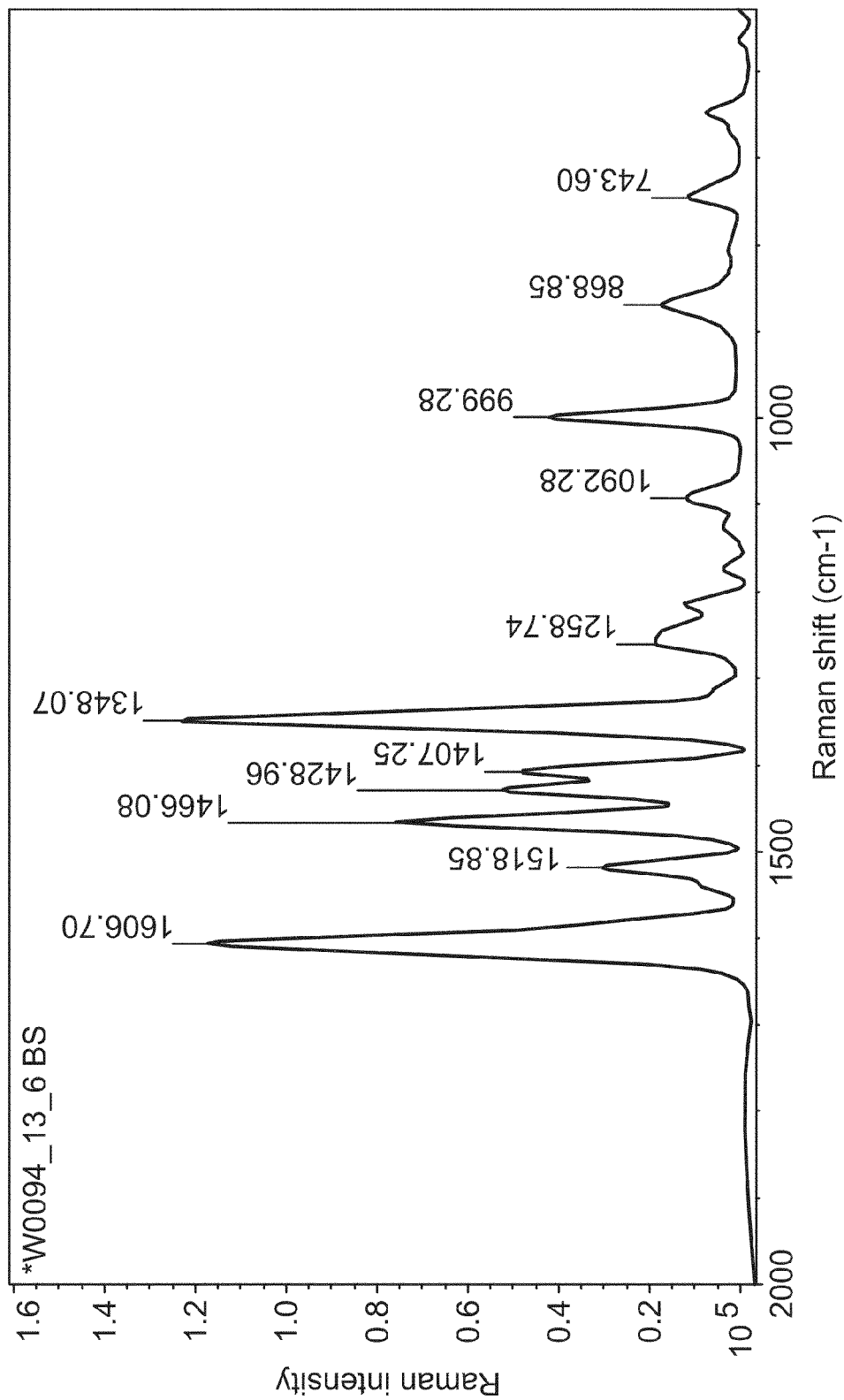
FIG. 44 depicts Raman spectra for the magnesium salt polymorph form XIX-B.

The Polarized light microscopy (PLM) shown in FIG. 42 (from a 1:1 ratio of Mg to compound I) indicates crystalline needles and/or plates of the Form XIX polymorphs from EtOH, iPrOH, 2-BuOH, iPrOH:H$_2$O, and DMF. The Raman spectra for the Form XIX-A polymorph is shown in FIG. 43 indicating peak assignments at e.g., about 1702.54, 1605.02, 1522.54, 1473.77, 1426.08, 1346.07, 1286.22, 1234.83, 1158.82, 1091.77, 996.94, 844.82 and 747.62 cm$^{-1}$. The Raman spectra for the Form XIX-B polymorph from these solvents is shown in FIG. 44 indicating peak assignments at e.g., about 1606.70, 1518.85, 1466.08, 1428.96, 1407.25, 1348.07, 1258.74, 1092.28, 999.28, 868.85 and 743.60 cm$^{-1}$.

Crystalline Potassium Salt of 5-(3-chlorophenylamino)benzo[c][2,6]naphthyridine-8-carboxylic acid (Form XX)

The Form XX polymorph (potassium salt) of compound I can be made by following the general methods described below in the Experimental section.

Figure 46:
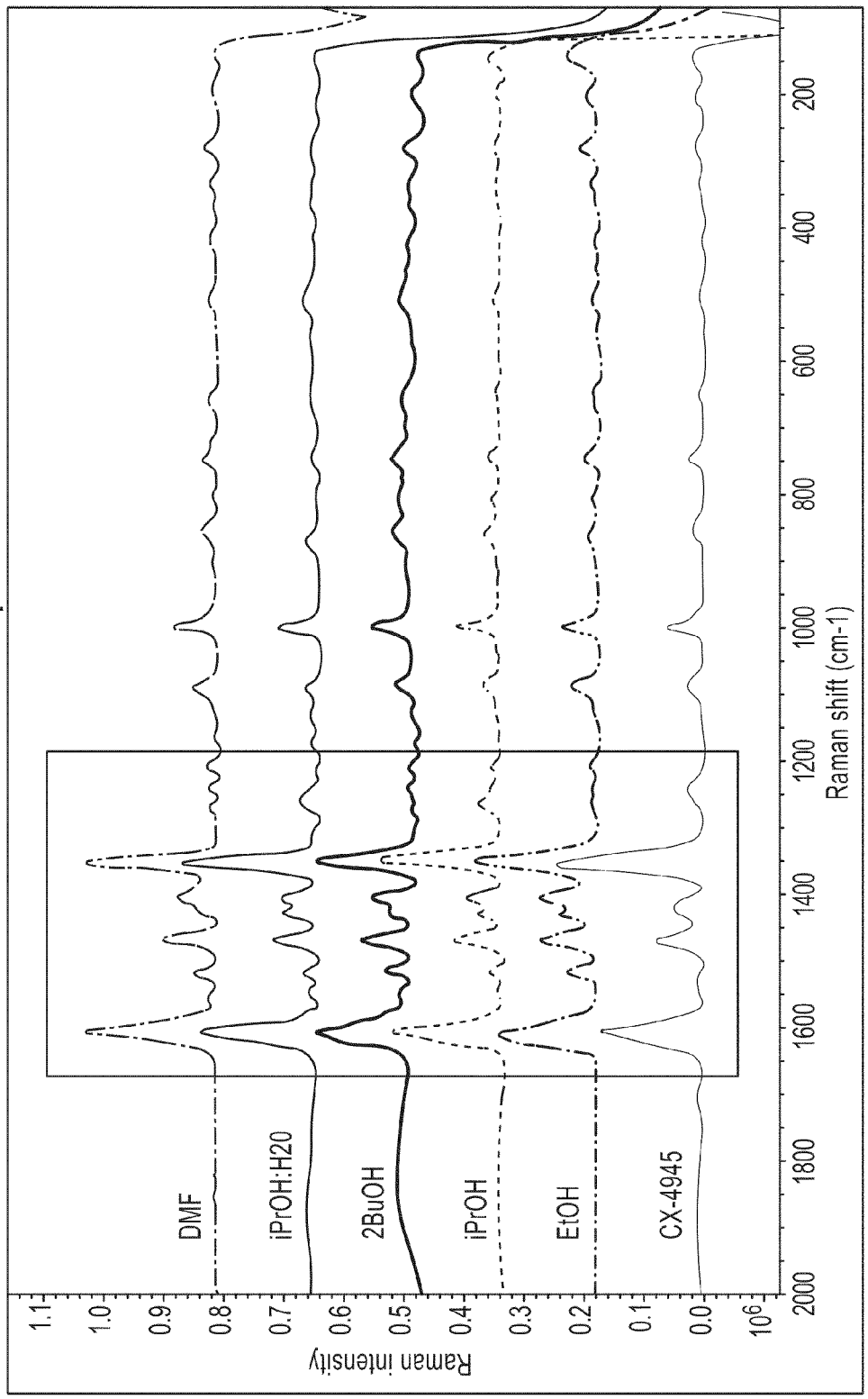
FIG. 46 depicts Raman spectra for the potassium salt polymorph from the indicated solvents.
Figure 47:
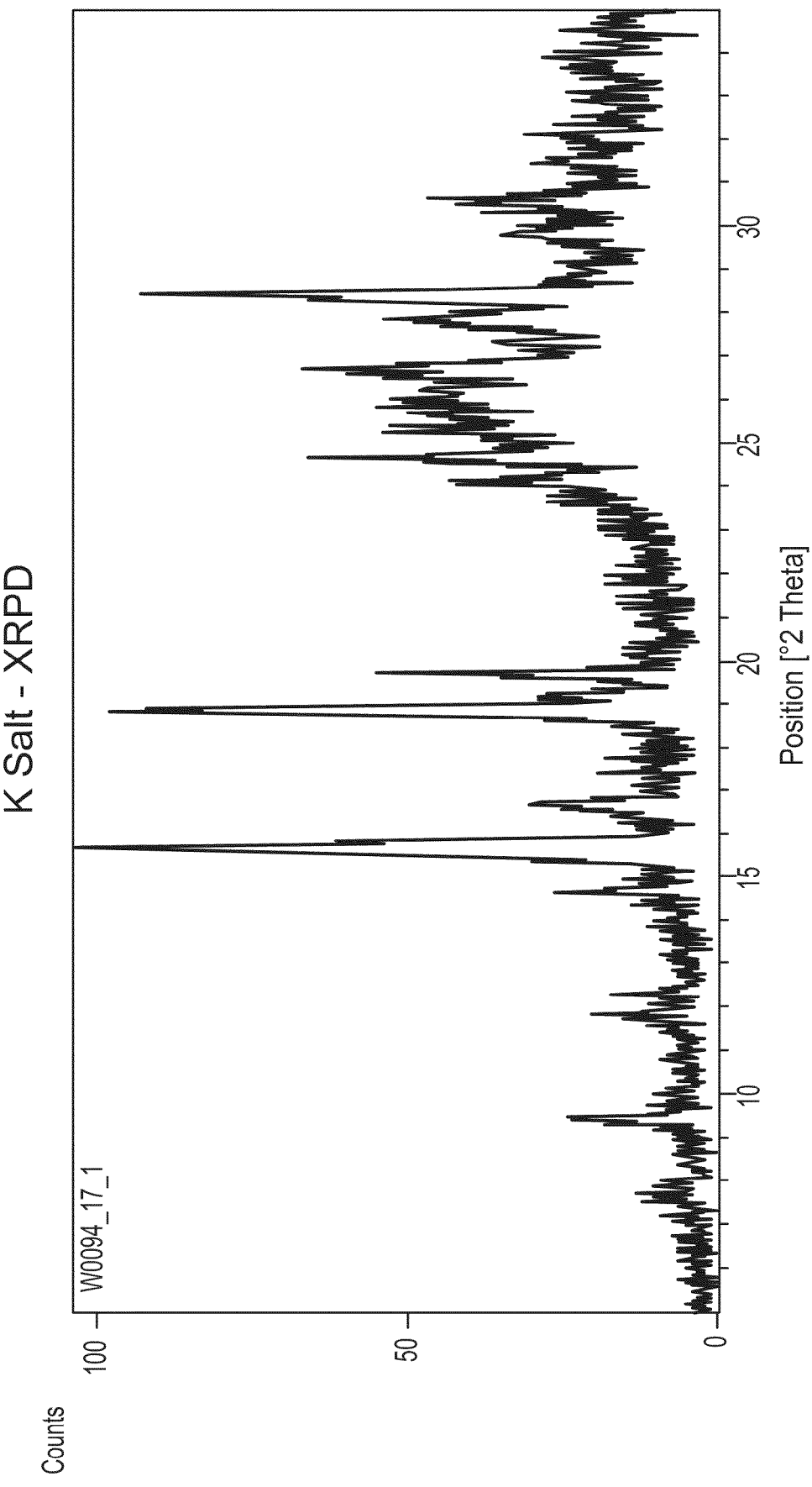
FIG. 47 depicts the powder x-ray diffraction pattern of the potassium salt polymorph.

The Polarized light microscopy (PLM) shown in FIG. 45 indicates crystalline solid as possible plates and/or needles of the Form XX polymorph from EtOH, iPrOH, 2-BuOH, iPrOH:H$_2$O and DMF. The Raman spectra for the Form XX polymorph from these solvents is shown in FIG. 46 indicating peak assignments at e.g., about 1609.15, 1518.91, 1472.84, 1411.87, 1360.91, 1093.93, 1001.52 and 754.45 cm$^{-1}$. The XRPD pattern of Form XX polymorph (FIG. 47) indicates 2θ diffraction lines at e.g., about 7.7°, 9.4°, 11.8°, 12.0°, 12.3°, 14.7°, 15.6°, 16.7°, 18.9°, 19.7°, 24.1°, 24.6°, 25.3°, 26.1°, 26.7°, 27.8°, 28.4°, 29.8°, 30.6°, 31.5°, 32.1° and 33.7°, with major 2θ diffraction lines at e.g., about 15.6°, 18.9°, and 28.4°.

Figure 48:
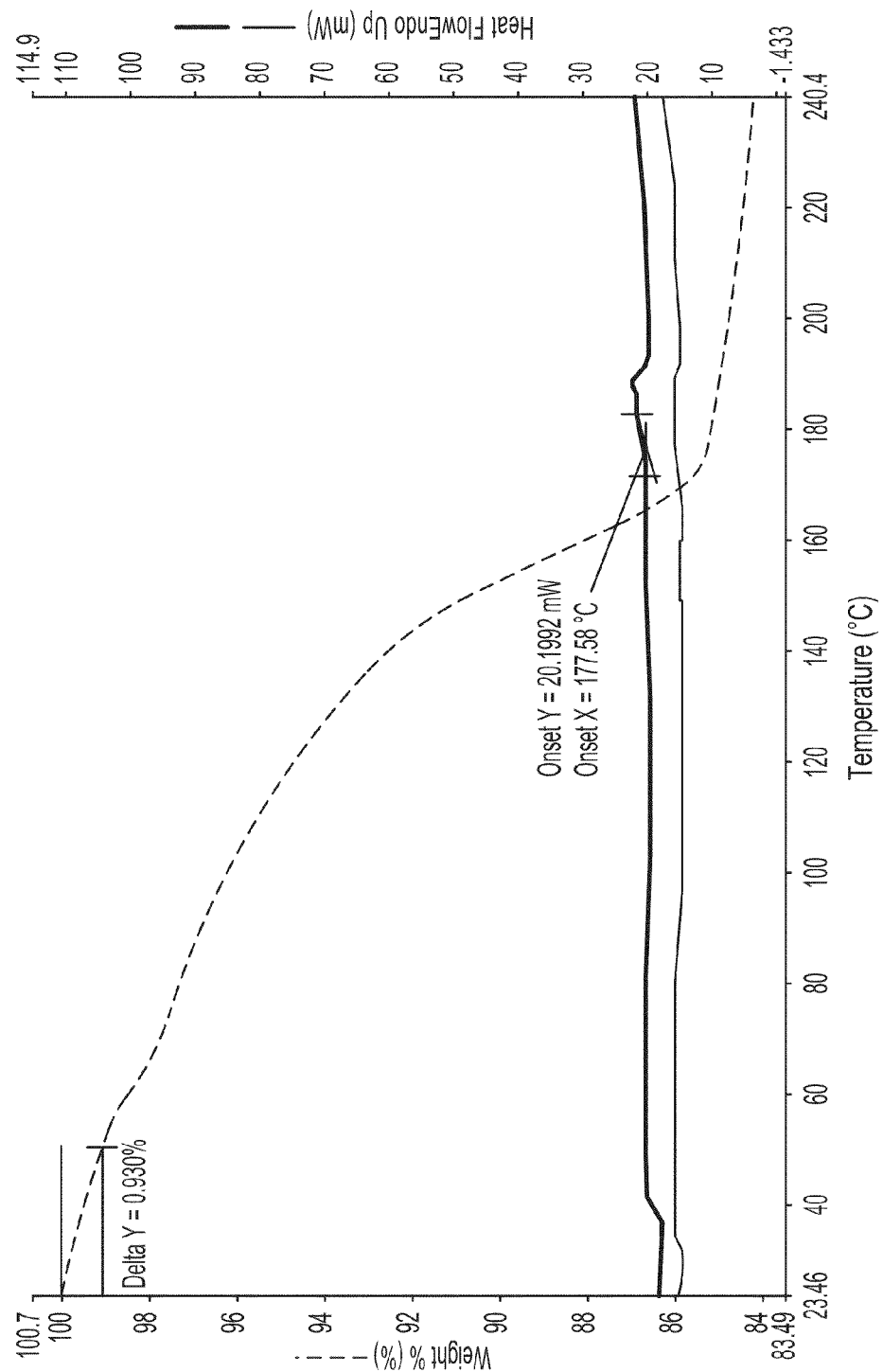
FIG. 48 depicts TGA and DSC data of the potassium salt polymorph.

Thermogravimetric Analysis (TGA) data for Form XX (see FIG. 48) indicates a small initial weight loss of about 0.9% up to about 50° C., (possible surface solvents) and a larger weight loss of about 14% from about 50° C. to about 180° C. (mono solvate and/or decomposition of the salt). Differential Scanning Calorimetry (DSC) data for Form XX (see FIG. 48) shows a very broad endotherm at about 170° C. to about 180° C. at 10° C./min scan rate (possible melting of potassium salt and/or degradation).

Crystalline L-Arginine Salt of 5-(3-chlorophenylamino)benzo[c][2,6]naphthyridine-8-carboxylic acid (Form XXI)

The Form XXI polymorph (L-Arginine salt) of compound I can be made by following the methods described below in the Experimental section.

Figure 50:
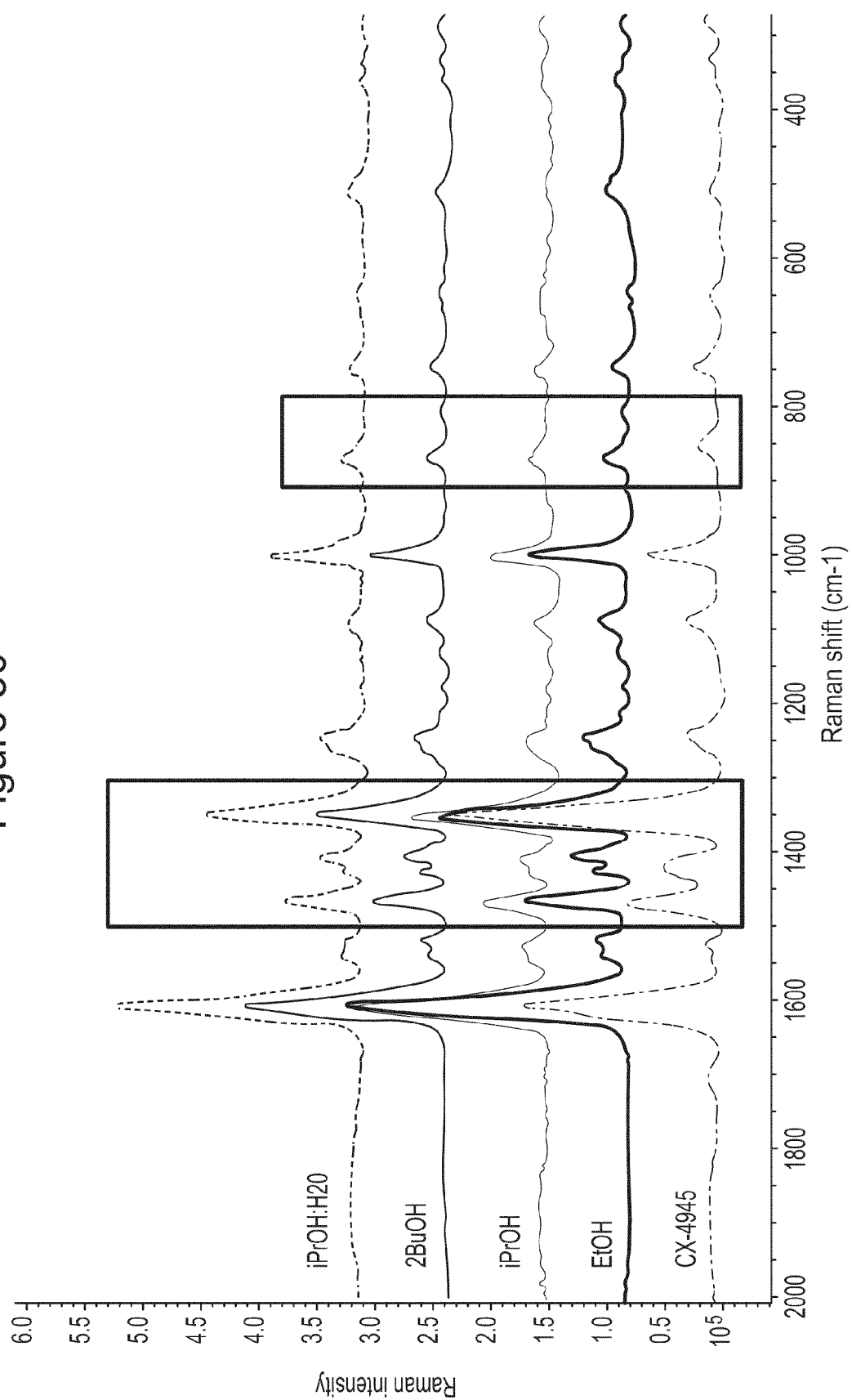
FIG. 50 depicts Raman spectra for the L-Arginine salt polymorph from the indicated solvents.
Figure 51:
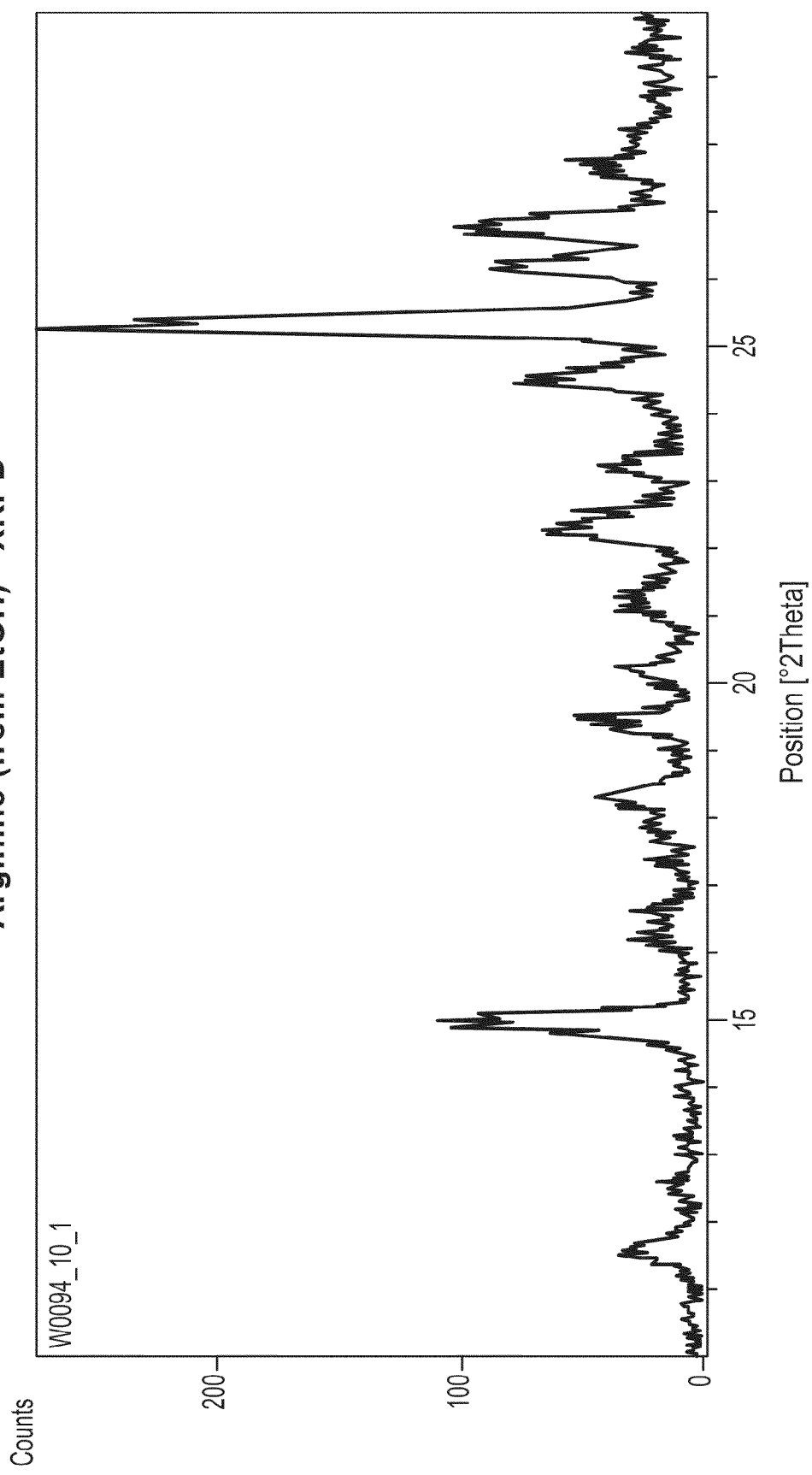
FIG. 51 depicts the powder x-ray diffraction pattern of the L-Arginine salt polymorph.

The Polarized light microscopy (PLM) shown in FIG. 49 indicates crystalline plates of the Form XXI polymorph from EtOH, iPrOH, 2-BuOH, and iPrOH:H$_2$O. The Raman spectra for the Form XXI polymorph from these solvents is shown in FIG. 50 indicating peak assignments at e.g., about 3085.30, 1606.60, 1518.54, 1405.94, 1348.18, 1245.94, 1087.86, 998.66, 868.84, 745.58 and 509.15 cm$^{-1}$. The XRPD pattern of Form XXI polymorph from EtOH (FIG. 51) indicates 2θ diffraction lines at e.g., about 10.5°, 11.6°, 15.0°, 16.3°, 16.6°, 18.3°, 19.4°, 20.2°, 21.2°, 22.3°, 23.2°, 24.5°, 25.3°, 26.2°, 26.8° and 27.7°, with major 2θ diffraction lines at e.g., about 15.0° and 25.3°.

Figure 52:
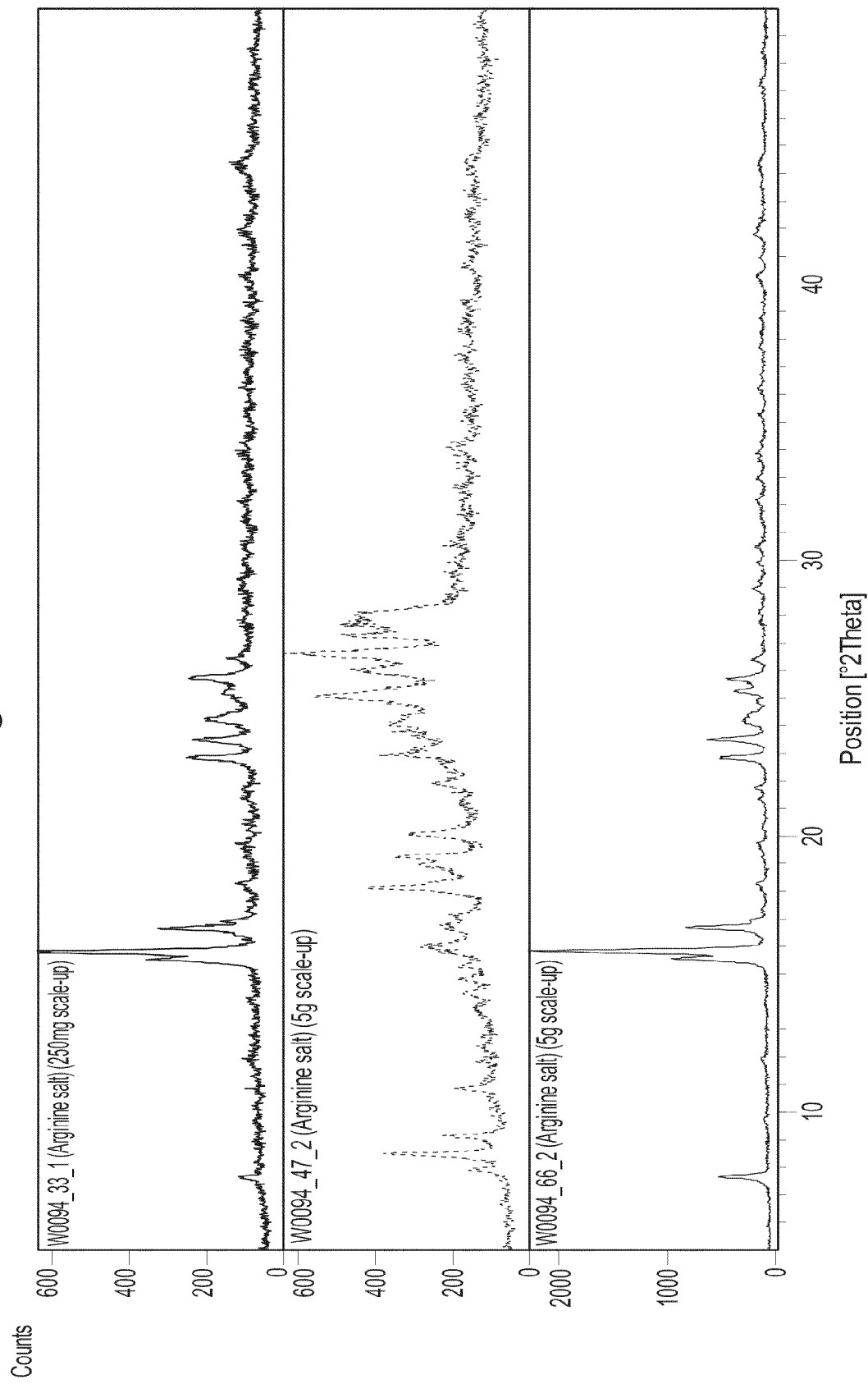
FIG. 52 depicts the powder x-ray diffraction patterns for the L-Arginine salt polymorph in a 250 mg scale-up (top), an initial 5 g scale-up (middle), and a 5 g scale-up following slurry in MeOH/H$_2$O (bottom).
Figure 53:
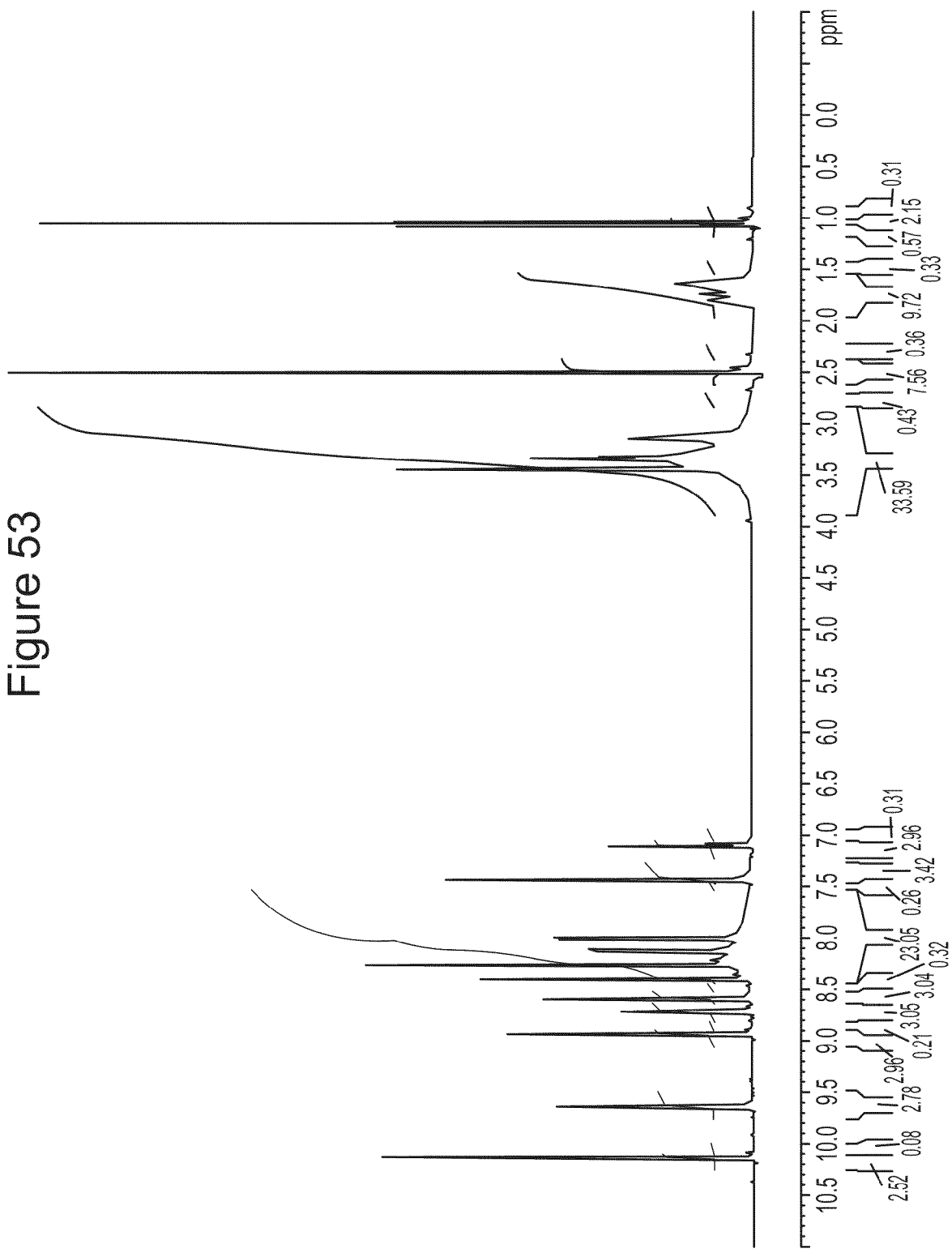
FIG. 53 depicts a solution NMR of the L-Arginine salt polymorph after scale-up.
Figure 54:
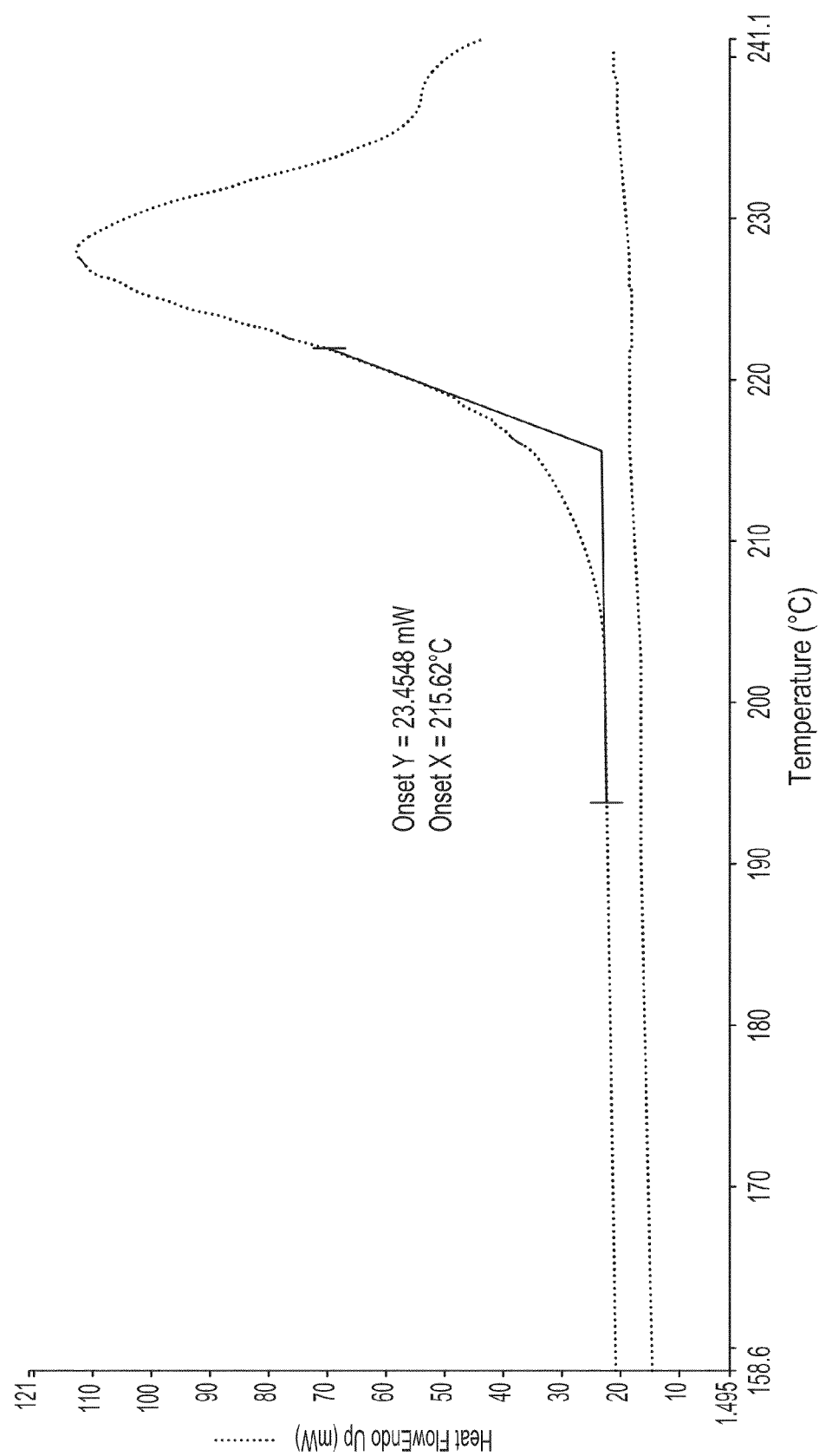
FIG. 54 depicts the DSC thermogram of the L-Arginine salt polymorph after scale-up.
Figure 79:
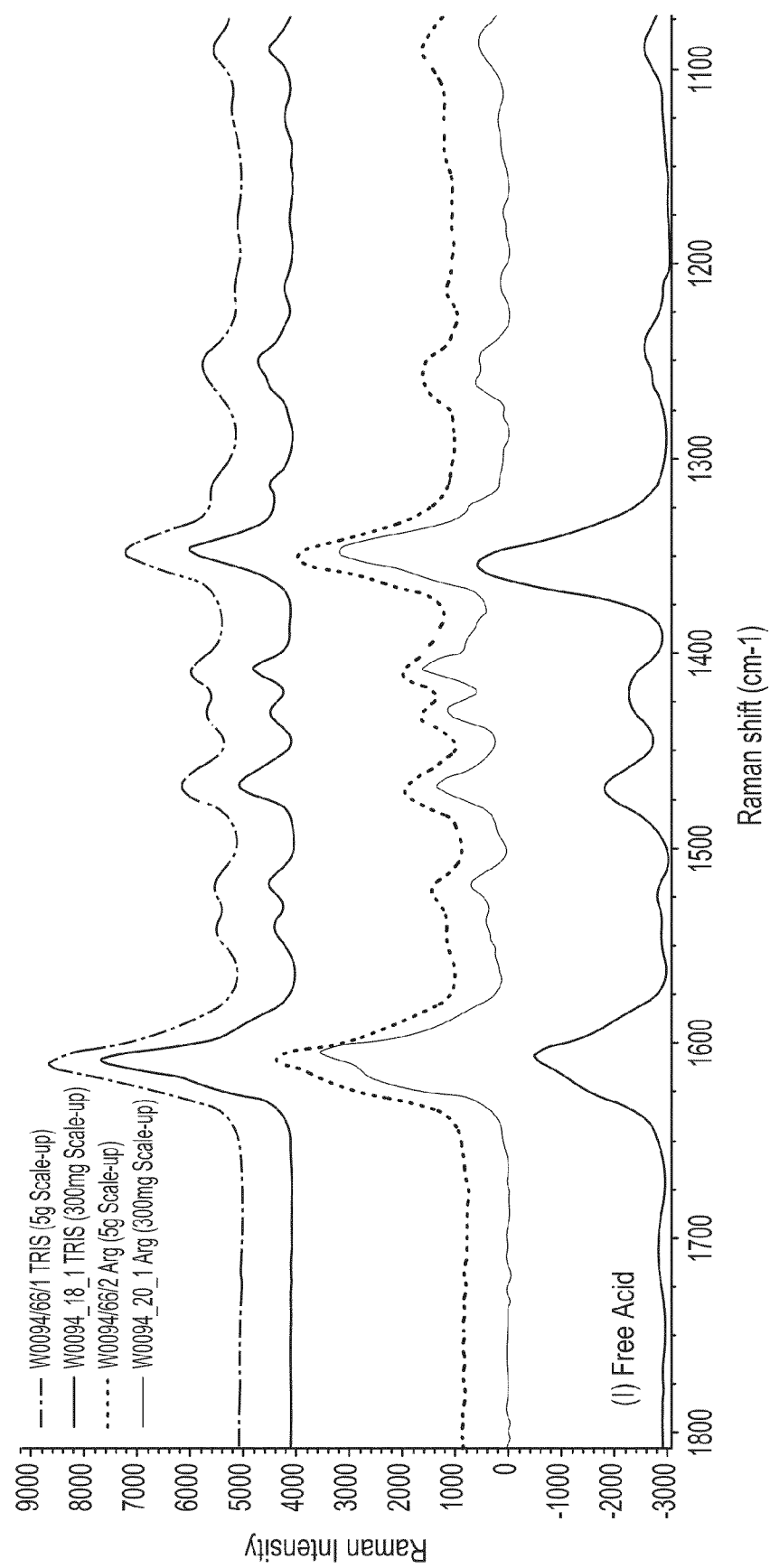
FIG. 79 depicts Raman spectra (bottom to top: free acid compound, L-Arginine salt polymorph; 300 mg scale, L-Arginine salt polymorph; 5 g scale, TRIS salt polymorph; 300 mg scale, TRIS salt polymorph; 5 g scale).
Figure 80:
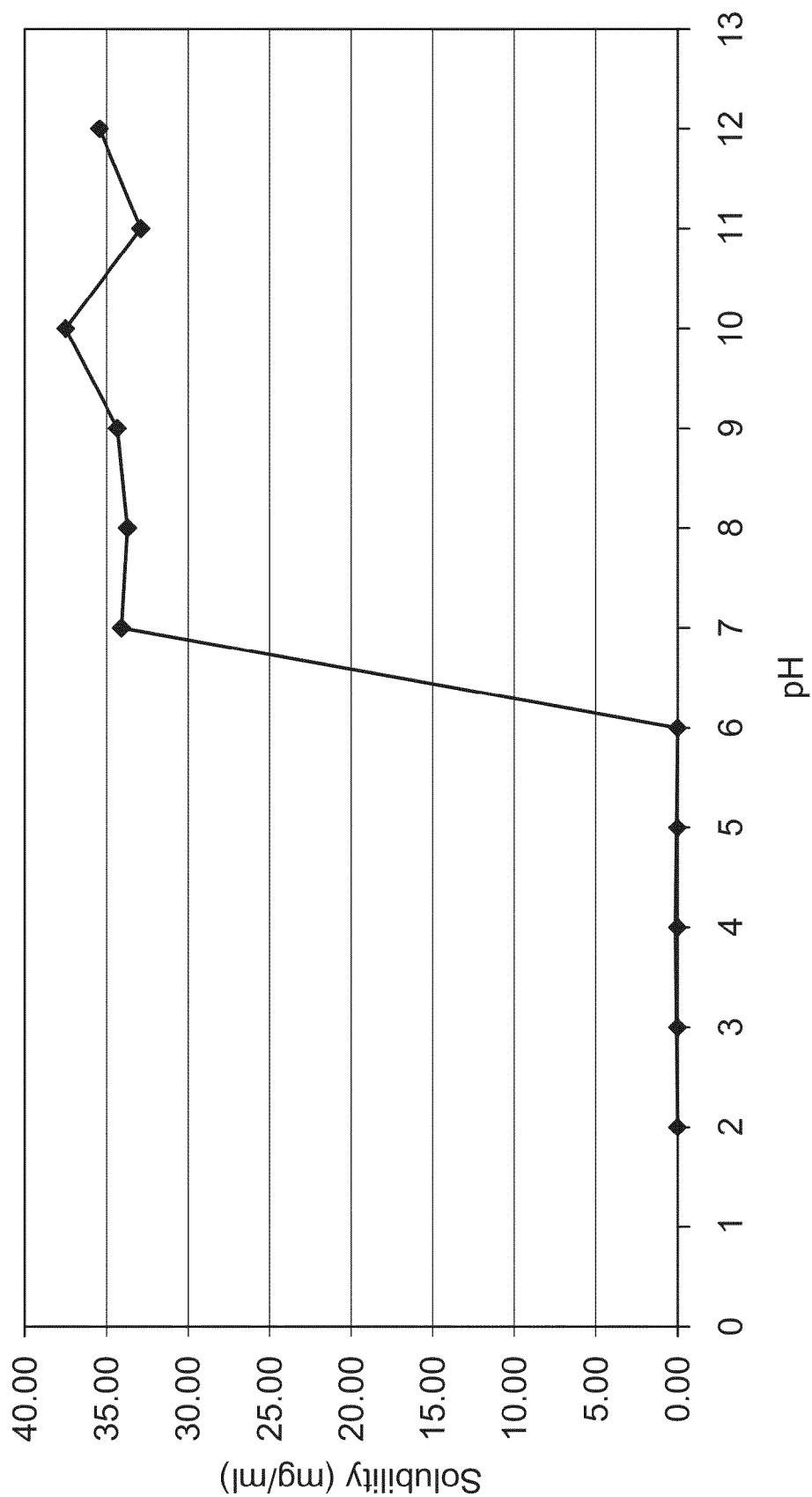
FIG. 80 depicts the aqueous solubility of the sodium salt of 5-(3-chlorophenylamino)benzo[c][2,6]naphthyridine-8-carboxylic acid (compound (I)).

The Form XXI polymorph was scaled-up to 5 g by following the methods described below in the Experimental section then analyzed by XRPD (FIG. 52), NMR (FIG. 53), Raman (FIG. 79), and HPLC. Raman and NMR spectra indicated that the Arginine 1:1 salt was made. The difference in XRPD for the initial 5 g scale-up material (Form XXI-B) can be seen in FIG. 52 (top vs. middle). The scaled-up material (Form XXI-B) was then slurried in MeOH/H$_2$O (90:10) by temperature cycling at 40° C. and RT, each period for 4 hours, for a total of 5 days, resulting in complete conversion to Form XXI as shown by XRPD (FIG. 52; bottom). Differential Scanning Calorimetry (DSC) data for the scaled-up Form XXI (see FIG. 54) shows an endotherm at about 215° C. (degradation occurred just after the melting point). By comparison, no endothermic event at about 215° C. (just a small lump) was found in the salt made in the 300 mg scale, likely due to the small particle size of the 300 mg scale salt and small quantity used for the DSC measurement. HPLC analysis showed no impurity in the 300 mg and 5 g samples.

Figure 55:
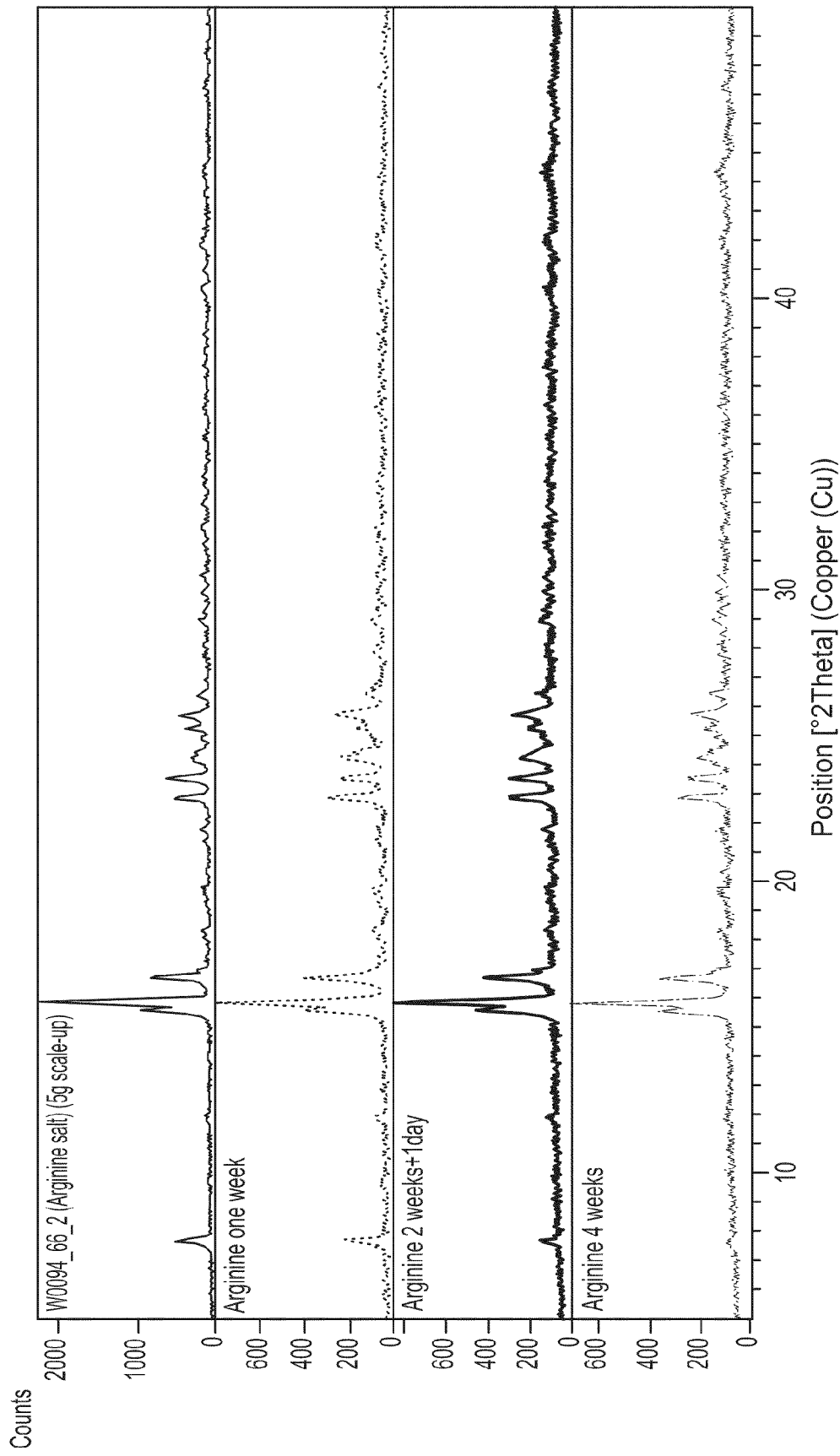
FIG. 55 depicts the powder x-ray diffraction pattern of the L-Arginine salt polymorph at time 0 (top), 1 week (middle-top), 2 weeks+1 day (middle-bottom), and 4 weeks (bottom).
Figure 56:
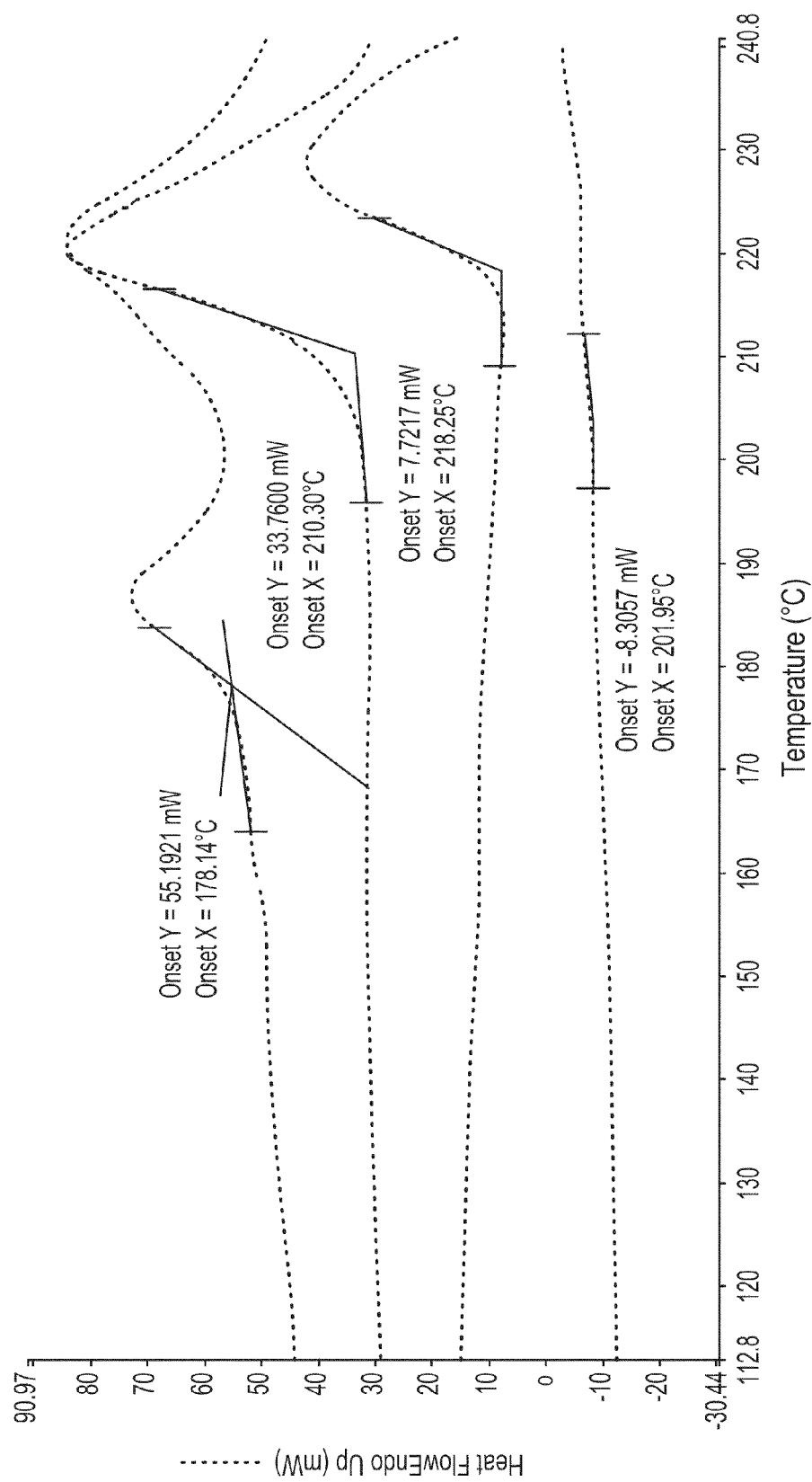
FIG. 56 depicts the DSC thermograms of the L-Arginine salt polymorph at various time points (bottom to top: time 0, 1 week, 2 weeks, and 4 weeks).

The stability of Form XXI polymorph was studied over a 4 week period using XRPD and DSC (FIGS. 55 and 56, respectively). Both XRPD and DSC showed no significant change. The difference in melting point between 4 samples in the DSC experiment is likely due to the different particle size of salts (as discussed herein). HPLC after 4 weeks confirmed no additional impurity.

Figure 57:
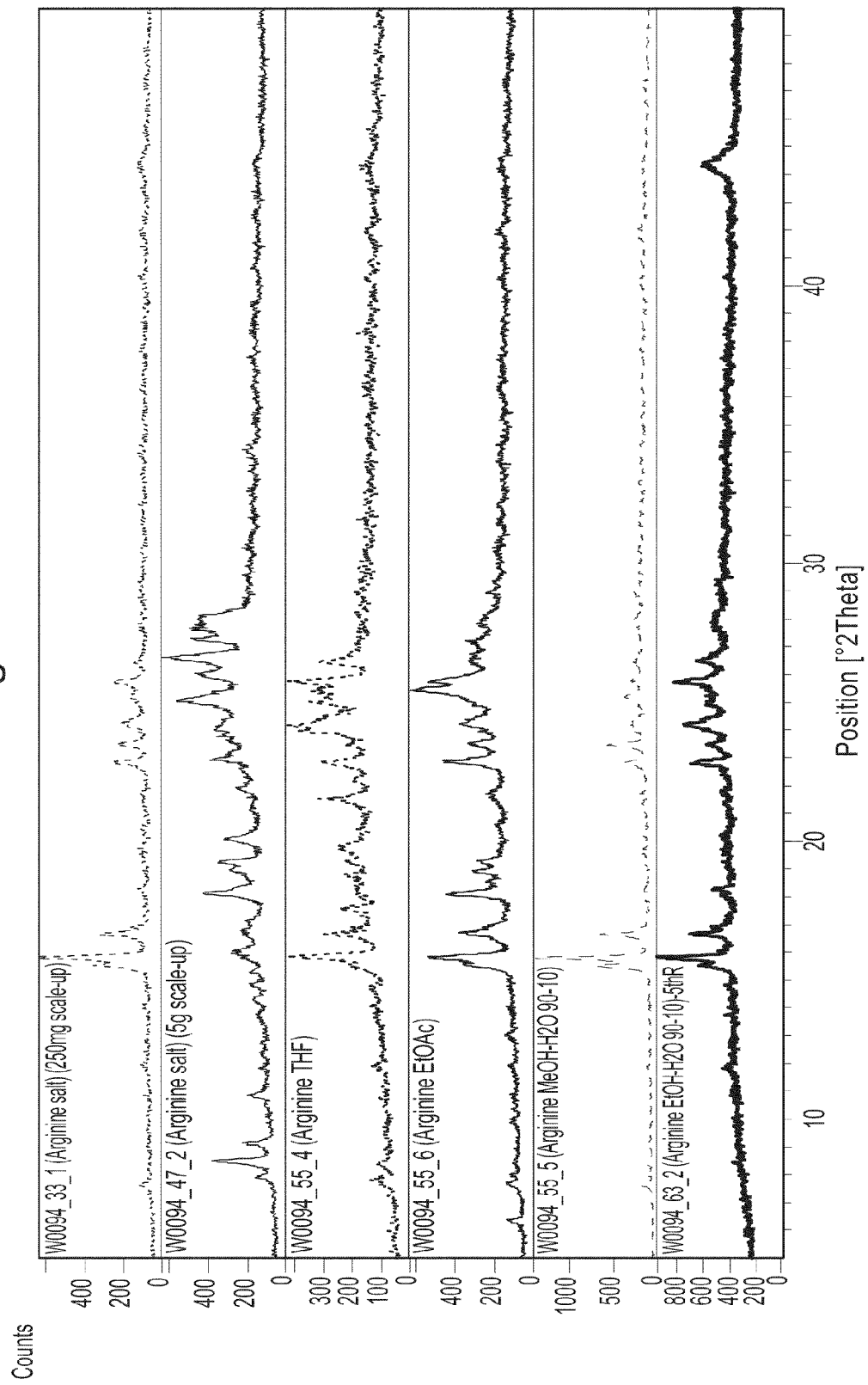
FIG. 57 depicts the powder x-ray diffraction pattern of the L-Arginine salt polymorph following slurry experiments in the indicated solvents.
Figure 58:
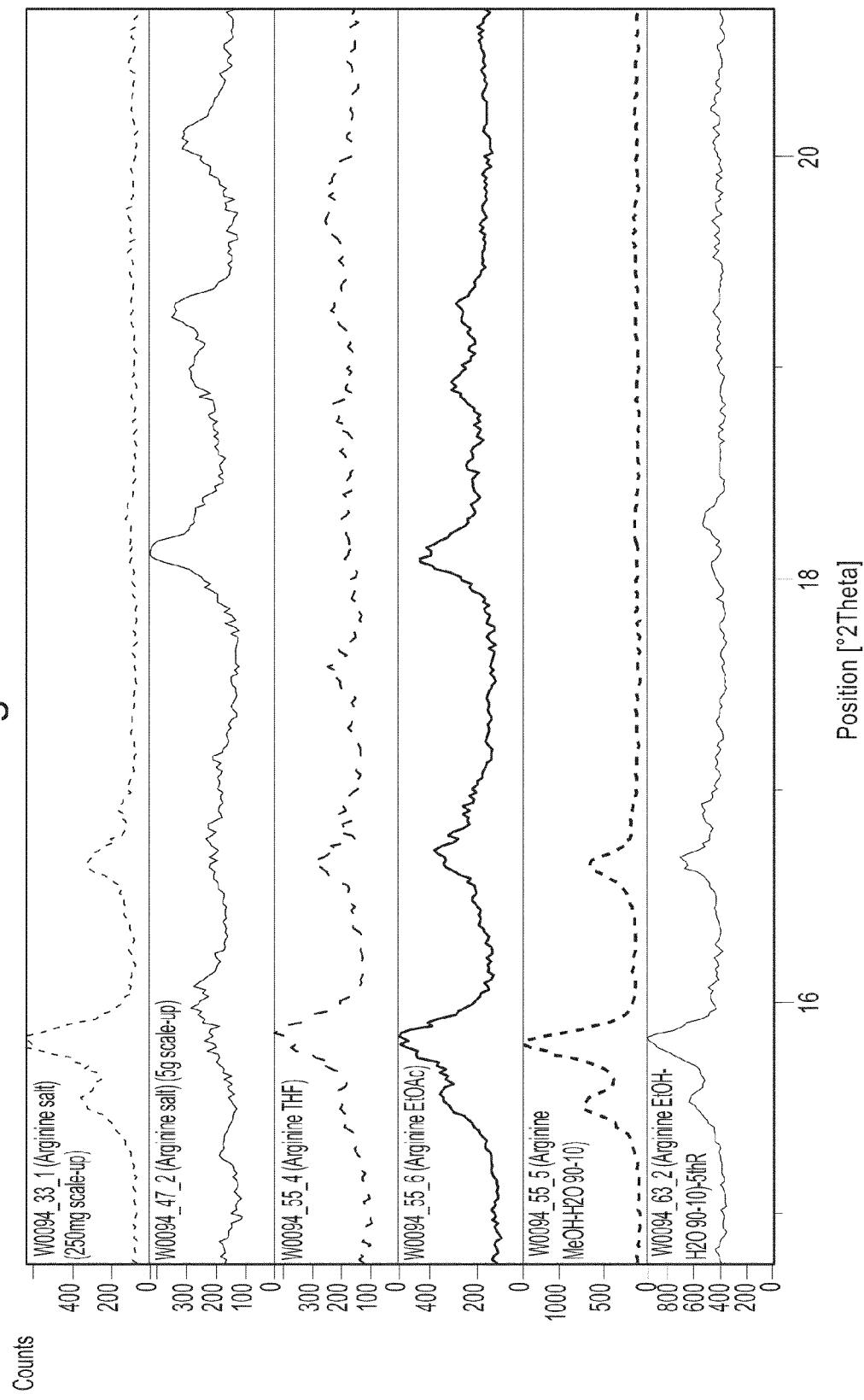
FIG. 58 depicts a zoomed-in version of FIG. 55.
Figure 59:
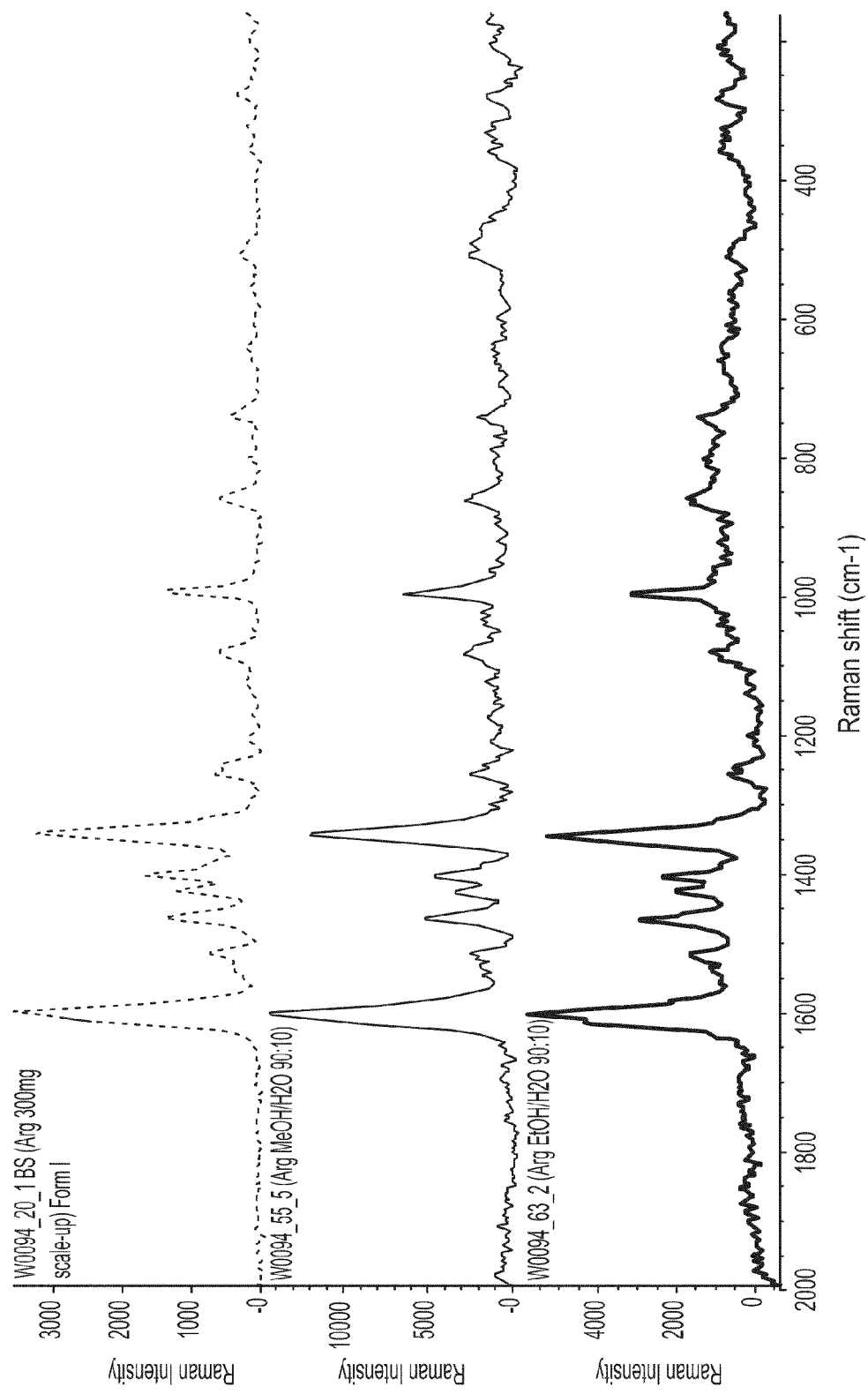
FIG. 59 depicts Raman spectra for the L-Arginine salt polymorph following slurry experiments in the indicated solvents.

Competitive slurry experiments for the Form XXI polymorph and the original Form XXI-B discuss above were carried out in various solvent systems and the results shown in Table 6. The Form XXI is more stable, as evidenced by the fact that the mixtures of two forms have all changed to Form XXI for each salt (slurry using MeOH/H$_2$O (90:10) and EtOH/H$_2$O (90:10)). Different polymorphic forms were also possibly formed from the slurry in THF or EtOAc (refer to FIGS. 57 and 58). Raman spectra of the slurry products from MeOH/H$_2$O (90:10) and EtOH/H$_2$O (90:10) compared to the 300 mg scale-up material are shown in FIG. 59.

TABLE 6

Competitive Slurry Experiments for Form XXI and Form XXI-B.

| | Solvent | | | |
|---|---|---|---|---|
| Starting material | MeOH/H$_2$O 90:10 | EtOH/H$_2$O 90:10 | THF | EtOAc |
| Form XXI + Form XXI-B | Form XXI | Form XXI | New form | New form |
| Form XXI + Form XXI-B | Form XXI | Form XXI | New form | New form |

Figure 61:
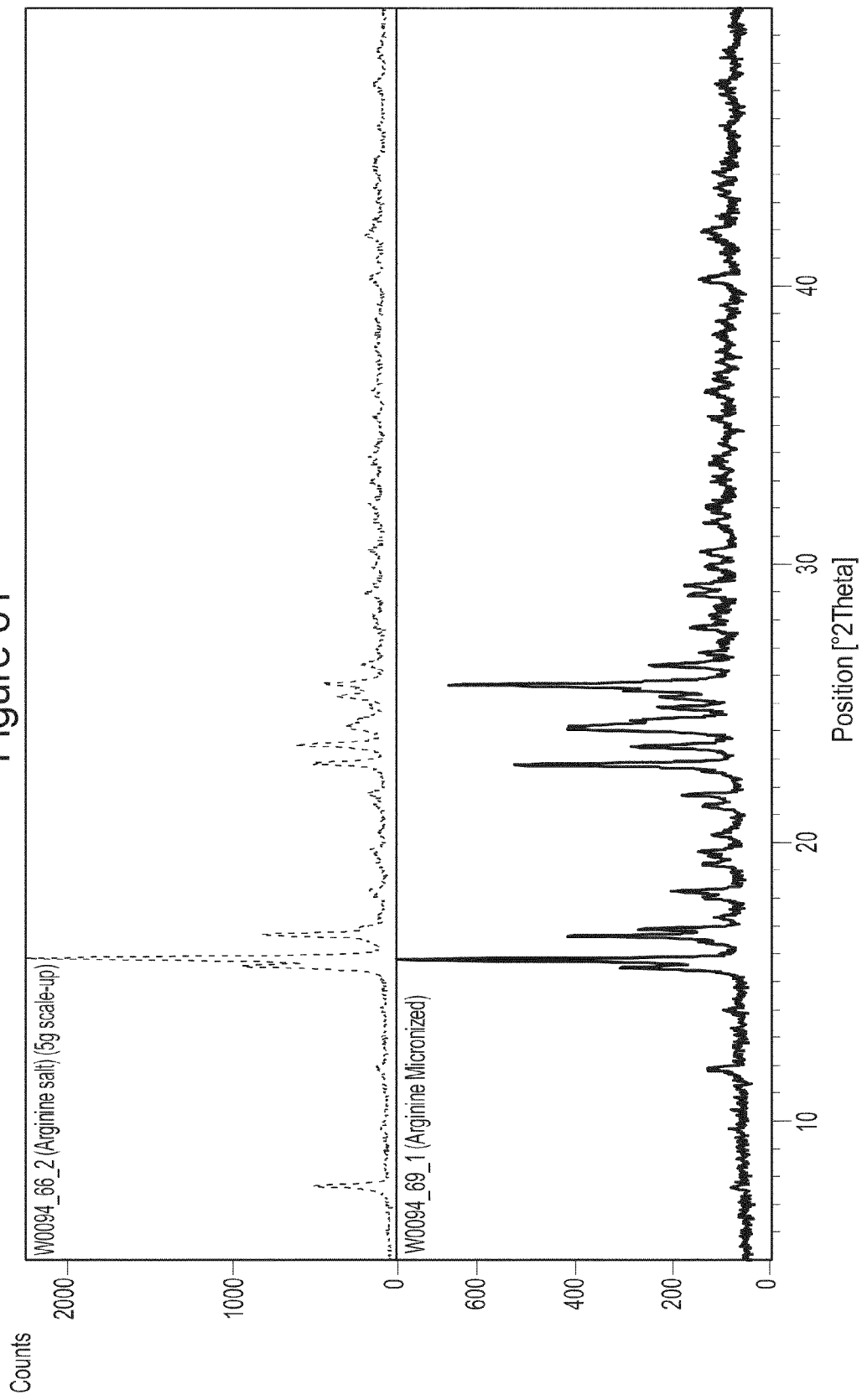
FIG. 61 depicts the powder x-ray diffraction pattern of the pre-micronized (top) and micronized (bottom) L-Arginine salt polymorph.
Figure 62:
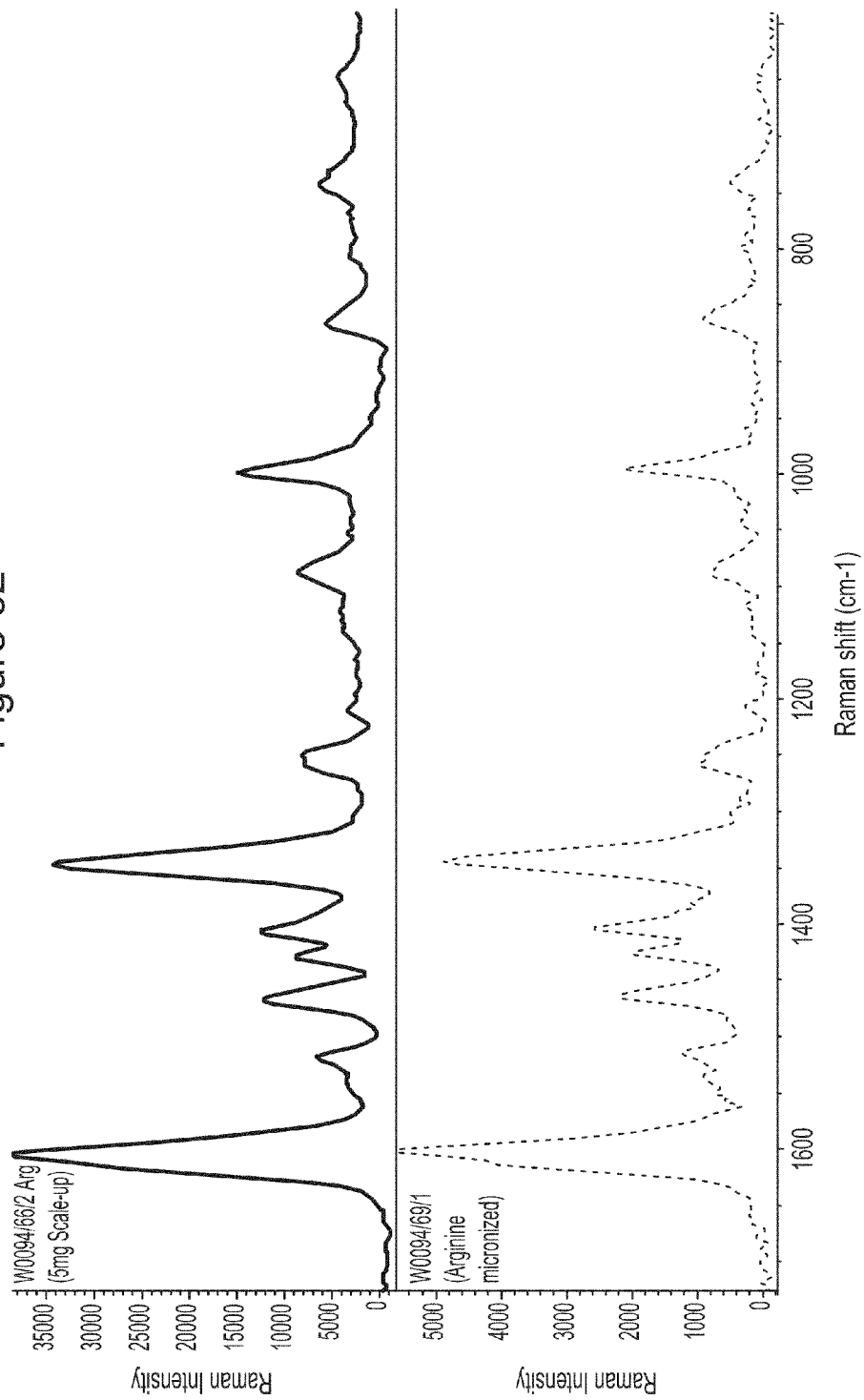
FIG. 62 depicts Raman spectra of the pre-micronized (top) and micronized (bottom) L-Arginine salt polymorph.
Figure 63:
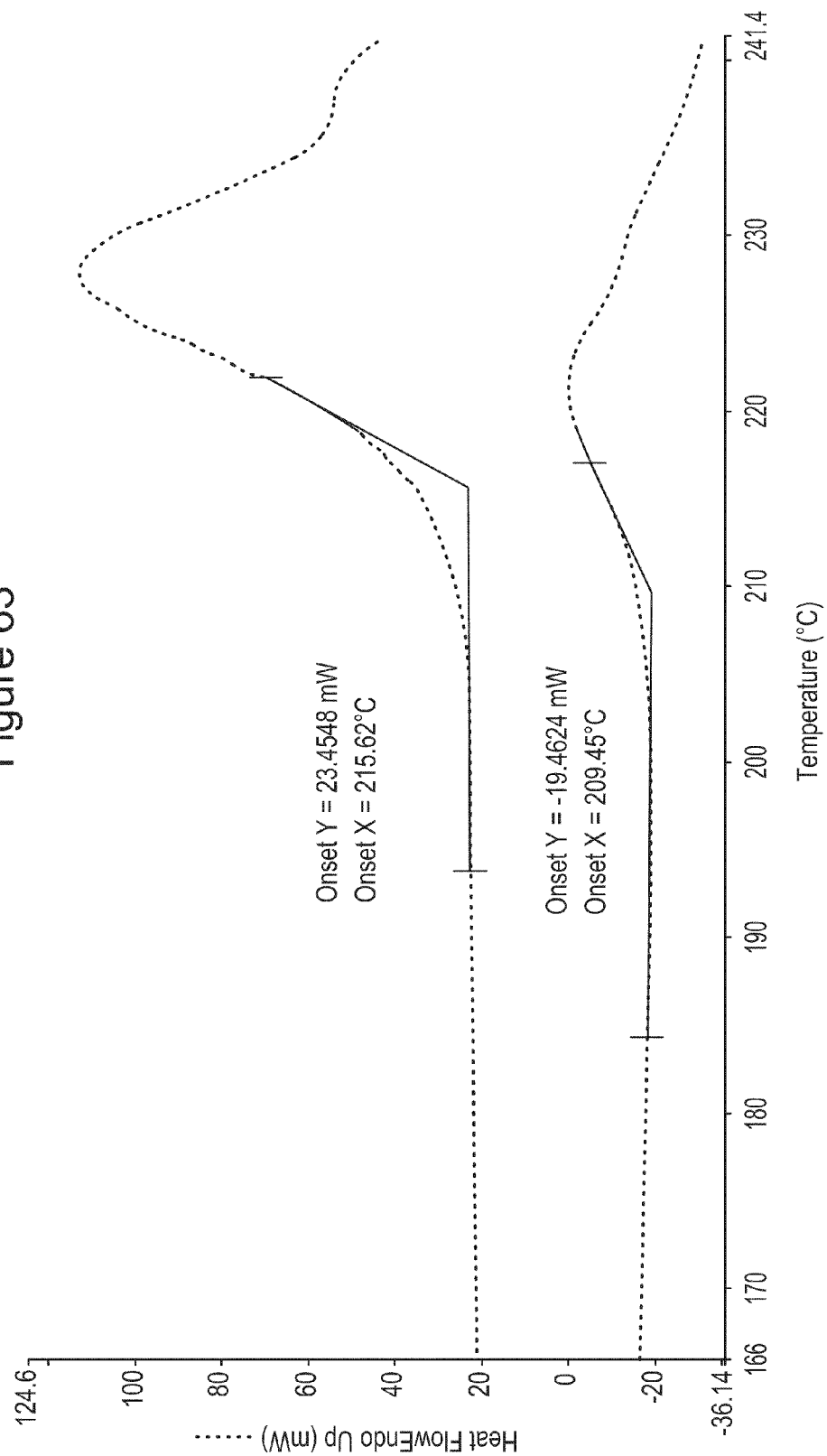
FIG. 63 depicts DSC thermograms of the pre-micronized (top) and micronized (bottom) L-Arginine salt polymorph.

Notes:
Form XXI: produced in 300 mg scale-up
Form XXI-B initial form produced in 5 g scale-up before conversion to Form XXI
New Form is different from Form XXI and Form XXI-B The Form XXI polymorph was micronized and size distribution was measured in comparison of pre-micronized and shown in Table 7 (see also FIG. 60). Micronized salts were also checked by XRPD, Raman, HPLC and DSC (see FIGS. 61-63). XRPD (FIG. 61) indicated no significant change in crystalline structure after micronization. DSC (FIG. 63) showed no significant change after micronization (although the melting point is shifted to a lower temperature). HPLC analysis showed no impurity after micronization. Particle size distribution indicated that the arginine salt can be micronized by grinding rather than using a micronizer.

TABLE 7

Polymorph Form XXI Particle Size Distribution.

| | d50 | | d90 | |
|---|---|---|---|---|
| Measured | 3 times (μm) | Average (μm) | 3 times (μm) | Average (μm) |
| pre-micronized | 19.97 21.13 23.60 | 21.6 | 62.36 70.79 79.85 | 71.0 |
| micronized | 3.98 4.04 4.14 | 4.1 | 7.90 7.94 8.13 | 8.0 |

Crystalline TRIS Salt of 5-(3-chlorophenylamino)benzo[c][2,6]naphthyridine-8-carboxylic acid (Form XXII)

The Form XXII polymorph (TRIS salt) of compound I can be made by following the methods described below in the Experimental section.

Figure 65:
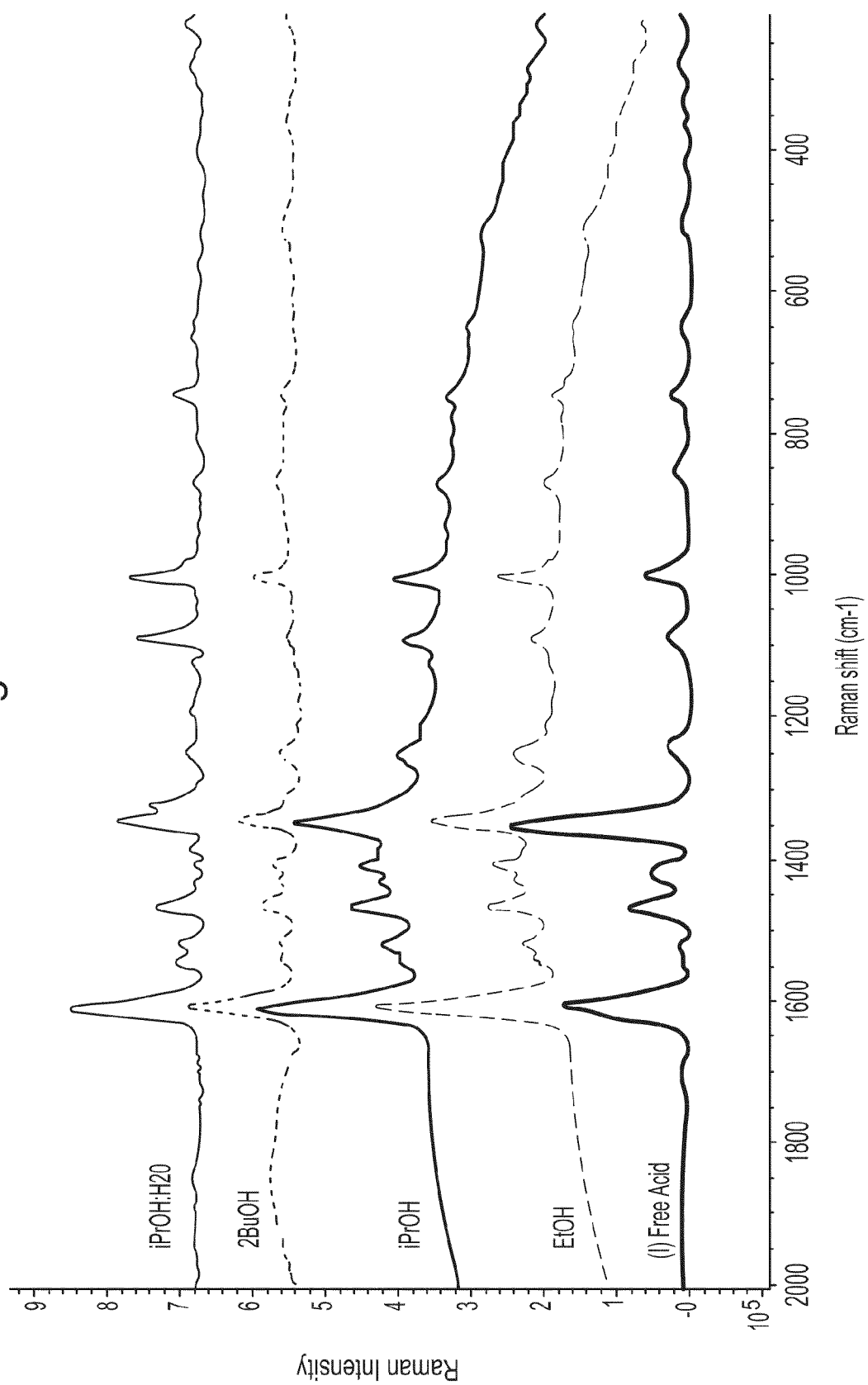
FIG. 65 depicts Raman spectra for the TRIS salt polymorph from the indicated solvents.
Figure 66:
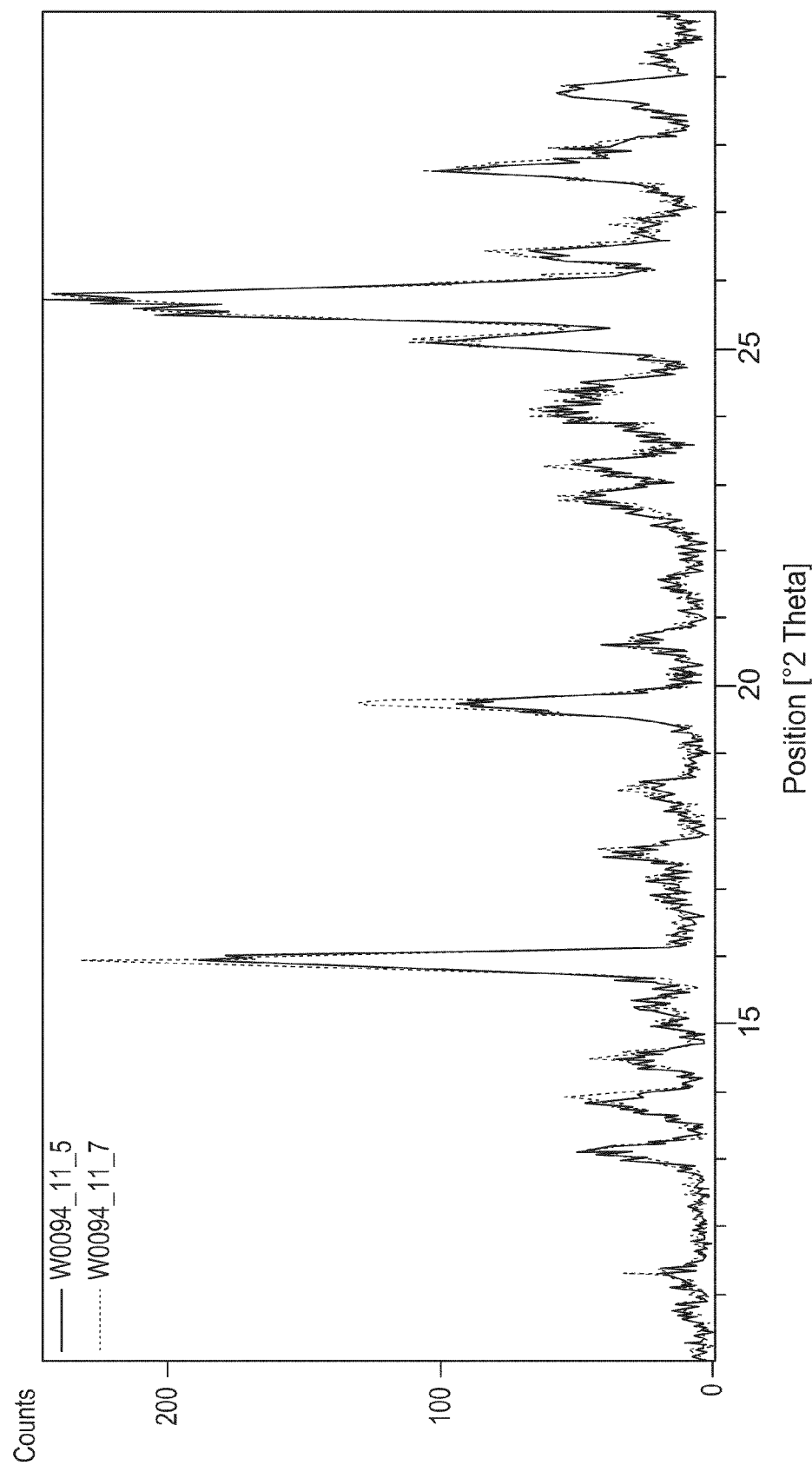
FIG. 66 depicts the powder x-ray diffraction pattern of the TRIS salt polymorph.

The Polarized light microscopy (PLM) shown in FIG. 64 indicates crystalline needles of the Form XXII polymorph from EtOH, iPrOH, 2-BuOH, and iPrOH:H$_2$O. The Raman spectra for the Form XXII polymorph from these solvents is shown in FIG. 65 indicating peak assignments at e.g., about 1609.28, 1519.81, 1468.75, 1408.47, 1347.48, 1251.07, 1089.83, 1002.87, 869.48, 746.14 and 514.45 cm$^{-1}$. The XRPD pattern of Form XXII polymorph from EtOH (FIG. 66) indicates 2θ diffraction lines at e.g., about 10.23°, 10.8°, 11.3°, 13.1°, 13.8°, 14.5°, 15.3°, 16.0°, 17.5°, 18.4°, 19.8°, 20.7°, 21.5°, 22.8°, 23.3°, 24.1°, 24.4°, 25.1°, 25.8°, 26.4°, 27.6° and 28.8°, with major 2θ diffraction lines at e.g., about 16.0°, 19.8° and 25.8°.

Figure 67:
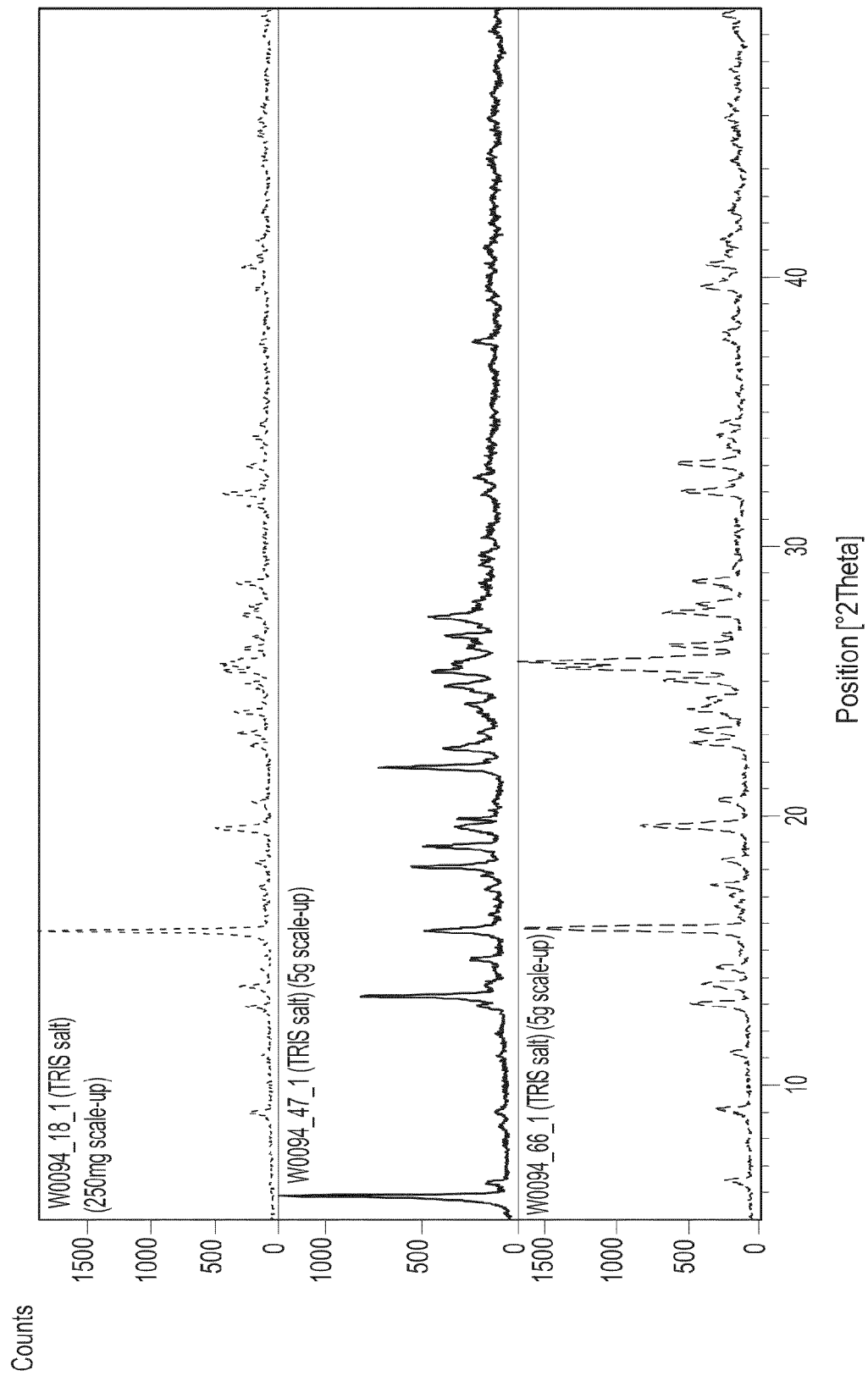
FIG. 67 depicts the powder x-ray diffraction patterns for the TRIS salt polymorph in a 250 mg scale-up (top), an initial 5 g scale-up (middle), and a 5 g scale-up following slurry in MeOH/H$_2$O (bottom).
Figure 68:
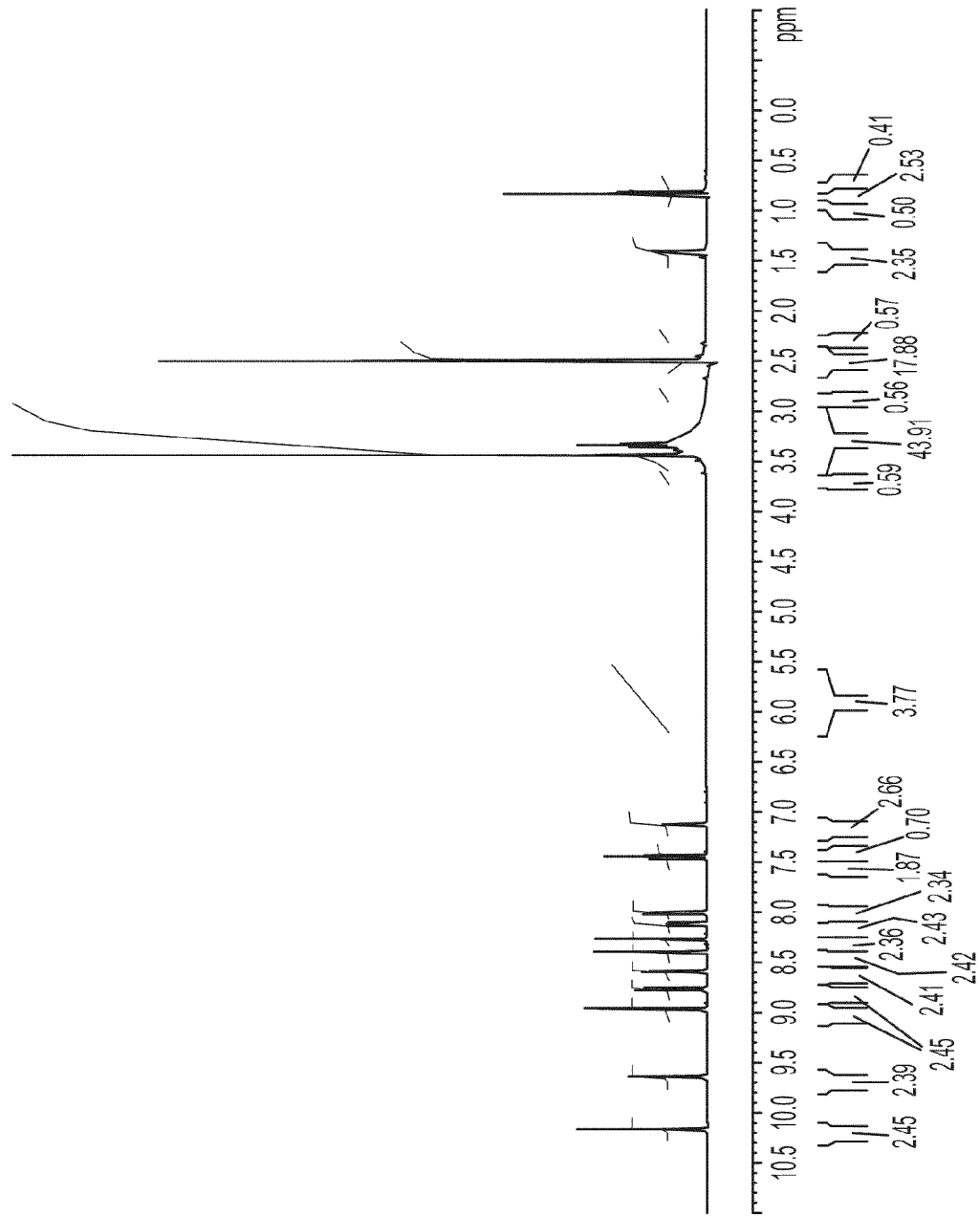
FIG. 68 depicts a solution NMR of the TRIS salt polymorph after scale-up.
Figure 69:
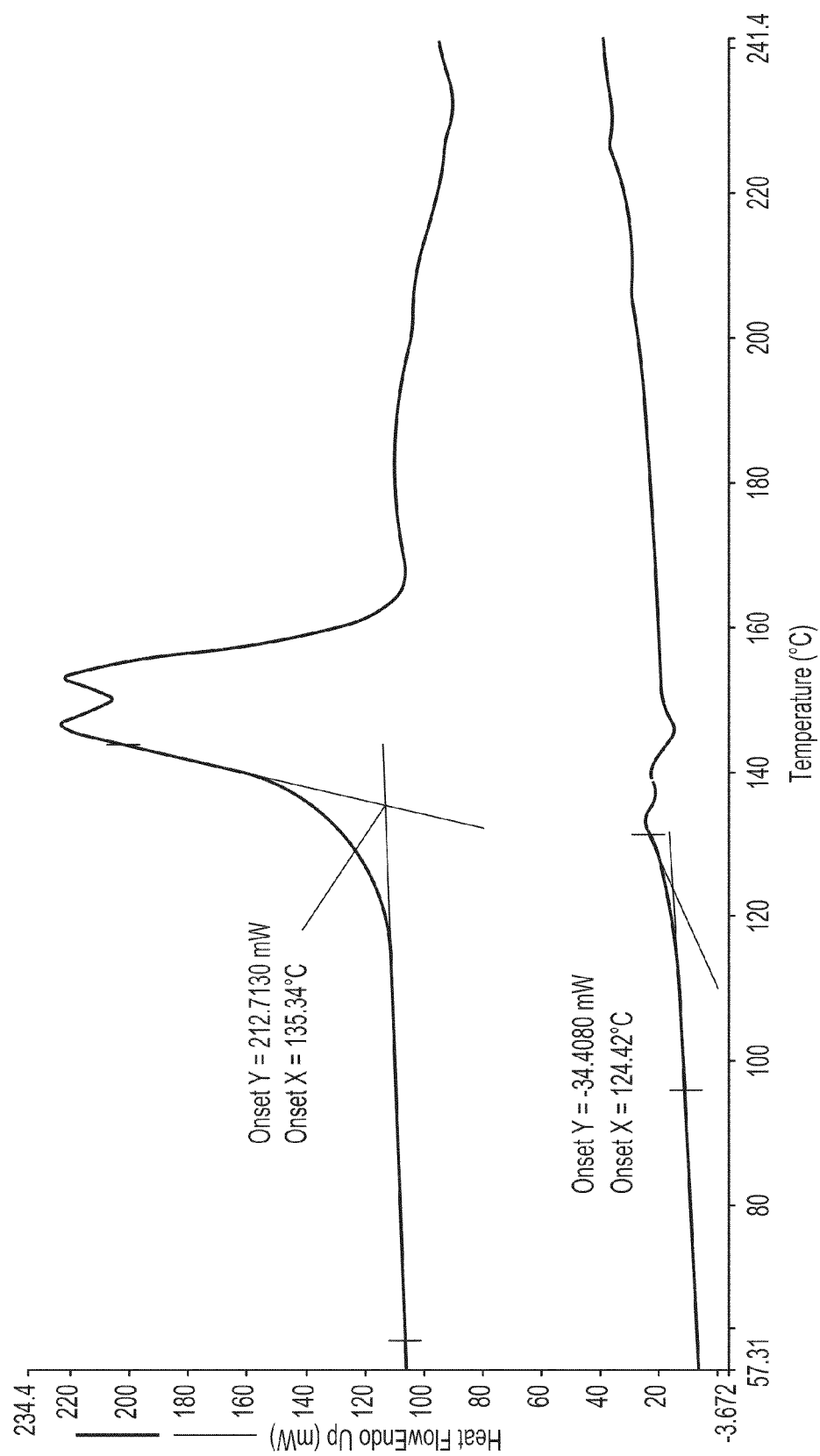
FIG. 69 depicts the DSC thermogram of the TRIS salt polymorph after scale-up.

The Form XXII polymorph was scaled-up to 5 g by following the methods described below in the Experimental section then analyzed by XRPD (FIG. 67), NMR (FIG. 68), Raman (FIG. 79), and HPLC. Raman and NMR spectra indicated that the TRIS 1:1 salt was made. The difference in XRPD for the initial 5 g scale-up material (Form XXII-B) can be seen in FIG. 67 (top vs. middle). The scaled-up material (Form XXII-B) was then slurried in MeOH/H$_2$O (90:10) by temperature cycling at 40° C. and RT, each period for 4 hours, for a total of 5 days, resulting in complete conversion to Form XXII as shown by XRPD (FIG. 67; bottom). Differential Scanning Calorimetry (DSC) data for both the 300 mg and 5 g scaled-up Form XXII (see FIG. 69) shows two endotherms: one at about 135° C. (melting point of the salt) and a second at a slightly higher temp as either degradation or conversion to a different form. The difference of melting points between the 300 mg and 5 g scale-up is likely due to differences in the particle size of the salts (as discussed below). HPLC analysis showed no impurity in the 300 mg and 5 g samples.

Figure 70:
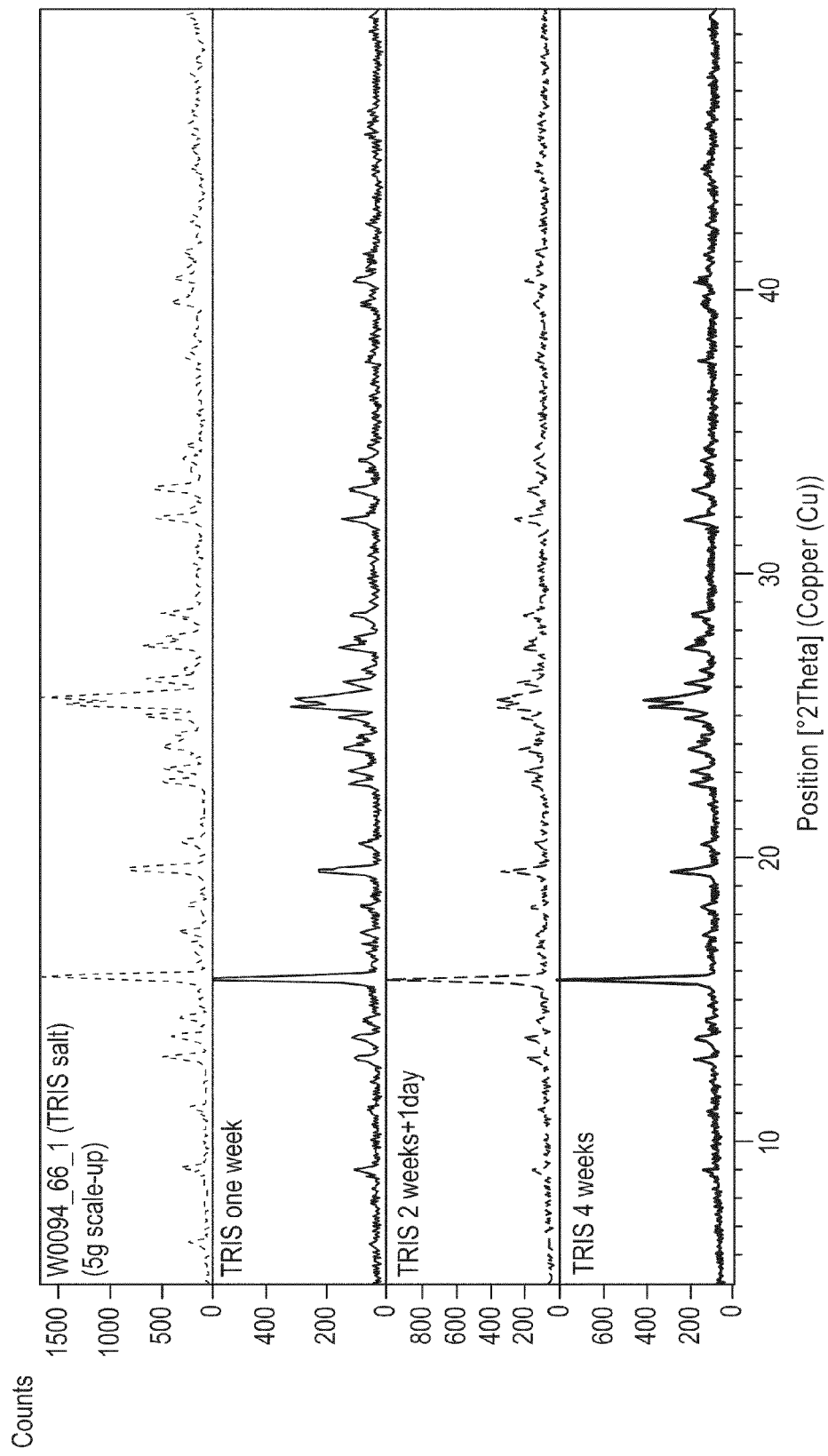
FIG. 70 depicts the powder x-ray diffraction pattern of the TRIS salt polymorph at time 0 (top), 1 week (middle-top), 2 weeks+1 day (middle-bottom), and 4 weeks (bottom).
Figure 71:
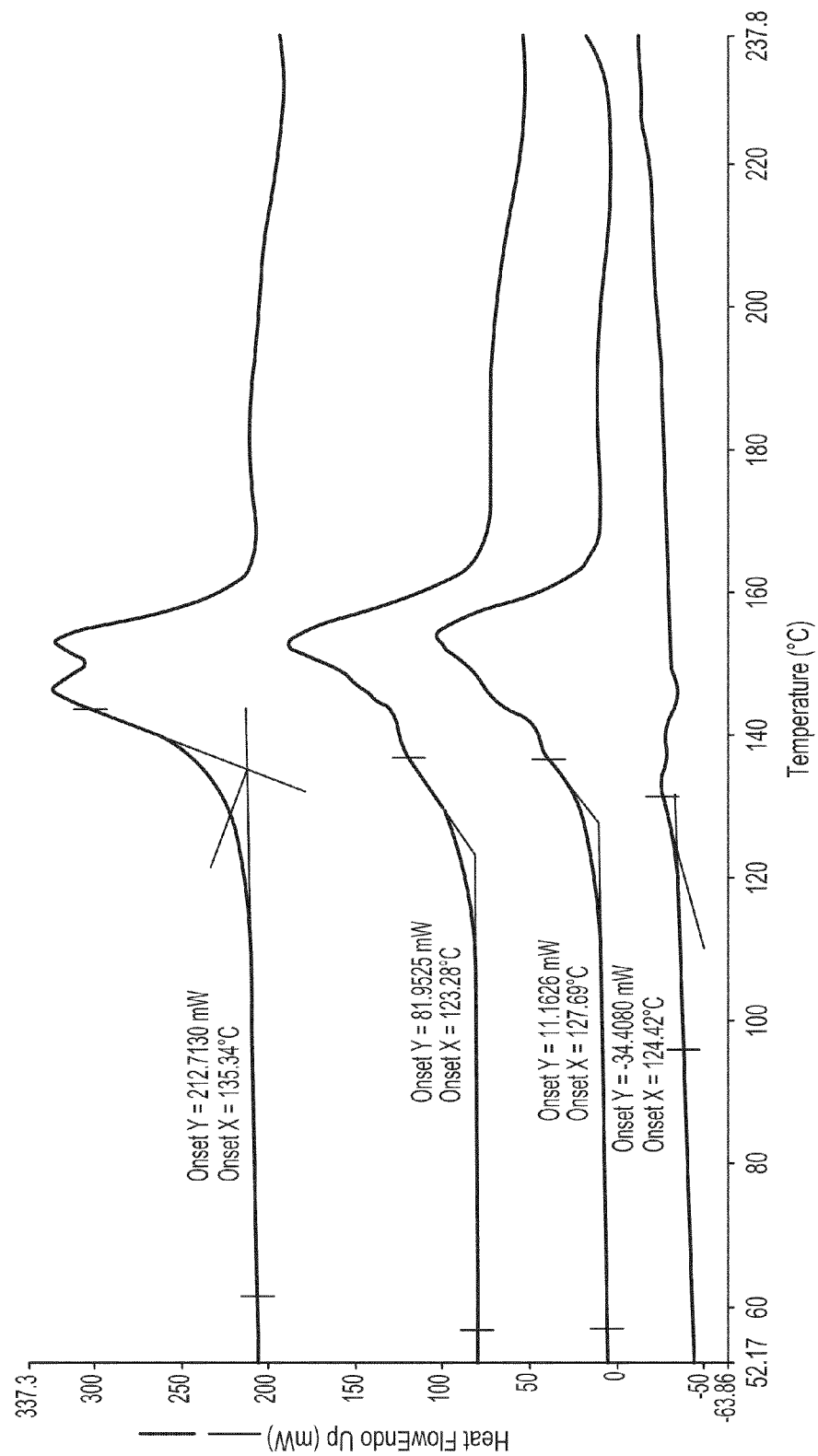
FIG. 71 depicts the DSC thermograms of the TRIS salt polymorph at various time points (bottom to top: time 0, 1 week, 2 weeks, and 4 weeks).

The stability of Form XXII polymorph was studied over a 4 week period using XRPD and DSC (FIGS. 70 and 71, respectively). Both XRPD and DSC showed no significant change. The difference in melting point between 4 samples in the DSC experiment is likely due to the different particle size of salts (as discussed herein). HPLC after 4 weeks confirmed no additional impurity.

Figure 72:
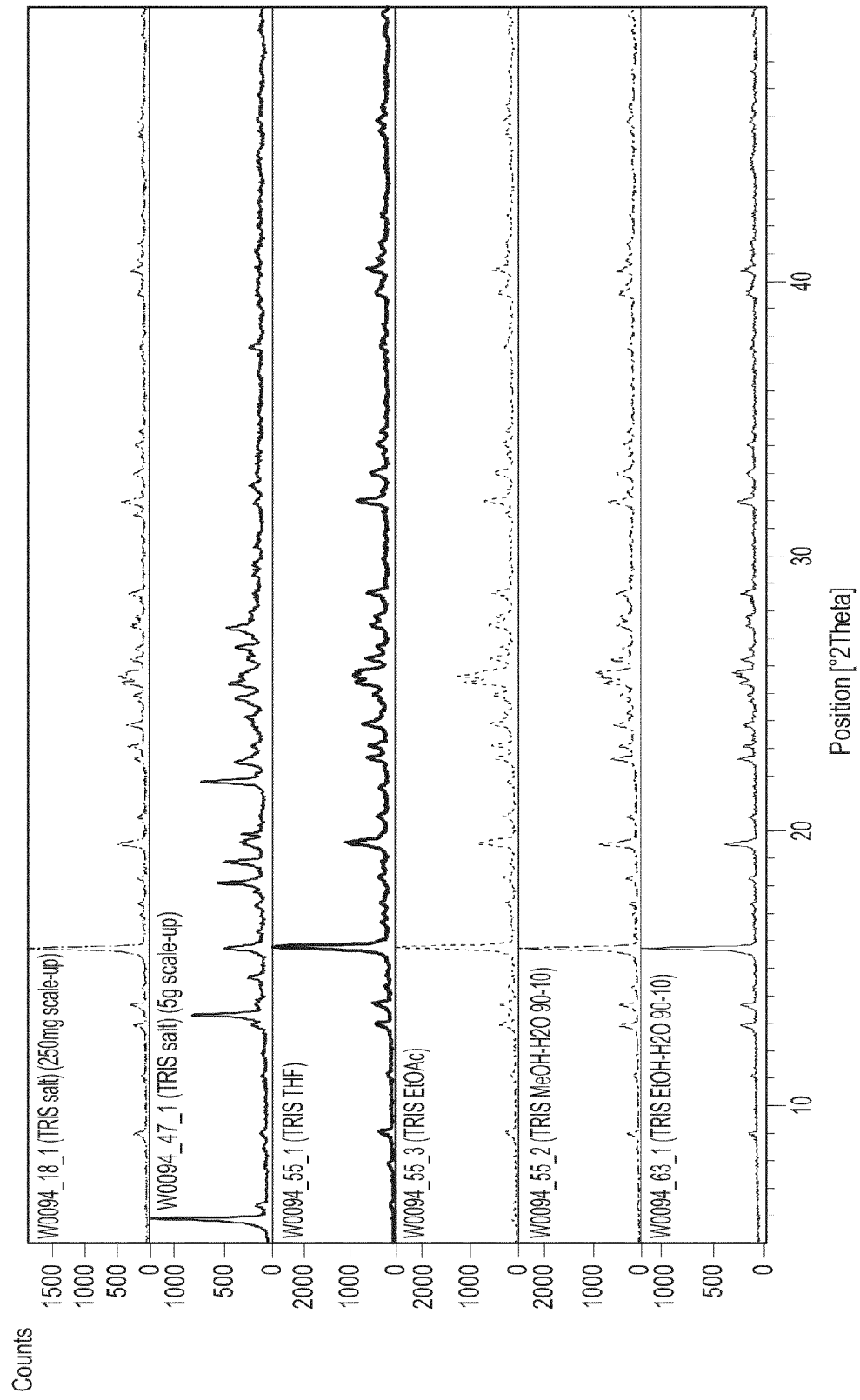
FIG. 72 depicts the powder x-ray diffraction pattern of the TRIS salt polymorph following slurry experiments in the indicated solvents.
Figure 73:
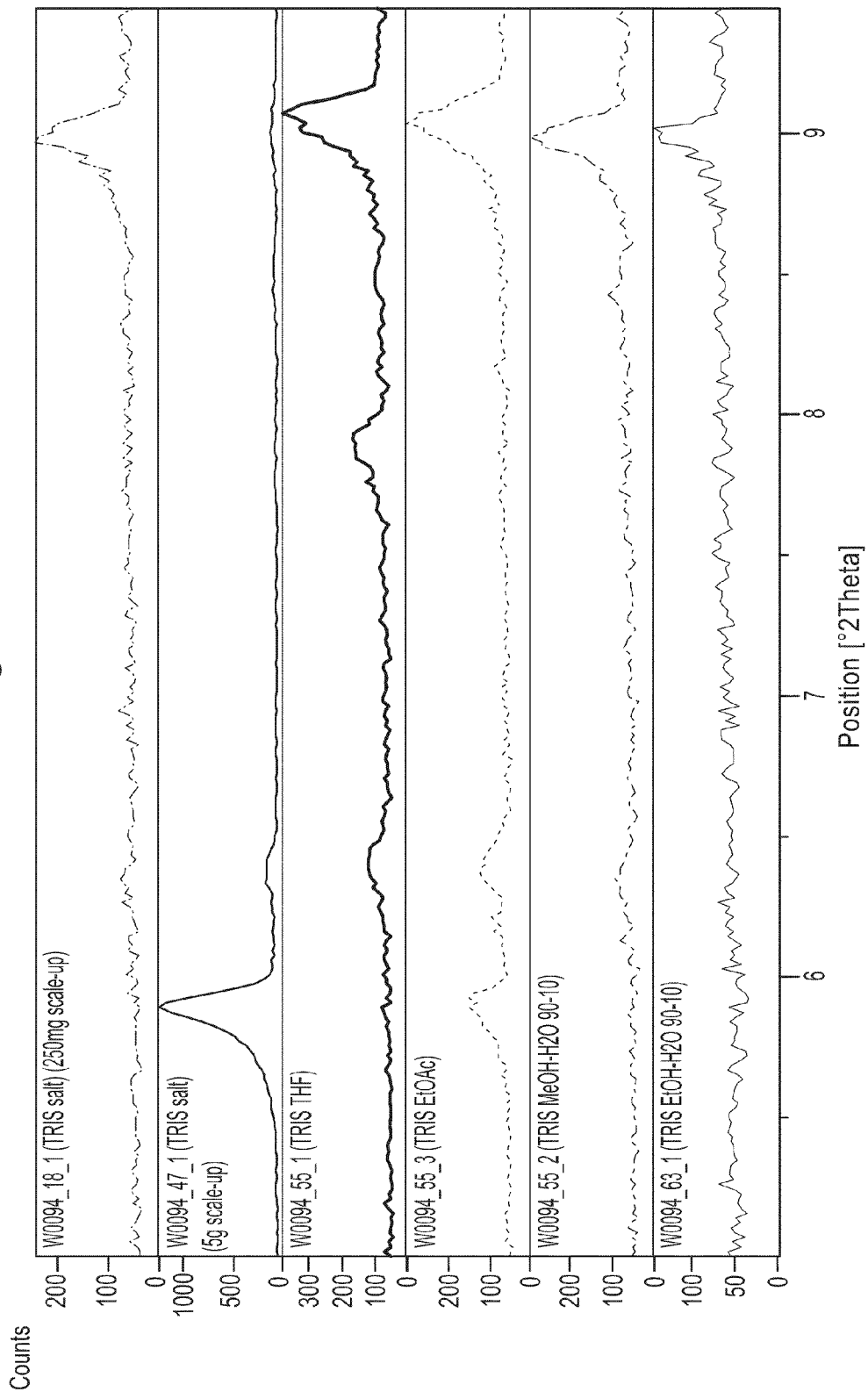
FIG. 73 depicts a zoomed in version of FIG. 71.
Figure 74:
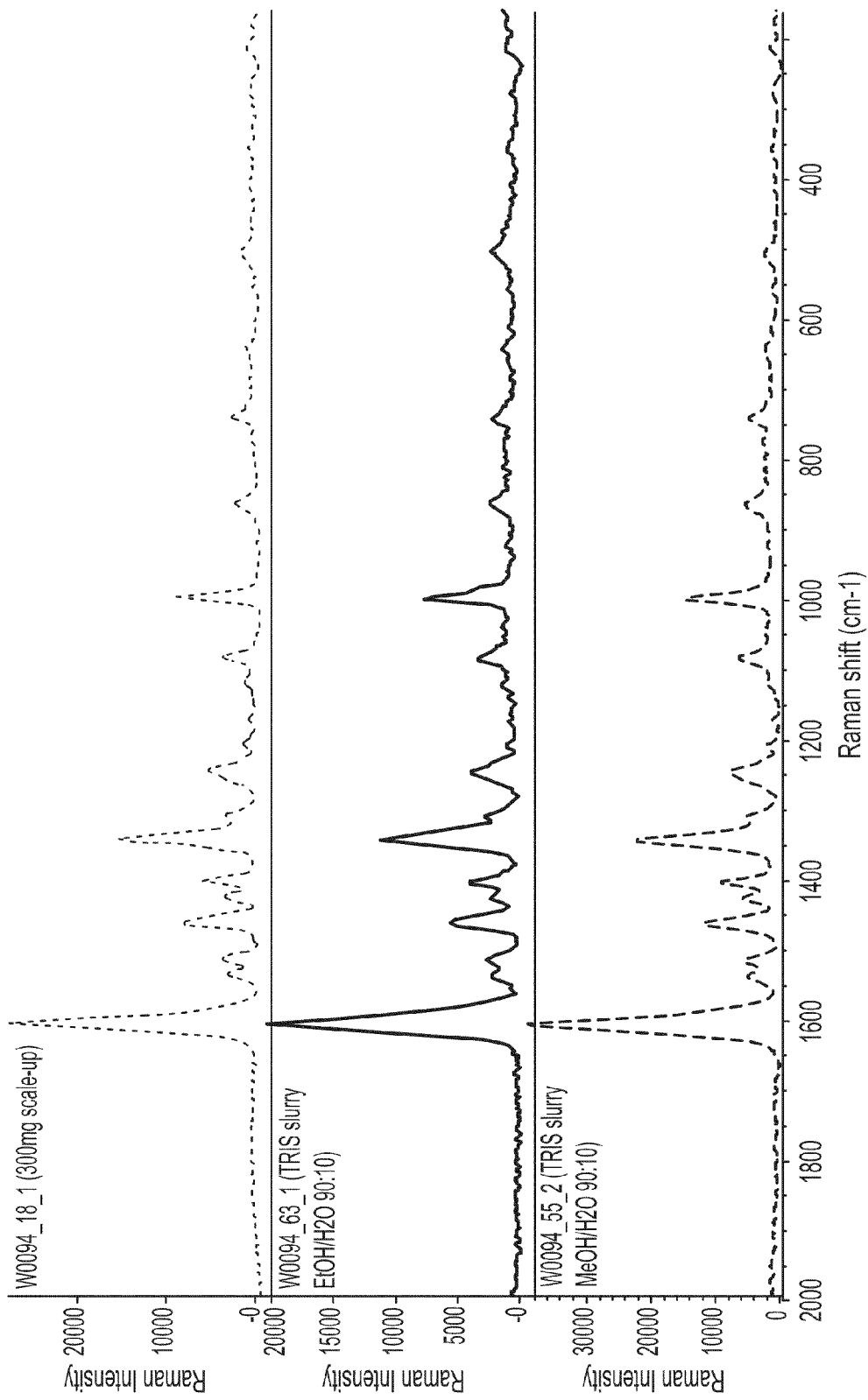
FIG. 74 depicts Raman spectra for the TRIS salt polymorph following slurry experiments in the indicated solvents.

Competitive slurry experiments for the Form XXII polymorph and the original Form XXII-B discuss above were carried out in various solvent systems and the results shown in Table 8. The Form XXII is more stable, as evidenced by the fact that the mixtures of two forms have all changed to Form XXII for each salt (slurry using MeOH/H$_2$O (90:10) and EtOH/H$_2$O (90:10)). Different polymorphic forms were also possibly formed from the slurry in THF or EtOAc (refer to FIGS. 72 and 73). Raman spectra of the slurry products from MeOH/H$_2$O (90:10) and EtOH/H$_2$O (90:10) compared to the 300 mg scale-up material are shown in FIG. 74.

TABLE 8

Competitive Slurry Experiments for Form XXII and Form XXII-B.

| | Solvent | | | |
|---|---|---|---|---|
| Starting material | MeOH/H$_2$O 90:10 | EtOH/H$_2$O 90:10 | THF | EtOAc |
| Form XXII + Form XXII-B | Form XXII | Form XXII | New form | New form |
| Form XXII + Form XXII-B | Form XXII | Form XXII | New form | New form |

Figure 76:
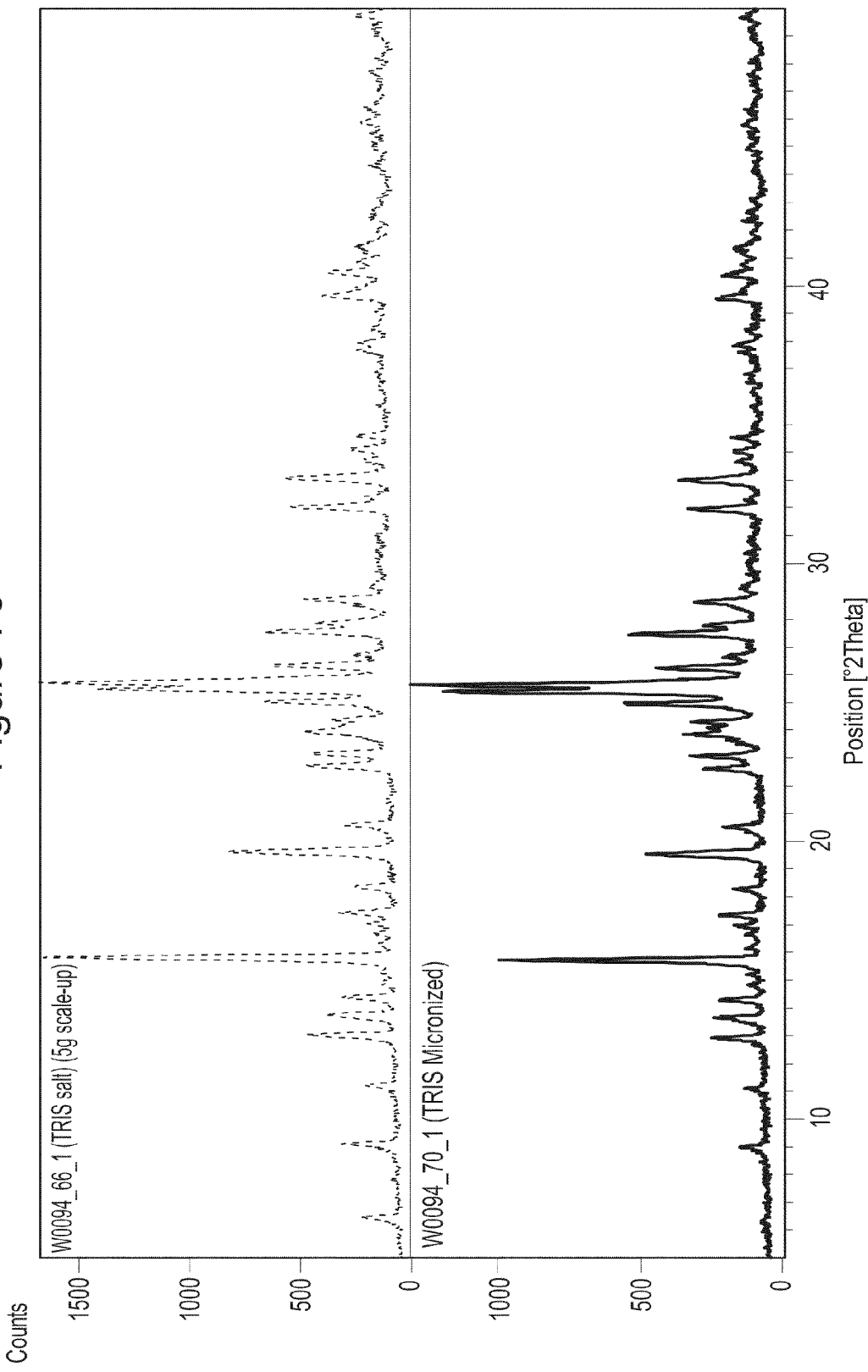
FIG. 76 depicts the powder x-ray diffraction pattern of the pre-micronized (top) and micronized (bottom) TRIS salt polymorph.
Figure 77:
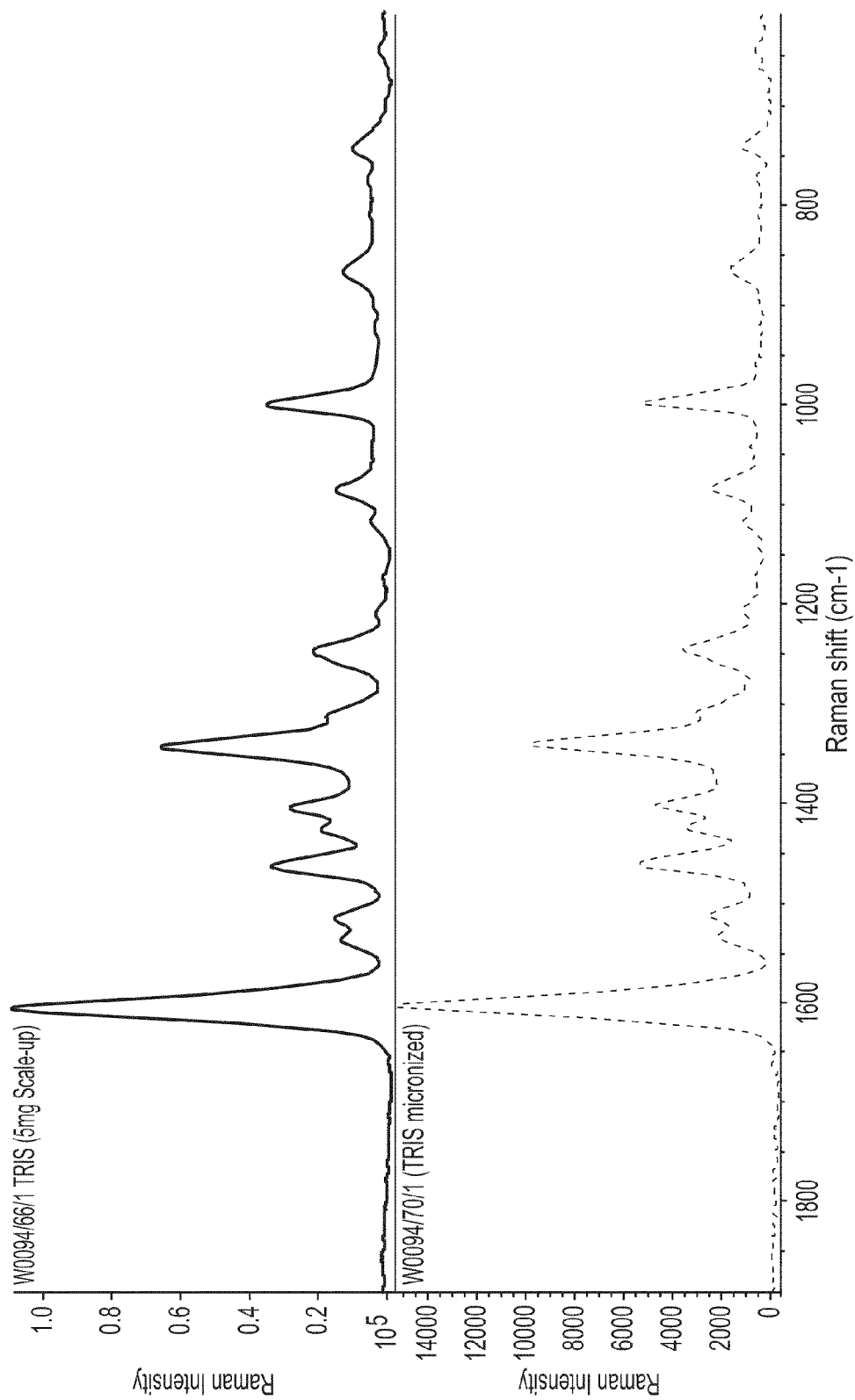
FIG. 77 depicts Raman spectra of the pre-micronized (top) and micronized (bottom) TRIS salt polymorph.
Figure 78:
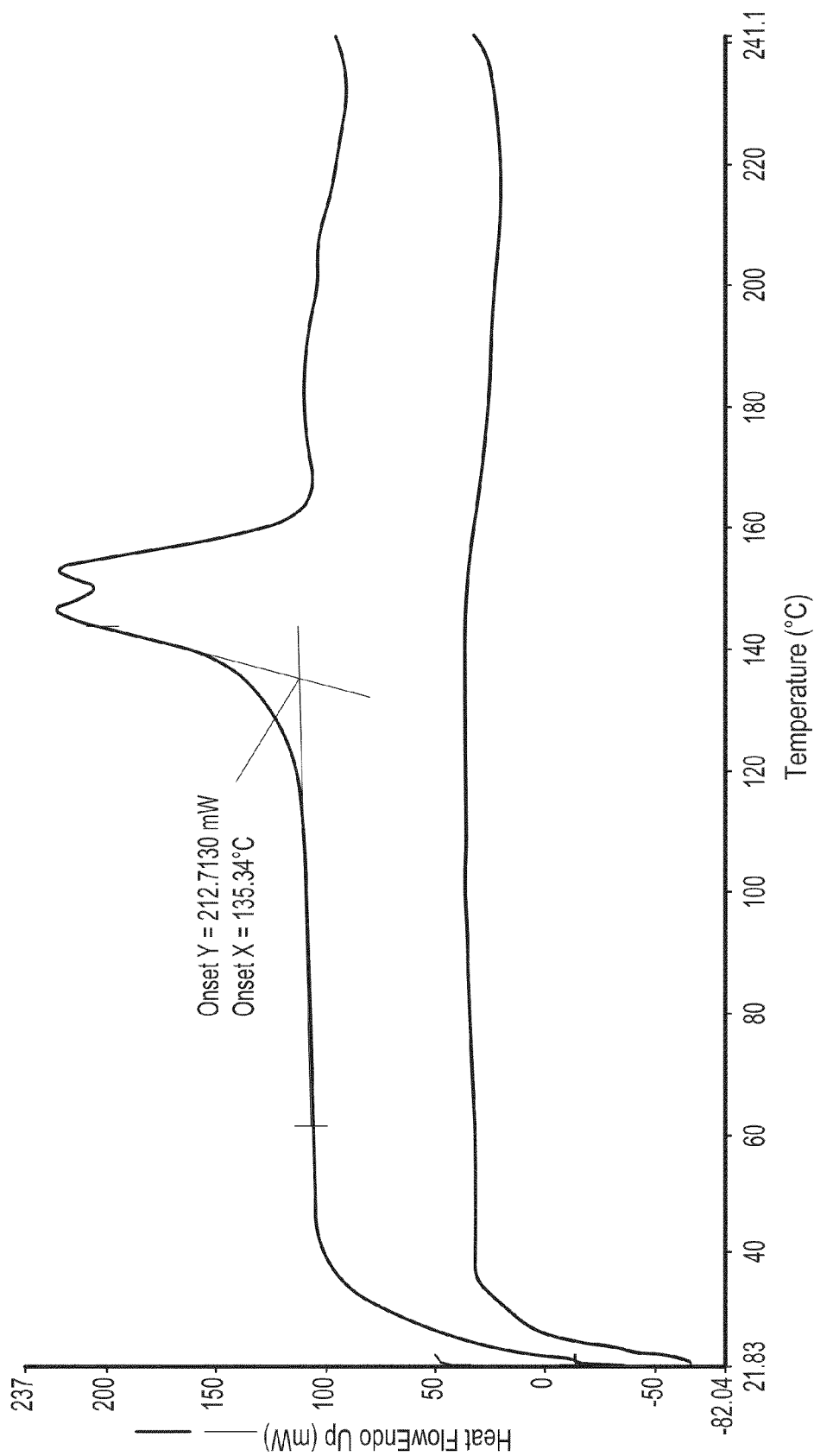
FIG. 78 depicts DSC thermograms of the pre-micronized (top) and micronized (bottom) TRIS salt polymorph.

Notes:
Form XXII: produced in 300 mg scale-up
Form XXII-B initial form produced in 5 g scale-up before conversion to Form XXII
New Form is different from Form XXII and Form XXII-B The Form XXII polymorph was micronized and size distribution was measured in comparison of pre-micronized and shown in Table 9 (see also FIG. 75). Micronized salts were also checked by XRPD, Raman, HPLC and DSC (see FIGS. 76-78). XRPD (FIG. 76) indicated no significant change in crystalline structure after micronization. DSC (FIG. 78) showed no significant change after micronization (although the melting point is shifted to a lower temperature). HPLC analysis showed no impurity after micronization. Particle size distribution indicated that the TRIS salt can be micronized by grinding rather than using a micronizer.

TABLE 9

Polymorph Form XXII Particle Size Distribution.

| Measured | d50 | | d90 | |
|---|---|---|---|---|
| | 3 times (μm) | Average (μm) | 3 times (μm) | Average (μm) |
| pre-micronized | 9.97 | 10.0 | 23.26 | 23.4 |
| | 9.98 | | 23.15 | |
| | 10.06 | | 23.68 | |
| micronized | 6.12 | 6.0 | 10.72 | 10.5 |
| | 6.03 | | 10.51 | |
| | 5.99 | | 10.41 | |

The polymorphs of compound (I) described above (e.g., polymorph Form II, III, IV, V, VI, VII, VIII, IX, X, XI, XII, XIII, XIV, XV, XVI, XVII, XVIII, XIX, XX, XXI, or XXII) may be substantially pure form. Unless otherwise stated, "substantially pure" intends a preparation of the specified polymorph that contains no more than 15% impurity, wherein the impurity intends compounds other than the desired polymorph of compound (I), (e.g., impurities such as an undesired polymorph of compound (I), amorphous compound (I), or a compound other than compound (I)). In one variation, a preparation of substantially pure polymorph (e.g., polymorph Form II, III, IV, V, VI, VII, VIII, IX, X, XI, XII, XIII, XIV, XV, XVI, XVII, XVIII, XIX, XX, XXI, or XXII) is provided wherein the preparation contains no more than 25% impurity, or no more than 20% impurity, or no more than 10% impurity, or no more than 5% impurity, or no more than 3% impurity, or no more than 1% impurity, or no more than 0.5% impurity. To determine if a composition of a polymorph were described as "substantially pure" the skilled artisan, particularly in view of the teaching provided herein, could perform routine XRPD assay to detect the absence of unwanted polymorph(s) in the composition. Additionally, as will be appreciated by the skilled artisan, DSC and FT-IR may also be used. Similarly, HPLC (including HPLC/MS, LC/NIS/MS, etc.), thin layer chromatography, mass spectrometry, gas-chromatography-mass spectrometry, or others analytical methods known to the skilled artisan could be performed on a composition of polymorph to detect the presence of compounds other than compound (I) (e.g., synthetic impurities, degradation products, etc.).

Compositions

The salt forms described herein, such as an amorphous salt form or crystalline polymorph salt form (e.g., polymorph Form II, III, IV, V, VI, VII, VIII, IX, X, XI, XII, XIII, XIV, XV, XVI, XVII, XVIII, XIX, XX, XXI, or XXII) may be used in the preparation of a composition, such as a pharmaceutical composition, by combining the described polymorph with one or more pharmaceutical acceptable carriers, excipients, stabilizing agents and/or other agents, which are known in the art, for use in the methods of treatment, methods of administration, and dosage regimes described herein. The compositions may vary or be tailored according to the condition to be treated, the amount of compound to be administered, the condition of the individual, and other variables that will readily be apparent to one of ordinary skill in the art in view of the teachings provided herein. The polymorphs may be formulated, for example, as a solid, semi-solid, and liquid dosage forms, such as tablets, pills, powders, liquid solutions or suspensions (e.g., when formulated with a surface interaction inhibitor), suppositories, injectable and infusible solutions, and sprays. The preferred form depends on the intended mode of administration and therapeutic application. The following compositions, additives, and methods are merely exemplary and are in no way limiting.

Additives used with the salt forms described herein, such as an amorphous salt form or crystalline polymorph salt form (e.g., polymorph Form II, III, IV, V, VI, VII, VIII, IX, X, XI, XII, XIII, XIV, XV, XVI, XVII, XVIII, XIX, XX, XXI, or XXII) include, for example, one or more excipients (e.g., one or more excipients), antioxidants (e.g., one or more antioxidants), stabilizers (e.g., one or more stabilizers), preservatives (e.g., one or more preservatives), pH adjusting and buffering agents (e.g., one or more pH adjusting and/or buffering agents), tonicity adjusting agents (e.g., one or more tonicity adjusting agents), thickening agents (e.g., one or more thickening agents), suspending agents (e.g., one or more suspending agents), binding agents (e.g., one or more binding agents, viscosity-increasing agents (e.g., one or more viscosity-increasing agents), surface interaction inhibitors, and the like, either alone or together with one or more additional pharmaceutical agents, provided that the additional components are pharmaceutically acceptable for the particular disease to be treated (e.g., cancer). In some embodiments, the composition may include combinations of two or more of the additional components as described herein (e.g., 2, 3, 4, 5, 6, 7, 8, or more additional components). In some embodiments, the composition may comprise a polymorph combined with a surface interaction inhibitor, which creates a physical barrier between adjacent particles. In some embodiments, the additives include processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-β-cyclodextrin, polyvinylpyrrolidinone, low melting waxes, ion exchange resins, and the like, as well as combinations of any two or more thereof. Other suitable pharmaceutically acceptable excipients are described in REMINGTON'S PHARMACEUTICAL SCIENCES, Marck Pub. Co., New Jersey $18^{th}$ edition (1996), and REMINGTON: THE SCIENCE AND PRACTICE OF PHARMACY, Lippincott Williams & Wilkins, Philadelphia, $20^{th}$ edition (2003) and $21^{st}$ edition (2005).

Compositions suitable for oral administration may comprise, for example, (a) liquid solutions (e.g., a polymorph combined with one or more solvents with a surface interaction inhibitor), such as an effective amount of the compound dissolved in diluents, such as water, saline, or orange juice, (b) capsules, sachets or tablets, each containing a predetermined amount of the active ingredient, as solids or granules, (c) suspensions (including microsuspensions) in an appropriate liquid, (d) suitable emulsions, and (e) powders. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

The salt forms described herein, such as an amorphous salt form or crystalline polymorph salt form (e.g., polymorph Form II, III, IV, V, VI, VII, VIII, IX, X, XI, XII, XIII, XIV, XV, XVI, XVII, XVIII, XIX, XX, XXI, or XXII) may be enclosed in a hard or soft capsule, may be compressed into tablets, or may be incorporated with beverages or food or otherwise incorporated into the diet. Capsules may be formulated by mixing the polymorph with an inert pharmaceutical diluent and inserting the mixture into a hard gelatin capsule of the appropriate size. If soft capsules are desired, a slurry of the polymorph with an acceptable vegetable oil, light petroleum or other inert oil can be encapsulated by machine into a gelatin capsule.

Liquid dosage forms for oral administration may include pharmaceutically acceptable emulsions, solutions, suspensions, syrups, and elixirs containing inert diluents commonly used in the art, such as water. Such formulations may also comprise adjuvants, such as surface interaction inhibitors, wetting agents, emulsifying and suspending agents, cyclodextrins, and sweetening, flavoring, and perfuming agents. The skilled artisan will appreciate that complete solvation of crystalline or amorphous solids is not encompassed by the instant invention and the polymorph should be insoluble in the carrier to preserve the polymorph that is to be employed in the specific composition.

Compositions suitable for parenteral administration include aqueous and non-aqueous, isotonic sterile injection solutions, which can contain anti-oxidants, buffers, bacteriostats, and solutes that render the formulation compatible with the blood of the intended recipient, and aqueous and non-aqueous sterile suspensions that can include suspending agents, solubilizers, thickening agents, stabilizing agents, and preservatives. The compositions may be presented in unit-dose or multi-dose sealed containers, such as ampules and vials, and can be stored in a freeze-dried (lyophilized) condition requiring only the addition of the sterile liquid excipient methods of treatment, methods of administration, and dosage regimes described herein (i.e., water) for injection, immediately prior to use. Extemporaneous injection solutions and suspensions may be prepared from sterile powders, granules, and tablets of the kind previously described.

Injectable preparations (for example, sterile injectable aqueous or oleaginous suspensions) may be formulated according to the known art using suitable dispersing or wetting agents and suspending agents. In some embodiments, the salt forms described herein, such as an amorphous salt form or crystalline polymorph salt form (e.g., polymorph Form II, III, IV, V, VI, VII, VIII, IX, X, XI, XII, XIII, XIV, XV, XVI, XVII, XVIII, XIX, XX, XXI, or XXII) is formulated as a microsuspension (e.g., for parenteral administration, oral administration, or otherwise). Microsuspensions are thermodynamically stable dispersions of microcrystals, which may be stabilized by an interfacial film of surfactant molecules functioning as a dispersing agent (*Encyclopedia of Pharmaceutical Technology* (New York: Marcel Dekker, 1992), volume 9, the content of which is hereby incorporated by reference).

The sterile injectable preparation may also be a sterile injectable solution or suspension in a nontoxic parenterally acceptable diluent or solvent, for example, as a solution in propylene glycol. The sterile injectable preparation may also be a sterile powder to be reconstituted using acceptable vehicles prior to administration. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid may be used in the preparation of injectables.

Compositions derived the salt forms described herein, such as an amorphous salt form or crystalline polymorph salt form (e.g., polymorph Form II, III, IV, V, VI, VII, VIII, IX, X, XI, XII, XIII, XIV, XV, XVI, XVII, XVIII, XIX, XX, XXI, or XXII) formulated in liquid form (for oral administration, parenteral administration, or otherwise) may have a pH in the range of about 4.5 to about 9.0, including for example pH ranges of any of about 5.0 to about 8.0, about 6.5 to about 7.5, and about 6.5 to about 7.0. In some embodiments, the pH of the composition is formulated to no less than about 6, including for example no less than about any of 6.5, 7, or 8 (e.g., about 8). The composition can also be made to be isotonic with blood by the addition of a suitable tonicity modifier, such as glycerol.

The salt forms described herein, such as an amorphous salt form or crystalline polymorph salt form (e.g., polymorph composition containing Form II, III, IV, V, VI, VII, VIII, IX, X, XI, XII, XIII, XIV, XV, XVI, XVII, XVIII, XIX, or XX) may also be formulated for administration by inhalation. Compositions suitable for aerosol administration which comprise the polymorph may include, for example, aqueous and non-aqueous, isotonic sterile solutions, which can contain anti-oxidants, buffers, bacteriostats, and solutes, as well as aqueous and non-aqueous sterile suspensions that can include suspending agents, solubilizers, thickening agents, stabilizing agents, and preservatives, alone or in combination with other suitable components, which can be made into aerosol compositions to be administered via inhalation. These aerosol formulations can be placed into pressurized acceptable propellants, such as dichlorodifluoromethane, propane, nitrogen, and the like. They also can be formulated as pharmaceuticals for non-pressured preparations, such as in a nebulizer or an atomizer.

Various sustained release systems for drugs have also been devised, and can be applied to Salt forms of the invention. See, for example, U.S. Pat. No. 5,624,677, the methods of which are incorporated herein by reference.

The salt forms described herein, such as an amorphous salt form or crystalline polymorph salt form (e.g., polymorph Form II, III, IV, V, VI, VII, VIII, IX, X, XI, XII, XIII, XIV, XV, XVI, XVII, XVIII, XIX, XX, XXI, or XXII) may also be formulated in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The salt forms described herein, such as an amorphous salt form or crystalline polymorph salt form (e.g., polymorph Form II, III, IV, V, VI, VII, VIII, IX, X, XI, XII, XIII, XIV, XV, XVI, XVII, XVIII, XIX, XX, XXI, or XXII) may also be formulated for topical administration, especially when the target of treatment includes areas or organs readily accessible by topical application, including diseases of the eye, the skin, or the lower intestinal tract. Suitable topical compositions are readily prepared for each of these areas or organs.

Topical application for the lower intestinal tract can be effected in a rectal suppository formulation (see above) or in a suitable enema formulation. Topically-transdermal patches may also be used.

Also provided are unit dosage forms comprising the compositions described herein (e.g., compositions comprising a salt form described herein, such as an amorphous salt form or crystalline polymorph salt form, such as Form II, III, IV, V, VI, VII, VIII, IX, X, XI, XII, XIII, XIV, XV, XVI, XVII, XVIII, XIX, or XX). These unit dosage forms can be stored in a suitable packaging in single or multiple unit dosages and may also be further sterilized and sealed. For example, the pharmaceutical formulation (e.g., a dosage or unit dosage form of a pharmaceutical composition) may include (i) a polymorph and (ii) a pharmaceutically acceptable carrier. In some embodiments, the pharmaceutical composition also includes one or more other compounds (or pharmaceutically acceptable salts thereof) that are useful fdr treating a particular condition (e.g., cancer). In various variations, the amount of polymorph in the composition is included in any of the following ranges: about 5 to about 50 mg, about 20 to about 50 mg, about 50 to about 100 mg, about 100 to about 125 mg, about 125 to about 150 mg, about 150 to about 175 mg, about 175 to about 200 mg, about 200 to about 225 mg, about 225 to about 250 mg, about 250 to about 300 mg, about 300 to about 350 mg, about 350 to about 400 mg, about 400 to about 450 mg, or about 450 to about 500 mg. In some embodiments, the amount of polymorph in the composition (e.g., a dosage or unit dosage form) is in the range of about 5 mg to about 500 mg, such as about 30 mg to about 300 mg or about 50 mg to about 200 mg. In some embodiments, the composition and carrier are suitable for oral administration. In some embodiments, the polymorph is the only pharmaceutically active agent for the treatment of the condition (e.g., cancer) that is contained in the composition.

Kits

Also provided are kits containing materials useful for the treatment of a disease (e.g., cancer) that is responsive to salt forms described herein, such as an amorphous salt form or crystalline polymorph salt form. The kits may contain a polymorph (e.g., polymorph Form II, III, IV, V, VI, VII, VIII, IX, X, XI, XII, XIII, XIV, XV, XVI, XVII, XVIII, XIX, XX, XXI, or XXII) and optionally contain instructions for use (e.g., instructions for preparation and/or administration of a composition comprising the polymorph). Information detailing possible side effects of the composition, and any other relevant information may also be enclosed. The instructions may be in any suitable format, including, but not limited to, printed matter, videotape, computer readable disk, optical disc or directions to internet-based instructions.

In one aspect, is provided a kit for treating an individual who suffers from or is susceptible to the disease or conditions described herein (e.g., cancer), comprising a first container comprising a dosage amount of a formulation as disclosed herein, and instructions for use. The container may be any of those known in the art and appropriate for storage and delivery of intravenous formulation. In certain embodiments the kit further comprises a second container comprising a pharmaceutically acceptable carrier, diluent, adjuvant, etc. for preparation of the formulation to be administered to the individual.

In some embodiments, the kits comprise a container with a label. Suitable containers include, for example, bottles, vials, and test tubes. The containers may be formed from a variety of materials such as glass or plastic. The containers may hold a salt forms described herein, such as an amorphous salt form or crystalline polymorph salt form (e.g., polymorph Form II, III, IV, V, VI, VII, VIII, IX, X, XI, XII, XIII, XIV, XV, XVI, XVII, XVIII, XIX, XX, XXI, or XXII) or a composition thereof. The label on the container may indicate that the polymorph, the composition, or the pharmaceutically active agent (compound (I)) is used for treating or suppressing a condition that is responsive to compound (I) (e.g., cancer), and may also indicate directions for either in vivo or in vitro use, such as those described herein.

The kit may further include other materials desirable from a commercial and user standpoint, including other buffers, diluents, filters, needles, syringes, and package inserts with instructions for performing any methods described herein. In some embodiments, the kit comprises the container described above and a second container comprising a buffer.

The kits may include additional pharmaceutical agents for use in conjunction with the formulation described herein. In some variations, the additional pharmaceutical agent(s) may be one or more anticancer drug(s). These agents may be provided in a separate form, or mixed with the polymorphs described herein, provided such mixing does not reduce the effectiveness of either the pharmaceutical agent or formulation described herein and is compatible with the route of administration. Similarly the kits may include additional agents for adjunctive therapy or other agents known to the skilled artisan as effective in the treatment or prevention of the conditions described herein (e.g., cancer).

Kits may also be provided that contain sufficient dosages of the compounds described herein (including compositions thereof) to provide effective treatment for an individual for an extended period, such as 1-3 days, 1-5 days, a week, 2 weeks, 3, weeks, 4 weeks, 6 weeks, 8 weeks, 3 months, 4 months, 5 months, 6 months, 7 months, 8 months, 9 months or more.

The kits may include the composition as described herein packaged in either a unit dosage form or in a multi-use form. The kits may also include multiple units of the unit dose form. The kits may be used for any of the methods described herein, including, for example, to treat an individual with cancer, or to delay cancer. In certain embodiments the kits may include a dosage amount of at least one formulation as disclosed herein. Kits may also comprise a means for the delivery of the composition thereof.

Methods of Treatment

The salt forms described herein, such as an amorphous salt form or crystalline polymorph salt form (e.g., polymorph Form II, III, IV, V, VI, VII, VIII, IX, X, XI, XII, XIII, XIV, XV, XVI, XVII, XVIII, XIX, XX, XXI, or XXII) may be used in various methods, e.g., as described in copending U.S. application Ser. No. 11/849,230 (US2009/0105233) and U.S. application Ser. No. 12/396,084 (Protein Kinase Modulators). The content of both of these applications, particularly with respect to methods of treatment, is hereby incorporated by reference.

In one aspect is are provided methods for modulating (e.g., inhibiting) the activity of a CK2 protein or PARP protein, which comprises contacting a system comprising the protein with an effective amount of compound (I):

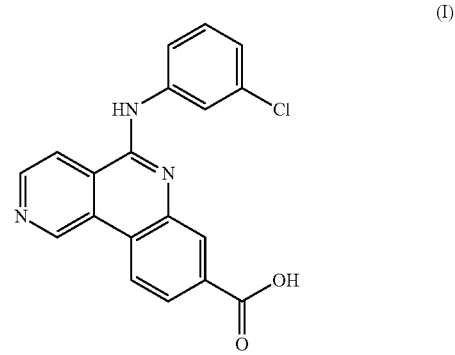 [SMILES: O=C(O)c1ccc2c(c1)nc(Nc1cccc(Cl)c1)c1ccncc12]

(I)

wherein compound (I) is derived from a salt form described herein, such as an amorphous salt form or crystalline polymorph salt form (e.g., polymorph Form II, III, IV, V, VI, VII, VIII, IX, X, XI, XII, XIII, XIV, XV, XVI, XVII, XVIII, XIX, XX, XXI, or XXII). The system in such embodiments can be a cell-free system or a system comprising cells. Also provided are methods for reducing cell proliferation, and optionally inducing apoptosis, which comprises contacting cells with a compound (I) in an amount effective to reduce proliferation of the cells, wherein compound (I) is derived from a salt form described herein, such as an amorphous salt form or crystalline polymorph salt form (e.g., polymorph Form II, III, IV, V, VI, VII, VIII, IX, X, XI, XII, XIII, XIV, XV, XVI, XVII, XVIII, XIX, XX, XXI, or XXII). The cells in such embodiments can be in a cell line, in a tissue or in a subject (e.g., a research animal or human). In related embodiments, provided are compositions comprising compound (I) described herein in combination with a protein or cell, such as an isolated protein (e.g., isolated CK2 or other serine-threonine protein kinase protein or PARP protein) or a cell in a cell line (e.g., HCT-116 cell line), wherein compound (I) is derived from a polymorph described herein.

Provided also are methods for modulating a serine-threonine protein kinase activity. Serine-threonine protein kinases catalyze the transfer of a gamma phosphate from adenosine triphosphate to a serine or threonine amino acid in a peptide or protein substrate. Thus, included herein are methods which comprise contacting a system comprising a serine-threonine protein kinase protein with compound (I) in an amount effective for modulating (e.g., inhibiting) the activity of the protein, wherein compound (I) is derived from a polymorph described herein. In some embodiments, the activity of the serine-threonine protein kinase is the catalytic activity of the protein (e.g., catalyzing the transfer of a gamma phosphate from adenosine triphosphate to a peptide or protein substrate). In certain embodiments, provided are methods for identifying a candidate molecule that interacts with a serine-threonine protein kinase, which comprise: contacting a composition containing a serine-threonine protein kinase and compound (I), wherein compound (I) is derived from a polymorph described herein, with a candidate molecule under conditions in which compound (I) and the protein interact, and determining whether the amount of compound (I) that interacts with the protein is modulated relative to a control interaction between compound (I) and the protein without the candidate molecule, whereby a candidate molecule that modulates the amount of compound (I) interacting with the protein relative to the control interaction is identified as a candidate molecule that interacts with the protein. Systems in such embodiments can be a cell-free system or a system comprising cells (e.g., in vitro). The protein, compound (I) or the molecule in some embodiments is in association with a solid phase. In certain embodiments, the interaction between compound (I) and the protein is detected via a detectable label, where in some embodiments the protein comprises a detectable label and in certain embodiments the compound comprises a detectable label. The interaction between compound (I) and the protein sometimes is detected without a detectable label.

The serine-threonine protein kinase can be from any source, such as a mammal, ape or human, for example. Examples of serine-threonine protein kinases that can be inhibited by compounds disclosed herein include without limitation human versions of CK2, CK2α2, Pim-1, CDK1/cyclinB, c-RAF, Mer, MELK, DYRK2, Flt3, Flt3 (D835Y), Flt4, HIPK3, HIPK2, ZIPK and ZIPK. A serine-threonine protein kinase sometimes is a member of a sub-family containing one or more of the following amino acids at positions corresponding to those listed in human CK2: leucine at position 45, methionine at position 163 and isoleucine at position 174. Examples of such protein kinases include without limitation human versions of CK2, STK 10, HIPK2, HIPK3, DAPK3, DYK2 and PIM-1. Nucleotide and amino acid sequences for serine-threonine protein kinases and reagents are publicly available (e.g., World Wide Web URLs ncbi.nlm.nih.gov/sites/entrez/ and Invitrogen.com).

Also provided are methods for treating a condition related to aberrant cell proliferation. For example, provided are methods of treating a cell proliferative condition in a subject, which comprises administering a salt form described herein, such as an amorphous salt form or crystalline polymorph salt form (e.g., polymorph Form II, III, IV, V, VI, VII, VIII, IX, X, XI, XII, XIII, XIV, XV, XVI, XVII, XVIII, XIX, XX, XXI, or XXII) to a subject in need thereof in an amount effective to treat the cell proliferative condition. The subject may be a research animal (e.g., rodent, dog, cat, monkey), optionally containing a tumor such as a xenograft tumor (e.g., human tumor), for example, or may be a human. A cell proliferative condition sometimes is a tumor or non-tumor cancer, including but not limited to, cancers of the colorectum, breast, lung, liver, pancreas, lymph node, colon, prostate, brain, head and neck, skin, liver, kidney, blood and heart (e.g., leukemia, lymphoma, carcinoma).

Also provided are methods for treating a condition related to inflammation or pain using a salt form described herein, such as an amorphous salt form or crystalline polymorph salt form (e.g., polymorph Form II, III, IV, V, VI, VII, VIII, IX, X, XI, XII, XIII, XIV, XV, XVI, XVII, XVIII, XIX, XX, XXI, or XXII). For example, provided are methods of treating pain in a subject, which comprise administering a polymorph described herein to a subject in need thereof in an amount effective to treat the pain. Provided also are methods of treating inflammation in a subject, which comprises administering a polymorph described herein to a subject in need thereof in an amount effective to treat the inflammation. The subject may be a research animal (e.g., rodent, dog, cat, monkey), for example, or may be a human. Conditions associated with inflammation and pain include without limitation acid reflux, heartburn, acne, allergies and sensitivities, Alzheimer's disease, asthma, atherosclerosis, bronchitis, carditis, celiac disease, chronic pain, Crohn's disease, cirrhosis, colitis, dementia, dermatitis, diabetes, dry eyes, edema, emphysema, eczema, fibromyalgia, gastroenteritis, gingivitis, heart disease, hepatitis, high blood pressure, insulin resistance, interstitial cystitis, joint pain/arthritis/rheumatoid arthritis, metabolic syndrome (syndrome X), myositis, nephritis, obesity, osteopenia, osteoporosis, Parkinson's disease, periodontal disease, polyarteritis, polychondritis, psoriasis, scleroderma, sinusitis, Sjögren's syndrome, spastic colon, systemic candidiasis, tendonitis, urinary track infections, vaginitis, inflammatory cancer (e.g., inflammatory breast cancer) and the like.

Methods for determining effects of the salts described herein on, e.g., pain or inflammation are known. For example, formalin-stimulated pain behaviors in research animals can be monitored after administration of a polymorph described herein to assess treatment of pain (e.g., Li et al., Pain 115(1-2): 182-90 (2005)). Also, modulation of pro-inflammatory molecules (e.g., IL-8, GRO-alpha, MCP-1, TNFalpha and iNOS) can be monitored after administration of a polymorph described herein to assess treatment of inflammation (e.g., Parhar et al., Int J Colorectal Dis. 22(6): 601-9 (2006)), for example. Non-limiting examples of pain signals are formalin-stimulated pain behaviors and examples of inflammation signals include without limitation a level of a pro-inflammatory molecule.

Also provided are methods for modulating angiogenesis in a subject, and methods for treating a condition associated with aberrant angiogenesis in a subject. Thus, provided are methods for determining whether a polymorph herein modulates angiogenesis, which comprise contacting or providing to a system a polymorph described herein (or compound (I) derived from a polymorph described herein) in an amount effective for modulating (e.g., inhibiting) angiogenesis or a signal associated with angiogenesis. Signals associated with angiogenesis are levels of a pro-angiogenesis growth factor such as VEGF. Methods for assessing modulation of angiogenesis also are known, such as analyzing human endothelial tube formation (BD BioCoat™ Angiogenesis System from BD Biosciences). Also provided are methods for treating an angiogenesis condition, which comprise administering a salt form described herein, such as an amorphous salt form or crystalline polymorph salt form (e.g., polymorph Form II, III, IV, V, VI, VII, VIII, IX, X, XI, XII, XIII, XIV, XV, XVI, XVII, XVIII, XIX, XX, XXI, or XXII) to a subject in need thereof in an amount effective to treat the angiogenesis condition. Angiogenesis conditions include without limitation solid tumor cancers, varicose disease and the like.

In some embodiments, the methods and/or compositions related to the salt forms described herein, such as an amorphous salt form or crystalline polymorph salt form (e.g., polymorph Form II, III, IV, V, VI, VII, VIII, IX, X, XI, XII, XIII, XIV, XV, XVI, XVII, XVIII, XIX, XX, XXI, or XXII) reduce the severity of one or more symptoms associated with the condition (e.g., condition such as cell proliferation, pain, inflammation, angiogenesis, etc.) by at least about any of 10%, 20%, 30%, 40%, 50%, 60%, 70%, 80%, 90%, 95%, or 100% compared to the corresponding symptom in the same individual prior to treatment or compared to the corresponding symptom in other individuals not receiving the methods and/or compositions.

As described herein, any suitable composition of a polymorph described above can be prepared for administration. Briefly, any suitable route of administration may be used, including, but not limited to, oral, parenteral, intravenous, intramuscular, transdermal, topical and subcutaneous routes. Depending on the subject to be treated, the mode of administration, and the type of treatment desired e.g., prevention, prophylaxis, therapy; the compounds are formulated in ways consonant with these parameters. Preparation of suitable compositions and formulations for each route of administration are known in the art.

For administration to animal or human subjects, the appropriate dosage of the a polymorph described above often is 0.01-15 mg/kg, and sometimes 0.1 10 mg/kg. Dosage levels are dependent on the nature of the condition, drug efficacy, the condition of the patient, the judgment of the practitioner, and the frequency and mode of administration; however, optimization of such parameters is within the ordinary level of skill in the art. An expanded description of contemplated dosages is described below.

Combination Therapy

The salt forms described herein, such as an amorphous salt form or crystalline polymorph salt form (e.g., polymorph Form II, III, IV, V, VI, VII, VIII, IX, X, XI, XII, XIII, XIV, XV, XVI, XVII, XVIII, XIX, XX, XXI, or XXII) may be formulated and/or administered in conjunction with one or more additional pharmaceutical agents, as described herein and as known in the art, including one or more additional pharmaceutical agents to further reduce the occurrence and/or severity of symptoms and/or clinical manifestations thereof, as well as additional pharmaceutical agents that treat or prevent the underlying conditions, and/or in conjunction with (e.g., prior to, concurrently with, or after) additional treatment modalities.

As used herein, the term "additional treatment modality" refers to treatment/prevention of the conditions described herein without the use of a pharmaceutical agent (e.g., surgery, radiotherapy, etc.). Where combinations of pharmaceutical agent(s) and/or additional treatment modality(ies) are used, they may be, independently, administered prior to, concurrently with, or after administration of one or more of the polymorphs (or compositions thereof) as described herein.

In some embodiments, the salt forms described herein, such as an amorphous salt form or crystalline polymorph salt form (e.g., polymorph Form II, III, IV, V, VI, VII, VIII, IX, X, XI, XII, XIII, XIV, XV, XVI, XVII, XVIII, XIX, XX, XXI, or XXII) may be used in combination with one or more additional pharmaceutical agents. The polymorphs may also be administered in conjunction with (e.g., prior to, concurrently with, or after) agents to alleviate the symptoms associated with either the disease or the treatment regimen. In some embodiments, the polymorph is used in combination with another polymorph described herein (e.g., polymorph Form II, III, IV, V, VI, VII, VIII, IX, X, XI, XII, XIII, XIV, XV, XVI, XVII, XVIII, XIX, XX, XXI, or XXII) and/or an amorphous form of a compound of formula (I) (e.g., the amorphous sodium salt of 5-(3-chlorophenylamino)benzo[c][2,6]naphthyridine-8-carboxylic acid).

As described, the salt forms described herein, such as an amorphous salt form or crystalline polymorph salt form (e.g., polymorph Form II, III, IV, V, VI, VII, VIII, IX, X, XI, XII, XIII, XIV, XV, XVI, XVII, XVIII, XIX, XX, XXI, or XXII) or salts of compound (I) described herein may be used alone or in combination with an additional pharmaceutical agent. As such, provided are methods to treat conditions such as cancer, inflammation and immune disorders by administering to a individual in need thereof an effective amount of a polymorph form described herein useful for treating said condition and administering to the same individual an effective amount of a modulator. A CK2, Pim or Flt modulator is an agent that inhibits or enhances a biological activity of a CK2 protein, a Pim protein or a Flt protein, and is generically referred to hereafter as a "modulator." The polymorph and the modulator may be administered together, either as separate pharmaceutical compositions or admixed in a single pharmaceutical composition. The polymorph and the modulator may also be administered separately, including at different times and with different frequencies. The modulator may be administered by any known route, such as orally, intravenously, intramuscularly, nasally, and the like; and the polymorph may also be administered by any conventional route. In many embodiments, at least one and optionally both of the modulator and the polymorph may be administered orally.

When used in combination, in some embodiments the polymorphic form described herein may be administered as a single pharmaceutical dosage composition that contains both the polymorph and another therapeutic agent. In other embodiments, separate dosage composition are administered; the polymorph and the other additional pharmaceutical agent may be, administered at essentially the same time, for example, concurrently, or at separately staggered times, for example, sequentially. In certain examples, the individual components of the combination may be administered separately, at different times during the course of therapy, or concurrently, in divided or single combination forms. Also provided are, for example, simultaneous, staggered, or alternating treatment. Thus, the polymorphs may be administered at the same time as an additional pharmaceutical agent, in the same pharmaceutical composition; the polymorph may be administered in separate pharmaceutical composition; the polymorph may be administered before the additional pharmaceutical agent, or the additional pharmaceutical agent may be administered before the polymorph, for example, with a time difference of seconds, minutes, hours, days, or weeks. In examples of a staggered treatment, a course of therapy with the polymorph may be administered, followed by a course of therapy with the additional pharmaceutical agent, or the reverse order of treatment may be used, more than one series of treatments with each polymorph may be used. In certain examples, one component, for example, the polymorph or the additional pharmaceutical agent, is administered to an individual (e.g., a mammal) while the other component, or its derivative products, remains in the bloodstream of the individual. In other examples, the second component is administered after all, or most of the first component, or its derivatives, have left the bloodstream of the individual.

Salt forms of the invention may be used alone or in combination with another therapeutic agent. The invention provides methods to treat conditions such as cancer, inflammation and immune disorders by administering to a subject in need of such treatment a therapeutically effective amount of a therapeutic agent useful for treating said disorder and administering to the same subject a therapeutically effective amount of a modulator of the present invention, i.e., a compound of the invention. The therapeutic agent and the modulator may be "co-administered", i.e, administered together, either as separate pharmaceutical compositions or admixed in a single pharmaceutical composition. By "administered together", the therapeutic agent and the modulator may also be administered separately, including at different times and with different frequencies. The modulator may be administered by any known route, such as orally, intravenously, intramuscularly, nasally, and the like; and the therapeutic agent may also be administered by any conventional route. In many embodiments, at least one and optionally both of the modulator and the therapeutic agent may be administered orally. Preferably, the modulator is an inhibitor, and it may inhibit either one of CK2 and Pim, or both of them to provide the treatment effects described herein.

In certain embodiments, a "modulator" as described above may be used in combination with a therapeutic agent that can act by binding to regions of DNA that can form certain quadruplex structures. In such embodiments, the therapeutic agents have anticancer activity on their own, but their activity is enhanced when they are used in combination with a modulator. This synergistic effect allows the therapeutic agent to be administered in a lower dosage while achieving equivalent or higher levels of at least one desired effect.

A modulator may be separately active for treating a cancer. For combination therapies described above, when used in combination with a therapeutic agent, the dosage of a modulator will frequently be two-fold to ten-fold lower than the dosage required when the modulator is used alone to treat the same condition or subject. Determination of a suitable amount of the modulator for use in combination with a therapeutic agent is readily determined by methods known in the art.

Salt forms and compositions of the invention may be used in combination with anticancer or other agents, such as palliative agents, that are typically administered to a patient being treated for cancer. Such "anticancer agents" include, e.g., classic chemotherapeutic agents, as well as molecular targeted therapeutic agents, biologic therapy agents, and radiotherapeutic agents.

When a salt form or composition of the invention is used in combination with an anticancer agent to another agent, the present invention provides, for example, simultaneous, staggered, or alternating treatment. Thus, The salt form of the invention may be administered at the same time as an anticancer agent, in the same pharmaceutical composition; The salt form of the invention may be administered at the same time as the anticancer agent, in separate pharmaceutical compositions; The salt form of the invention may be administered before the anticancer agent, or the anticancer agent may be administered before The salt form of the invention, for example, with a time difference of seconds, minutes, hours, days, or weeks.

In examples of a staggered treatment, a course of therapy with The salt form of the invention may be administered, followed by a course of therapy with the anticancer agent, or the reverse order of treatment may be used, and more than one series of treatments with each component may also be used. In certain examples of the present invention, one component, for example, The salt form of the invention or the anticancer agent, is administered to a mammal while the other component, or its derivative products, remains in the bloodstream of the mammal. For example, the present compound may be administered while the anticancer agent or its derivative products remains in the bloodstream, or the anticancer agent may be administered while the present compound or its derivatives remains in the bloodstream. In other examples, the second component is administered after all, or most of the first component, or its derivatives, have left the bloodstream of the mammal.

The salt form of the invention and the anticancer agent may be administered in the same dosage form, e.g., both administered as intravenous solutions, or they may be administered in different dosage forms, e.g., one compound may be administered topically and the other orally. A person of ordinary skill in the art would be able to discern which combinations of agents would be useful based on the particular characteristics of the drugs and the cancer involved.

Anticancer agents useful in combination with the compounds of the present invention may include agents selected from any of the classes known to those of ordinary skill in the art, including, but not limited to, antimicrotubule agents such as diterpenoids and vinca alkaloids; platinum coordination complexes; alkylating agents such as nitrogen mustards, oxazaphosphorines, alkylsulfonates, nitrosoureas, and triazenes; antibiotic agents such as anthracyclins, actinomycins and bleomycins; topoisomerase II inhibitors such as epipodophyllotoxins; antimetabolites such as purine and pyrimidine analogues and anti-folate compounds; topoisomerase I inhibitors such as camptothecins; hormones and hormonal analogues; signal transduction pathway inhibitors; nonreceptor tyrosine kinase angiogenesis inhibitors; immunotherapeutic agents; pro-apoptotic agents; and cell cycle signaling inhibitors; and other agents described below.

Anti-microtubule or anti-mitotic agents are phase specific agents that are typically active against the microtubules of tumor cells during M or the mitosis phase of the cell cycle. Examples of anti-microtubule agents include, but are not limited to, diterpenoids and vinca alkaloids.

Plant alkaloid and terpenoid derived agents include mitotic inhibitors such as the vinca alkaloids vinblastine, vincristine, vindesine, and vinorelbine; and microtubule polymer stabilizers such as the taxanes, including, but not limited to paclitaxel, docetaxel, larotaxel, ortataxel, and tesetaxel.

Diterpenoids, which are derived from natural sources, are phase specific anti-cancer agents that are believed to operate at the G2/M phases of the cell cycle. It is believed that the diterpenoids stabilize the p-tubulin subunit of the microtubules, by binding with this protein. Disassembly of the protein appears then to be inhibited with mitosis being arrested and cell death following.

Examples of diterpenoids include, but are not limited to, taxanes such as paclitaxel, docetaxel, larotaxel, ortataxel, and tesetaxel. Paclitaxel is a natural diterpene product isolated from the Pacific yew tree *Taxus brevifolia* and is commercially available as an injectable solution TAXOL®. Docetaxel is a semisynthetic derivative of paclitaxel q. v., prepared using a natural precursor, 10-deacetyl-baccatin III, extracted from the needle of the European Yew tree. Docetaxel is commercially available as an injectable solution as TAXOTERE®.

Vinca alkaloids are phase specific anti-neoplastic agents derived from the periwinkle plant. Vinca alkaloids that are believed to act at the M phase (mitosis) of the cell cycle by binding specifically to tubulin. Consequently, the bound tubulin molecule is unable to polymerize into microtubules. Mitosis is believed to be arrested in metaphase with cell death following. Examples of vinca alkaloids include, but are not limited to, vinblastine, vincristine, vindesine, and vinorelbine. Vinblastine, vincaleukoblastine sulfate, is commercially available as VELBAN® as an injectable solution. Vincristine, vincaleukoblastine 22-oxo-sulfate, is commercially available as ONCOVIN® as an injectable solution. Vinorelbine, is commercially available as an injectable solution of vinorelbine tartrate (NAVELBINE®), and is a semisynthetic vinca alkaloid derivative.

Platinum coordination complexes are non-phase specific anti-cancer agents, which are interactive with DNA. The platinum complexes are believed to enter tumor cells, undergo, aquation and form intra- and interstrand crosslinks with DNA causing adverse biological effects to the tumor. Platinum-based coordination complexes include, but are not limited to cisplatin, carboplatin, nedaplatin, oxaliplatin, satraplatin, and (SP-4-3)-(cis)-amminedichloro-[2-methylpyridine] platinum(II). Cisplatin, cis-diamminedichloroplatinum, is commercially available as PLATINOL® as an injectable solution. Carboplatin, platinum, diammine[1,1-cyclobutane-dicarboxylate(2-)-0,0'], is commercially available as PARAPLATIN® as an injectable solution.

Alkylating agents are generally non-phase specific agents and typically are strong electrophiles. Typically, alkylating agents form covalent linkages, by alkylation, to DNA through nucleophilic moieties of the DNA molecule such as phosphate, amino, sulfhydryl, hydroxyl, carboxyl, and imidazole groups. Such alkylation disrupts nucleic acid function leading to cell death. Examples of alkylating agents include, but are not limited to, alkyl sulfonates such as busulfan; ethyleneimine and methylmelamine derivatives such as altretamine and thiotepa; nitrogen mustards such as chlorambucil, cyclophosphamide, estramustine, ifosfamide, mechlorethamine, melphalan, and uramustine; nitrosoureas such as carmustine, lomustine, and streptozocin; triazenes and imidazotetrazines such as dacarbazine, procarbazine, temozolamide, and temozolomide. Cyclophosphamide, 2-[bis(2-chloroethyl)-amino] tetrahydro-2H-1,3,2-oxazaphosphorine 2-oxide monohydrate, is commercially available as an injectable solution or tablets as CYTOXAN®. Melphalan, 4-[bis(2-chloroethyl) amino]-L-phenylalanine, is commercially available as an injectable solution or tablets as ALKERAN®. Chlorambucil, 4-[bis(2-chloroethyl)amino]-benzenebutanoic acid, is commercially available as LEUKERAN® tablets. Busulfan, 1,4-butanediol dimethanesulfonate, is commercially available as MYLERAN® TABLETS. Carmustine, 1,3-[bis(2-chloroethyl)-1-nitrosourea, is commercially available as single vials of lyophilized material as BiCNU®, 5-(3,3-dimethyl-1-triazeno)-imidazole-4-carboxamide, is commercially available as single vials of material as DTIC-Dome®. Furthermore, alkylating agents include (a) alkylating-like platinum-based chemotherapeutic agents such as cisplatin, carboplatin, nedaplatin, oxaliplatin, satraplatin, and (SP-4-3)-(cis)-amminedichloro-[2-methylpyridine] platinum(II); (b) alkyl sulfonates such as busulfan; (c) ethyleneimine and methylmelamine derivatives such as altretamine and thiotepa; (d) nitrogen mustards such as chlorambucil, cyclophosphamide, estramustine, ifosfamide, mechlorethamine, trofosamide, prednimustine, melphalan, and uramustine; (e) nitrosoureas such as carmustine, lomustine, fotemustine, nimustine, ranimustine and streptozocin; (f) triazenes and imidazotetrazines such as dacarbazine, procarbazine, temozolamide, and temozolomide.

Anti-tumor antibiotics are non-phase specific agents which are believed to bind or intercalate with DNA. This may result in stable DNA complexes or strand breakage, which disrupts ordinary function of the nucleic acids, leading to cell death. Examples of anti-tumor antibiotic agents include, but are not limited to, anthracyclines such as daunorubicin (including liposomal daunorubicin), doxorubicin (including liposomal doxorubicin), epirubicin, idarubicin, and valrubicin; streptomyces-related agents such as bleomycin, actinomycin, mithramycin, mitomycin, porfiromycin; and mitoxantrone. Dactinomycin, also know as Actinomycin D, is commercially available in injectable form as COSMEGEN®. Daunorubicin, (8S-cis+8-acetyl-10-[(3-amino-2,3,6-trideoxy-α-L-lyxohexopyranosyl)oxy]-7,8,9,10-tetrahydro-6,8,11-trihydroxy-1-methoxy-5,12-naphthacenedione hydrochloride, is commercially available as a liposomal injectable form as DAUNOXOME® or as an injectable as CERUBIDINE®. Doxorubicin, (8S,10S)-10-[(3-amino-2,3,6-trideoxy-α-L-lyxohexopyranosyl)oxy]-8-glycoloyl, 7,8,9,10-tetrahydro-6, 8,11-trihydroxy-1-methoxy-5,12-naphthacenedione hydrochloride, is commercially available in an injectable form as RUBEX® or ADRIAMYCIN RDF®. Bleomycin, a mixture of cytotoxic glycopeptide antibiotics isolated from a strain of *Streptomyces verticillus*, is commercially available as BLENOXANE®.

Topoisomerase inhibitors include topoisomerase I inhibitors such as camptothecin, topotecan, irinotecan, rubitecan, and belotecan; and topoisomerase II inhibitors such as etoposide, teniposide, and amsacrine.

Topoisomerase II inhibitors include, but are not limited to, epipodophyllotoxins, which are phase specific anti-neoplastic agents derived from the mandrake plant. Epipodophyllotoxins typically affect cells in the S and G2 phases of the cell cycle by forming a ternary complex with topoisomerase II and DNA causing DNA strand breaks. The strand breaks accumulate and cell death follows. Examples of epipodophyllotoxins include, but are not limited to, etoposide, teniposide, and amsacrine. Etoposide, 4'-demethyl-epipodophyllotoxin 9[4,6-0-(R)-ethylidene-β-D-glucopyranoside], is commercially available as an injectable solution or capsules as VePESID® and is commonly known as VP-16. Teniposide, 4'-demethyl-epipodophyllotoxin 9[4,6-0-(R)-thenylidene-β-D-glucopyranoside], is commercially available as an injectable solution as VUMON® and is commonly known as VM-26.

Topoisomerase I inhibitors including, camptothecin and camptothecin derivatives. Examples of topoisomerase I inhibitors include, but are not limited to camptothecin, topotecan, irinotecan, rubitecan, belotecan and the various optical forms (i.e., (R), (S) or (R,S)) of 7-(4-methylpiperazino-methylene)-10,11-ethylenedioxy-camptothecin, as described in U.S. Pat. Nos. 6,063,923; 5,342,947; 5,559,235; 5,491,237 and pending U.S. patent application Ser. No. 08/977,217 filed Nov. 24, 1997. Irinotecan HCl, (4S)-4,11-diethyl-4-hydroxy-9-[(4-piperidinopiperidino)-carbonyloxy]-1H-yrano[3',4',6, 7]indolizino[1,2-b]quinoline-3,14(4H, 12H)-dione hydrochloride, is commercially available as the injectable solution CAMPTOSAR®. Irinotecan is a derivative of camptothecin which binds, along with its active metabolite SN-38, to the topoisomerase I-DNA complex. Topotecan HCl, (S)-10-[(dimethylamino)methyl]-4-ethyl-4,9-dihydroxy-1H-pyrano [3',4',6,7]indolizino[1,2-b]quinoline-3,14-(4H, 12H)-dione monohydrochloride, is commercially available as the injectable solution HYCAMTIN®.

Anti-metabolites include (a) purine analogs such as fludarabine, cladribine, chlorodeoxyadenosine, clofarabine, mercaptopurine, pentostatin, and thioguanine; (b) pyrimidine analogs such as fluorouracil, gemcitabine, capecitabine, cytarabine, azacitidine, edatrexate, floxuridine, and troxacitabine; (c) antifolates, such as methotrexate, pemetrexed, raltitrexed, and trimetrexate. Anti-metabolites also include thymidylate synthase inhibitors, such as fluorouracil, raltitrexed, capecitabine, floxuridine and pemetrexed; and ribonucleotide reductase inhibitors such as claribine, clofarabine and fludarabine. Antimetabolite neoplastic agents are phase specific anti-neoplastic agents that typically act at S phase (DNA synthesis) of the cell cycle by inhibiting DNA synthesis or by inhibiting purine or pyrimidine base synthesis and thereby limiting DNA synthesis. Consequently, S phase does not proceed and cell death follows. Anti-metabolites, include purine analogs, such as fludarabine, cladribine, chlorodeoxyadenosine, clofarabine, mercaptopurine, pentostatin, erythrohydroxynonyladenine, fludarabine phosphate and thioguanine; pyrimidine analogs such as fluorouracil, gemcitabine, capecitabine, cytarabine, azacitidine, edatrexate, floxuridine, and troxacitabine; antifolates, such as methotrexate, pemetrexed, raltitrexed, and trimetrexate. Cytarabine, 4-amino-1-p-D-arabinofuranosyl-2 (1H)-pyrimidinone, is commercially available as CYTOSAR-U® and is commonly known as Ara-C. Mercaptopurine, 1,7-dihydro-6H-purine-6-thione monohydrate, is commercially available as PURINETHOL®. Thioguanine, 2-amino-1,7-dihydro-6H-purine-6-thione, is commercially available as TABLOID®. Gemcitabine, 2'-deoxy-2',2'-difluorocytidine monohydrochloride (p-isomer), is commercially available as GEMZAR®.

Hormonal therapies include (a) androgens such as fluoxymesterone and testolactone; (b) antiandrogens such as bicalutamide, cyproterone, flutamide, and nilutamide; (c) aromatase inhibitors such as aminoglutethimide, anastrozole, exemestane, formestane, and letrozole; (d) corticosteroids such as dexamethasone and prednisone; (e) estrogens such as diethylstilbestrol; (f) antiestrogens such as fulvestrant, raloxifene, tamoxifen, and toremifine; (g) LHRH agonists and antagonists such as buserelin, goserelin, leuprolide, and triptorelin; (h) progestins such as medroxyprogesterone acetate and megestrol acetate; and (i) thyroid hormones such as levothyroxine and liothyronine. Hormones and hormonal analogues are useful compounds for treating cancers in which there is a relationship between the hormone(s) and growth and/or lack of growth of the cancer. Examples of hormones and hormonal analogues useful in cancer treatment include, but are not limited to, androgens such as fluoxymesterone and testolactone; antiandrogens such as bicalutamide, cyproterone, flutamide, and nilutamide; aromatase inhibitors such as aminoglutethimide, anastrozole, exemestane, formestane, vorazole, and letrozole; corticosteroids such as dexamethasone, prednisone and prednisolone; estrogens such as diethylstilbestrol; antiestrogens such as fulvestrant, raloxifene, tamoxifen, toremifene, droloxifene, and iodoxyfene, as well as selective estrogen receptor modulators (SERMS) such those described in U.S. Pat. Nos. 5,681,835, 5,877,219, and 6,207,716; 5α-reductases such as finasteride and dutasteride; gonadotropin-releasing hormone (GnRH) and analogues thereof which stimulate the release of leutinizing hormone (LH) and/or follicle stimulating hormone (FSH), for example LHRH agonists and antagonists such as buserelin, goserelin, leuprolide, and triptorelin; progestins such as medroxyprogesterone acetate and megestrol acetate; and thyroid hormones such as levothyroxine and liothyronine.

Signal transduction pathway inhibitors are those inhibitors, which block or inhibit a chemical process which evokes an intracellular change, such as cell proliferation or differentiation. Signal tranduction inhibitors useful in the present invention include, e.g., inhibitors of receptor tyrosine kinases, non-receptor tyrosine kinases, SH2/SH3 domain blockers, serine/threonine kinases, phosphotidyl inositol-3 kinases, myo-inositol signaling, and Ras oncogenes.

Molecular targeted agents include (a) receptor tyrosine kinase ('RTK') inhibitors, such as inhibitors of EGFR, including erlotinib, gefitinib, and neratinib; inhibitors of VEGFR including vandetanib, semaxinib, and cediranib; and inhibitors of PDGFR; further included are RTK inhibitors that act at multiple receptor sites such as lapatinib, which inhibits both EGFR and HER2, as well as those inhibitors that act at each of C-kit, PDGFR and VEGFR, including but not limited to axitinib, sunitinib, sorafenib and toceranib; also included are inhibitors of BCR-ABL, c-kit and PDGFR, such as imatinib; (b) FKBP binding agents, such as an immunosuppressive macrolide antibiotic, including bafilomycin, rapamycin (sirolimus) and everolimus; (c) gene therapy agents, antisense therapy agents, and gene expression modulators such as the retinoids and rexinoids, e.g. adapalene, bexarotene, trans-retinoic acid, 9-cis-retinoic acid, and N-(4-hydroxyphenyl)retinamide; (d) phenotype-directed therapy agents, including monoclonal antibodies such as alemtuzumab, bevacizumab, cetuximab, ibritumomab tiuxetan, rituximab, and trastuzumab; (e) immunotoxins such as gemtuzumab ozogamicin; (f) radioimmunoconjugates such as 131I-tositumomab; and (g) cancer vaccines.

Several protein tyrosine kinases catalyse the phosphorylation of specific tyrosyl residues in various proteins involved in the regulation of cell growth. Such protein tyrosine kinases can be broadly classified as receptor or non-receptor kinases. Receptor tyrosine kinases are transmembrane proteins having an extracellular ligand binding domain, a transmembrane domain, and a tyrosine kinase domain. Receptor tyrosine kinases are involved in the regulation of cell growth and are sometimes termed growth factor receptors.

Inappropriate or uncontrolled activation of many of these kinases, for example by over-expression or mutation, has been shown to result in uncontrolled cell growth. Accordingly, the aberrant activity of such kinases has been linked to malignant tissue growth. Consequently, inhibitors of such kinases could provide cancer treatment methods.

Growth factor receptors include, for example, epidermal growth factor receptor (EGFr), platelet derived growth factor receptor (PDGFr), erbB2, erbB4, vascular endothelial growth factor receptor (VEGFr), tyrosine kinase with immunoglobulin-like and epidermal growth factor homology domains (TIE-2), insulin growth factor-I (IGFI) receptor, macrophage colony stimulating factor (cfms), BTK, ckit, cmet, fibroblast growth factor (FGF) receptors, Trk receptors (TrkA, TrkB, and TrkC), ephrin (eph) receptors, and the RET protooncogene.

Several inhibitors of growth receptors are under development and include ligand antagonists, antibodies, tyrosine kinase inhibitors and anti-sense oligonucleotides. Growth factor receptors and agents that inhibit growth factor receptor function are described, for instance, in Kath, John C., *Exp. Opin. Ther. Patents* (2000) 10(6):803-818; Shawver et al., *Drug Discov. Today* (1997), 2(2):50-63; and Lofts, F. J. et al., "Growth factor receptors as targets", New Molecular Targets for Cancer Chemotherapy, ed. Workman, Paul and Kerr, David, CRC press 1994, London. Specific examples of receptor tyrosine kinase inhibitors include, but are not limited to, sunitinib, erlotinib, gefitinib, and imatinib.

Tyrosine kinases which are not growth factor receptor kinases are termed non-receptor tyrosine kinases. Non-receptor tyrosine kinases useful in the present invention, which are targets or potential targets of anti-cancer drugs, include cSrc, Lck, Fyn, Yes, Jak, cAbl, FAK (Focal adhesion kinase), Brutons tyrosine kinase, and Bcr-Abl. Such non-receptor kinases and agents which inhibit non-receptor tyrosine kinase function are described in Sinh, S. and Corey, S. J., *J. Hematotherapy & Stem Cell Res*. (1999) 8(5): 465-80; and Bolen, J. B., Brugge, J. S., *Annual Review of Immunology*. (1997) 15: 371-404.

SH2/SH3 domain blockers are agents that disrupt SH2 or SH3 domain binding in a variety of enzymes or adaptor proteins including, PI3-K p85 subunit, Src family kinases, adaptor molecules (Shc, Crk, Nck, Grb2) and Ras-GAP. SH2/SH3 domains as targets for anti-cancer drugs are discussed in Smithgall, T. E., *J. Pharmacol. Toxicol. Methods*. (1995), 34(3): 125-32. Inhibitors of Serine/Threonine Kinases including MAP kinase cascade blockers which include blockers of Raf kinases (rafk), Mitogen or Extracellular Regulated Kinase (MEKs), and Extracellular Regulated Kinases (ERKs); and Protein kinase C family member blockers including blockers of PKCs (alpha, beta, gamma, epsilon, mu, lambda, iota, zeta). IkB kinase family (IKKa, IKKb), PKB family kinases, AKT kinase family members, and TGF beta receptor kinases. Such Serine/Threonine kinases and inhibitors thereof are described in Yamamoto, T., Taya, S., Kaibuchi, K., *J. Biochemistry*. (1999) 126 (5): 799-803; Brodt, P, Samani, A, & Navab, R, *Biochem. Pharmacol*. (2000) 60:1101-1107; Massague, J., Weis-Garcia, F., *Cancer Surv*. (1996) 27:41-64; Philip, P. A, and Harris, A L, *Cancer Treat. Res*. (1995) 78: 3-27; Lackey, K. et al. *Bioorg. Med. Chem. Letters*, (2000) 10(3): 223-226; U.S. Pat. No. 6,268,391; and Martinez-Lacaci, I., et al., *Int. J. Cancer* (2000), 88(1): 44-52. Inhibitors of Phosphotidyl inositol-3 Kinase family members including blockers of PI3-kinase, ATM, DNA-PK, and Ku are also useful in the present invention. Such kinases are discussed in Abraham, R T. *Current Opin. Immunol*. (1996), 8(3): 412-8; Carman, C. E., Lim, D. S., Oncogene (1998) 17(25): 3301-8; Jackson, S. P., *Int. J. Biochem. Cell Biol*. (1997) 29(7):935-8; and Thong, H. et al., *Cancer Res*. (2000) 60(6):1541-5. Also useful in the present invention are Myo-inositol signaling inhibitors such as phospholipase C blockers and Myoinositol analogues. Such signal inhibitors are described in Powis, G., and Kozikowski A, (1994) New Molecular Targets for Cancer Chemotherapy, ed., Paul Workman and David Kerr, CRC Press 1994, London.

Another group of signal transduction pathway inhibitors are inhibitors of Ras Oncogene. Such inhibitors include inhibitors of farnesyltransferase, geranyl-geranyl transferase, and CAAX proteases as well as anti-sense oligonucleotides, ribozymes and immunotherapy. Such inhibitors have been shown to block ras activation in cells containing wild type mutant ras, thereby acting as antiproliferation agents. Ras oncogene inhibition is discussed in Scharovsky, O. G., Rozados, V. R, Gervasoni, S I, Matar, P., *J. Biomed. Sci*. (2000) 7(4): 292-8; Ashby, M. N., *Curr. Opin. Lipidol*. (1998) 9(2): 99-102; and Oliff, A., *Biochim. Biophys. Acta*, (1999) 1423 (3):C19-30.

As mentioned above, antibody antagonists to receptor kinase ligand binding may also serve as signal transduction inhibitors. This group of signal transduction pathway inhibitors includes the use of humanized antibodies to the extracellular ligand binding domain of receptor tyrosine kinases. For example Imclone C225 EGFR specific antibody (see Green, M. C. et al., *Cancer Treat. Rev*., (2000) 26(4): 269-286); Herceptin® erbB2 antibody (see Stern, D F, *Breast Cancer Res*. (2000) 2(3):176-183); and 2CB VEGFR2 specific antibody (see Brekken, R. A. et al., *Cancer Res*. (2000) 60(18): 5117-24).

Non-receptor kinase angiogenesis inhibitors may also find use in the present invention. Inhibitors of angiogenesis related VEGFR and TIE2 are discussed above in regard to signal transduction inhibitors (both receptors are receptor tyrosine kinases). Angiogenesis in general is linked to erbB2/EGFR signaling since inhibitors of erbB2 and EGFR have been shown to inhibit angiogenesis, primarily VEGF expression. Thus, the combination of an erbB2/EGFR inhibitor with an inhibitor of angiogenesis makes sense. Accordingly, non-receptor tyrosine kinase inhibitors may be used in combination with the EGFR/erbB2 inhibitors of the present invention. For example, anti-VEGF antibodies, which do not recognize VEGFR (the receptor tyrosine kinase), but bind to the ligand; small molecule inhibitors of integrin (alphav beta3) that will inhibit angiogenesis; endostatin and angiostatin (non-RTK) may also prove useful in combination with the disclosed erb family inhibitors. (See Bruns, C J et al., *Cancer Res*. (2000), 60(11): 2926-2935; Schreiber A B, Winkler M E, & Derynck R., *Science* (1986) 232(4755):1250-53; Yen L. et al., *Oncogene* (2000) 19(31): 3460-9).

Agents used in immunotherapeutic regimens may also be useful in combination with the compounds of formula (I). There are a number of immunologic strategies to generate an immune response against erbB2 or EGFR. These strategies are generally in the realm of tumor vaccinations. The efficacy of immunologic approaches may be greatly enhanced through combined inhibition of erbB2/EGFR signaling pathways using a small molecule inhibitor. Discussion of the immunologic/tumor vaccine approach against erbB2/EGFR are found in Reilly R T, et al., *Cancer Res*. (2000) 60(13): 3569-76; and Chen Y, et al., *Cancer Res*. (1998) 58(9):1965-71.

Agents used in pro-apoptotic regimens (e.g., bcl-2 antisense oligonucleotides) may also be used in the combination of the present invention. Members of the Bcl-2 family of proteins block apoptosis. Upregulation of bcl-2 has therefore been linked to chemoresistance. Studies have shown that the epidermal growth factor (EGF) stimulates anti-apoptotic members of the bcl-2 family. Therefore, strategies designed to downregulate the expression of bcl-2 in tumors have demonstrated clinical benefit and are now in Phase II/III trials, namely Genta's G3139 bcl-2 antisense oligonucleotide. Such pro-apoptotic strategies using the antisense oligonucleotide strategy for bcl-2 are discussed in Waters J S, et al., *J. Clin. Oncol*. (2000) 18(9): 1812-23; and Kitada S, et al. *Antisense Res. Dev*. (1994) 4(2): 71-9.

Cell cycle signalling inhibitors inhibit molecules involved in the control of the cell cycle. A family of protein kinases called cyclin dependent kinases (CDKs) and their interaction with a family of proteins termed cyclins controls progression through the eukaryotic cell cycle. The coordinate activation and inactivation of different cyclin/CDK complexes is necessary for normal progression through the cell cycle. Several inhibitors of cell cycle signalling are under development. For instance, examples of cyclin dependent kinases, including CDK2, CDK4, and CDK6 and inhibitors for the same are described in, for instance, Rosania G R & Chang Y-T., *Exp. Opin. Ther. Patents* (2000) 10(2):215-30.

Other molecular targeted agents include FKBP binding agents, such as the immunosuppressive macrolide antibiotic, rapamycin; gene therapy agents, antisense therapy agents, and gene expression modulators such as the retinoids and rexinoids, e.g. adapalene, bexarotene, trans-retinoic acid, 9-cisretinoic acid, and N-(4 hydroxyphenyl)retinamide; phenotype-directed therapy agents, including: monoclonal antibodies such as alemtuzumab, bevacizumab, cetuximab, ibritumomab tiuxetan, rituximab, and trastuzumab; immunotoxins such as gemtuzumab ozogamicin, radioimmunoconjugates such as 131-tositumomab; and cancer vaccines.

Anti-tumor antibiotics include (a) anthracyclines such as daunorubicin (including liposomal daunorubicin), doxorubicin (including liposomal doxorubicin), epirubicin, idarubicin, and valrubicin; (b) streptomyces-related agents such as bleomycin, actinomycin, mithramycin, mitomycin, porfiromycin; and (c) anthracenediones, such as mitoxantrone and pixantrone. Anthracyclines have three mechanisms of action: intercalating between base pairs of the DNA/RNA strand; inhibiting topoiosomerase II enzyme; and creating iron-mediated free oxygen radicals that damage the DNA and cell membranes. Anthracyclines are generally characterized as topoisomerase II inhibitors.

Monoclonal antibodies include, but are not limited to, murine, chimeric, or partial or fully humanized monoclonal antibodies. Such therapeutic antibodies include, but are not limited to antibodies directed to tumor or cancer antigens either on the cell surface or inside the cell. Such therapeutic antibodies also include, but are not limited to antibodies directed to targets or pathways directly or indirectly associated with CK2. Therapeutic antibodies may further include, but are not limited to antibodies directed to targets or pathways that directly interact with targets or pathways associated with the compounds of the present invention. In one variation, therapeutic antibodies include, but are not limited to anticancer agents such as Abagovomab, Adecatumumab, Afutuzumab, Alacizumab pegol, Alemtuzumab, Altumomab pentetate, Anatumomab mafenatox, Apolizumab, Bavituximab, Belimumab, Bevacizumab, Bivatuzumab mertansine, Blinatumomab, Brentuximab vedotin, Cantuzumab mertansine, Catumaxomab, Cetuximab, Citatuzumab bogatox, Cixutumumab, Clivatuzumab tetraxetan, Conatumumab, Dacetuzumab, Detumomab, Ecromeximab, Edrecolomab, Elotuzumab, Epratuzumab, Ertumaxomab, Etaracizumab, Farletuzumab, Figitumumab, Fresolimumab, Galiximab, Glembatumumab vedotin, Ibritumomab tiuxetan, Intetumumab, Inotuzumab ozogamicin, Ipilimumab, Iratumumab, Labetuzumab, Lexatumumab, Lintuzumab, Lucatumumab, Lumiliximab, Mapatumumab, Matuzumab, Milatuzumab, Mitumomab, Nacolomab tafenatox, Naptumomab estafenatox, Necitumumab, Nimotuzumab, Ofatumumab, Olaratumab, Oportuzumab monatox, Oregovomab, Panitumumab, Pemtumomab, Pertuzumab, Pintumomab, Pritumumab, Ramucirumab, Rilotumumab, Rituximab, Robatumumab, Sibrotuzumab, Tacatuzumab tetraxetan, Taplitumomab paptox, Tenatumomab, Ticilimumab, Tigatuzumab, Tositumomab, Trastuzumab, Tremelimumab, Tucotuzumab celmoleukin, Veltuzumab, Volociximab, Votumumab, Zalutumumab, and Zanolimumab. In some embodiments, such therapeutic antibodies include, alemtuzumab, bevacizumab, cetuximab, daclizumab, gemtuzumab, ibritumomab tiuxetan, pantitumumab, rituximab, tositumomab, and trastuzumab; in other embodiments, such monoclonal antibodies include alemtuzumab, bevacizumab, cetuximab, ibritumomab tiuxetan, rituximab, and trastuzumab; alternately, such antibodies include daclizumab, gemtuzumab, and pantitumumab. In yet another embodiment, therapeutic antibodies useful in the treatment of infections include but are not limited to Afelimomab, Efungumab, Exbivirumab, Felvizumab, Foravirumab, Ibalizumab, Libivirumab, Motavizumab, Nebacumab, Pagibaximab, Palivizumab, Panobacumab, Rafivirumab, Raxibacumab, Regavirumab, Sevirumab, Tefibazumab, Tuvirumab, and Urtoxazumab. In a further embodiment, therapeutic antibodies can be useful in the treatment of inflammation and/or autoimmune disorders, including, but are not limited to, Adalimumab, Atlizumab, Atorolimumab, Aselizumab, Bapineuzumab, Basiliximab, Benralizumab, Bertilimumab, Besilesomab, Briakinumab, Canakinumab, Cedelizumab, Certolizumab pegol, Clenoliximab, Daclizumab, Denosumab, Eculizumab, Edobacomab, Efalizumab, Erlizumab, Fezakinumab, Fontolizumab, Fresolimumab, Gantenerumab, Gavilimomab, Golimumab, Gomiliximab, Infliximab, Inolimomab, Keliximab, Lebrikizumab, Lerdelimumab, Mepolizumab, Metelimumab, Muromonab-CD3, Natalizumab, Ocrelizumab, Odulimomab, Omalizumab, Otelixizumab, Pascolizumab, Priliximab, Reslizumab, Rituximab, Rontalizumab, Rovelizumab, Ruplizumab, Sifalimumab, Siplizumab, Solanezumab, Stamulurnab, Talizumab, Tanezumab, Teplizumab, Tocilizumab, Toralizumab, Ustekinumab, Vedolizumab, Vepalimomab, Visilizumab, Zanolimumab, and Zolimomab aritox. In yet another embodiment, such therapeutic antibodies include, but are not limited to adalimumab, basiliximab, certolizumab pegol, eculizumab, efalizumab, infliximab, muromonab-CD3, natalizumab, and omalizumab. Alternately the therapeutic antibody can include abciximab or ranibizumab. Generally a therapeutic antibody is non-conjugated, or is conjugated with a radionuclide, cytokine, toxin, drug-activating enzyme or a drug-filled liposome.

Akt inhibitors include IL6-Hydroxymethyl-chiro-inositol-2-(R)-2-O-methyl-3-O-octadecyl-sn-glycerocarbonate, SH-5 (Calbiochem Cat. No. 124008), SH-6 (Calbiochem Cat. No. Cat. No. 124009), Calbiochem Cat. No. 124011, Triciribine (NSC 154020, Calbiochem Cat. No. 124012), 10-(4'-(N-diethylamino)butyl)-2-chlorophenoxazine, $Cu(II)Cl_2$(3-Formylchromone thiosemicarbazone), 1,3-dihydro-1-(1-((4-(6-phenyl-1H-imidazo[4,5-g]quinoxalin-7-yl)phenyl) methyl)-4-piperidinyl)-2H-benzimidazol-2-one, GSK690693 (4-(2-(4-amino-1,2,5-oxadiazol-3-yl)-1-ethyl-7-{[(3S)-3-piperidinylmethyl]oxy}-1H-imidazo[4,5-c]pyridin-4-yl)-2-methyl-3-butyn-2-ol), SR13668 ((2,10-dicarbethoxy-6-methoxy-5,7-dihydro-indolo[2,3-b]carbazole), GSK2141795, Perifosine, GSK21110183, XL418, XL147, PF-04691502, BEZ-235 [2-Methyl-2-[4-(3-methyl-2-oxo-8-quinolin-3-yl-2,3-dihydro-imidazo[4,5-c]quinolin-1-yl)-phenyl]-propionitrile], PX-866 ((acetic acid (1S,4E,10R, 11R,13S,14R)-[4-diallylaminomethylene-6-hydroxy-1-methoxymethyl-10,13-dimethyl-3,7,17-trioxo-1,3,4,7,10, 11,12,13,14,15,16,17-dodecahydro-2-oxa-cyclopenta[a] phenanthren-11-yl ester)], D-106669, CAL-101, GDC0941 (2-(1H-indazol-4-yl)-6-(4-methanesulfonyl-piperazin-1-yl-methyl)-4-morpholin-4-yl-thieno[3,2-d]pyrimidine), SF1126, SF1188, SF2523, TG100-115 [3-[2,4-diamino-6-(3-hydroxyphenyl)pteridin-7-yl]phenol]. A number of these inhibitors, such as, for example, BEZ-235, PX-866, D 106669, CAL-101, GDC0941, SF1126, SF2523 are also identified in the art as PI3K/mTOR inhibitors; additional examples, such as PI-103 [3-[4-(4-morpholinylpyrido[3',2': 4,5]furo[3,2-d]pyrimidin-2-yl]phenol hydrochloride] are well-known those of skill in the art. Additional well-known PI3K inhibitors include LY294002 [2-(4-morpholinyl)-8-phenyl-4H-1-benzopyran-4-one] and wortmannin. mTOR inhibitors known to those of skill in the art include temsirolimus, deforolimus, sirolimus, everolimus, zotarolimus, and biolimus A9. A representative subset of such inhibitors includes temsirolimus, deforolimus, zotarolimus, and biolimus A9.

HDAC inhibitors include (i) hydroxamic acids such as Trichostatin A, vorinostat (suberoylanilide hydroxamic acid (SAHA)), panobinostat (LBH589) and belinostat (PXD101) (ii) cyclic peptides, such as trapoxin B, and depsipeptides, such as romidepsin (NSC 630176), (iii) benzamides, such as MS-275 (3-pyridylmethyl-N-{4-[(2-aminophenyl)-carbamoyl]-benzyl}-carbamate), CI994 (4-acetylamino-N-(2aminophenyl)-benzamide) and MGCD0103 (N-(2-aminophenyl)-4-((4-(pyridin-3-yl)pyrimidin-2-ylamino)methyl) benzamide), (iv) electrophilic ketones, (v) the aliphatic acid compounds such as phenylbutyrate and valproic acid.

Hsp90 inhibitors include benzoquinone ansamycins such as geldanamycin, 17-DMAG (17-Dimethylamino-ethylamino-17-demethoxygeldanamycin), tanespimycin (17-AAG, 17-allylamino-17-demethoxygeldanamycin), EC5, retaspimycin (IPI-504, 18,21-didehydro-17-demethoxy-18,21-dideoxo-18,21-dihydroxy-17-(2-propenylamino)-geldanamycin), and herbimycin; pyrazoles such as CCT 018159 (4-[4-(2,3-dihydro-1,4-benzodioxin-6-yl)-5-methyl-1H-pyrazol-3-yl]-6-ethyl-1,3-benzenediol); macrolides, such as radicocol; as well as BIIB021 (CNF2024), SNX-5422, STA-9090, and AUY922.

Miscellaneous agents include altretamine, arsenic trioxide, gallium nitrate, hydroxyurea, levamisole, mitotane, octreotide, procarbazine, suramin, thalidomide, lenalidomide, photodynamic compounds such as methoxsalen and sodium porfimer, and proteasome inhibitors such as bortezomib.

Biologic therapy agents include: interferons such as interferon-α2a and interferon-α2b, and interleukins such as aldesleukin, denileukin diftitox, and oprelvekin.

In addition to these anticancer agents intended to act against cancer cells, combination therapies including the use of protective or adjunctive agents, including: cytoprotective agents such as armifostine, dexrazonxane, and mesna, phosphonates such as parmidronate and zoledronic acid, and stimulating factors such as epoetin, darbepoetin, filgrastim, PEG-filgrastim, and sargramostim, are also envisioned.

Additional therapeutic combinations applicable to the polymorphs described herein are detailed in copending U.S. application Ser. No. 11/849,230 (US2009/0105233) and U.S. application Ser. No. 12/396,084 (Protein Kinase Modulators). The contents of both of these applications, particularly with respect to combination formulations and method of uses thereof, are hereby incorporated by reference in their entireties for all purposes.

Dosing and Methods of Administration

The amount of the polymorph administered to an individual (such as a human) may vary with the particular composition, the method of administration, and the particular type of condition being treated, and should be sufficient to produce a desirable beneficial effect. The amount administered in order to achieve an effective amount will depend upon a variety of factors, including, for example, the particular polymorph/polymorph composition being administered, the particular condition being treated, the frequency of administration, the severity of the condition being treated and the age, weight and general health of the individual, the adverse effects experienced by the individual being treated, etc. A pharmaceutical unit dosage chosen may be fabricated and administered to provide a defined final concentration of drug in the blood, tissues, organs, or other targeted region of the body. Determination of an effective amount for a given situation can be readily determined by routine experimentation (e.g., using in vivo animal models) and is within the skill and judgment of the ordinary clinician, particularly in view of the teachings provided herein.

In some embodiments, the amount of administered salt form described herein, such as an amorphous salt form or crystalline polymorph salt form (e.g., polymorph Form II, III, IV, V, VI, VII, VIII, IX, X, XI, XII, XIII, XIV, XV, XVI, XVII, XVIII, XIX, XX, XXI, or XXII) is effective to result in an objective response (such as a partial response or a complete response). In some embodiments, the amount of the polymorph is sufficient to result in a complete response in the individual. In some embodiments, the amount of the polymorph is sufficient to result in a partial response in the individual. In some embodiments, the amount of the polymorph administered alone is sufficient to produce an overall response rate and/or clinical benefit of more than about any of about 10%, 20%, 30%, 40%, 50%, 60%, 70%, 80%, 90%, or 95% among a population of individuals treated with the polymorph. Responses of an individual to the treatment of the methods described herein may easily determined by one of skill in the art (e.g., based on RECIST or CA-125 level in the case of cancer). A partial response can be defined as a sustained over 50% reduction from the pretreatment value.

In some embodiments, the amount of administered salt form described herein, such as an amorphous salt form or crystalline polymorph salt form (e.g., polymorph Form II, III, IV, V, VI, VII, VIII, IX, X, XI, XII, XIII, XIV, XV, XVI, XVII, XVIII, XIX, XX, XXI, or XXII) is sufficient to prolong progress-free survival of the individual (for example as measured by RECIST or CA-125 changes). In some embodiments, the amount of the polymorph is sufficient to prolong overall survival of the individual.

In some embodiments, the amount of administered polymorph is below the level that induces a toxicological effect (i.e., an effect above a clinically acceptable level of toxicity) or is at a level where a potential side effect can be controlled or tolerated when the polymorph is administered to the individual. In some embodiments, the amount of the polymorph is close to a maximum tolerated dose (MTD) of the polymorph following the same dosing regime. In some embodiments, the amount of the polymorph is more than about any of 80%, 90%, 95%, or 98% of the MTD.

In some embodiments, the amount of administered salt form is an amount sufficient to decrease the size of a tumor, decrease the number of cancer cells, or decrease the growth rate of a tumor by at least about any of 10%, 20%, 30%, 40%, 50%, 60%, 70%, 80%, 90%, 95% or 100% compared to the corresponding tumor size, number of cancer cells, or tumor growth rate in the same subject prior to treatment or compared to the corresponding activity in other subjects not receiving the treatment. Standard methods can be used to measure the magnitude of this effect, such as in vitro assays with purified enzyme, cell-based assays, animal models, or human testing.

In some embodiments, the amount of administered salt form described herein, such as an amorphous salt form or crystalline polymorph salt form (e.g., polymorph Form II, III, IV, V, VI, VII, VIII, IX, X, XI, XII, XIII, XIV, XV, XVI, XVII, XVIII, XIX, XX, XXI, or XXII) is included in any of the following ranges: about 0.5 to about 5 mg, about 5 to about 10 mg, about 10 to about 15 mg, about 15 to about 20 mg, about 20 to about 25 mg, about 20 to about 50 mg, about 25 to about 50 mg, about 50 to about 75 mg, about 50 to about 100 mg, about 75 to about 100 mg, about 100 to about 125 mg, about 125 to about 150 mg, about 150 to about 175 mg, about 175 to about 200 mg, about 200 to about 225 mg, about 225 to about 250 mg, about 250 to about 300 mg, about 300 to about 350 mg, about 350 to about 400 mg, about 400 to about 450 mg, or about 450 to about 500 mg. In some embodiments, the amount of polymorph in the effective amount of the composition (e.g., a unit dosage form) is in the range of about 5 mg to about 500 mg, such as about 30 mg to about 300 mg or about 50 mg to about 200 mg.

In some variations of any of the embodiments herein, the effective amount of salt form described herein, such as an amorphous salt form or crystalline polymorph salt form (e.g., polymorph Form II, III, IV, V, VI, VII, VIII, IX, X, XI, XII, XIII, XIV, XV, XVI, XVII, XVIII, XIX, XX, XXI, or XXII) and/or the amount of administered salt form includes at least about any of 1 mg/kg, 2.5 mg/kg, 3.5 mg/kg, 5 mg/kg, 6.5 mg/kg, 7.5 mg/kg, 10 mg/kg, 15 mg/kg, or 20 mg/kg. In various variations, the amount of polymorph includes less than about any of 350 mg/kg, 300 mg/kg, 250 mg/kg, 200 mg/kg, 150 mg/kg, 100 mg/kg, 50 mg/kg, 25 mg/kg, 20 mg/kg, 10 mg/kg, 7.5 mg/kg, 6.5 mg/kg, 5 mg/kg, 3.5 mg/kg, 2.5 mg/kg, or 1 mg/kg. In some embodiments, the amount of polymorph is about 0.01-15 mg/kg, or about 0.1-10 mg/kg, or about 0.2-8 mg/kg, or about 0.5-5 mg/kg, or about 0.75-2.75 mg/kg.

Exemplary dosing frequencies include, but are not limited to, weekly without break; weekly, three out of four weeks; once every three weeks; once every two weeks; weekly, two out of three weeks. In some embodiments, the salt form (e.g., polymorph) is administered about once every 2 weeks, once every 3 weeks, once every 4 weeks, once every 6 weeks, or once every 8 weeks. In some embodiments, the polymorph is administered at least about any of 1×, 2×, 3×, 4×, 5×, 6×, or 7× (i.e., daily) a week. In some embodiments, the intervals between each administration are less than about any of 6 months, 3 months, 1 month, 20 days, 15, days, 12 days, 10 days, 9 days, 8 days, 7 days, 6 days, 5 days, 4 days, 3 days, 2 days, or 1 day. In some embodiments, the intervals between each administration are more than about any of 1 month, 2 months, 3 months, 4 months, 5 months, 6 months, 8 months, or 12 months. In some embodiments, there is no break in the dosing schedule. In some embodiments, the interval between each administration is no more than about a week. The administration of the polymorph can be extended over an extended period of time, such as from about a month up to about seven years. In some embodiments, the composition is administered over a period of at least about any of 2, 3, 4, 5, 6, 7, 8, 9, 10, 11, 12, 18, 24, 30, 36, 48, 60, 72, or 84 months.

Any of the salt forms described herein, such as an amorphous salt form or crystalline polymorph salt form (e.g., polymorph Form II, III, IV, V, VI, VII, VIII, IX, X, XI, XII, XIII, XIV, XV, XVI, XVII, XVIII, XIX, XX, XXI, or XXII) can be administered to an individual (such as human) via various routes, including, for example, intravenous, intra-arterial, intraperitoneal, intrapulmonary, oral, inhalation, intravesicular, intramuscular, intra-tracheal, subcutaneous, intraocular, intrathecal, transmucosal, and transdermal. In some embodiments, sustained continuous release formulation of the composition may be used. In one variation, polymorph can be administered by any acceptable route including, but not limited to, orally, intramuscularly, transdermally, intravenously, through an inhaler or other air borne delivery systems and the like. Additional methods of administration are known in the art.

The salt forms described herein may be well-suited for oral administration due to favorable physiochemical properties. In some embodiments, compositions comprising the one or more polymorphs are suitable for oral administration. In some embodiments, a salt forms described herein, such as an amorphous salt form or crystalline polymorph salt form (e.g., polymorph Form II, III, IV, V, VI, VII, VIII, IX, X, XI, XII, XIII, XIV, XV, XVI, XVII, XVIII, XIX, XX, XXI, or XXII) is administered to an individual (e.g. a human) orally.

As described herein, the polymorphs may be administered with an additional pharmaceutical agent and/or an additional treatment modality. The dosing frequency of the polymorph and the additional pharmaceutical agent may be adjusted over the course of the treatment based on the judgment of the administering physician. In some embodiments, the polymorph and the additional pharmaceutical agent are administered simultaneously, sequentially, or concurrently. When administered separately, the polymorph and the additional pharmaceutical agent can be administered at different dosing frequency or intervals. For example, the polymorph can be administered weekly, while the additional pharmaceutical agent can be administered more or less frequently. In some embodiments, sustained continuous release formulation of the polymorph and/or the additional pharmaceutical agent may be used. Various formulations and devices for achieving sustained release are known in the art. A combination of the administration configurations described herein can be used.

The present invention will be understood more readily by reference to the following examples, which are provided by way of illustration and are not intended to be limiting of the present invention.

EXAMPLES

Example 1

Synthesis of 5-(3-chlorophenylamino)benzo[c][2,6]naphthyridine-8-carboxylic acid (compound (I))

The synthesis of compound (I) from 3-bromoisonicotinic acid has been described in copending U.S. application Ser. No. 11/849,230 (US2009/0105233) and U.S. application Ser. No. 12/396,084 (Protein Kinase Modulators). The content of both of these applications is hereby incorporated by reference. Synthetic details of compound (I) of this synthesis are also described below.

Example 1.1 ethyl 3-bromoisonicotinate

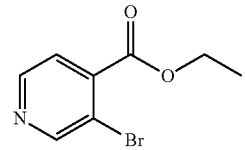

3-bromoisonicotinic acid (3.0 g, 14.9 mmol) in ethanol (100 mL) was treated with concentrated sulfuric acid (5 mL). The mixture was brought to reflux at which time everything went into solution. After 12 hours at reflux, LCMS indicated that the reaction was complete. The reaction mixture was cooled to room temperature and concentrated on a rotary evaporator to a third of its original volume. The mixture was then diluted with 250 mL of ethyl acetate and washed twice with saturated aqueous sodium bicarbonate. Concentration on a rotary evaporator yielded 3.25 g of ethyl 3-bromoisonicotinate as a yellowish oil which was sufficiently pure enough for subsequent chemical transformations. LCMS (ESI) 216.2 (M+1)+.

Example 1.2 methyl 5-oxo-5,6-dihydrobenzo[c][2,6]naphthyridine-8-carboxylate

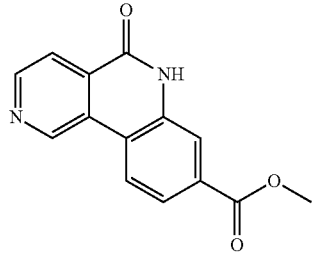 [SMILES: COC(=O)c1ccc2c(c1)[nH]c(=O)c1ccncc12]

Ethyl 3-bromoisonicotinate (1.15 g, 5.0 mmol), 2-amino-4-(methoxycarbonyl)phenylboronic acid (1.04 g, 4.5 mmol), sodium acetate (1.64 g, 20 mmol), 1,1'-bis(diphenylphosphino)ferrocene palladium (II) chloride (complexed with dichloromethane), (182 mg, 0.25 mmol) and dimethylformamide (7.5 mL) were combined in a flask. The flask was evacuated and filled with nitrogen twice and heated to 125° C. with stirring for 12 hours or until LCMS indicated the absence of any starting material. The mixture was cooled to room temperature and water (100 mL) was added to form a brown precipitate. The precipitate was filtered to yield 637 mg of methyl 5-oxo-5,6-dihydrobenzo[c][2,6]naphthyridine-8-carboxylate. LCMS (ESI) 255.4 (M+1)+.

Example 1.3 methyl 5-chlorobenzo[c][2,6]naphthyridine-8-carboxylate

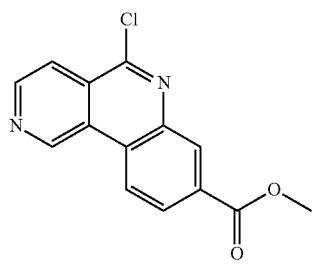 [SMILES: COC(=O)c1ccc2c(c1)nc(Cl)c1ccncc12]

Methyl 5-oxo-5,6-dihydrobenzo[c][2,6]naphthyridine-8-carboxylate (200 mg, 0.787 mmol) was combined with phosphorus oxychloride (1 mL) and heated to reflux. After 2 hours, LCMS indicated the absence of any starting material. The volatiles were removed under reduced pressure. The residue was taken up in dichloromethane (50 mL) and washed twice with saturated aqueous sodium bicarbonate. The organic phase was dried over sodium sulfate and concentrated on a rotary evaporator to give methyl 5-chlorobenzo[c][2,6]naphthyridine-8-carboxylate (140 mg) as a grayish solid. LCMS (ESI) 273.3 (M+1)+.

Example 1.4

5-(3-chlorophenylamino)benzo[c][2,6]naphthyridine-8-carboxylic acid

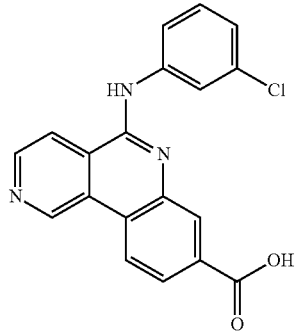 [SMILES: O=C(O)c1ccc2c(c1)nc(Nc1cccc(Cl)c1)c1ccncc12]

Methyl 5-chlorobenzo[c][2,6]naphthyridine-8-carboxylate (232 mg, 0.853 mmol) was combined with meta-chloroaniline (217 mg, 1.71 mmol) and N-methyl pyrrolidinone (1 mL) in a flask and the mixture was heated to 80° C. for 2 hours at which time LCMS indicated that the reaction was complete as indicated by the absence of any starting material. The mixture was dissolved in CH$_2$Cl$_2$, washed with saturated aqueous sodium bicarbonate and dried over Na$_2$SO$_4$. The material was purified by flash chromatography (SiO$_2$, 1:1 to 9:1 gradient of EtOAc/Hexanes) to obtain the ester. The material was dissolved in methanol and 6N aqueous NaOH and the mixture stirred at 50° C. for 30 minutes. The volatiles were removed in vacuo. The residue was triturated from acetic acid/THF/methanol using a mixture of hexanes and ethylacetate. Filtration and drying provided 147 mg of 5-(3-chlorophenylamino)benzo[c][2,6]naphthyridine-8-carboxylic acid. LCMS (ESI) 350 (M+1)+. $^1$HNMR (400 MHz, DMSO-d$_6$) δ 10.21 (s, 1H), 9.72 (br s, 1H), 9.02 (d, J=5.6, 1H), 8.89 (d, J=8.8, 1H), 8.62 (d, J=5.6, 1H), 8.31 (br s, 1H), 8.28 (d, J=1.6, 1H), 8.10 (br d, J=8, 1H), 7.99 (dd, J=2, J=8.4, 1H), 7.46 (t, J=8.0, 1H), 7.16 (br d, J=7.2, 1H) ppm.

Example 2

General Method for Salt Polymorph Formation

Approximately 10 mg of compound I was dissolved/suspended in 50-200 μL of solvent (EtOH, iPrOH, 2-BuOH, DMF, or iPrOH:H$_2$O). Approximately one equivalent of the desired base solution containing the counter ion (1.0M in water) was added to the solution/suspension comprising compound I. If no precipitate resulted after approximately 2 hr of slurrying, the material was temperature cycled one or more times. If a solid was then obtained, the solvent was allowed to evaporate. If no crystalline material developed after evaporation, anti-solvent addition methods are performed. The results of several polymorph salts are shown below in Table 10.

TABLE 10

Polymorph Salt formation conditions.

| No. | Counter-ion | EtOH | iPrOH | 2-BuOH | iPrOH:H$_2$O (1:1) | DMF |
|---|---|---|---|---|---|---|
| 1 | L-Arginine | | | | | |
| 2 | L-Lysine | | | | | |
| 3 | Zinc | | | | | |
| 4 | N-methyl glucamine | | | | | |
| 5 | TRIS | | | | | |
| 6 | Ammonium | | | | | |
| 7 | Choline | | | | | |
| 8 | Calcium (1 equiv.) | | | | | |
| 9 | Calcium (2 equiv.) | | | | | |
| 10 | Magnesium (1 equiv.) | | | | | |
| 11 | Magnesium (2 equiv.) | | | | | |
| 12 | Potassium | | | | | |

 = Birefringent salt - solid hit obtained after temp cycling & solvent evaporation. confirmed by opticalmicroscopy and Raman

 = Clear Yellow solution - after temperature cycling

= Yellow gum - after temperature cycling and solvent evaporation

Example 3

Scale Up of Arginine and TRIS Salts (5 g Scale)

Arginine and TRIS salts of compound I were prepared following the procedure as shown below:
(i) A stock solution of compound I in PrOH (for TRIS salt) and EtOH (for Arginine salt) was respectively prepared.
(ii) The required weight of base (TRIS and Arginine) equating to 1:1 molar equivalents was respectively added to the compound I stock solutions.
(iii) After the addition of counter-ions, the samples were sealed and temperature cycled for up to ~3 days (40° C./RT, 4 hour periods at each temperature) and checked periodically for crystalline material.
(viii) Solid materials were then filtered and dried in a desiccator.

Example 4

Short Term Accelerated Stability Study of Arginine and TRIS Salts

Arginine and TRIS salts of compound I prepared as described above were stored at 40° C./75% RH. Each sample was assessed at 0,1 week, 2 weeks and 4 weeks by XRPD, DSC and HPLC assess the stability of each salt.

Example 5

Slurry of Arginine and TRIS Salts to Determine Stability

Both Arginine and TRIS salt forms of compound I prepared as described above were slurried in 2~4 different solvents including aqueous mixes to further determine the stability of the new salt forms. The solids were then dried and analyzed by XRPD and Raman to check for changes in physical and/or chemical form.

Example 6

Micronization of Arginine and TRIS Salts and Full Physical Characterization

Both Arginine and TRIS salt forms of compound I prepared as described above were micronized at Pharmaterials in preparation for PK studies. Particle size reduction was done using a Sturtevant Qualification Micronizer® (Sturtevant Inc. Hanover Mass., USA) with dry nitrogen gas as feed and grind gas. To avoid clogging of the venturi and feed nozzle, the polymorph was initially ground using a pestle and motor to break down large particles. Grinding was done at room temperature using the following settings:
Feed air pressure: 80 psi
Grind air pressure: 100 psi The micronized polymorph was collected from the exhaust bag and put in a glass vial pending further analysis. The material was then analyzed for particle size distribution based on a method established and applied to each batch. The material post micronization was also analyzed using XRPD, Raman and DSC to check the physical form (as there is significant risk of formation of amorphous content during the micronization process, which can lead to large variability in the PK results over time). The samples were also analyzed by HPLC to determine chemical purity.

Example 7

HPLC of Arginine and TRIS Polymorphs of Compound I

The details of the HPLC method used to determine the purity is outlined below.
Column: Phenomenax Gemini C18, 100*4.6 mm, 3 5μ, 110° A
Mobile Phase A: 0.1% v/v TFA in Water
Mobile Phase B: 0.05% TFA in Acetonitrile
Flow Rate: 1.2 mL/min
Column Temperature: 0° C.
Detection: UV 227 nm
Injection volume: 10 μL
Run time: 15 minutes
Sample Solvent: % TFA in Acetonitrile
Gradient Conditions: See Table 7.

TABLE 11

HPLC Gradient Conditions

| Time (minutes) | Flow rate (ml/min) | Mobile Phase A (%) | Mobile phase B (%) |
|---|---|---|---|
| 0.0 | 1.2 | 90 | 10 |
| 2.0 | 1.2 | 50 | 50 |
| 6.0 | 1.2 | 35 | 65 |
| 8.0 | 1.2 | 90 | 10 |
| 12.0 | 1.2 | 90 | 10 |

Approximately 10 mg of each of Arginine and TRIS polymorph salt was weighed in separate 100 mL volumetric flask, dissolved and diluted to volume with sample solvent to obtain a concentration of about 0.1 mg/mL. The resulting solution was analyzed by HPLC.

The details of the HPLC method used for assay of arginine counter ion in the polymorph salt is outlined below.
Column: Kromasil C18, 250*4.6 mm, 5μ
Mobile Phase: 10 mM Ammonium Bicarbonate (pH 10): Methanol (990:10)
Flow Rate: 1.0 mL/min
Column Temperature: 25° C.
Detection: UV 215 nm
Injection volume: 10 μL
Run time: 10 minutes
Sample Solvent: Water Approximately 10 mg of Arginine salt was weighed in 100 mL volumetric flask, dissolved and diluted to volume with sample solvent to get concentration of about 0.1 mg/mL.

The details of the HPLC method used for assay of TRIS counter ion in the polymorph salt is outlined below.
Column: Zorbax NH2 5 μm, 150*4.6 mm
Mobile Phase: Acetonitrile: Water (80:20)
Flow Rate: 1.0 mL/min
Column Temperature: 25° C.
Detection: UV 225 nm
Injection volume: 10 μL
Run time: 10 minutes
Sample Solvent: Acetonitrile: Water (80:20)

Approximately 25 mg of TRIS polymorph salt was weighed in 50 mL volumetric flask, dissolved and diluted to volume with sample solvent to get concentration of about 0.5 g/mL.

The resulting solutions of two salts were respectively analyzed by HPLC.

Example 8

X-Ray Powder Diffraction (XRPD)

Approximately 5 mg of sample was gently compressed on the XRPD zero background single obliquely cut silica sample holder. The sample was then loaded into a Philips X-Pert MPD diffractometer and analyzed using the following experimental conditions;
Tube anode: Cu
Generator tension: 40 kV
Tube current: 40 mA
Wavelength alpha1: 1.5406 Å
Wavelength alpha2: 1.5444 Å
Start angle [2 theta]: 5
End angle [2 theta]: 50
Time per step: 2.5 seconds
Scan step size: 0.06

Example 9

Differential Scanning Calorimetry (DSC)

Approximately 2 mg of sample was weighed into an aluminum DSC pan and sealed with an aluminum lid non-hermetically. The sample was then loaded into a Perkin-Elmer Diamond DSC (equipped with a liquid-nitrogen cooling unit) cooled and held at 25° C. Once a stable heat-flow response was obtained, the sample was then heated to 240° C. at scan rate of 200° C./min and the resulting heat flow response monitored. A 20 $cm^3$/min helium purge was used to prevent thermally induced oxidation of the sample during heating and also to reduce the thermal lag through the sample to increase the instrument sensitivity. Prior to analysis, the instrument was temperature and heat-flow calibrated using an indium reference standard.

Example 10

Raman Spectroscopy

Raman spectra were recorded on a confocal Nicolet Almega XR dispersive Raman spectrometer. Raman spectrum was measured under following conditions:
Exposure Time: 1.0 sec
Number of exposures: 10
Laser: 633 nm He/Ne laser at 100% power
Spectrograph aperture: 100 μm pinhole
Wavelength: whole (single grating)
Objective: 20×/0.25

The measured Raman spectra were corrected by baseline subtraction using the software OMNIC™ v7.3.

Example 11

Nuclear Magnetic Resonance (NMR)

Solution (DMSO d6) 1H nuclear magnetic resonance (NMR) and 13C NMR spectra were acquired with a JEOL Eclipse 400 spectrometer operating at 400.13 and 100.52 MHz, respectively; tetramethylsilane (TMS) was employed as the internal standard.

Example 12

Determination of Particle Size Distribution

Particle size analysis of the pre-milled and post-milled TRIS and arginine salts was carried out using the Malvern Mastersizer, Model Micro Plus. Backgrounds were first measured using the appropriate vehicle solution as diluent (Dimethyl Siloxane). The samples were added drop-wise until a suitable obscuration value was achieved, and particle size distribution measured. A minimum of three analyses were made for each sample.

Example 13

Thermodynamic Stability Studies on Sodium Salt Polymorphic Forms

The amorphous material Form I, polymorph Form II, polymorph Form III and polymorph Form IV were slurried together in pairs in ethanol, isopropanol, or ethyl acetate at 25° C.; and 60° C. All materials were isolated and analyzed by XRPD.

The results from the competitive slurry experiments in different solvents and temperatures are shown below in Table 12. For most mixtures, higher temperature at 60° C. did not change forms. In most slurries in EtOH and IPA, the mixtures convert to Form III at both 25° C. and 60° C., whereas in EtOAc all slurry mixtures convert to Form IV.

TABLE 12

Resulting Polymorph Competitive Slurry Experiments

| Forms slurried | EtOH @ 25° C. | EtOH @ 60° C. | IPA @ 25° C. | IPA @ 60° C. | EtOAc 25° C. | EtOAc @ 60° C. |
|---|---|---|---|---|---|---|
| Form I + II | mostly Form IV | | Form III | Form III | Form IV | Form IV |
| Form I + III | Form III | Form III | Form III | Form III | Form IV | Form IV |
| Form I + IV | — | Form III | Form III | Form III | Form IV | Form IV |
| Form II + III | Form III | Form III | Form III | Form III | Changed upon heating | Form IV |
| Form II + IV | mostly Form III | | Form III | Form III | Form IV | Form IV |
| Form III + IV | Form III | Form III | Form III | Form III | Form IV | Form IV |

Citation of the above patents, patent applications, publications and documents is not an admission that any of the foregoing is pertinent prior art, nor does it constitute any admission as to the contents or date of these publications or documents. Furthermore, the contents of the patents, patent applications, publications and documents cited herein are incorporated by reference in their entirety for all purposes to the same extent as each and everyone of them is incorporated by references specifically.

Modifications may be made to the foregoing without departing from the basic aspects of the invention. Although the invention has been described in substantial detail with reference to one or more specific embodiments, those of ordinary skill in the art will recognize that changes may be made to the embodiments specifically disclosed in this application, and yet these modifications and improvements are within the scope and spirit of the invention. The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. Thus, the terms and expressions which have been employed are used as terms of description and not of limitation, equivalents of the features shown and described, or portions thereof, are not excluded, and it is recognized that various modifications are possible within the scope of the invention.

What is claimed is:

1. A crystalline polymorph of a salt of compound (I):

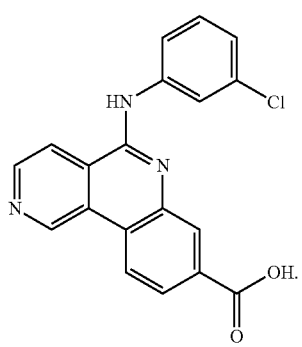

(I)

characterized by having powder X-ray diffraction pattern peaks of 2θ at about:
  (a) 26.2°, and 27.2°, the salt being sodium salt Form II; or
  (b) 25.9°, 27.1° and 27.9°, the salt being sodium salt Form III; or
  (c) 22.8°, and 25.3°, the salt being sodium salt Form IV; or
  (d) 12.3° and 31.3°, the salt being sodium salt Form V; or
  (e) 20.7° and 26.0°, the salt being sodium salt Form VI; or
  (f) 12.2° and 17.7°, the salt being sodium salt Form VII; or
  (g) 24.4° and 25.4°, the salt being sodium salt Form VIII; or
  (h) 15.8° and 16.5°, the salt being sodium salt Form IX; or
  (i) 23.6° and 28.4°, the salt being sodium salt Form X; or
  (j) 24.4°, 24.9° and 26.4°, the salt being sodium salt Form XI; or
  (k) 26.3° and 30.7°, the salt being sodium salt Form XII.

2. The crystalline polymorph of claim 1, wherein the sodium salt Form II is characterized by having powder X-ray diffraction pattern peaks of 2θ at about 10.4°, 11.9°, 15.1°, 15.6°, 26.2°, and 27.2°.

3. The crystalline polymorph of claim 1, wherein the sodium salt Form II is characterized by having the powder X-ray diffraction pattern substantially as shown in FIG. 2.

4. The crystalline polymorph of claim 1, wherein the sodium salt Form II is further characterized by having a water content between about 13% and about 17%.

5. The crystalline polymorph of claim 4, wherein the sodium salt Form II has a water content of about 15%.

6. The crystalline polymorph of claim 1, wherein the sodium salt Form II is further characterized by having an endotherm at about 90° C. as shown by DSC.

7. The crystalline polymorph of claim 1, wherein the sodium salt Form III is characterized by having powder X-ray diffraction pattern peaks of 2θ at about 8.2°, 25.9°, 26.1°, 27.1°, and 27.9°.

8. The crystalline polymorph of claim 1, wherein the sodium salt Form III is characterized by having the powder X-ray diffraction pattern substantially as shown in FIG. 7.

9. The crystalline polymorph of claim 1, wherein the sodium salt Form III is further characterized by having a water content between about 3% and about 7%.

10. The crystalline polymorph of claim 9, wherein the sodium salt Form III has a water content of about 5%.

11. The crystalline polymorph of claim 1, wherein the sodium salt Form III is further characterized by having an endotherm at about 120° C. as shown by DSC.

12. The crystalline polymorph of claim 1, wherein the sodium salt Form IV is characterized by having powder X-ray diffraction pattern peaks of 2θ at about 19.5°, 21.6°, 22.8°, 24.1°, 24.6°, 26.9°, and 29.5°.

13. The cc polymorph of claim 1, wherein the sodium salt Form IV is characterized by having the powder X-ray diffraction pattern substantially as shown in FIG. 11.

14. The crystalline polymorph of claim 1, wherein the sodium salt Form IV is further characterized by having a water content of less than about 5%.

15. The crystalline polymorph of claim 14, wherein the sodium salt Form IV has a water content of about 2%.

16. The crystalline polymorph of claim 1, wherein the sodium salt Form IV is further characterized by having endotherm at about 100° C. as shown by DSC.

17. The crystalline polymorph of claim 1, wherein the sodium salt Form V is characterized by having powder X-ray diffraction pattern peaks of 2θ at about 12.3°, 21.8°, 224°, and 31.3°.

18. The crystalline polymorph of claim 1, wherein the sodium salt Form V is characterized by having powder X-ray diffraction pattern substantially as shown in FIG. 16.

19. The crystalline polymorph of claim 1, wherein the sodium salt Form VI is characterized by having powder X-ray diffraction pattern peaks of 2θ at about 11.4°, 14.6°, 16.1°, 20.7°, and 26.0°.

20. The crystalline polymorph of claim 1, wherein the sodium salt Form VI is characterized by having the powder X-ray diffraction pattern substantially as shown in FIG. 17.

21. The crystalline polymorph of claim 1, wherein the sodium salt Form VII is characterized by having powder X-ray diffraction pattern peaks of 2θ at about 11.7°, 12.2°, 13.8°, 14.4°, 15.9°, 17.7°, 18.5°, 19.7°.

22. The crystalline polymorph of claim 1, wherein the sodium salt Form VII is characterized by having the powder X-ray diffraction pattern substantially as shown in FIG. 18.

23. The crystalline polymorph of claim 1, wherein the sodium salt Form VII is further characterized by having a water content between about 3% and about 7%.

24. The crystalline polymorph of claim 23, wherein the sodium salt Form VII has a water content of about 5%.

25. The crystalline polymorph of claim 1, wherein the sodium salt Form VIII is characterized by having powder X-ray diffraction pattern peaks of 2θ at about 10.2°, 14.0°, 14.4°, 18.4°, 24.4°, 24.9°, and 25.4°.

26. The crystalline polymorph of claim 1, wherein the sodium salt Form VIII is characterized by having the powder X-ray diffraction pattern substantially as shown in FIG. 19.

27. The crystalline polymorph of claim 1, wherein the sodium salt Form IX is characterized by having powder X-ray diffraction pattern peaks of 2θ at about 14.2°, 15.8°, 16.0° and 16.5°.

28. The crystalline polymorph of claim 1, wherein the sodium salt Form IX is characterized by having the powder X-ray diffraction pattern substantially as shown in FIG. 21.

29. The crystalline polymorph of claim 1, wherein the sodium salt Form X is characterized by having powder X-ray diffraction pattern peaks of 2θ at about 13.8°, 23.6°, 25.3° and 28.4°.

30. The crystalline polymorph of claim 1, wherein the sodium salt Form X is characterized by having the powder X-ray diffraction pattern substantially as shown in FIG. 22.

31. The crystalline polymorph of claim 1, wherein the sodium salt Form XI is characterized by having powder X-ray diffraction pattern peaks of 2θ at about 22.6°, 24.4°, 24.9°, 26.4°, 28.5° and 30.7°.

32. The crystalline polymorph of claim 1, wherein the sodium salt Form XI is characterized by having the powder X-ray diffraction pattern substantially as shown in FIG. 23.

33. The crystalline polymorph of claim 1, wherein the sodium salt Form XII is characterized by having powder X-ray diffraction pattern peaks of 2θ at about 14.8°, 21.9°, 23.8°, 26.3°, 27.6°, and 30.7°.

34. The crystalline polymorph of claim 1, wherein the sodium salt Form XII is characterized by having the powder X-ray diffraction pattern substantially as shown in FIG. 24.

35. The crystalline polymorph of claim 1, wherein the crystalline polymorph is substantially pure.

36. A composition comprising a crystalline polymorph of claim 1, and a pharmaceutically acceptable carrier.

\* \* \* \* \*